US008629158B2

(12) United States Patent
Guzzo et al.

(10) Patent No.: US 8,629,158 B2
(45) Date of Patent: Jan. 14, 2014

(54) AZABICYCLOALKANE-INDOLE AND AZABICYCLOALKANE-PYRROLO-PYRIDINE MCH-1 ANTAGONISTS, METHODS OF MAKING, AND USE THEREOF

(75) Inventors: Peter R. Guzzo, Niskayuna, NY (US); Matthew David Surman, Albany, NY (US); Alan John Henderson, Albany, NY (US); Mark Hadden, Albany, NY (US); Emily Elizabeth Freeman, Guilderland, NY (US)

(73) Assignee: Albany Molecular Research, Inc., Albany, NY (US)

( * ) Notice: Subject to any disclaimer, the term of this patent is extended or adjusted under 35 U.S.C. 154(b) by 306 days.

(21) Appl. No.: 12/828,855

(22) Filed: Jul. 1, 2010

(65) Prior Publication Data

US 2011/0003737 A1 Jan. 6, 2011
US 2012/0058939 A9 Mar. 8, 2012

Related U.S. Application Data

(60) Provisional application No. 61/222,440, filed on Jul. 1, 2009, provisional application No. 61/329,428, filed on Apr. 29, 2010.

(51) Int. Cl.
*A61K 31/437* (2006.01)
*A61K 31/4412* (2006.01)
*C07D 471/18* (2006.01)

(52) U.S. Cl.
USPC ............... 514/286; 546/61; 546/62; 546/63; 514/279; 514/285

(58) Field of Classification Search
USPC ............ 546/61, 62, 64, 70, 63; 514/279, 285, 514/287, 286
See application file for complete search history.

(56) References Cited

U.S. PATENT DOCUMENTS

| | | |
|---|---|---|
| 3,514,462 A | 5/1970 | Hester |
| 4,978,669 A | 12/1990 | Barchas et al. |
| 4,985,422 A | 1/1991 | North et al. |
| 5,013,733 A | 5/1991 | Coates et al. |
| 5,162,336 A | 11/1992 | Molino et al. |
| 5,169,852 A | 12/1992 | Barchas et al. |
| 5,183,820 A | 2/1993 | Coates et al. |
| 5,187,180 A | 2/1993 | Gillard |
| 5,223,625 A | 6/1993 | Van Wijngaarden et al. |
| 5,225,407 A | 7/1993 | Oakley et al. |
| 5,424,314 A | 6/1995 | Clemence et al. |
| 5,466,688 A | 11/1995 | Commons et al. |
| 5,506,234 A | 4/1996 | Huth et al. |
| 5,527,794 A | 6/1996 | Commons et al. |
| 5,563,147 A | 10/1996 | Gilmore et al. |
| 5,569,661 A | 10/1996 | Haffer et al. |
| 5,767,131 A | 6/1998 | Gluchowski et al. |
| 5,811,551 A | 9/1998 | Chen et al. |
| 5,854,245 A | 12/1998 | Duggan et al. |
| 5,932,582 A | 8/1999 | Young et al. |
| 5,972,980 A | 10/1999 | Cornicelli et al. |
| 6,001,866 A | 12/1999 | Cornicelli et al. |
| 6,177,440 B1 | 1/2001 | Bach et al. |
| 6,255,306 B1 | 7/2001 | Macor |
| 6,407,092 B1 | 6/2002 | Hester et al. |
| 6,548,493 B1 | 4/2003 | Robichaud et al. |
| 6,552,017 B1 | 4/2003 | Robichaud et al. |
| 6,605,639 B1 | 8/2003 | Tamura et al. |
| 6,610,684 B2 | 8/2003 | Zaharevitz et al. |
| 6,653,304 B2 | 11/2003 | Leftheris et al. |
| 6,699,852 B2 | 3/2004 | Robichaud et al. |
| 6,713,471 B1 | 3/2004 | Robichaud et al. |
| 6,713,645 B1 | 3/2004 | Bach et al. |
| 6,727,264 B1 | 4/2004 | Marzabadi et al. |
| 6,838,456 B2 | 1/2005 | Orme et al. |
| 6,849,619 B2 | 2/2005 | Robichaud et al. |
| 6,849,640 B2 | 2/2005 | Ennis et al. |
| 6,872,721 B2 | 3/2005 | Orme et al. |
| 6,872,743 B2 | 3/2005 | Beight et al. |
| 6,875,762 B2 | 4/2005 | Hester et al. |
| 6,890,933 B1 | 5/2005 | Feng et al. |
| 6,906,095 B2 | 6/2005 | Cole et al. |
| 6,927,222 B2 | 8/2005 | Hansen et al. |
| 6,927,223 B1 | 8/2005 | Meadows et al. |
| 6,943,188 B2 | 9/2005 | Eriksson et al. |
| 6,951,874 B2 | 10/2005 | Hansen et al. |
| 6,951,881 B2 | 10/2005 | Cole et al. |
| 6,992,192 B2 | 1/2006 | Sawyer et al. |
| 7,022,856 B2 | 4/2006 | Orme et al. |
| 7,115,621 B2 | 10/2006 | Sawyer et al. |
| 7,122,554 B2 | 10/2006 | Sawyer et al. |
| 7,193,079 B1 | 3/2007 | Tepe |

(Continued)

FOREIGN PATENT DOCUMENTS

CA 2597193 A1 2/2009
CN 101074207 A 11/2007

(Continued)

OTHER PUBLICATIONS

Extended European Search Report for corresponding EP Application No. 10794771.5 (mailed Oct. 16, 2012).
Kokkotou et al., "Melanin-Concentrating Hormone as a Mediator of Intestinal Inflammation," PNAS 105 (30):10613-10618 (2008).
International Search Report for International Patent Application No. PCT/US10/40800 (Aug. 30, 2010).
Written Opinion of the International Patent Searching Authority for International Patent Application No. PCT/US10/40800 (Aug. 30, 2010).
International Search Report for International Patent Application No. PCT/US10/40809 (Aug. 30, 2010).

(Continued)

*Primary Examiner* — Golam M M Shameem
(74) *Attorney, Agent, or Firm* — LeClairRyan, a Professional Corporation

(57) ABSTRACT

Novel MCH-1 receptor antagonists are disclosed. These compounds are used in the treatment of various disorders, including obesity, anxiety, depression, non-alcoholic fatty liver disease, and psychiatric disorders. Methods of making these compounds are also described in the present invention.

28 Claims, No Drawings

(56) References Cited

U.S. PATENT DOCUMENTS

| | | |
|---|---|---|
| 7,196,103 B2 | 3/2007 | Nazare et al. |
| 7,250,514 B1 | 7/2007 | Xiao |
| 7,332,519 B2 | 2/2008 | Hinze et al. |
| 7,335,769 B2 | 2/2008 | Tepe |
| 7,385,055 B2 | 6/2008 | Tepe |
| 7,482,360 B2 | 1/2009 | Burnett et al. |
| 7,485,634 B2 | 2/2009 | Martin et al. |
| 7,872,017 B2 | 1/2011 | Ji et al. |
| 8,067,590 B2 | 11/2011 | Stenkamp et al. |
| 8,101,632 B2 | 1/2012 | Guzzo et al. |
| 8,158,643 B2 | 4/2012 | Andres-Gil et al. |
| 8,268,868 B2 | 9/2012 | Guzzo et al. |
| 8,273,770 B2 | 9/2012 | Guzzo et al. |
| 2002/0013333 A1 | 1/2002 | Batty et al. |
| 2002/0099068 A1 | 7/2002 | Ritzeler et al. |
| 2002/0173503 A1 | 11/2002 | Robichaud et al. |
| 2003/0022819 A1 | 1/2003 | Ling et al. |
| 2003/0095958 A1 | 5/2003 | Bhisetti et al. |
| 2003/0130293 A1 | 7/2003 | Bamdad |
| 2003/0144267 A1 | 7/2003 | Hansen et al. |
| 2003/0149047 A1 | 8/2003 | Eriksson et al. |
| 2003/0158225 A1 | 8/2003 | Hansen et al. |
| 2003/0225058 A1 | 12/2003 | Frank et al. |
| 2003/0232843 A1 | 12/2003 | Cole et al. |
| 2004/0002527 A1 | 1/2004 | Cole et al. |
| 2004/0023947 A1 | 2/2004 | Martin et al. |
| 2004/0116458 A1 | 6/2004 | Sawyer et al. |
| 2004/0122035 A1 | 6/2004 | Orme et al. |
| 2004/0186094 A1 | 9/2004 | Robichaud et al. |
| 2004/0235820 A1 | 11/2004 | Tepe |
| 2005/0004156 A1 | 1/2005 | Feng et al. |
| 2005/0026941 A1 | 2/2005 | Sawyer et al. |
| 2005/0033049 A1 | 2/2005 | Nazare et al. |
| 2005/0054634 A1 | 3/2005 | Busch et al. |
| 2005/0176775 A1 | 8/2005 | Devadas et al. |
| 2005/0187387 A1 | 8/2005 | Lynch et al. |
| 2005/0192333 A1 | 9/2005 | Hinze et al. |
| 2005/0215580 A1 | 9/2005 | Wang et al. |
| 2006/0004041 A1 | 1/2006 | Cummings et al. |
| 2006/0019952 A1 | 1/2006 | Distefano et al. |
| 2006/0128711 A1 | 6/2006 | Gallego et al. |
| 2006/0167259 A1 | 7/2006 | Chao et al. |
| 2006/0189639 A1 | 8/2006 | Stewart et al. |
| 2006/0235012 A1 | 10/2006 | Davidson et al. |
| 2006/0247228 A1 | 11/2006 | Umeda et al. |
| 2006/0276451 A1 | 12/2006 | Tepe |
| 2006/0281786 A1 | 12/2006 | Hamprecht et al. |
| 2006/0281796 A1 | 12/2006 | Edmondson et al. |
| 2006/0287296 A1 | 12/2006 | Tepe |
| 2006/0293305 A1 | 12/2006 | Tepe |
| 2007/0004765 A1 | 1/2007 | Graffner-Nordberg et al. |
| 2007/0027178 A1 | 2/2007 | Lee |
| 2007/0037791 A1 | 2/2007 | Rawson et al. |
| 2007/0049575 A1 | 3/2007 | Tepe |
| 2007/0049593 A1 | 3/2007 | Oka et al. |
| 2007/0149557 A1 | 6/2007 | Collins et al. |
| 2007/0173537 A1 | 7/2007 | Takemiya et al. |
| 2007/0185184 A1 | 8/2007 | Hanson et al. |
| 2007/0213351 A1 | 9/2007 | Sundermann et al. |
| 2007/0254877 A1 | 11/2007 | Nishikimi et al. |
| 2007/0293491 A1 | 12/2007 | Shafer et al. |
| 2008/0045539 A1 | 2/2008 | Ji et al. |
| 2008/0103164 A1 | 5/2008 | Gudmundsson et al. |
| 2008/0124319 A1 | 5/2008 | Pothoulakis et al. |
| 2008/0125475 A1 | 5/2008 | Linz et al. |
| 2008/0194803 A1 | 8/2008 | Sinclair et al. |
| 2008/0207594 A1 | 8/2008 | Mussmann et al. |
| 2008/0221141 A1 | 9/2008 | Friderichs et al. |
| 2008/0269055 A1 | 10/2008 | Bastiaans et al. |
| 2008/0287423 A1 | 11/2008 | Mussmann et al. |
| 2008/0292626 A1 | 11/2008 | Wang et al. |
| 2008/0312218 A1 | 12/2008 | Burnett et al. |
| 2009/0012062 A1 | 1/2009 | Andres-Gil et al. |
| 2009/0012077 A1 | 1/2009 | Dossetter et al. |
| 2009/0069367 A1 | 3/2009 | Bamdad |
| 2009/0075996 A1 | 3/2009 | Alper et al. |
| 2009/0232879 A1 | 9/2009 | Cable et al. |
| 2009/0264426 A1 | 10/2009 | Sakuraba et al. |
| 2010/0105679 A1 | 4/2010 | Guzzo et al. |
| 2010/0249105 A1 | 9/2010 | Schrimpf et al. |
| 2010/0331339 A9 | 12/2010 | Guzzo et al. |
| 2011/0003737 A1 | 1/2011 | Guzzo et al. |
| 2011/0003738 A1 | 1/2011 | Guzzo et al. |
| 2011/0003739 A1 | 1/2011 | Guzzo et al. |
| 2011/0003793 A1 | 1/2011 | Guzzo et al. |
| 2012/0035102 A9 | 2/2012 | Guzzo et al. |
| 2012/0058940 A9 | 3/2012 | Guzzo et al. |
| 2012/0157460 A1 | 6/2012 | Surman et al. |
| 2012/0157469 A1 | 6/2012 | Surman et al. |

FOREIGN PATENT DOCUMENTS

| | | |
|---|---|---|
| EP | 950661 A1 | 10/1999 |
| EP | 1462103 A1 | 9/2004 |
| EP | 1757607 A1 | 2/2007 |
| EP | 2003129 A1 | 12/2008 |
| GB | 2120662 A | 12/1983 |
| IN | 2000CH01126 | 3/2005 |
| JP | 2951434 B2 | 11/2004 |
| WO | 92/00295 A1 | 1/1992 |
| WO | WO 9422829 A2 | 10/1994 |
| WO | WO 9611197 A1 | 4/1996 |
| WO | WO 9612721 A1 | 5/1996 |
| WO | WO 9633211 A1 | 10/1996 |
| WO | WO 9712613 A1 | 4/1997 |
| WO | WO 9723458 A1 | 7/1997 |
| WO | WO 9731910 A1 | 9/1997 |
| WO | 98/00401 A1 | 1/1998 |
| WO | WO 9800134 A1 | 1/1998 |
| WO | WO 9947521 A1 | 9/1999 |
| WO | WO 0064899 A1 | 11/2000 |
| WO | WO 0077002 A1 | 12/2000 |
| WO | WO 0105793 A1 | 1/2001 |
| WO | 01/58869 A2 | 8/2001 |
| WO | WO 0164680 A1 | 9/2001 |
| WO | WO 0168648 A1 | 9/2001 |
| WO | WO 0187038 A2 | 11/2001 |
| WO | WO 0187883 A1 | 11/2001 |
| WO | WO 0194345 A2 | 12/2001 |
| WO | WO 0204456 A1 | 1/2002 |
| WO | WO 0204457 A1 | 1/2002 |
| WO | WO 0224701 A2 | 3/2002 |
| WO | WO 0228859 A2 | 4/2002 |
| WO | WO 0228865 A2 | 4/2002 |
| WO | 02/50034 A2 | 6/2002 |
| WO | 02/064590 A2 | 8/2002 |
| WO | 02/064591 A2 | 8/2002 |
| WO | WO 02059082 A2 | 8/2002 |
| WO | WO 02059129 A2 | 8/2002 |
| WO | 02/088101 A2 | 11/2002 |
| WO | 02/088123 A1 | 11/2002 |
| WO | 02/098875 A1 | 12/2002 |
| WO | 03/014118 A1 | 2/2003 |
| WO | WO 03099821 A1 | 12/2003 |
| WO | WO 2004030629 A2 | 4/2004 |
| WO | WO 2004081010 A1 | 9/2004 |
| WO | 2005/070930 A2 | 8/2005 |
| WO | 2005/107471 A1 | 11/2005 |
| WO | 2005/108367 A1 | 11/2005 |
| WO | WO 2005118587 A1 | 12/2005 |
| WO | 2006/015035 A1 | 2/2006 |
| WO | WO 2006018184 A2 | 2/2006 |
| WO | WO 2006064355 A2 | 6/2006 |
| WO | WO 2006064757 A1 | 6/2006 |
| WO | WO 2006089874 A1 | 8/2006 |
| WO | 2006/122931 A1 | 11/2006 |
| WO | WO 2006117548 A1 | 11/2006 |
| WO | WO 2007002051 A1 | 1/2007 |
| WO | WO 2007009120 A2 | 1/2007 |
| WO | 2007/024004 A1 | 3/2007 |
| WO | 2007/035620 A2 | 3/2007 |
| WO | WO 2007062175 A2 | 5/2007 |
| WO | WO 2007070796 A1 | 6/2007 |
| WO | WO 2007120333 A2 | 10/2007 |

(56) References Cited

FOREIGN PATENT DOCUMENTS

| WO | WO 2007124903 A1 | 11/2007 |
| --- | --- | --- |
| WO | 2007/142217 A1 | 12/2007 |
| WO | WO 2007141200 A1 | 12/2007 |
| WO | WO 2008011805 A1 | 1/2008 |
| WO | WO 2008024029 A1 | 2/2008 |
| WO | WO 2008046155 A1 | 4/2008 |
| WO | WO 2008060190 A2 | 5/2008 |
| WO | WO 2008081282 A2 | 7/2008 |
| WO | WO 2008101659 A1 | 8/2008 |
| WO | WO 2008101660 A1 | 8/2008 |
| WO | WO 2008103470 A3 | 8/2008 |
| WO | WO 2008106594 A2 | 9/2008 |
| WO | WO 2008112280 A1 | 9/2008 |
| WO | WO 2009003003 A2 | 12/2008 |
| WO | WO 2009022104 A1 | 2/2009 |
| WO | WO 2009032123 A2 | 3/2009 |
| WO | 2009/089482 | 7/2009 |
| WO | WO 2011003005 A1 | 1/2011 |
| WO | WO 2011003007 A1 | 1/2011 |
| WO | WO 2011003012 A1 | 1/2011 |
| WO | WO 2011003021 A1 | 1/2011 |

OTHER PUBLICATIONS

Written Opinion of the International Searching Authority for International Patent Application No. PCT/US10/40809 (Aug. 30, 2010).
International Search Report for International Patent Application No. PCT/US2010/040803 (Aug. 30, 2010).
Written Opinion for International Patent Application No. PCT/US2010/040803 (Aug. 30, 2010).
International Search Report for International Patent Application No. PCT/US10/40820 (Aug. 30, 2010).
Written Opinion of the International Searching Authority for International Patent Application No. PCT/US10/40820 (Aug. 18, 2010).
BE 896590 to Gadient (Oct. 28, 1983) (abstract only).
CN 101074207 to Deng et al. (Nov. 21, 2007) (abstract only).
IN 2000CH01126 to Bipul et al. (Mar. 4, 2005) (abstract only).
JP 04319958 to Ito, A. (Nov. 10, 1992) (abstract only).
JP 2951434 to Ito, A. (Sep. 20, 1999) (abstract only).
International Search Report for International Patent Application No. PCT/US2009/030646 (Apr. 2, 2009).
Written Opinion of the International Searching Authority for International Patent Application No. PCT/US2009/030646 (Apr. 2, 2009).
Hadden et al., "Synthesis and SAR of 4-aryl-1-(indazol-5-yl)pyridin-2(1H)ones as MCH-1 Antagonists for the Treatment of Obesity," Bioorg. Med. Chem. Lett. 20:7020-7023 (2010).
Sargent et al., "New Central Targets for the Treatment of Obesity," Br. J. Clin. Pharmacol. 68(6):852-860 (2009).
Henderson et al., "Tetrahydrocarboline Analogs as MCH-1 Antagonists," Bioorg. Med. Chem. Lett. 20:7024-7028 (2010).
Surman et al., "5-(Pyridinon-1-yl)indazoles and 5-(furopyridinon-5-yl)indazoles as MCH-1 Antagonists," Bioorg. Med. Chem. Lett. 20:7015-7019 (2010).
Viggers et al., "Development and Validation of a Radioligand Receptor Binding Assay for MCH-1 Receptors Using [3H]AMR-MCH-1 In Vitro and Ex Vivo," Abstract 584.27/SS8, Society for Neuroscience Annual Meeting (2008).
Lakaye et al., "Melanin-Concentrating Hormone and Immune Function," Peptides 30:2076-2080 (2009).
Kokkotou et al., "Melanin-Concentrating Hormone (MCH) Modulates C Difficile Toxin A-Mediated Enteritis in Mice," Gut. 58(1):34-40 (2009).
Office Action dated Jan. 24, 2012 for U.S. Appl. No. 12/351,561.
Office Action dated Mar. 7, 2012 for Chinese Application No. 200980105529.7.
Office Action dated Jan. 30, 2013 for U.S. Appl. No. 12/828,890.
Office Action dated Feb. 20, 2013 for U.S. Appl. No. 12/828,955.
Patent Examination Report dated Oct. 22, 2012 for Australian Application No. 2009204048.
Office Action dated Jan. 5, 2013 for Chinese Application No. 200980105529.7.
Translation of Office Action dated Oct. 30, 2012 for Israeli Application No. 206594.
Office Action dated Feb. 17, 2011 for New Zealand Application No. 586120.
Office Action dated May 30, 2012 for New Zealand Application No. 586120.
Extended Search Report dated Jun. 7, 2012 for European Application No. 12163813.4.
Office Action dated Jul. 2, 2012 for U.S. Appl. No. 12/828,807.
Jantzen and Robinson, Modern Pharmaceutics, 596 (1996).
STN Registry Database, RN 1260582-72-6, available online Jan. 27, 2011.
Office Action for U.S. Appl. No. 13/330,989 (Jul. 19, 2013).
"Burger's Medicinal Chemistry and Drug Discovery" edited by Manfred E. Wolff, 5th Ed. Part 1, pp. 975-977 (1995).
Banker et al., "Modern Parmaceutics," 3rd Ed., p. 451, 596 (1996).
Carpenter et al., "Melanin-Concentrating Hormone Receptor Antagonists as Potential Antiobesity Agents," Expert Opin. Ther. Patents 12(11):1639-1646 (2002).
Dyke et al., "Recent Developments in the Discovery of MCH-1R Antagonists for the Treatment of Obesity—An Update," Expert Opin. Ther. Patents 15(10):1303-1313 (2005).
Johansson, "Recent Progress in the Discovery of Melanin-Concentrating Hormone 1-Receptor Antagonists," Expert Opin. Ther. Patents 21(6):905-925 (2011).
Vippagunta et al., "Crystalline Solids," Adv. Drug Del. Rev. 48:3-26 (2001).
International Search Report and Written Opinion for PCT/US2011/066027 (Aug. 14, 2012).
International Search Report and Written Opinion for PCT/US2011/066177 (Jun. 28, 2012).
Translation of Office Action dated Oct. 3, 2013 for Japanese Application No. 2010-542381.

AZABICYCLOALKANE-INDOLE AND AZABICYCLOALKANE-PYRROLO-PYRIDINE MCH-1 ANTAGONISTS, METHODS OF MAKING, AND USE THEREOF

This application claims benefit of U.S. Provisional Patent Application Ser. No. 61/222,440, filed Jul. 1, 2009, and U.S. Provisional Patent Application Ser. No. 61/329,428, filed Apr. 29, 2010, which are hereby incorporated by reference in their entirety.

FIELD OF THE INVENTION

The present invention relates to azabicycloalkane-indoles, which are melanin-concentrating hormone (MCH-1) receptor antagonists, pharmaceutical compositions including these compounds, and methods of preparation and use thereof. The compounds are useful in the treatment of obesity, anxiety, depression, non-alcoholic fatty liver disease, and psychiatric disorders.

BACKGROUND OF THE INVENTION

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Obesity has associated with it, economic and social costs. Obese people, an increasing proportion of most western societies, are regarded as having out of control feeding habits often associated with low self-esteem. Moreover, obese persons are more likely to have medical problems associated with or exacerbated by the excess body weight. Examples of medical conditions caused, exacerbated, or triggered by excessive weight include bone fractures, pains in the knee joints, arthritis, increased risk of hypertension, artherosclerosis, stroke, and diabetes.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, "Chronic Infusion of MCH Causes Obesity in Mice," *Am. J. Physiol. Endocrinol. Metab.*, 284:E583 (2002)). Mice lacking MCH are hypophagic and lean with increased metabolic rate, whereas animals over-expressing MCH gain excess weight on both standard and high fat diets. MCH is thought to have effects on other nervous system functions as well (Rocksz, "Biological Examination of Melanin Concentrating Hormone 1: Multi-tasking from the Hypothalamus," *Drug News Perspect.*, 19(5):273 (2006)). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, "Recent Advances in the Discovery of Melanin-Concentrating Hormone Receptor Antagonists," *Curr. Opin. Drug Disc. & Dev.*, 9(4):496 (2006)).

The current preferred treatment for obesity as well as Type II non-insulin dependent diabetes is diet and exercise with a view toward weight reduction and improved insulin sensitivity for diabetics. Patient compliance, however, is usually poor.

The problem is compounded by the fact that there are currently only two medications approved for the treatment of obesity (sibutramine (MERIDIA™) and orlistat (XENICAL™)).

The present invention is directed to overcoming these and other deficiencies in the art.

SUMMARY OF THE INVENTION

The present invention relates to compounds of formula I:

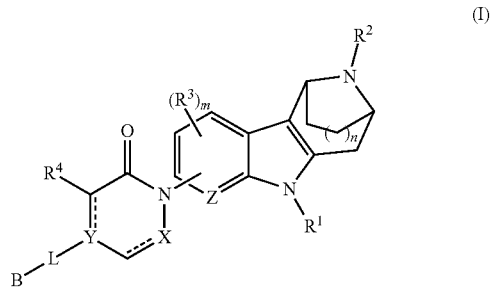

wherein
$R^1$ is selected from the group consisting of H, —S(O)$_q$R$^6$, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;
$R^2$ is selected from the group consisting of H, —S(O)$_q$R$^6$, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;
$R^3$ is independently selected at each location from the group consisting of H, halogen, —OR$^5$, —NR$^5$R$^6$, —NR$^5$C(O)R$^6$, —NR$^5$C(O)$_2$R$^6$, —NR$^6$C(O)NR$^6$R$^7$, —S(O)$_q$R$^6$, CN, C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

$R^4$ is selected from the group consisting of H, halogen, —$OR^5$, —$NR^5R^6$, —$NR^5C(O)R^6$, —$NR^5C(O)_2R^6$, $NR^6C(O)NR^6R^7$, —$S(O)_qR^6$, —CN, —$C(O)R^6$, —$C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^8$, —$NR^8R^9$, and phenyl which is optionally substituted 1-3 times with halogen, $C_1$-$C_4$ alkyl, $C_1$-$C_4$ haloalkyl, $C_1$-$C_4$ alkoxy, —CN, —$OR^8$, or —$NR^8R^9$;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^7$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^6$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^7$ is $C_1$-$C_4$ alkyl, $C_1$-$C_4$ haloalkyl, or phenyl;

$R^8$ and $R^9$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^7$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^{10}$ is selected from the group consisting of H, halogen, —$OR^5$, —$NR^5R^6$, —$NR^5C(O)R^6$, —$NR^5C(O)_2R^6$, $NR^6C(O)NR^6R^7$, —$S(O)_qR^6$, CN, $C(O)R^6$, $C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^8$, —$NR^8R^9$, and phenyl which is optionally substituted 1-3 times with halogen, $C_1$-$C_4$ alkyl, $C_1$-$C_4$ haloalkyl, $C_1$-$C_4$ alkoxy, —CN, —$OR^8$, or —$NR^8R^9$;

X is $CR^{10}$, $C(R^{10})_2$, N, or $NR^{10}$;
Y is $CR^{10}$, C, or N;
Z is C, CH, or N;
L is —$(CH_2)_p$—O—, —$(CH_2)_p$—, —CH=CH—, or a bond;
B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S-alkyl, optionally substituted $C_1$-$C_6$ alkyl, halogen, —$CF_3$, and —CN;
n is 1 or 2;
m is 0, 1, 2, or 3;
p is from 1 to 4;
q is 0, 1, or 2; and
----- represents an optional double bond,
or an oxide thereof, a pharmaceutically acceptable salt thereof, a solvate thereof, or prodrug thereof.

Additional aspects of the present invention include pharmaceutical compositions comprising a compound of the invention and a pharmaceutically acceptable carrier and, optionally, one or more additional additive agent(s) as discussed below.

The present invention also relates to a method of treating a disease or condition which is susceptible to treatment with a MCH-1 receptor antagonist. This method involves selecting a patient with a disease or condition which is susceptible to treatment with a MCH-1 antagonist and administering to the patient a therapeutically effective amount of a compound of formula I or a pharmaceutically acceptable salt thereof.

Another aspect of the present invention relates to a method of treating obesity in a subject in need of weight loss. This method involves selecting a patient in need of weight loss and administering to the patient a therapeutically effective amount of a compound of formula I or a pharmaceutically acceptable salt thereof.

Yet another aspect of the present invention relates to a method of treating obesity in a subject who has experienced weight loss. This method involves selecting a patient who has experienced weight loss and administering to the patient a therapeutically effective amount of a compound of formula I or a pharmaceutically acceptable salt thereof.

A further aspect of the present invention relates to a method of treating anxiety. This method involves selecting a patient with anxiety and administering to the patient a therapeutically effective amount of a compound of formula I or a pharmaceutically acceptable salt thereof.

The present invention also relates to a method of treating depression. This method involves selecting a patient with depression and administering to the patient a therapeutically effective amount of a compound of formula I or a pharmaceutically acceptable salt thereof.

Another aspect of the present invention relates to a method of treating non-alcoholic fatty liver disease. This method involves selecting a patient who has non-alcoholic fatty liver disease and administering to the patient a therapeutically effective amount of a compound of formula I or a pharmaceutically acceptable salt thereof.

A further aspect of the present invention relates to a process for preparation of a compound of formula I which includes treating a first intermediate compound of formula II:

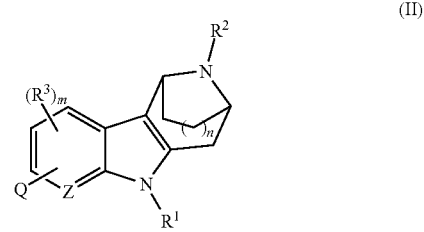

(II)

wherein Q is a halogen, under conditions effective to produce the product compound.

It has now been found that compounds of formula I are MCH-1 receptor antagonists. This invention provides compounds that bind to the MCH-1 receptor with high affinity. The compounds provided by formula I are useful for the treatment of obesity, anxiety, depression, psychiatric disorders, and other disorders described herein. In particular, it is contemplated that the compounds of this invention will be effective in treating obesity, including weight loss and maintenance of weight loss in patients who have been diagnosed with obesity by the one or more of the following measurements: an increased body mass index, increased waist circumference (an indicator of intra-abdominal fat), Dual Energy X-Ray Absorptiometry (DEXA), and truncal (android) fat mass. It is further contemplated that the compounds of the invention will be effective in inducing improvements in certain factors measured in these tests.

DETAILED DESCRIPTION OF THE INVENTION

The present invention relates to compounds of formula I:

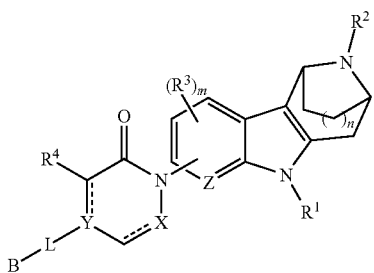

(I)

wherein $R^1$ is selected from the group consisting of H, $-S(O)_qR^6$, $-C(O)R^6$, $-C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl is optionally substituted with from 1 to 3 substituents independently selected at each occurrence thereof from $C_1$-$C_3$ alkyl, halogen, $-CN$, $-OR^8$, $-NR^8R^9$, and phenyl which is optionally substituted 1-3 times with halogen, $C_1$-$C_4$ alkyl, $C_1$-$C_4$ haloalkyl, $C_1$-$C_4$ alkoxy, $-CN$, $-OR^8$, or $-NR^8R^9$;

$R^2$ is selected from the group consisting of H, $-S(O)_qR^6$, $-C(O)R^6$, $-C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, $-CN$, $-OR^8$, $-NR^8R^9$, and phenyl which is optionally substituted 1-3 times with halogen, $C_1$-$C_4$ alkyl, $C_1$-$C_4$ haloalkyl, $C_1$-$C_4$ alkoxy, $-CN$, $-OR^8$, or $-NR^8R^9$;

$R^3$ is independently selected at each location from the group consisting of H, halogen, $OR^5$, $-NR^5R^6$, $-NR^5C(O)R^6$, $-NR^5C(O)_2R^6$, $-NR^6C(O)NR^6R^7$, $-S(O)_qR^6$, $-CN$, $-C(O)R^6$, $-C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, $-CN$, $-OR^8$, $-NR^8R^9$, and phenyl which is optionally substituted 1-3 times with halogen, $C_1$-$C_4$ alkyl, $C_1$-$C_4$ haloalkyl, $C_1$-$C_4$ alkoxy, $-CN$, $-OR^8$, or $-NR^8R^9$;

$R^4$ is selected from the group consisting of H, halogen, $-OR^5$, $-NR^5R^6$, $-NR^5C(O)R^6$, $-NR^5C(O)_2R^6$, $-NR^6C(O)NR^6R^7$, $-S(O)_qR^6$, $-CN$, $-C(O)R^6$, $-C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, $-CN$, $-OR^8$, $-NR^8R^9$, and phenyl which is optionally substituted 1-3 times with halogen, $C_1$-$C_4$ alkyl, $C_1$-$C_4$ haloalkyl, $C_1$-$C_4$ alkoxy, $-CN$, $-OR^8$, or $-NR^8R^9$;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, $-C(O)R^7$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^6$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^7$ is $C_1$-$C_4$ alkyl, $C_1$-$C_4$ haloalkyl, or phenyl;

$R^8$ and $R^9$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, $-C(O)R^7$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^{10}$ is selected from the group consisting of H, halogen, $-OR^5$, $-NR^5R^6$, $-NR^5C(O)R^6$, $-NR^5C(O)_2R^6$, $-NR^6C(O)NR^6R^7$, $-S(O)_qR^6$, $-CN$, $-C(O)R^6$, $-C(O)NR^5R^6$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, $-CN$, $-OR^8$, $-NR^8R^9$, and phenyl which is optionally substituted 1-3 times with halogen, $C_1$-$C_4$ alkyl, $C_1$-$C_4$ haloalkyl, $C_1$-$C_4$ alkoxy, $-CN$, $-OR^8$, or $-NR^8R^9$;

X is $CR^{10}$, $C(R^{10})_2$, N, or $NR^{10}$;

Y is $CR^{10}$, C, or N;

Z is C, CH, or N;

L is $-(CH_2)_p-O-$, $-(CH_2)_p-$, $-CH=CH-$, or a bond;

B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, $-S$-alkyl, optionally substituted $C_1$-$C_6$ alkyl, halogen, $-CF_3$, and $-CN$;

n is 1 or 2;

m is 0, 1, 2, or 3;

p is from 1 to 4;

q is 0, 1, or 2; and

- - - - - represents an optional double bond, or an oxide thereof, a pharmaceutically acceptable salt thereof, a solvate thereof, or prodrug thereof.

As used above, and throughout the description of the invention, the following terms, unless otherwise indicated, shall be understood to have the following meanings If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. In the present invention, the term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butyryl, 3-methylbutynyl, and n-pentynyl.

The term "aryl" means an aromatic monocyclic or multicyclic (polycyclic) ring system of 6 to about 19 carbon atoms, preferably of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

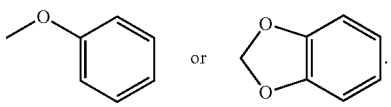

The term "compounds of the invention", and equivalent expressions, are meant to embrace compounds of general formula I as hereinbefore described, which expression includes the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of pharmaceutical compositions, methods of treatment, and compounds per se, is provided as the salt form. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The term "cycloalkyl" means a non-aromatic, saturated or unsaturated, mono- or multi-cyclic ring system of about 3 to about 7 carbon atoms, preferably of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means an cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined above.

The term "haloalkyl" means both branched and straight-chain alkyl substituted with one or more halogen, wherein the alkyl group is as herein described.

The term "halogen" means fluorine, chlorine, bromine, or iodine.

The term "heteroaryl" means an aromatic monocyclic or multi-cyclic ring system of about 5 to about 19 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl,

[1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this invention, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "method of treating" means amelioration or relief from the symptoms and/or effects associated with the disorders described herein. As used herein, reference to "treatment" of a patient is intended to include prophylaxis.

The term "monocyclic" used herein indicates a molecular structure having one ring.

The term "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "pharmaceutical composition" means a composition comprising a compound of formula I and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents, and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Commonly, the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs," p. 113-191 (1991); Advanced Drug Delivery Reviews, H. Bundgaard, 8, p. 1-38 (1992); *Journal of Pharmaceutical Sciences,* 77:285 (1988); Nakeya et al, *Chem. Pharm. Bull.,* 32:692 (1984); Higuchi et al., "Prodrugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "pharmaceutically acceptable salt" refers to salts prepared from pharmaceutically acceptable non-toxic acids or bases including inorganic acids and bases and organic acids and bases. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Pharmaceutically acceptable salts further include, but are not limited to, amine salts, such as but not limited to N,N' dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris(hydroxymethyl)aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amount" is meant to describe an amount of compound of the present invention effective producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Compounds described herein may contain one or more asymmetric centers and may thus give rise to enantiomers, diastereomers, and other stereoisomeric forms.

Each chiral center may be defined, in terms of absolute stereochemistry, as (R)- or (S)-.

The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

In accordance with one embodiment of the present invention, $R^1$ is H.

In accordance with another embodiment of the present invention, $R^1$ is $C_1$-$C_6$ alkyl, for example, methyl.

In accordance with one embodiment of the present invention, $R^2$ is H. In yet another embodiment, $R^2$ is optionally substituted alkyl. In a preferred embodiment, $R^2$ is methyl.

In accordance with one embodiment of the present invention, $R^3$ is H, halogen, or $C_1$-$C_6$ alkyl.

In accordance with one embodiment of the present invention, $R^4$ is H, halogen, or $C_1$-$C_6$ alkyl.

In accordance with one embodiment of the present invention, X is N, CH, or $CH_2$.

In accordance with one embodiment of the present invention, Y is N, C, or CH.

In accordance with one embodiment of the present invention, L is a bond. In accordance with another embodiment of the present invention, L is —$CH_2$—O—. In yet another embodiment, L is —$CH_2$—$CH_2$—.

In accordance with one embodiment of the present invention, B is aryl. In one preferred embodiment, B is phenyl. In accordance with another embodiment of the present invention, B is heteroaryl. In one preferred embodiment, B is pyridinyl, for example pyridin-2-yl or pyridin-3-yl, pyridazinyl, for example, pyridazin-3-yl, or pyrimidinyl, for example, pyrimidin-5-yl.

As described herein, B may be optionally substituted. In one preferred embodiment, B is unsubstituted. In another preferred embodiment, B is substituted with one substituent selected from methyl, trifluoromethyl, chloro, and fluoro. In yet another preferred embodiment, B is selected from phenyl, 5-(trifluoromethyl)pyridin-2-yl, 5-fluoropyridin-2-yl, 6-(trifluoromethyl)pyridazin-3-yl, 6-(trifluoromethyl)pyridin-3-yl, 2-(trifluoromethyl)pyrimidin-5-yl 6-methylpyridin-3-yl, pyridin-2-yl, 2,4-difluorophenyl, 4-chlorophenyl, 4-chloro-2-fluorophenyl, 2,4-dichlorophenyl, and 4-(trifluoromethyl) phenyl.

Within these embodiments, the selection of a particular preferred substituent at any one of $R^1$-$R^{10}$, X, Y, Z, L, L and B does not affect the selection of a substituent at any of the others of $R^1$-$R^{10}$, X, Y, Z, L, and B. That is, preferred compounds provided herein have any of the preferred substituents at any of the positions.

In accordance with one embodiment of the present invention, the compound has the formula:

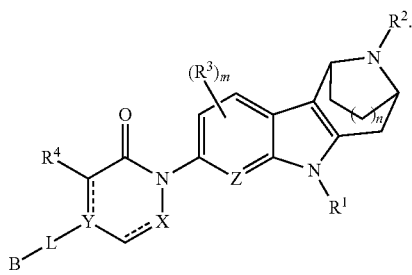

In accordance with one embodiment of the present invention, the compound is selected from

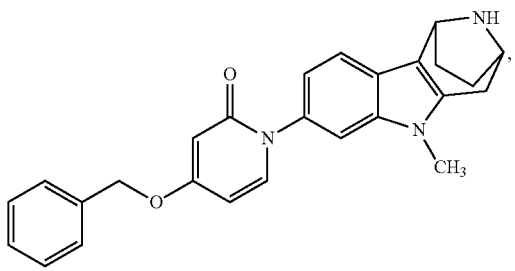

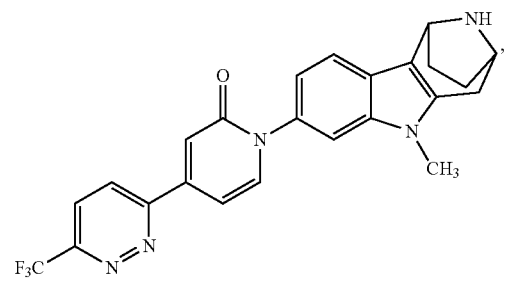

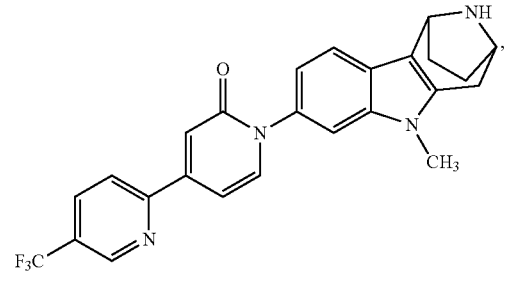

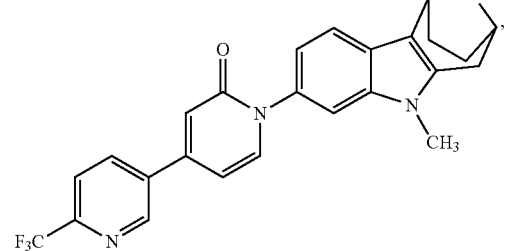

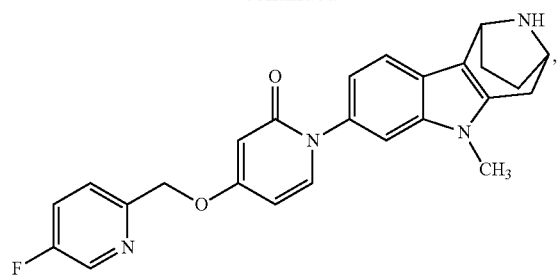
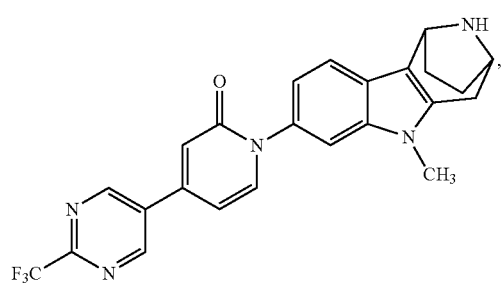
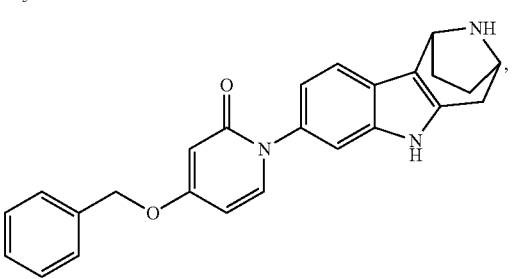
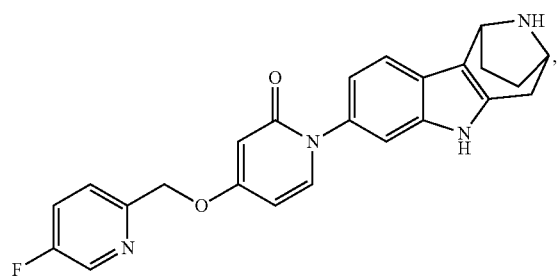
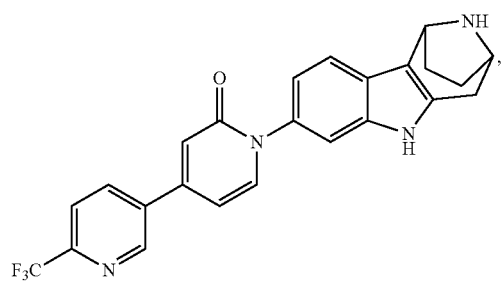
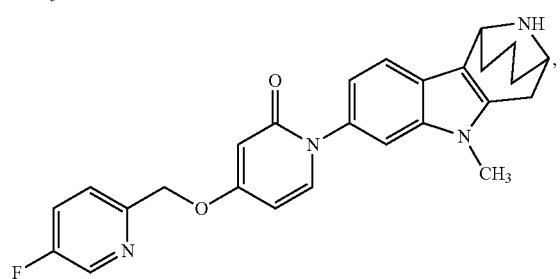
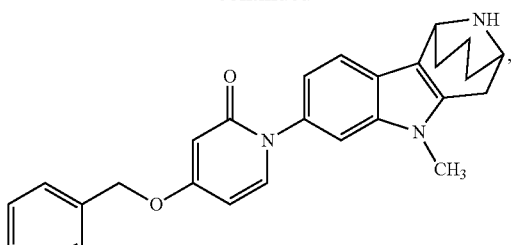
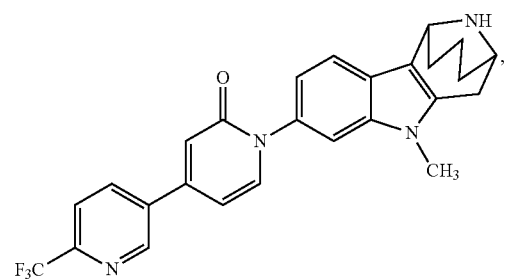
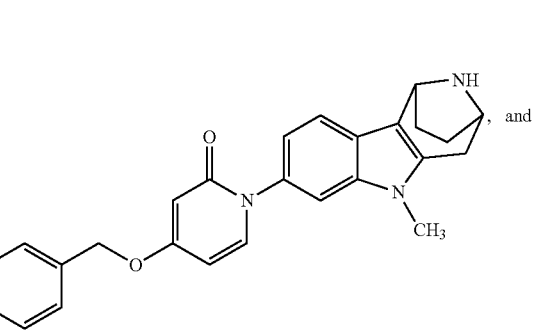
Enantiomer A
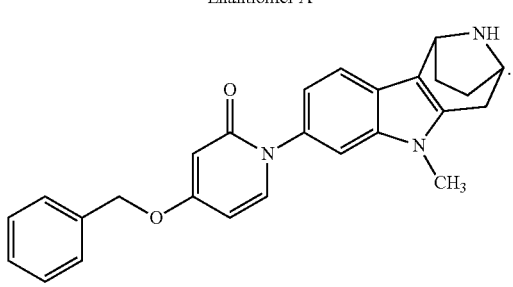
Enantiomer B
In accordance with another embodiment of the present invention, the compound is selected from
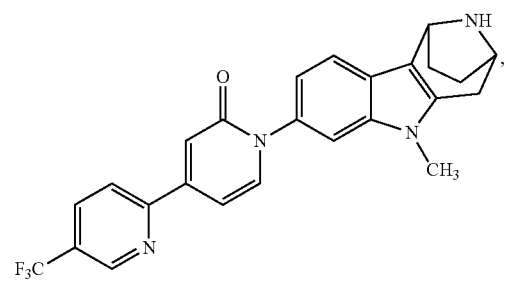
Enantiomer B

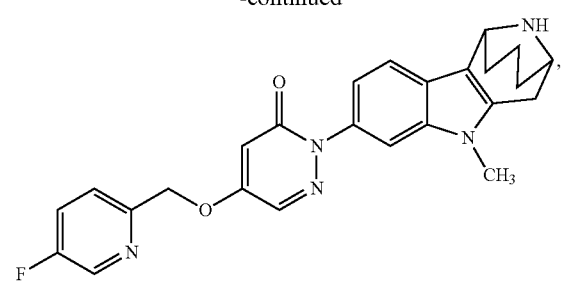
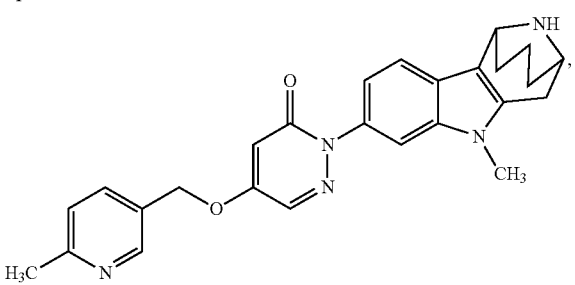
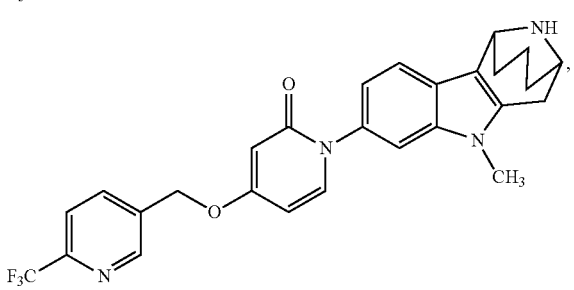
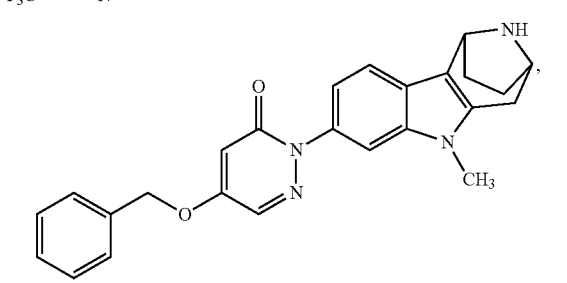
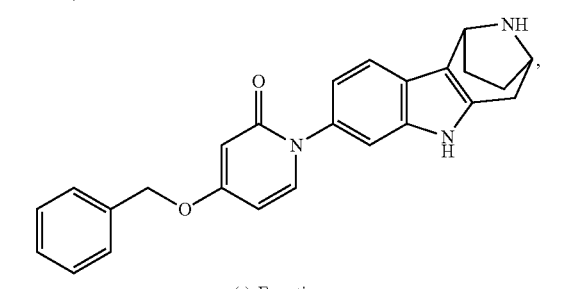
(−)-Enantiomer
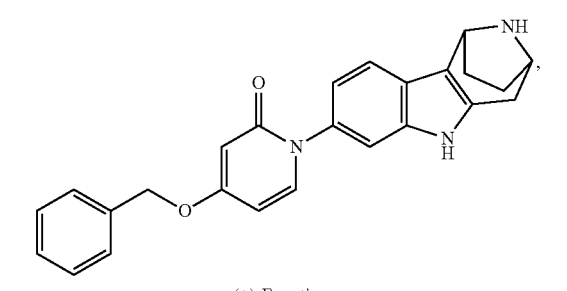
(+)-Enantiomer
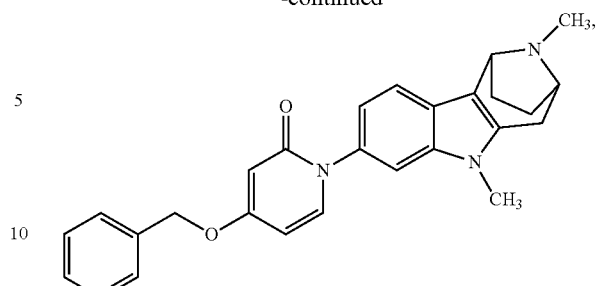
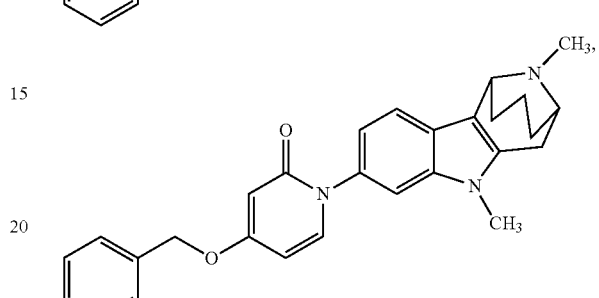
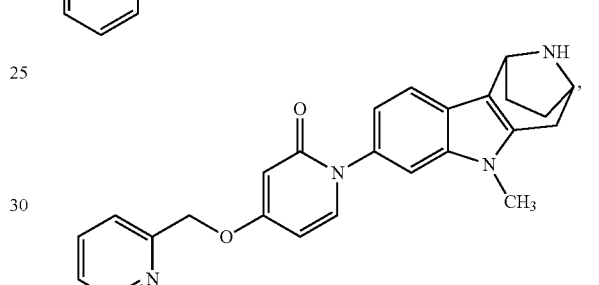
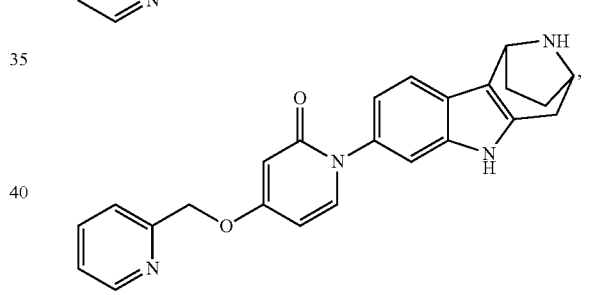
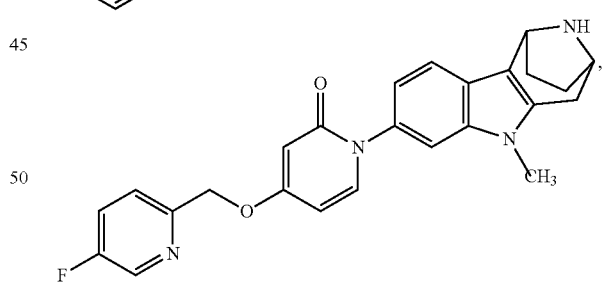
Enantiomer B
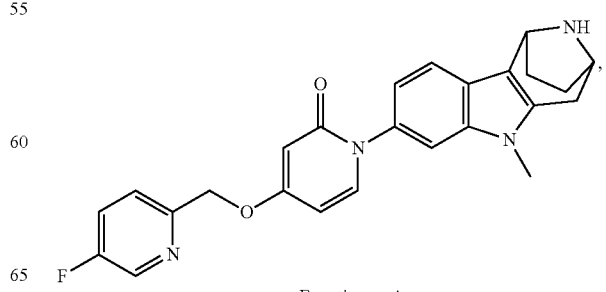
Enantiomer A

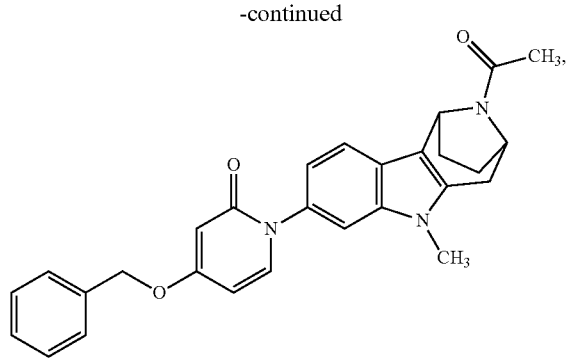
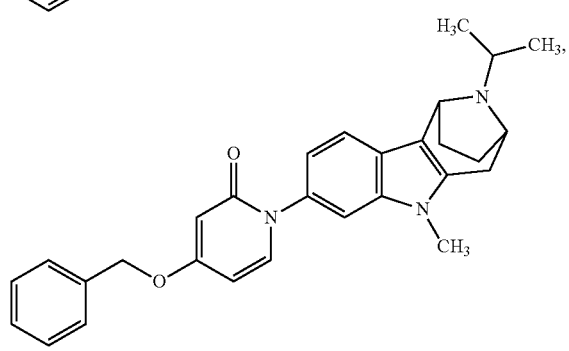
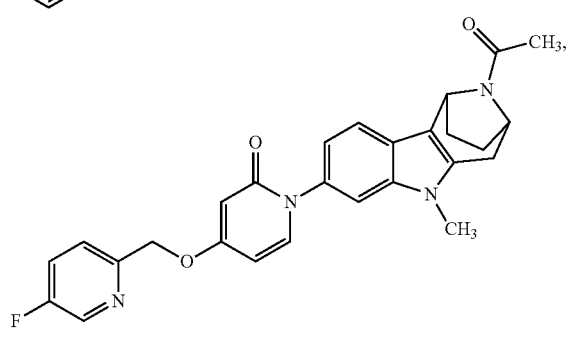
Enantiomer A
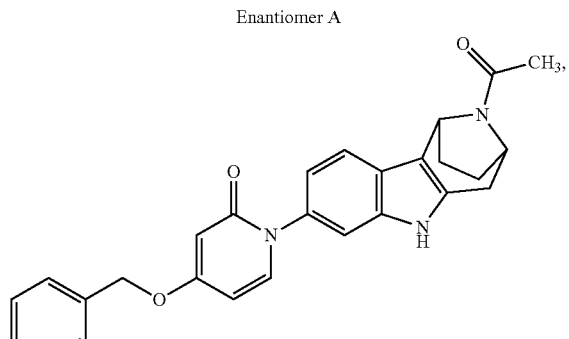
Enantiomer A
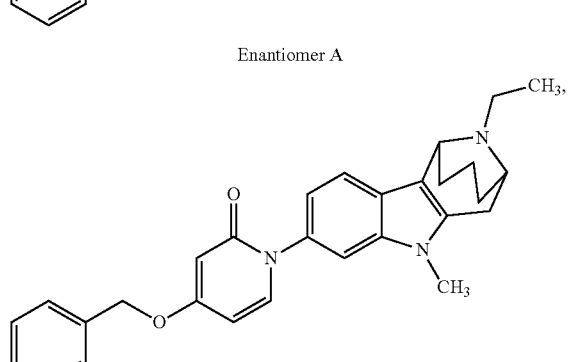
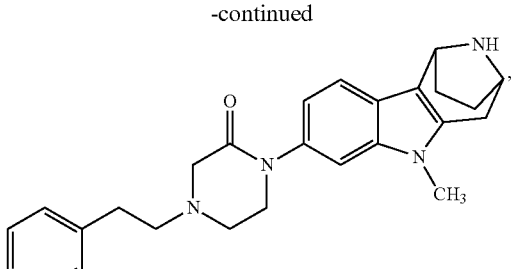
Enantiomer B
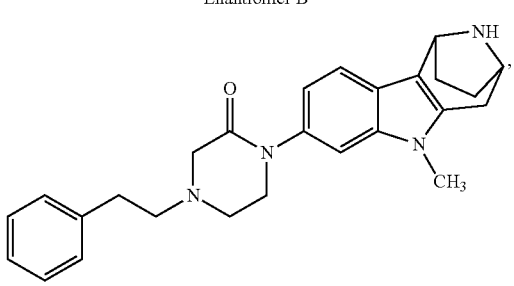
Enantiomer A
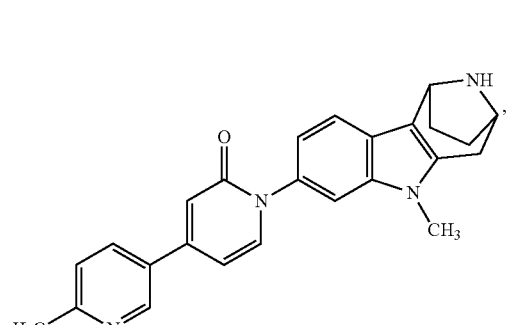
Enantiomer B
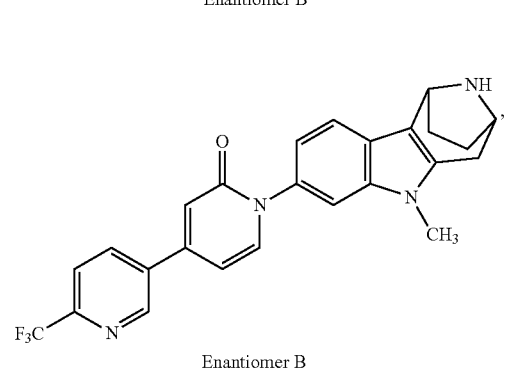
Enantiomer B
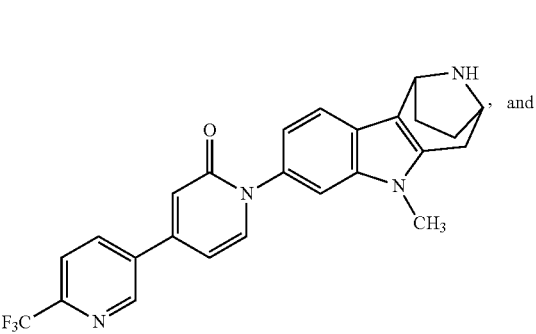
, and
Enantiomer A

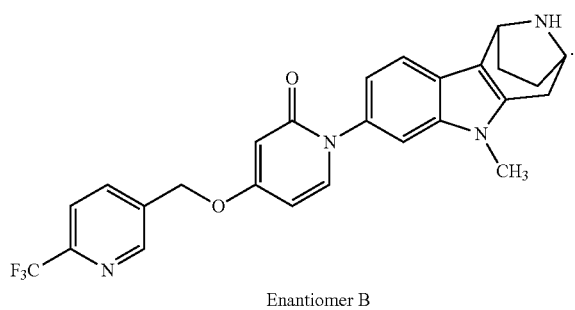
Enantiomer B
In accordance with another embodiment of the present invention, the compound is selected from
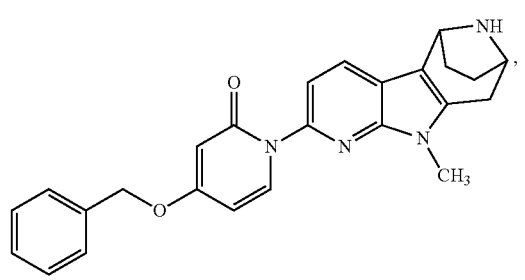
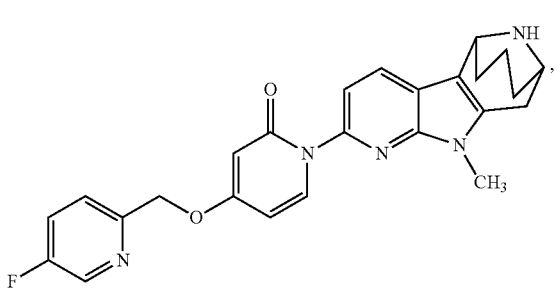
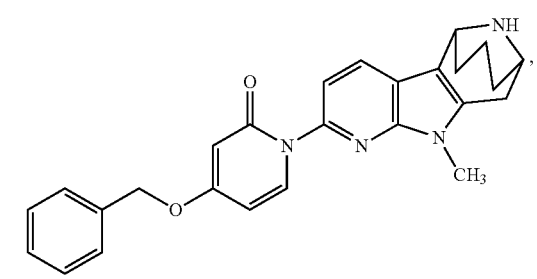
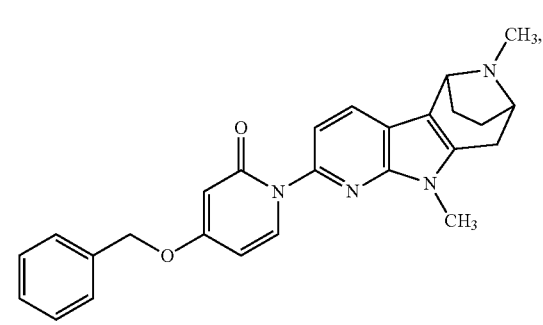
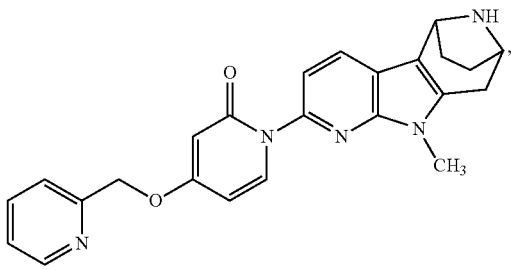
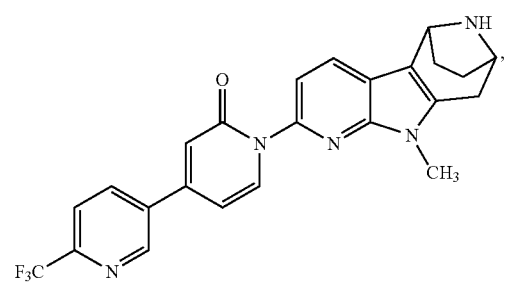
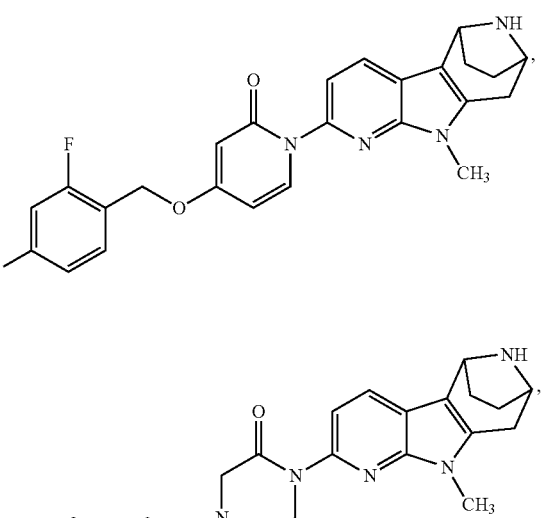
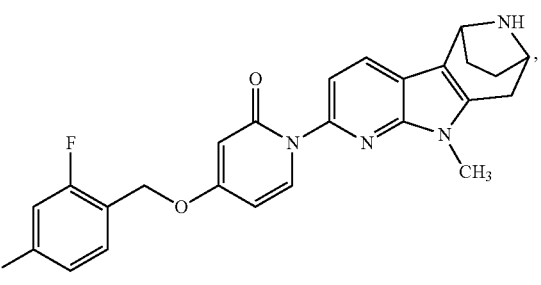
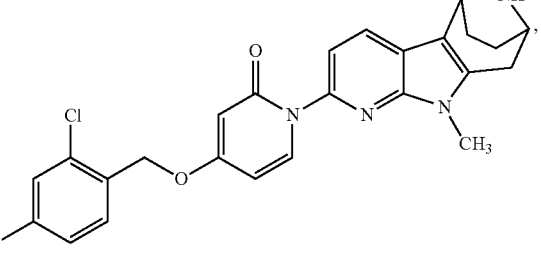

-continued

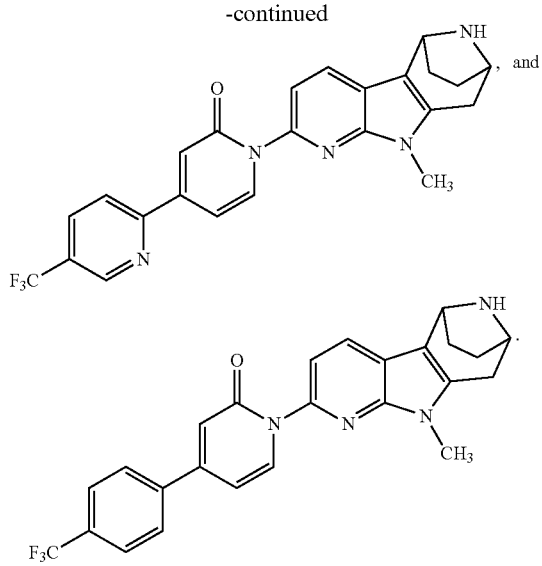

Table 1, infra, lists compounds representative of embodiments of the present invention.

One embodiment of the present invention relates to pharmaceutically acceptable salts, or non-salt forms, of any of the compounds of formula I described herein.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula I, wherein one or more of the atoms, e.g., C or H, are replaced by the corresponding radioactive isotopes of that atom (e.g., C replaced by $^{14}$C and H replaced by $^{3}$H), or a stable isotope of that atom (e.g., C replaced by $^{13}$C or H replaced by $^{2}$H). Radioisotopes of hydrogen, carbon, phosphorous fluorine iodine and chlorine include $^{3}$H, $^{14}$C, $^{35}$S, $^{18}$F, $^{32}$P, $^{33}$P, $^{125}$I and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the binding ability of a potential pharmaceutical. In addition, in the case of stable isotopes, such compounds may have the potential to favorably modify the biological properties, e.g., pharmacological and/or pharmacokinetic properties, of compounds of formula I. The details concerning selection of suitable sites for incorporating radioactive isotopes into the compounds are known to those skilled in the art.

Compounds of the present invention as described herein are useful as MCH-1 receptor antagonists. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all compounds of formula I, except those that are in the public's possession.

While it may be possible for compounds of formula I to be administered as the raw chemical, it will often be preferable to present them as part of a pharmaceutical composition. Accordingly, another aspect of the present invention is a pharmaceutical composition containing a therapeutically effective amount of a compound of formula I, or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

In one embodiment of the present invention, the pharmaceutical composition further comprises one or more other therapeutic adjuncts, e.g., other compounds effective in the treatment of obesity, anxiety, depression, or non-alcoholic fatty liver disease, that are known to persons of skill in the art. Such other therapeutic adjunts are described below.

Another aspect of the present invention relates to a method of treating a disease or condition which is susceptible to treatment with an MCH-1 receptor antagonist. This method involves selecting a patient with a disease or condition which is susceptible to treatment with an MCH-1 receptor antagonist and administering to the patient a therapeutically effective amount of a compound of formula I or a pharmaceutically acceptable salt thereof.

Diseases or conditions which are susceptible to treatment with an MCH-1 receptor antagonist in accordance with the present invention include, but are not limited to, obesity, general anxiety disorders, social phobias, vertigo, obsessive-compulsive disorders, panic disorders, post-traumatic stress disorders, Parkinson's Disease Psychosis, schizophrenia, cognitive decline and defects in schizophrenia, presenile dementias, Alzheimer's Disease, psychological disorders, depression, substance abuse disorders, dementia associated with neurodegenerative disease, cognition deficits, and epilepsy (see PCT Publication No. WO 2007/010275, which is hereby incorporated by reference in its entirety).

As described above, the compounds of the present invention are useful as MCH-1 antagonists. As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific, but by no means limiting, examples of well-known second messenger systems are adenylate cyclase, intracellular calcium mobilization, ion channel activation, guanylate cyclase, and inositol phospholipid hydrolysis.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which MCH-1 receptor activity is implicated.

In another embodiment of the present invention, the above method further involves administering a therapeutically effective amount of one or more therapeutic adjuncts. Suitable therapeutic adjuncts include, but are not limited to, anti-obesity and/or anorectic agents, anti-anxiety agents, anti-depression agents, and anti-non-alcoholic fatty liver disease agents.

Suitable anti-obesity and/or anorectic adjuncts include, but are not limited to, phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist or inverse agonist, a melanin concentrating hormone receptor antagonist, a serotonin 5-$HT_6$ receptor antagonist, a serotonin 5-$HT_{2C}$ receptor agonist, the OB protein (hereinafter referred to as "leptin"), a leptin analog, a leptin receptor agonist, the amylin peptide, an amylin analog, an amylin receptor agonist, a neuropeptide Y receptor modulator, a galanin antagonist, or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Suitable anti-anxiety adjuncts include, but are not limited to, an allosteric modulator of the $GABA_A$ receptor (such as diazepam, lorazepam, or alprazolam), a serotonin 5-$HT_{1A}$ receptor partial agonist (such as buspirone), a selective serotonin reuptake inhibitor (SSRI, such as citalopram, escitalopram, fluoxetine, paroxetine, or sertraline), a serotonin-norepinephrine reuptake inhibitor (SNRI, such as duloxetine or venlafaxine), a monoamine neurotransmitter reuptake inhibitor of the tricyclic antidepressant (TCA) class (such as amitriptyline, desipramine, or imipramine), a combined serotonin reuptake inhibitor and 5-$HT_{2C}$ antagonist (such as trazodone), and an $H_1$ receptor antagonist (such as hydroxyzine).

Suitable anti-depression adjuncts include, but are not limited to, a serotonin 5-$HT_{1A}$ receptor partial agonist (such as buspirone), a selective serotonin reuptake inhibitor (SSRI, such as citalopram, escitalopram, fluoxetine, paroxetine, or sertraline), a serotonin-norepinephrine reuptake inhibitor (SNRI, such as duloxetine or venlafaxine), a monoamine neurotransmitter reuptake inhibitor of the tricyclic antidepressant (TCA) class (such as amitriptyline, desipramine, or imipramine), a combined serotonin reuptake inhibitor and 5-$HT_{2C}$ antagonist (such as trazodone), a noradrenergic and specific serotonergic antidepressant (NaSSA, such as mianserin or mirtazapine), a norepinephrine reuptake inhibitor (NRI, such as atomoxetine or Mazindol), a norepinephrine-dopamine reuptake inhibitor (NDRI, such as bupropion), and a monoamine oxidase inhibitor (MAOI, such as isocarboxazid or moclobemide).

Suitable anti-non-alcoholic fatty liver disease adjuncts include, but are not limited to, an AMP-activated protein kinase (AMPK) agonist (such as metformin), a peroxisome proliferator-activated receptor (PPAR) gamma activator (such as rosiglitazone, pioglitazone, or troglitazone), a HMG-CoA reductase inhibitor (such as atorvastatin or simvastatin), and a PDE4 inhibitor (such as pentoxifylline).

In one embodiment, the patient is a mammal. The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

The present invention also relates to a method of treating obesity in a subject in need of weight loss. This method involves selecting a patient in need of weight loss and administering to the patient a therapeutically effective amount of a compound of formula I or a pharmaceutically acceptable salt thereof.

This method further involves administering an anti-obesity adjunct, as described above.

Yet another aspect of the present invention relates to a method of treating obesity in a subject who has experienced weight loss. This method involves selecting a patient who has experienced weight loss and administering to the patient a therapeutically effective amount of a compound of formula I or a pharmaceutically acceptable salt thereof.

A further aspect of the present invention relates to a method of treating anxiety. This method involves selecting a patient with anxiety and administering to the patient a therapeutically effective amount of a compound of formula I or a pharmaceutically acceptable salt thereof.

This method further involves administering an anti-anxiety adjunct, as described above.

The present invention also relates to a method of treating depression. This method involves selecting a patient with depression and administering to the patient a therapeutically effective amount of a compound of formula I or a pharmaceutically acceptable salt thereof.

This method further involves administering an anti-depression adjunct, as described above.

Another aspect of the present invention relates to a method of treating non-alcoholic fatty liver disease. This method involves selecting a patient who has non-alcoholic fatty liver disease and administering to the patient a therapeutically effective amount of a compound of formula I or a pharmaceutically acceptable salt thereof.

This method further involves administering an anti-nonalcoholic fatty liver disease adjunct, as described above.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Another aspect of the present invention relates to a process of preparing a product compound of formula I:

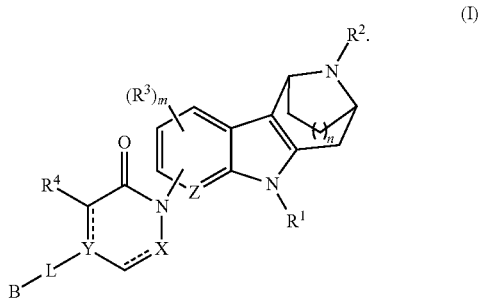

(I)

This process involves treating a first intermediate compound of formula II:

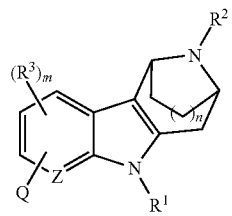

(II)

wherein Q is a halogen, under conditions effective to produce the product compound. $R^1$-$R^4$, X, Y, Z, L, and B are as defined above.

In one embodiment, treating comprises reacting the first intermediate with a second intermediate having the structure:

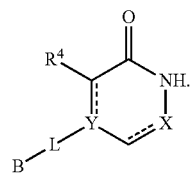

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula I including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice and as described above.

The novel MCH-1 antagonists of formula I of this invention can be prepared by the methods illustrated in the general reaction schemes as, for example, described below, or by modifications thereof, using readily available starting materials, reagents, and conventional synthesis procedures. In these reactions, it is also possible to make use of variants that are known in the art but are not mentioned here. Although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

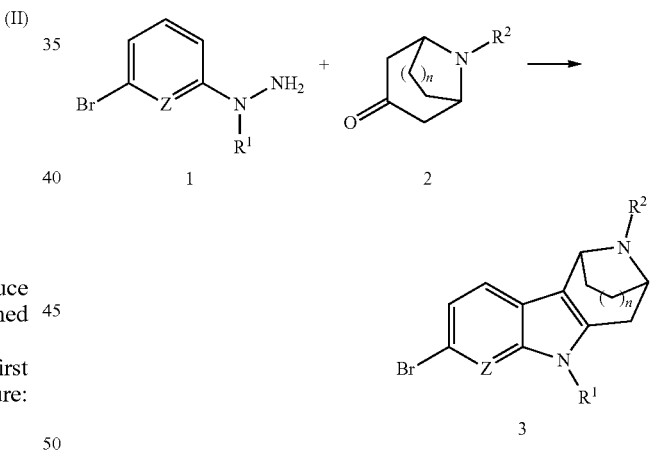

Scheme 1

Compounds of formula 3 (wherein $R^1$ is H or alkyl; $R^2$ is H or a protecting group such as tert-butoxycarbonyl or benzyloxycarbonyl; and n is 1 or 2) can be prepared from compounds of formula 1 (or a salt thereof, wherein $R^1$ is H or alkyl and Z is CH or N) and compounds of formula 2 (or a salt thereof, wherein $R^2$ is H or a protecting group such as tert-butoxycarbonyl or benzyloxycarbonyl; and n is 1 or 2) under heated acidic conditions. In the case where $R^1$ is H, optional alkylation or protection of compound 3 can provide compounds of formula 3 wherein $R^1$ is alkyl or a protecting group such as tert-butoxycarbonyl, benzyloxycarbonyl or p-toluenesulfonyl. In the case where $R^2$ is H, reductive amination, alkylation or protection of the secondary amine can provide compounds of formula 3 wherein $R^2$ is alkyl or a protecting group such as tert-butoxycarbonyl, benzyloxycarbonyl, or p-toluenesulfonyl.

Scheme 2

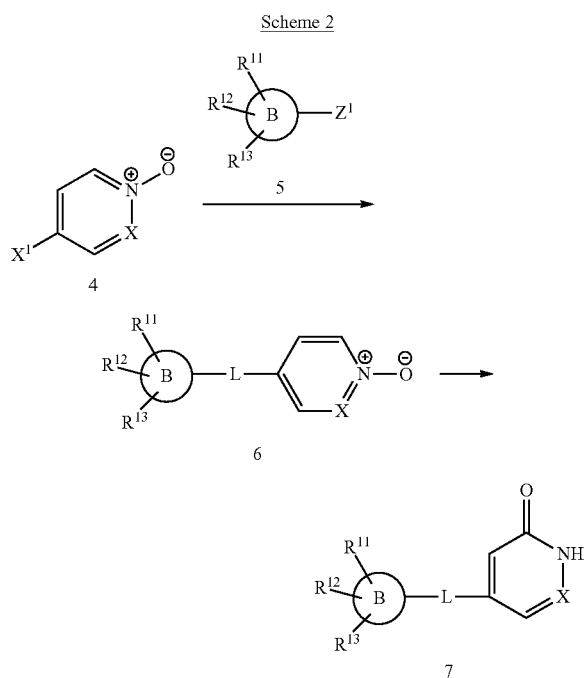

Compounds of formula 7 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; and X is CH) can be prepared by treating compounds of formula 4 (wherein $X^1$ is chlorine, bromine or iodine and X is CH) with compounds of formula 5 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; $Z^1$ is —$B(OH)_2$, —$B(OR^{14})_2$, —$SnR^{14}{}_3$ or the like; and $R^{14}$ is alkyl), a catalyst such as palladium(0), and a base such as potassium carbonate to give compounds of formula 6, wherein L is a direct bond. Alternatively, in the case where $Z^1$ is —$CH_2$—OH and B is aryl, heteroaryl, heterocyclyl, or cycloalkyl, compounds of formula 5 can be treated with a base such as sodium hydride and compounds of formula 4 under heated conditions to give compounds of formula 6, wherein L is —$CH_2$—O—. In turn, compounds of formula 6 can be treated with acetic anhydride under heated conditions followed by methanol and water or methanol and sodium hydroxide under ambient to heated conditions to provide compounds of formula 7, wherein L is —$CH_2$—O— or a direct bond.

Scheme 3

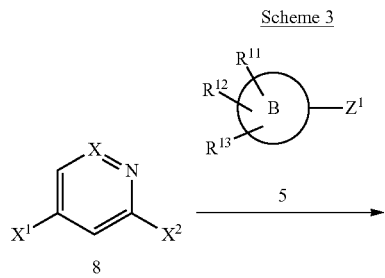

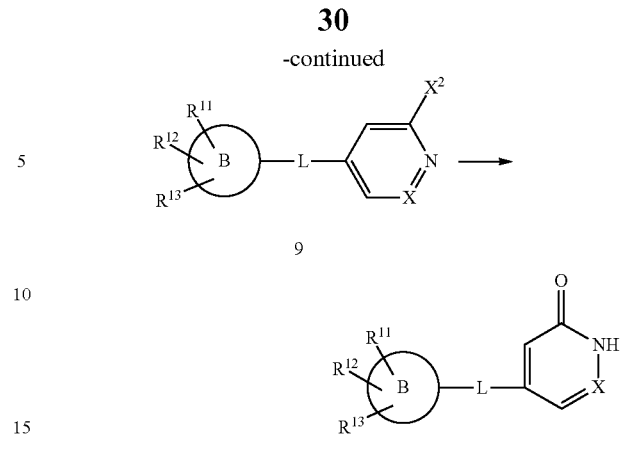

Alternatively, compounds of formula 7 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; and X is CH) can be prepared by treating compounds of formula 8 (wherein $X^1$ is chlorine, bromine or iodine; $X^2$ is —O—$CH_3$ or chlorine; and X is CH) with compounds of formula 5 (wherein $Z^1$ is —$B(OH)_2$, —$B(OR^{14})_2$, —$SnR^{14}{}_3$ or the like; and $R^{14}$ is alkyl), a catalyst such as palladium(0), and a base such as potassium carbonate to give compounds of formula 9, wherein L is a direct bond. Alternatively, in the case where $Z^1$ is —$CH_2$—OH, compounds of formula 5 can be treated with compounds of formula 8, a catalyst such as copper iodide, a ligand such as 3,4,7,8-tetramethylphenanthroline, and a base such as cesium carbonate under heated conditions to give compounds of formula 9, wherein L is —$CH_2$—O—. In turn, compounds of formula 9 can be heated under acid conditions to provide compounds of formula 7, wherein L is —$CH_2$—O— or a direct bond.

Scheme 4

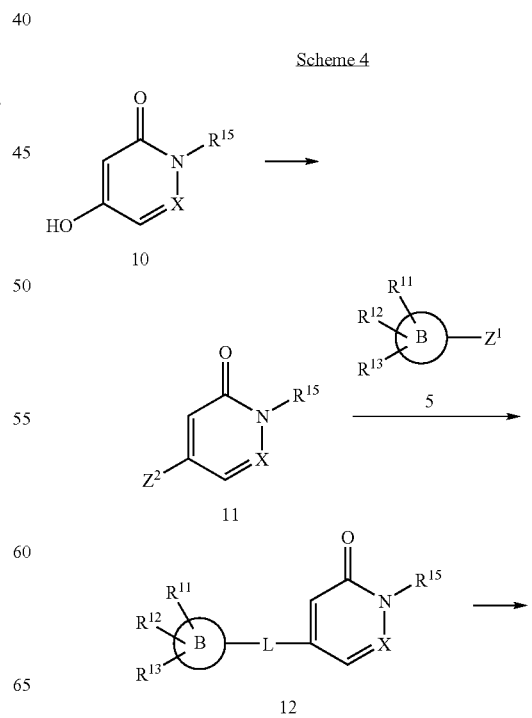

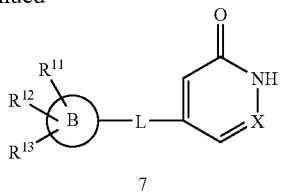

Alternatively, compounds of formula 7 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; and X is N) can be prepared from compounds of formula 10 (wherein X is N and $R^{15}$ is a protecting group such as tetrahydropyran-2-yl). The hydroxyl group on compound 10 can be converted to an appropriate activating group to give compounds of formula 11. In the case where $Z^2$ is triflate, compounds of formula 10 can be treated with trifluoromethylsulfonic anhydride or N-phenyl trifluoromethanesulfonamide and a base such as triethylamine, pyridine, or lithium bis(trimethylsilyl)amide under cooled conditions to give compounds of formula 11. Treatment of compounds of formula 11 with compounds of formula 5 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; $Z^1$=B $(OH)_2$, $B(OR^{14})_2$, $SnR^{14}_3$ or the like, and $R^{14}$=alkyl), a catalyst such as palladium(0), and a base such as potassium carbonate under heated conditions can provide compounds of formula 12, wherein L a direct bond. Alternatively, in the case where $Z^1$ is —$CH_2$—Br, compounds of formula 5 can be treated with compounds of formula 10 and a base such as potassium carbonate to give compounds of formula 12, wherein L is —$CH_2$—O—. Removal of the protecting group $R^{15}$ on compound 12 can provide compounds of formula 7, wherein L is —$CH_2$—O— or a direct bond.

Scheme 5

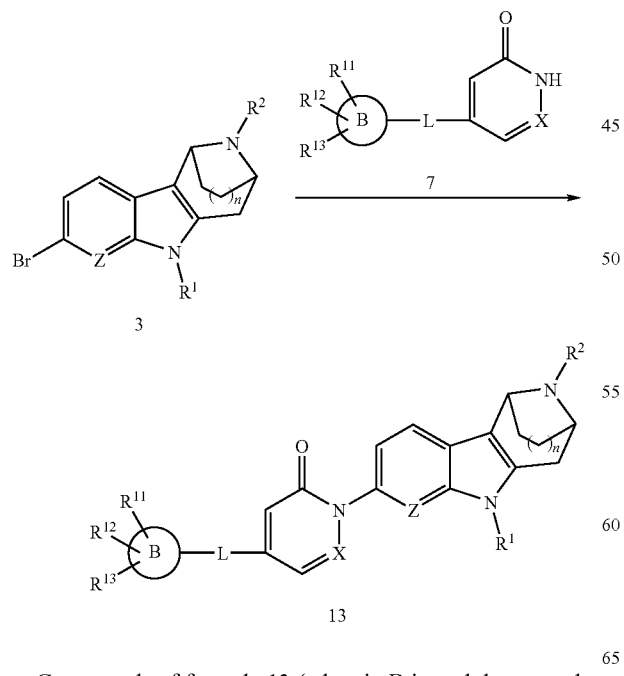

Compounds of formula 13 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; L is —$CH_2$—O— or a direct bond; X is CH or N; Z is CH or N; $R^1$ is H, alkyl, or a protecting group such as tert-butoxycarbonyl, benzyloxycarbonyl or p-toluenesulfonyl; $R^2$ is H, alkyl, or a protecting group such as tert-butoxycarbonyl, or benzyloxycarbonyl; and n is 1 or 2) can be prepared by treating compounds of formula 3 (wherein $R^1$ is alkyl or a protecting group such as tert-butoxycarbonyl, benzyloxycarbonyl, or p-toluenesulfonyl; $R^2$ is alkyl or a protecting group such as tert-butoxycarbonyl or benzyloxycarbonyl; Z is CH or N; and n is 1 or 2) under heated conditions with a catalyst such as copper iodide, a ligand such as trans-1,2-diaminocyclohexane or 8-hydroxyquinoline, a base such as potassium carbonate, cesium carbonate or potassium phosphate, and compounds of formula 7 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; L is —$CH_2$—O— or a direct bond; and X is CH or N). In the case where $R^2$ is a protecting group, the protecting group can be removed to give compounds of formula 13 wherein $R^2$ is H. In the case where $R^2$ is H, reductive amination or alkylation can provide compounds of formula 13, wherein $R^2$ is an alkyl group. Additionally, in the case where $R^1$ is a protecting group, the protecting group can be removed to give compounds of formula 13 wherein $R^1$ is H. Alternatively, following removal of the $R^1$ protecting group, N-alkylation can give compounds of formula 13 wherein $R^2$ is an alkyl group.

Scheme 6

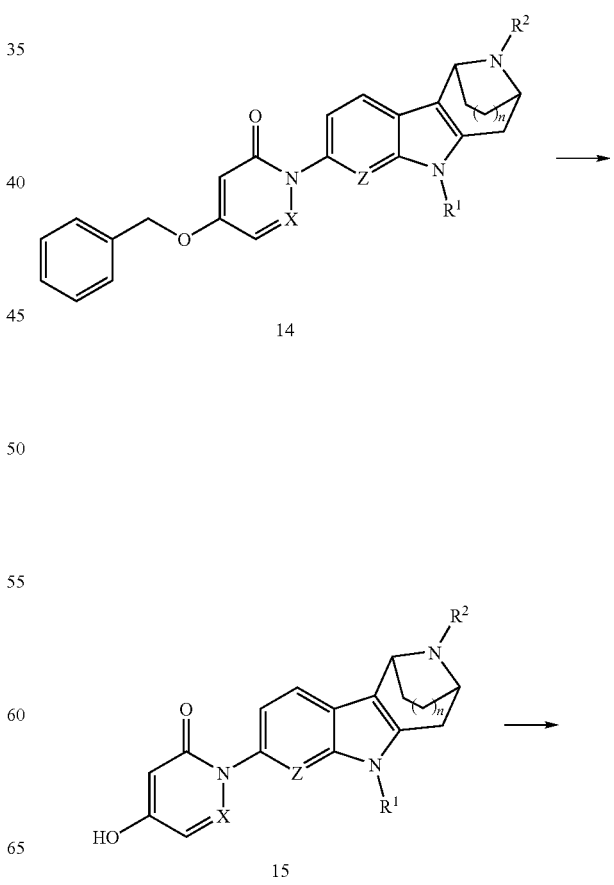

33

-continued

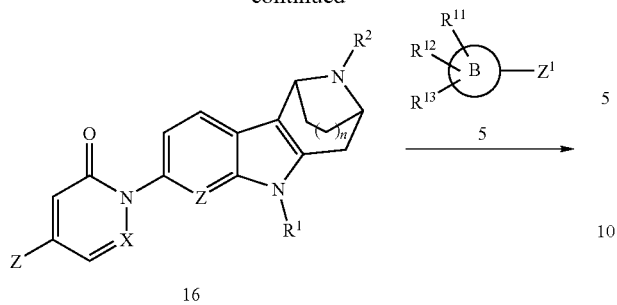

16

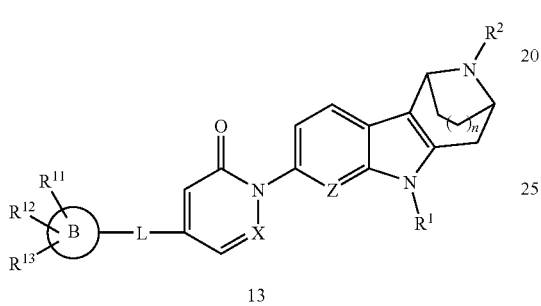

13

Compounds of formula 14 (wherein X is CH or N; $R^1$ is alkyl or a protecting group such as tert-butoxycarbonyl, benzyloxycarbonyl, or p-toluenesulfonyl; $R^2$ is alkyl or a protecting group such as tert-butoxycarbonyl or benzyloxycarbonyl; and n is 1 or 2) can be treated with hydrogen and a catalyst such as palladium on carbon to provide compounds of formula 15. The hydroxyl group on compounds of formula 15 can be converted to an appropriate activating group to give compounds of formula 16. In the case where $Z^2$ is triflate, compounds of formula 15 can be treated with trifluoromethylsulfonic anhydride or N-phenyl trifluoromethanesulfonamide and a base such as pyridine or lithium bis(trimethylsilyl) amide under cooled conditions to give compounds of formula 16. Treatment of compounds of formula 16 with compounds of formula 5 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; $Z^1$=B(OH)$_2$, B(OR$^{14}$)$_2$, SnR$^{14}_3$ or the like; and $R^{14}$=alkyl), a catalyst such as palladium(0), and a base such as potassium carbonate under heated conditions can provide compounds of formula 13, wherein L is a direct bond.

Scheme 7

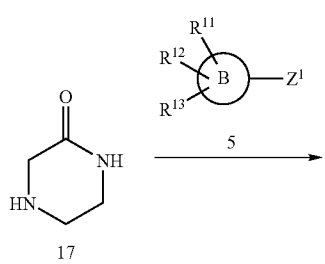

34

-continued

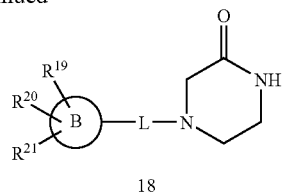

18

Compounds of formula 17 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; and L is —$CH_2$—$CH_2$—) can be prepared by treating piperazin-2-one 17 with compounds of formula 5 (wherein $Z^1$ is —$CH_2$—$CH_2$—$X^1$; and $X^1$ is a leaving group such as chlorine, bromine, iodine or the like) and a base such as di-isopropylamine to give compounds of formula 18, wherein L is —$CH_2$—$CH_2$—.

Scheme 8

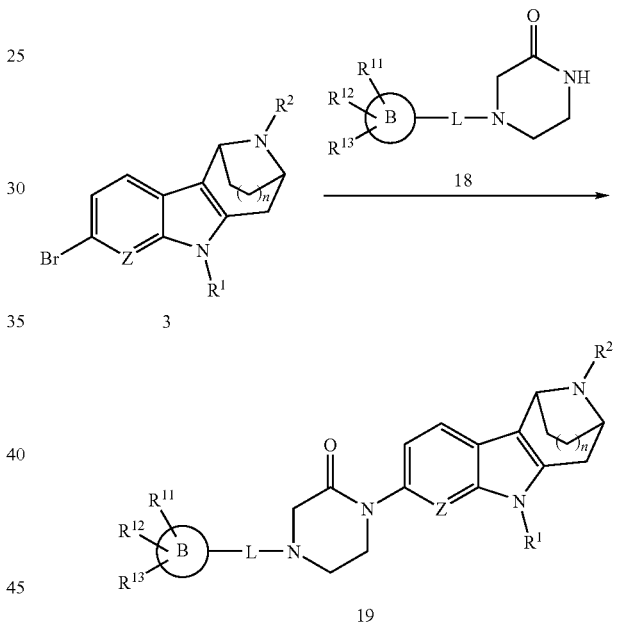

Compounds of formula 19 (wherein B is aryl, heteroaryl, heterocyclyl, or cycloalkyl; $R^{11}$, $R^{12}$, and $R^{13}$ are each independently selected from H, alkoxy, —S-alkyl, alkyl, halo, —$CF_3$, and —CN; L is —$CH_2$—$CH_2$—; Z is CH or N; $R^1$ is H, alkyl or a protecting group such as tert-butoxycarbonyl, benzyloxycarbonyl or p-toluenesulfonyl; $R^2$ is H, alkyl, or a protecting group such as tert-butoxycarbonyl, or benzyloxycarbonyl; and n is 1 or 2) can be prepared by treating compounds of formula 3 (wherein Z is CH or N; $R^1$ is H, alkyl or a protecting group such as tert-butoxycarbonyl, benzyloxycarbonyl or p-toluenesulfonyl; $R^2$ is H, alkyl, or a protecting group such as tert-butoxycarbonyl, or benzyloxycarbonyl; and n is 1 or 2) under heated conditions with a catalyst such as copper iodide, a ligand such as trans-1,2-bis(methylamino)cyclohexane or 8-hydroxyquinoline, a base such as potassium carbonate, cesium carbonate or potassium phosphate and compounds of formula 18 (wherein B is aryl, heteroaryl, heterocyclyl, or cycloalkyl; $R^{11}$, $R^{12}$, and $R^{13}$ are each independently selected from H, alkoxy, —CF$_3$, and —CN; and L is —CH$_2$—CH$_2$—). In the case where R$^2$ is a protecting group, the protecting group can be removed to give compounds of formula 19 wherein R$^2$ is H. In the case where R$^2$ is H, reductive amination or alkylation can provide compounds of formula 19, wherein R$^2$ is an alkyl group. Additionally, in the case where R$^1$ is a protecting group, the protecting group can be removed to give compounds of formula 19 wherein R$^1$ is H.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining one or more active ingredients useful in treating the disease. A kit may provide (alone or in combination with a pharmaceutically acceptable diluent or carrier) the compounds of formula I and an additional active ingredient (alone or in combination with diluent or carrier), as described above.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The formulations of compounds of formula I include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. It will be understood, however, that the specific dose level for any particular patient will depend upon a variety of factors including the activity of the specific compound employed, the age, body weight, general health, sex, diet time of administration, route of administration, rate of excretion, drug combination, and the severity of the particular disease undergoing therapy.

The amount of active ingredient that may be combined with the carrier materials to produce a single dosage form will vary depending upon the host treated and the particular mode of administration. For example, a formulation intended for the oral administration of humans may vary from about 5 to about 95% of the total composition.

A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

For additional information about pharmaceutical compositions and their formulation, see, for example, Remington, *The Science and Practice of Pharmacy*, 20$^{th}$ Edition (2000), which is hereby incorporated by reference in its entirety.

The compounds of formula 1 can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula I can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula I can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., *Nature Reviews Drug Discovery* 3:115 (2004), which is hereby incorporated by reference in its entirety)). The agents can be administered locally. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in PCT Publication Nos. WO 00/45792, WO 00/53160, and WO 02/19989, which are hereby incorporated by reference in their entirety. An example of a transdermal formulation containing plaster and the absorption promoter dimethylisosorbide can be found in PCT Publication No. WO 89/04179, which is hereby incorporated by reference in its entirety. PCT Publication No. WO 96/11705, which is hereby incorporated by reference in its entirety, provides formulations suitable for transdermal administration.

The compounds can be administered in the form a suppository or by other vaginal or rectal means. The compounds can be administered in a transmembrane formulation as described in PCT Publication No. WO 90/07923, which is hereby incorporated by reference in its entirety. The compounds can be administered non-invasively via the dehydrated particles described in U.S. Pat. No. 6,485,706, which is hereby incorporated by reference in its entirety. The compound can be administered in an enteric-coated drug formulation as described in PCT Publication No. WO 02/49621, which is hereby incorporated by reference in its entirety. The compounds can be administered intranasaly using the formulation described in U.S. Pat. No. 5,179,079, which is hereby incorporated by reference in its entirety. Formulations suitable for parenteral injection are described in PCT Publication No. WO 00/62759, which is hereby incorporated by reference in its entirety. The compounds can be administered using the casein formulation described in U.S. Patent Application Publication No. 20030206939 and PCT Publication No. WO 00/06108, which are hereby incorporated by reference in their entirety. The compounds can be administered using the particulate formulations described in U.S. Patent Application Publication No. 20020034536, which is hereby incorporated by reference in its entirety.

The compounds, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs), and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include but are not limited to bile salts and those described in U.S. Pat. No. 6,524,557 and references therein, which is hereby incorporated by reference in its entirety. The surfactants described in U.S. Pat. No. 6,524,557, which is hereby incorporated by reference in its entirety, e.g., a $C_8$-$C_{16}$ fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers that can be added to dry powder formulations of the present invention include those described in U.S. Pat. No. 6,632,456, which is hereby incorporated by reference in its entirety. PCT Publication No. WO 02/080884, which is hereby incorporated by reference in its entirety, describes new methods for the surface modification of powders. Aerosol formulations may include U.S. Pat. No. 5,230,884, U.S. Pat. No. 5,292,499, PCT Publication No. WO 017/8694, PCT Publication No. WO 01/78696, U.S. Patent Application Publication No. 2003019437, U.S. Patent Application Publication No. 20030165436, and PCT Publication No. WO 96/40089 (which includes vegetable oil), which are hereby incorporated by reference in their entirety. Sustained release formulations suitable for inhalation are described in U.S. Patent Application Publication Nos. 20010036481A1, 20030232019A1, and 20040018243A1 as well as in PCT Publication Nos. WO 01/13891, WO 02/067902, WO 03/072080, and WO 03/079885, which are hereby incorporated by reference in their entirety.

Pulmonary formulations containing microparticles are described in PCT Publication No. WO 03/015750, U.S. Patent Application Publication No. 20030008013, and PCT Publication No. WO 00/00176, which are hereby incorporated by reference in their entirety. Pulmonary formulations containing stable glassy state powder are described in U.S. Patent Application Publication No. 20020141945 and U.S. Pat. No. 6,309,671, which are hereby incorporated by reference in their entirety. Other aerosol formulations are described in EP 1338272A1, PCT Publication No. WO 90/09781, U.S. Pat. No. 5,348,730, U.S. Pat. No. 6,436,367, PCT Publication No. WO 91/04011, and U.S. Pat. No. 6,294,153, which are hereby incorporated by reference in their entirety, and U.S. Pat. No. 6,290,987, which is hereby incorporated by reference in its entirety, describes a liposomal based formulation that can be administered via aerosol or other means.

Powder formulations for inhalation are described in U.S. Patent Application Publication No. 20030053960 and PCT Publication No. WO 01/60341, which are hereby incorporated by reference in their entirety. The compounds can be administered intranasally as described in U.S. Patent Application Publication No. 20010038824, which is hereby incorporated by reference in its entirety.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy, which are hereby incorporated by reference in their entirety.

Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington, which are hereby incorporated by reference in their entirety.

Compounds of formula I can be incorporated into a liposome to improve half-life. Compounds of formula I can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula I can also be administered via a nanocochleate or cochleate delivery vehicle (BioDelivery Sciences International, Raleigh, N.C.). Compounds of formula I can also be delivered using nanoemulsion formulations.

EXAMPLES

The Examples set forth below are for illustrative purposes only and are not intended to limit, in any way, the scope of the present invention.

Example 1

Analytical Methods and Materials

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex) or a Gemini C18 column (250×4.6 mm, Phenomenex) with UV detection at 254 nm or 223 nm using a standard solvent gradient program (Method A, B, C, or D).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 98.0 | 2.0 |
| 25 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid Method C:

| Time (min) | Flow (mL/min) | % A | % B |
|---|---|---|---|
| 0.0 | 1.0 | 98.0 | 2.0 |
| 20 | 1.0 | 2.0 | 98.0 |
| 25 | 1.0 | 2.0 | 98.0 |

A = Water with 0.025% Trifluoroacetic Acid
B = Acetonitrile with 0.025% Trifluoroacetic Acid Method D:

| Time (min) | Flow (mL/min) | % A | % B |
|---|---|---|---|
| 0.0 | 1.0 | 98.0 | 2.0 |
| 10 | 1.0 | 5.0 | 95.0 |
| 15 | 1.0 | 5.0 | 95.0 |

A = Water with 0.05% Trifluoroacetic Acid
B = Acetonitrile with 0.05% Trifluoroacetic Acid Example 2

Preparation of 4-(Benzyloxy)-1-(5-methyl-5,6,7,8,9,10-hexahydro-7,10-iminocyclohept[b]indol-3-yl)pyridin-2(1H)-one hydrochloride a) tert-Butyl 3-bromo-5,6,7,8,9,10-hexahydro-7,10-iminocyclohept[b]indole-11-carboxylate

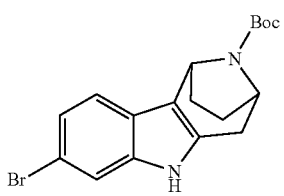

Chemical Formula: $C_{18}H_{21}BrN_2O_2$
Exact Mass: 376.08
Molecular Weight: 377.28

3-Bromophenylhydrazine hydrochloride (919 mg, 4.12 mmol) and nortropanone hydrochloride (1000 mg, 6.18 mmol) were dissolved in ethanol (5 mL), and conc. HCl (2 mL) was added. The reaction mixture was heated at reflux for 18 h and then concentrated. The residue was suspended in a mixture of isopropanol (25 mL) and water (15 ml) and $K_2CO_3$ (1.70 g, 12.3 mmol) and $Boc_2O$ (1.79 g, 8.24 mmol) were added. After 18 h, the mixture was diluted with $CH_2Cl_2$ and the organic phase removed, dried over $Na_2SO_4$ and concentrated. The resulting mixture of regioisomers was purified by flash column chromatography (silica gel, hexanes/EtOAc, 100:0 to 50:50) to give the more polar title compound (240 mg, 15%) as a yellow solid: $^1H$ NMR (500 MHz, $CDCl_3$) δ 7.92-7.64 (br s, 1H), 7.42 (s, 1H), 7.34 (d, J=8.4 Hz, 1H), 7.19 (d, J=8.4 Hz, 1H), 5.29-5.11 (br m, 1H), 4.69-4.65 (br m, 1H), 3.52-3.27 (br m, 1H), 2.44 (d, J=15.9 Hz, 1H), 2.34-2.24 (m, 1H), 2.19-2.14 (m, 1H), 1.93 (t, J=9.8 Hz, 1H), 1.46-1.43 (m, 1H), 1.43 (s, 9H).

b) tert-Butyl 3-bromo-5-methyl-5,6,7,8,9,10-hexahydro-7,10-iminocyclohept[b]indole-11-carboxylate

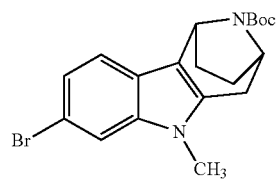

Chemical Formula: $C_{19}H_{23}BrN_2O_2$
Exact Mass: 390.09
Molecular Weight: 391.30

Sodium hydride (60% weight dispersion in mineral oil, 38 mg, 0.95 mmol) was added to a solution of tert-butyl 3-bromo-5,6,7,8,9,10-hexahydro-7,10-iminocyclohept[b]indole-11-carboxylate (240 mg, 0.636 mmol) in DMF (4 mL) at room temperature under $N_2$. After 1 h, methyl iodide (130 mg, 0.058 mL, 0.94 mmol) was added, and the reaction was allowed to proceed for an additional 1 h. The mixture was quenched with $H_2O$, upon which a solid precipitated out of solution. The solids were filtered off to provide the title compound (248 mg, 100%) as a brown solid: $^1H$ NMR (300 MHz, $CDCl_3$) δ 7.40 (s, 1H), 7.35 (d, J=8.5 Hz, 1H), 7.19 (d, J=8.5 Hz, 1H), 5.30-5.10 (br m, 1H), 4.76-4.56 (br m, 1H), 3.54 (s, 3H), 3.49-3.19 (br m, 1H), 2.46 (d, J=16.0 Hz, 1H), 2.37-2.08 (m, 2H), 1.97-1.86 (m, 1H), 1.69-1.57 (m, 1H), 1.50 (s, 9H).

c) tert-Butyl 3-(4-(benzyloxy)-2-oxopyridin-1(2H)-yl)-5-methyl-5,6,7,8,9,10-hexahydro-7,10-iminocyclohept[b]indole-11-carboxylate

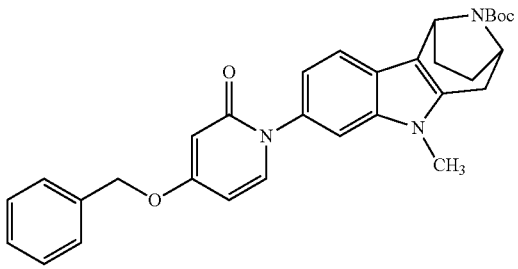

Chemical Formula: $C_{31}H_{33}N_3O_4$
Exact Mass: 511.25
Molecular Weight: 511.61 tert-Butyl 3-bromo-5-methyl-5,6,7,8,9,10-hexahydro-7,10-iminocyclohept[b]indole-11-carboxylate (120 mg, 0.30 mmol) and 4-(benzyloxy)pyridin-2(1H)-one (67 mg, 0.33 mmol), CuI (62 mg, 0.33 mmol), 8-hydroxyquinoline (10 mg, 0.06 mmol) and $K_2CO_3$ (45 mg, 0.33 mmol) in DMSO (5 mL) was degassed under reduced pressure for 45 min. The suspension was put under Ar and stirred at 135° C. overnight. The suspension was cooled, 9:0.9:0.1 $CH_2Cl_2$/MeOH/$NH_4OH$ (10 mL) was added and the resulting suspension was stirred at 25° C. for 30 min. The suspension was passed through a plug of silica gel and the filtrate was washed with brine. The resulting solution was dried over Na₂SO₄ and concentrated under reduced pressure. Flash chromatography (silica gel, (1:1 EtOAc/hexanes)/(9:0.9:0.1 CH₂Cl₂/MeOH/NH₄OH), 100:0 to 90:10) afforded the title compound (65 mg, 42%) as a green oil: ¹H NMR (300 MHz, CDCl₃) δ 7.55 (d, J=8.3 Hz, 1H), 7.46-7.33 (m, 6H), 7.30 (d, J=8.0 Hz, 1H), 7.00 (d, J=6.2 Hz, 1H), 6.09 (d, J=2.5 Hz, 1H), 6.09-6.03 (dd, J=7.5, 2.6 Hz, 1H), 5.23-5.15 (br m, 1H), 5.05 (s, 2H), 4.75-4.56 (br m, 1H), 3.57 (s, 3H), 3.51-3.23 (m, 1H), 2.49 (d, J=15.7 Hz, 1H), 2.37-2.12 (m, 2H), 1.98-1.88 (m, 1H), 1.66-1.54 (m, 1H), 1.38 (s, 9H).

d) 4-(Benzyloxy)-1-(5-methyl-5,6,7,8,9,10-hexahydro-7,10-iminocyclohept[b]indol-3-yl)pyridin-2(1H)-one hydrochloride

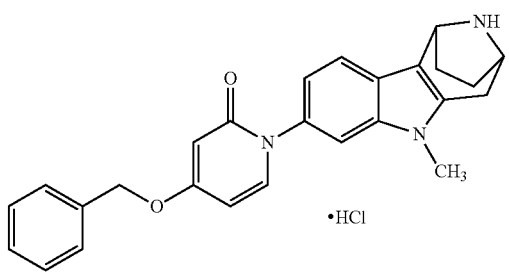 [SMILES: Cn1c2c(c3ccc(-n4ccc(OCc5ccccc5)cc4=O)cc31)C1CCC(C2)N1 ; Cl]

Chemical Formula: C₂₆H₂₆ClN₃O₂
Exact Mass: 447.17
Molecular Weight: 447.96

TFA (1 ml) was added to a solution of tert-butyl 3-(4-(benzyloxy)-2-oxopyridin-1(2H)-yl)-5-methyl-5,6,7,8,9,10-hexahydro-7,10-iminocyclohept[b]indole-11-carboxylate (65 mg, 0.12 mmol) in CH₂Cl₂ (2 mL) under N₂, and the resulting solution was stirred for 1 h at 25° C. Saturated NaHCO₃ solution was added, and the phases were separated. The aqueous phase was extracted with CH₂Cl₂, and the combined organic extracts were dried over Na₂SO₄. The resulting solution was concentrated under reduced pressure. Flash chromatography (silica gel, CH₂Cl₂/(9:1 MeOH/NH₄OH), 100:0 to 80:20) afforded 20 mg of a yellow solid. 2 N HCl in Et₂O (0.024 mL, 0.048 mmol) was added to a solution of the solid in MeOH (1 mL). Concentration under vacuum provide the title compound (21 mg, 40%) as a pink solid: ¹H NMR (300 MHz, CD₃OD) δ 7.64 (d, J=8.4 Hz, 1H), 7.58 (d, J=7.6 Hz, 1H), 7.49-7.30 (m, 6H), 7.07-7.04 (dd, J=8.3, 1.7 Hz, 1H), 6.33-6.30 (dd, J=7.6, 2.6 Hz, 1H), 6.14 (d, J=2.6 Hz, 1H), 5.23 (d, J=4.6 Hz, 1H), 5.19 (s, 2H), 4.59-4.48 (m, 1H), 3.69 (s, 3H), 3.55-3.46 (dd, J=17.3, 4.4 Hz, 1H), 3.05 (d, J=17.3 Hz, 1H), 2.53-2.23 (m, 3H), 2.04-1.90 (m, 1H); ESI MS m/z 412 [M+H]⁺; HPLC (Method B) 97.3% (AUC), t_R=12.9 min.

Example 3

Preparation of 1-(5-Methyl-5,6,7,8,9,10-hexahydro-7,10-iminocyclohept[b]indol-3-yl)-4-(6-(trifluoromethyl)pyridazin-3-yl)pyridin-2(1H)-one hydrochloride a) 3-(2-Methoxypyridin-4-yl)-6-(trifluoromethyl)pyridazine (CAS Registry Number 1173155-65-1) (WO 2009/089482 to Guzzo et al., which is hereby incorporated by reference in its entirety)

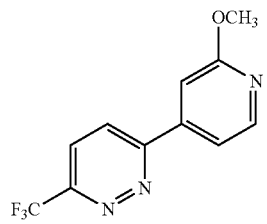

Chemical Formula: C₁₁H₈F₃N₃O
Exact Mass: 255.06
Molecular Weight: 255.20

3-Chloro-6-(trifluoromethyl)pyridazine (137 mg, 0.751 mmol), 2-methoxy-4-(4,4,5,5-tetramethyl-1,3,2-dioxaborolan-2-yl)pyridine (176 mg, 0.749 mmol), K₂CO₃ (310 mg, 2.25 mmol) and PdCl₂(dppf) (61 mg, 0.075 mmol) were stirred in DMSO (4 mL). The reaction mixture was degassed, then back-filled with N₂. The reaction mixture was stirred at 80° C. in a pre-heated oil bath for 2 hours. After cooling, the reaction was quenched with water and extracted with CH₂Cl₂. The organic layer was washed with H₂O and 5% LiCl solution, dried with Na₂SO₄, filtered and concentrated. Flash chromatography (silica gel, hexanes/EtOAc), 100:0 to 50:50) afforded the title compound (115 mg, 60%) as a white solid: ¹H NMR (500 MHz, CDCl₃) δ 8.39 (d, J=5.8 Hz, 1H), 8.05 (d, J=8.8 Hz, 1H), 7.94 (d, J=8.8 Hz, 1H), 7.62 (dd, J=5.4, 1.5 Hz, 1H), 7.45 (s, 1H), 4.03 (s, 3H).

b) 4-(6-(Trifluoromethyl)pyridazin-3-yl)pyridin-2(1H)-one (CAS Registry Number 1173155-66-2) (WO 2009/089482 to Guzzo et al., which is hereby incorporated by reference in its entirety)

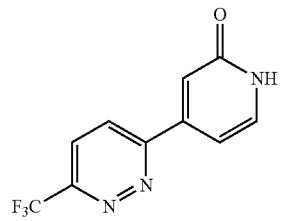

Chemical Formula: C₁₀H₆F₃N₃O
Exact Mass: 241.05
Molecular Weight: 241.17

3-(2-Methoxypyridin-4-yl)-6-(trifluoromethyl)pyridazine (115 mg, 0.451 mmol) was stirred in concentrated hydrochloric acid (20 mL) at 120° C. for 18 h and then concentrated. The residue was adjusted to pH 8 with 6 N NaOH solution, and the solids were filtered off, washed with water and dried under vacuum to provide the title compound (120 mg, quant) as a white solid: $^1$H NMR (500 MHz, DMSO-$d_6$) δ 11.87 (s, 1H), 8.61 (d, J=8.9 Hz, 1H), 8.42 (d, J=8.9 Hz, 1H), 7.62 (d, J=6.8 Hz, 1H), 7.19 (s, 1H), 7.01 (dd, J=6.8, 1.6 Hz, 1H).

c) tert-Butyl 5-methyl-3-(2-oxo-4-(6-(trifluoromethyl)pyridazin-3-yl)pyridin-1(2H)-yl)-5,6,7,8,9,10-hexahydro-7,10-iminocyclohept[b]indole-11-carboxylate

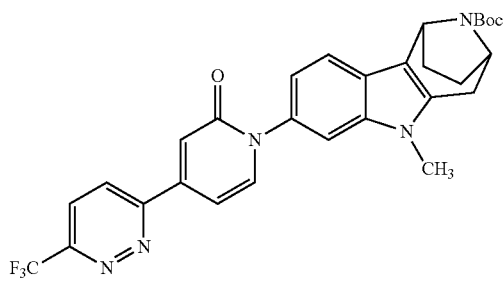

Chemical Formula: $C_{29}H_{28}F_3N_5O_3$
Exact Mass: 551.21
Molecular Weight: 551.56 tert-Butyl 3-bromo-5-methyl-5,6,7,8,9,10-hexahydro-7,10-iminocyclohept[b]indole-11-carboxylate (120 mg, 0.30 mmol) and 4-(6-(trifluoromethyl)pyridazin-3-yl)pyridin-2(1H)-one (73 mg, 0.30 mmol) were reacted following the procedure for Example 2 (step c) to provide the title compound (57 mg, 34%) as a yellow oil: $^1$H NMR (300 MHz, CDCl$_3$) δ 8.10 (d, J=8.9 Hz, 1H), 7.97 (d, J=8.9 Hz, 1H), 7.65 (d, J=6.7 Hz, 1H), 7.61 (d, J=8.4 Hz, 1H), 7.34 (d, J=1.7 Hz, 1H), 7.28-7.20 (m, 2H), 7.08 (d, J=7.6 Hz, 1H), 5.34-5.16 (br m, 1H), 4.76-4.57 (br m, 1H), 3.61 (s, 3H), 3.53-3.26 (br m, 1H), 2.51 (d, J=16.1 Hz, 1H), 2.40-2.11 (m, 2H), 2.00-1.90 (m, 1H), 1.68-1.51 (m, 1H), 1.38 (s, 9H).

d) 1-(5-Methyl-5,6,7,8,9,10-hexahydro-7,10-iminocyclohept[b]indol-3-yl)-4-(6-(trifluoromethyl)pyridazin-3-yl)pyridin-2(1H)-one hydrochloride

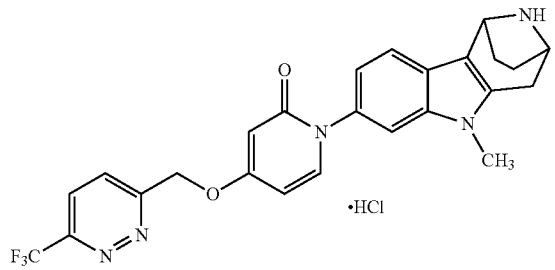

Chemical Formula: $C_{24}H_{21}ClF_3N_5O$
Exact Mass: 487.14
Molecular Weight: 487.90 tert-Butyl 5-methyl-3-(2-oxo-4-(6-(trifluoromethyl)pyridazin-3-yl)pyridin-1(2H)-yl)-5,6,7,8,9,10-hexahydro-7,10-iminocyclohept[b]indole-11-carboxylate (56 mg, 0.12 mmol) was deprotected and converted to the hydrochloride salt according to the procedure for Example 2 (step d) to provide the title compound (34 mg, 58%) as a yellow solid: mp 235-245° C.; $^1$H NMR (300 MHz, CD$_3$OD) δ 8.53 (d, J=8.9 Hz, 1H), 8.27 (d, J=8.9 Hz, 1H), 7.90 (d, J=7.1 Hz, 1H), 7.71 (d, J=8.4 Hz, 1H), 7.58 (d, J=1.3 Hz, 1H), 7.43 (d, J=1.3 Hz, 1H), 7.35-7.32 (dd, J=7.1, 2.0 Hz, 1H), 7.19-7.15 (dd, J=8.4, 1.8 Hz, 1H), 5.26 (d, J=4.6 Hz, 1H), 4.57-4.54 (m, 1H), 3.78 (s, 3H), 3.55-3.48 (dd, J=17.0, 4.6 Hz, 1H), 3.09 (d, J=17.5 Hz, 1H), 2.53-2.24 (m, 3H), 2.06-1.95 (m, 1H); ESI MS m/z 452 [M+H]$^+$; HPLC (Method B)>99% (AUC), $t_R$=12.4 min Example 4

Preparation of 1-(5-Methyl-5,6,7,8,9,10-hexahydro-7,10-iminocyclohept[b]indol-3-yl)-4-(5-(trifluoromethyl)pyridin-2-yl)pyridin-2(1H)-one dihydrochloride a) 2'-Methoxy-5-(trifluoromethyl)-2,4'-bipyridine (CAS Registry Number 1108184-24-2) (WO 2009/015037 to Guzzo et al., which is hereby incorporated by reference in its entirety)

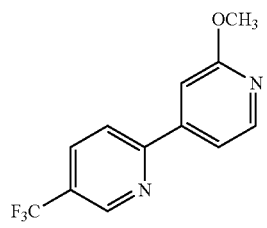

Chemical Formula: $C_{12}H_9F_3N_2O$
Exact Mass: 254.07
Molecular Weight: 254.21

2-Bromo-5-trifluoromethylpyridine (410 mg, 2.13 mmol) and 2-methoxy-4-(4,4,5,5-tetramethyl-1,3,2-dioxaborolan-2-yl)pyridine (500 mg, 1.81 mmol) were reacted according to Example 3 (step a) to provide the title compound (337 mg, 62%) as a white solid: $^1$H NMR (300 MHz, CDCl$_3$) δ 8.96 (s, 1H), 8.31 (d, J=5.4 Hz, 1H), 8.04 (dd, J=8.3, 2.1 Hz, 1H), 7.87 (d, J=8.3 Hz, 1H), 7.51 (dd, J=5.4, 1.4 Hz, 1H), 7.36 (s, 1H), 3.52 (s, 3H).

b) 4-(5-(Trifluoromethyl)pyridin-2-yl)pyridin-2(1H)-one (CAS Registry Number 1108184-25-3) (WO 2009/015037 to Guzzo et al., which is hereby incorporated by reference in its entirety)

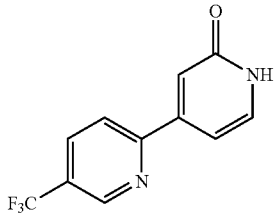

Chemical Formula : $C_{11}H_7F_3N_2O$
Exact Mass: 240.05
Molecular Weight: 240.18

2'-Methoxy-5-(trifluoromethyl)-2,4'-bipyridine (337 mg, 1.32 mmol) was reacted according to Example 3 (step b) to provide the title compound (289 mg, 89%) as a white solid: $^1$H NMR (300 MHz, DMSO-$d_6$) δ 11.08 (s, 1H) 9.10 (s, 1H), 8.35 (dd, J=8.4, 2.1 Hz, 1H), 8.25 (d, J=8.3 Hz, 1H), 7.53 (d, J=6.8, 1H), 7.09 (d, J=1.3 Hz, 1H), 6.90 (dd, J=6.8, 1.6 Hz, 1H).

c) tert-Butyl 5-methyl-3-(2-oxo-4-(5-(trifluoromethyl)pyridin-2-yl)pyridin-1(2H)-yl)-5,6,7,8,9,10-hexahydro-7,10-iminocyclohept[b]indole-11-carboxylate

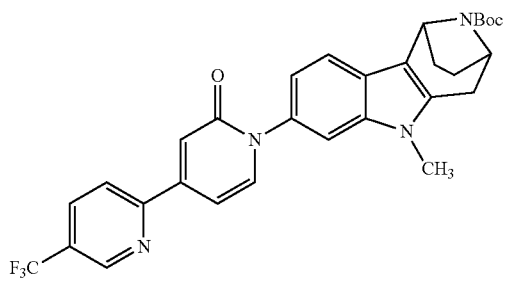

Chemical Formula: $C_{30}H_{29}F_3N_4O_3$
Exact Mass: 550.22
Molecular Weight: 550.57 tert-Butyl 3-bromo-5-methyl-5,6,7,8,9,10-hexahydro-7,10-iminocyclohept[b]indole-11-carboxylate (160 mg, 0.44 mmol) and 4-(5-(trifluoromethyl)pyridin-2-yl)pyridin-2(1H)-one (98 mg, 0.41 mmol) were reacted following the procedure for Example 2 (step c) to provide the title compound (60 mg, 26%) as a yellow oil: $^1$H NMR (500 MHz, CDCl$_3$) δ 9.00 (s, 1H), 8.07-8.05 (dd, J=8.2, 1.6 Hz, 1H), 7.92 (d, J=8.2 Hz, 1H), 7.62-7.52 (m, 2H), 7.34 (s, 1H), 7.26 (s, 1H), 7.20-7.01 (m, 2H), 5.35-5.21 (m, 1H), 4.72-4.62 (m, 1H), 3.60 (s, 3H), 3.51-3.30 (m, 1H), 2.51 (d, J=15.8 Hz, 1H), 2.36-2.27 (m, 1H), 2.24-2.16 (m, 1H), 1.95 (t, J=9.9 Hz, 1H), 1.65-1.54 (m, 1H), 1.38 (s, 9H).

d) 1-(5-Methyl-5,6,7,8,9,10-hexahydro-7,10-iminocyclohept[b]indol-3-yl)-4-(5-(trifluoromethyl)pyridin-2-yl)pyridin-2(1H)-one dihydrochloride

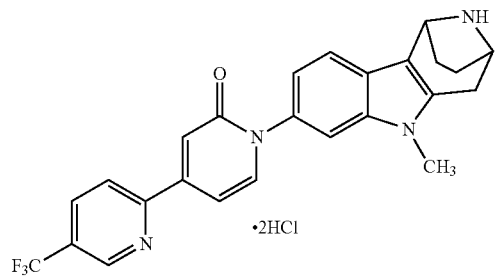 [SMILES: Cn1c2c(c3ccc(-n4ccc(-c5ccc(C(F)(F)F)cn5)cc4=O)cc31)C1CCC(C2)N1 ; "·2HCl"]

Chemical Formula: $C_{25}H_{23}Cl_2F_3N_4O$
Exact Mass: 522.12
Molecular Weight: 523.38 tert-Butyl 5-methyl-3-(2-oxo-4-(5-(trifluoromethyl)pyridin-2-yl)pyridin-1(2H)-yl)-5,6,7,8,9,10-hexahydro-7,10-iminocyclohept[b]indole-11-carboxylate (60 mg, 0.11 mmol) was deprotected and converted to the dihydrochloride salt according to the procedure for Example 2 (step d) to provide the title compound (16 mg, 28%) as a yellow solid: $^1$H NMR (500 MHz, CD$_3$OD) δ 9.05 (s, 1H), 8.29-8.27 (dd, J=8.4, 2.0 Hz, 1H), 8.23 (d, J=8.3 Hz, 1H), 7.82 (d, J=7.1 Hz, 1H), 7.70 (d, J=8.3 Hz, 1H), 7.55 (d, J=1.5 Hz, 1H), 7.39 (d, J=1.4 Hz, 1H), 7.25-7.24 (dd, J=7.1, 2.0 Hz, 1H), 7.17-7.14 (dd, J=8.3, 1.8 Hz, 1H), 5.26 (d, J=5.2 Hz, 1H), 4.58-4.53 (m, 1H), 3.72 (s, 3H), 3.53-3.49 (dd, J=17.2, 4.5 Hz, 1H), 3.09 (d, J=17.2 Hz, 1H), 2.53-2.35 (m, 2H), 2.32-2.27 (dd, J=11.7, 9.7 Hz, 1H), 2.03-1.96 (m, 1H); ESI MS m/z 451 [M+H]$^+$; HPLC (Method B) 98.6% (AUC), $t_R$=13.1 min.

Example 5

Preparation of 1-(5-Methyl-5,6,7,8,9,10-hexahydro-7,10-iminocyclohept[b]indol-3-yl)-4-(6-(trifluoromethyl)pyridin-3-yl)pyridin-2(1H)-one dihydrochloride a) 2'-Methoxy-6-(trifluoromethyl)-3,4'-bipyridine (CAS Registry Number 1173155-80-0) (WO 2009/089482 to Guzzo et al., which is hereby incorporated by reference in its entirety)

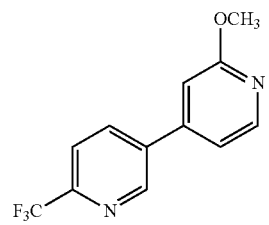

Chemical Formula: $C_{12}H_9F_3N_2O$
Exact Mass: 254.07
Molecular Weight: 254.21

2-Methoxy-4-(4,4,5,5-tetramethyl-1,3,2-dioxaborolan-2-yl)pyridine (1.24 g, 0.53 mmol) and 5-bromo-2-(trifluoromethyl)pyridine (2.4 g, 11 mmol) were reacted according to the procedure of Example 3 (step a) to provide the title compound (1.1 g, 81%) as a white solid: ESI MS m/z 255 [M+H].

b) 4-(6-(Trifluoromethyl)pyridin-3-yl)pyridin-2(1H)-one (CAS Registry Number 1173155-81-1) (WO 2009/089482 to Guzzo et al., which is hereby incorporated by reference in its entirety)

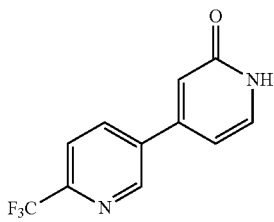

Chemical Formula: C₁₁H₇F₃N₂O
Exact Mass: 240.05
Molecular Weight: 240.18

2'-Methoxy-6-(trifluoromethyl)-3,4'-bipyridine (1.1 g, 4.3 mmol) was reacted according to the procedure of Example 3 (step b) to provide the title compound (522 mg, 50%) as a white solid: ¹H NMR (500 MHz, DMSO-d₆) δ 11.80 (br s, 1H), 9.10 (s, 1H), 8.40 (dd, J=8.1, 1.2 Hz, 1H), 8.00 (d, J=8.2 Hz, 1H), 7.56 (d, J=6.7 Hz, 1H), 6.81 (s, 1H), 6.63 (dd, J=6.7, 1.3 Hz, 1H).

c) tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate

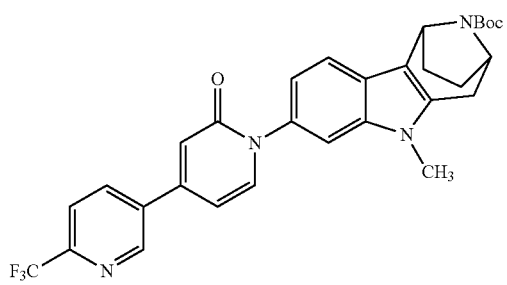

Chemical Formula: C₃₀H₂₉F₃N₄O₃
Exact Mass: 550.22
Molecular Weight: 550.57 tert-Butyl 3-bromo-5-methyl-5,6,7,8,9,10-hexahydro-7,10-iminocyclohept[b]indole-11-carboxylate (120 mg, 0.30 mmol) and 4-(6-(trifluoromethyl)pyridin-3-yl)pyridin-2(1H)-one (73 mg, 0.30 mmol) were reacted following the procedure for Example 2 (step c) to provide the title compound (90 mg, 54%) as a yellow oil: ¹H NMR (300 MHz, CDCl₃) δ 8.99 (s, 1H), 8.11-8.08 (dd, J=8.0, 1.7 Hz, 1H), 7.82 (d, J=8.0 Hz, 1H), 7.62-7.59 (m, 2H), 7.31 (d, J=1.5 Hz, 1H), 7.07-7.05 (m, 1H), 6.93 (d, J=1.5 Hz, 1H), 6.50-6.47 (dd, J=7.0, 1.6 Hz, 1H), 5.34-5.16 (br m, 1H), 4.77-4.60 (br m, 1H), 3.60 (s, 3H), 3.52-3.28 (br m, 1H), 2.51 (d, J=15.6 Hz, 1H), 2.39-2.21 (m, 2H), 1.95 (t, J=10.1 Hz, 1H), 1.65-1.54 (m, 1H), 1.38 (s, 9H).

d) 1-(5-Methyl-5,6,7,8,9,10-hexahydro-7,10-iminocyclohept[b]indol-3-yl)-4-(6-(trifluoromethyl)pyridin-3-yl)pyridin-2(1H)-one dihydrochloride

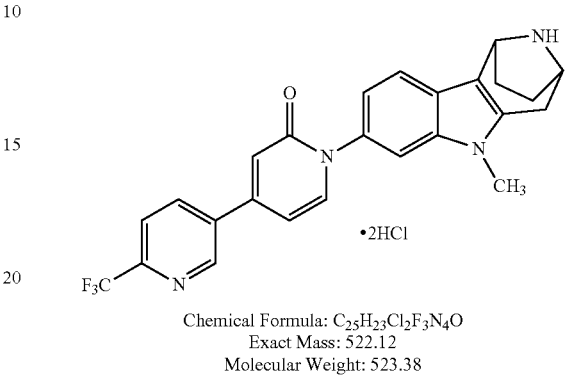

Chemical Formula: C₂₅H₂₃Cl₂F₃N₄O
Exact Mass: 522.12
Molecular Weight: 523.38 tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate (90 mg, 0.16 mmol) was deprotected and converted to the dihydrochloride salt according to the procedure for Example 2 (step d) to provide the title compound (40 mg, 47%) as a yellow solid: mp 228-233° C.; ¹H NMR (300 MHz, CD₃OD) δ 9.10 (s, 1H), 8.43-8.39 (dd, J=8.9, 1.9 Hz, 1H), 7.97 (d, J=8.2 Hz, 1H), 7.84 (d, J=7.1 Hz, 1H), 7.70 (d, J=8.4 Hz, 1H), 7.55 (d, J=1.5 Hz, 1H), 7.15 (dd, J=8.4, 1.8 Hz, 1H), 7.02 (d, J=1.6 Hz, 1H), 6.90-6.87 (dd, J=7.1, 2.0 Hz, 1H), 5.27 (d, J=4.7 Hz, 1H), 4.59-4.53 (m, 1H), 3.72 (s, 3H), 3.53-3.48 (dd, J=17.5, 4.5 Hz, 1H), 3.08 (d, J=17.1 Hz, 1H), 2.52-2.26 (m, 3H), 2.04-2.00 (m, 1H); ESI MS m/z 451 [M+H]⁺; HPLC (Method B)>99% (AUC), t_R=12.7 min.

Example 6

Preparation of 4-((5-Fluoropyridin-2-yl)methoxy)-1-(5-methyl-5,6,7,8,9,10-hexahydro-7,10-iminocyclohept[b]indol-3-yl)pyridin-2(1H)-one dihydrochloride a) 4-((5-Fluoropyridin-2-yl)methoxy)pyridine 1-oxide (CAS Registry Number 1173155-63-9) (WO 2009/089482 to Guzzo et al., which is hereby incorporated by reference in its entirety)

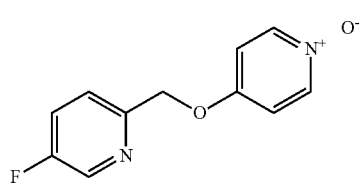

Chemical Formula: C₁₁H₉FN₂O₂
Exact Mass: 220.06
Molecular Weight: 220.20

5-Fluoro-2-pyridylbenzylalcohol (3.00 g, 23.6 mmol) was dissolved in DMF (20 mL), and NaH (60% weight dispersion in mineral oil, 0.92 g, 23 mmol) was added. After stirring for 30 minutes, 4-chloropyridine-N-oxide (2.03 g, 15.7 mmol) was added, and the reaction mixture was heated for 1 h at 120° C. Upon cooling, the mixture was diluted with methylene chloride and washed with 5% lithium chloride solution (5×), dried and concentrated. Purification by flash column chromatography (40 g ISCO column eluting with methylene chloride and a methanol/ammonia mixture (10:1); gradient 100% methylene chloride to 90% methylene chloride over 30 min at 40 mL/min) provided the title compound (1.76 g, 50%) as a tan solid: $^1$H NMR (300 MHz, CDCl$_3$) δ 8.48 (s, 1H), 8.12 (d, J=7.7 Hz, 2H), 7.48-7.46 (m, 2H), 6.90 (d, J=7.7 Hz, 2H), 5.20 (s, 2H).

b) 4-((5-Fluoroyridin-2-yl)methoxy)pyridin-2(1H)-one (CAS Registry Number 924311-90-0) (WO 2007/018248 to Ando et al., which is hereby incorporated by reference in its entirety)

Chemical Formula: C$_{11}$H$_9$FN$_2$O$_2$
Exact Mass: 220.06
Molecular Weight: 220.20

4-((5-Fluoropyridin-2-yl)methoxy)pyridine 1-oxide (1.76 g, 7.99 mmol) was heated to 140° C. in acetic anhydride (80 mL) for 5 h. The mixture was concentrated and then heated at 80° C. for 1 h in a mixture of MeOH (20 mL) and aqueous 1 N NaOH (15 mL). The resulting black solution was concentrated to a volume of 15 mL, and the solid was filtered off, rinsed with CH$_2$Cl$_2$ and dried under vacuum to provide the title compound (1.29 g, 73%) as a yellow solid: $^1$H NMR (500 MHz, DMSO-d$_6$) δ 11.12 (s, 1H), 8.59 (d, J=2.9 Hz, 1H), 7.79 (ddd, J=8.7, 8.7, 2.9 Hz, 1H), 7.60 (dd, J=8.7, 4.5 Hz, 1H), 7.26 (d, J=7.3 Hz, 1H), 5.95 (dd, J=7.4, 2.6 Hz, 1H), 5.78 (d, J=2.5 Hz, 1H), 5.12 (s, 2H).

c) tert-Butyl 3-(4-((5-fluoropyridin-2-yl)methoxy)-2-oxopyridin-1(2H)-yl)-5-methyl-5,6,7,8,9,10-hexahydro-7,10-iminocyclohept[b]indole-11-carboxylate Chemical Formula: C$_{30}$H$_{31}$FN$_4$O$_4$
Exact Mass: 530.23
Molecular Weight: 530.59 tert-Butyl 3-bromo-5-methyl-5,6,7,8,9,10-hexahydro-7,10-iminocyclohept[b]indole-11-carboxylate (140 mg, 0.36 mmol) and 4-((5-fluoropyridin-2-yl)methoxy)pyridin-2(1H)-one (96 mg, 0.43 mmol) were reacted following the procedure for Example 2 (step c) to provide the title compound (100 mg, 52%) as a yellow oil: ESI MS m/z 531 [M+H]$^+$.

d) 4-((5-Fluoropyridin-2-yl)methoxy)-1-(5-methyl-5,6,7,8,9,10-hexahydro-7,10-iminocyclohept[b]indol-3-yl)pyridin-2(1H)-one dihydrochloride Chemical Formula: C$_{25}$H$_{25}$Cl$_2$FN$_4$O$_2$
Exact Mass: 502.13
Molecular Weight: 503.40 tert-Butyl 3-(4-((5-fluoropyridin-2-yl)methoxy)-2-oxopyridin-1(2H)-yl)-5-methyl-5,6,7,8,9,10-hexahydro-7,10-iminocyclohept[b]indole-11-carboxylate (100 mg, 0.19 mmol) was deprotected and converted to the dihydrochloride salt according to the procedure for Example 2 (step d) to provide the title compound (37 mg, 39%) as a white solid: mp 180-190° C.; $^1$H NMR (300 MHz, CD$_3$OD) δ 8.54 (d, J=2.7 Hz, 1H), 7.79-7.63 (m, 4H), 7.46 (d, J=1.6 Hz, 1H), 7.08-7.04 (dd, J=8.4, 1.8 Hz, 1H), 6.40-6.37 (dd, J=7.6, 2.7 Hz, 1H), 6.18 (d, J=2.6 Hz, 1H), 5.29 (s, 2H), 5.24 (d, J=4.7 Hz, 1H), 4.58-4.50 (m, 1H), 3.70 (s, 3H), 3.54-3.46 (dd, J=17.2, 4.9 Hz, 1H), 3.07

(d, J=17.1 Hz, 1H), 2.51-2.23 (m, 3H), 2.02-1.99 (m, 1H); ESI MS m/z 431 [M+H]+; HPLC (Method B) 98.4% (AUC), $t_R$=11.8 min.

Example 7

Preparation of 1-(5-Methyl-5,6,7,8,9,10-hexahydro-7,10-iminocyclohept[b]indol-3-yl)-4-(2-(trifluoromethyl)pyrimidin-5-yl)pyridin-2(1H)-one hydrochloride a) 5-(2-Methoxypyridin-4-yl)-2-(trifluoromethyl)pyrimidine (CAS Registry Number 1173155-89-9) (WO 2009/089482 to Guzzo et al., which is hereby incorporated by reference in its entirety)

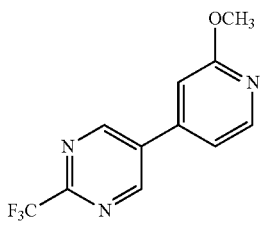

Chemical Formula: $C_{11}H_8F_3N_3O$
Exact Mass: 255.06
Molecular Weight: 255.20

2-Methoxy-4-(4,4,5,5-tetramethyl-1,3,2-dioxaborolan-2-yl)pyridine (2.0 g, 8.5 mmol) and 5-chloro-2-(trifluoromethyl)pyrimidine (2.3 g, 13 mmol) were reacted according to the procedure of Example 3 (step a) to provide the title compound (1.0 g, 46%) as a white solid: ¹H NMR (300 MHz, CDCl₃) δ 9.10 (s, 2H), 8.35 (d, J=5.5 Hz, 1H), 7.11 (dd, J=5.5, 1.6 Hz, 1H), 6.98 (d, J=1.6 Hz, 1H), 4.02 (s, 3H).

b) 4-(2-(Trifluoromethyl)pyrimidin-5-yl)pyridin-2(1H)-one (CAS Registry Number 1173155-90-2) (WO 2009/089482 to Guzzo et al., which is hereby incorporated by reference in its entirety)

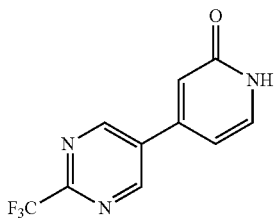

Chemical Formula: $C_{10}H_6F_3N_3O$
Exact Mass: 241.05
Molecular Weight: 241.17

5-(2-Methoxypyridin-4-yl)-2-(trifluoromethyl)pyrimidine (900 mg, 3.5 mmol) was reacted according to the procedure of Example 3 (step b) to provide the title compound (470 mg, 56%) as an orange solid: ¹H NMR (300 MHz, DMSO-d₆) δ 11.6 (br s, 1H), 9.41 (s, 2H), 7.61 (d, J=6.8 Hz, 1H), 6.91 (s, 1H), 6.68 (dd, J=6.8, 1.6 Hz, 1H).

c) tert-Butyl 5-methyl-3-(2-oxo-4-(2-(trifluoromethyl)pyrimidin-5-yl)pyridin-1(2H)-yl)-5,6,7,8,9,10-hexahydro-7,10-iminocyclohept[b]indole-11-carboxylate

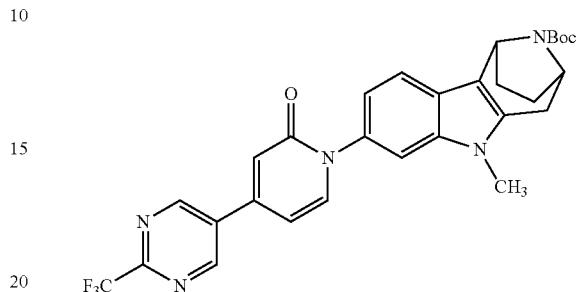

Chemical Formula: $C_{29}H_{28}F_3N_5O_3$
Exact Mass: 551.21
Molecular Weight: 551.56 tert-Butyl 3-bromo-5-methyl-5,6,7,8,9,10-hexahydro-7,10-iminocyclohept[b]indole-11-carboxylate (135 mg, 0.345 mmol) and 4-(2-(trifluoromethyl)pyrimidin-5-yl)pyridin-2(1H)-one (101 mg, 0.420 mmol) were reacted following the procedure for Example 2 (step c) to provide the title compound (69 mg, 36%) as a yellow oil: ¹H NMR (300 MHz, CDCl₃) δ 9.14 (s, 2H), 7.65-7.60 (m, 2H), 7.32 (s, 1H), 7.09-7.01 (m, 1H), 7.32 (s, 1H), 6.47 (d, J=6.2 Hz, 1H), 5.35-5.18 (br m, 1H), 4.76-4.58 (br m, 1H), 3.61 (s, 3H), 3.52-3.39 (br m, 1H), 2.51 (d, J=16.3 Hz, 1H), 2.37-2.17 (m, 2H), 1.99-1.89 (m, 1H), 1.67-1.53 (m, 1H), 1.38 (s, 9H).

d) 1-(5-Methyl-5,6,7,8,9,10-hexahydro-7,10-iminocyclohept[b]indol-3-yl)-4-(2-(trifluoromethyl)pyrimidin-5-yl)pyridin-2(1H)-one hydrochloride

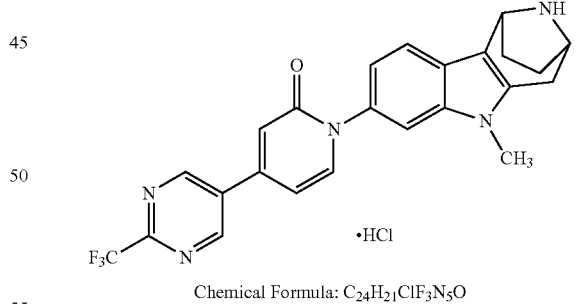

Chemical Formula: $C_{24}H_{21}ClF_3N_5O$
Exact Mass: 487.14
Molecular Weight: 487.90 tert-Butyl 5-methyl-3-(2-oxo-4-(2-(trifluoromethyl)pyrimidin-5-yl)pyridin-1(2H)-yl)-5,6,7,8,9,10-hexahydro-7,10-iminocyclohept[b]indole-11-carboxylate (69 mg, 0.13 mmol) was deprotected and converted to the hydrochloride salt according to the procedure for Example 2 (step d) to provide the title compound (30 mg, 49%) as a yellow solid: ¹H NMR (300 MHz, CD₃OD) δ 9.36 (s, 2H), 7.87 (d, J=7.1 Hz, 1H), 7.70 (d, J=8.4 Hz, 1H), 7.55 (d, J=1.5 Hz, 1H), 7.16-7.13 (dd, J=8.4, 1.8 Hz, 1H), 7.09 (d, J=1.5 Hz, 1H), 6.93-6.93 (dd, J=7.1, 2.0 Hz, 1H), 5.26 (d, J=4.7 Hz, 1H), 4.58-4.52 (m, 1H), 3.79 (s, 3H), 3.56-3.47 (dd, J=17.3, 4.4 Hz, 1H), 3.12 (dd, J=17.3, 1.4 Hz, 1H), 2.53-2.23 (m, 3H), 2.04-1.98 (m, 1H); ESI MS m/z 452 [M+H]⁺; HPLC (Method B)>99% (AUC), $t_R$=12.5 min.

Example 8

Preparation of 4-(Benzyloxy)-1-(5,6,7,8,9,10-hexahydro-7,10-iminocyclohept[b]indol-3-yl)pyridin-2(1H)-one hydrochloride a) tert-Butyl 3-bromo-5-tosyl-5,6,7,8,9,10-hexahydro-7,10-iminocyclohept[b]indole-11-carboxylate

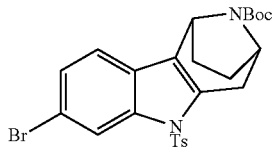

Chemical Formula: $C_{25}H_{27}BrN_2O_4S$
Exact Mass: 530.09
Molecular Weight: 531.46 tert-Butyl 3-bromo-5,6,7,8,9,10-hexahydro-7,10-iminocyclohept[b]indole-11-carboxylate (1.20 g, 3.18 mmol) and tosyl chloride (770 mg, 3.89 mmol) were added to a biphasic system of Bu₄NHSO₄ (50% weight solution in H₂O, 0.26 mL) in 5:3 toluene/(6 N NaOH in H₂O) (43 mL), and the resulting biphasic system was stirred at 25° C. for 1 h. The phases were separated. The organic phase was washed with H₂O, dried over Na₂SO₄ and concentrated under reduced pressure. Flash chromatography (silica gel, hexanes/(1:1 EtOAc/hexanes), 100:0 to 0:100) afforded the title compound (1.3 g, 77%) as an orange solid: ¹H NMR (300 MHz, CDCl₃) δ 8.30 (br m, 1H), 7.60 (br m, 2H), 7.35 (d, J=8.6 Hz, 1H), 7.27-7.23 (m, 1H), 7.19 (d, J=8.6 Hz, 2H), 5.09-4.97 (br m, 1H), 4.59-4.56 (m, 1H), 3.52-3.41 (m, 1H), 2.87 (d, J=17.5 Hz, 1H), 2.33-2.23 (m, 4H), 2.20-2.07 (m, 1H), 1.87 (t, J=9.6 Hz, 1H), 1.66-1.57 (m, 1H), 1.47-1.12 (br m, 9H).

b) tert-Butyl 3-(4-(benzyloxy)-2-oxopyridin-1(2H)-yl)-5-tosyl-5,6,7,8,9,10-hexahydro-7,10-iminocyclohept[b]indole-11-carboxylate

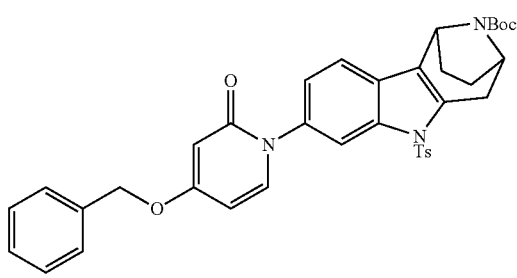

Chemical Formula: $C_{37}H_{37}N_3O_6S$
Exact Mass: 651.24
Molecular Weight: 651.77 tert-Butyl 3-bromo-5-tosyl-5,6,7,8,9,10-hexahydro-7,10-iminocyclohept[b]indole-11-carboxylate (400 mg, 0.75 mmol) and 4-(benzyloxy)pyridin-2(1H)-one (150 mg, 0.75 mmol) were reacted following the procedure for Example 2 (step c) to provide the title compound (190 mg, 39%) as a green foam: ¹H NMR (300 MHz, CDCl₃) δ 8.15 (br s, 1H), 7.67 (d, J=8.0 Hz, 2H), 7.50-7.34 (m, 6H), 7.31-7.16 (m, 4H), 6.09-6.08 (m, 2H), 5.14-4.97 (br m, 3H), 4.63-4.54 (m, 1H), 3.63-3.46 (m, 1H), 2.90 (d, J=17.5 Hz, 1H), 2.36-2.23 (m, 4H), 2.20-2.07 (m, 1H), 1.93-1.84 (m, 1H), 1.61-1.57 (m, 1H), 1.48-1.12 (br m, 9H).

c) 4-(Benzyloxy)-1-(5-tosyl-5,6,7,8,9,10-hexahydro-7,10-iminocyclohept[b]indol-3-yl)pyridin-2(1H)-one

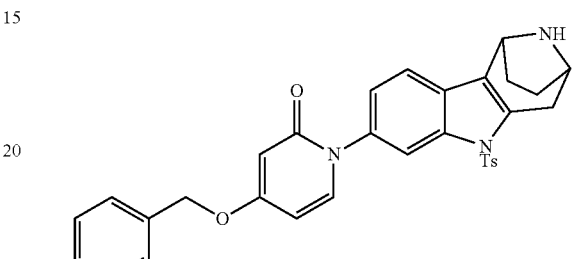

Chemical Formula: $C_{32}H_{29}N_3O_4S$
Exact Mass: 551.19
Molecular Weight: 551.66 tert-Butyl 3-(4-(benzyloxy)-2-oxopyridin-1(2H)-yl)-5-tosyl-5,6,7,8,9,10-hexahydro-7,10-iminocyclohept[b]indole-11-carboxylate (190 mg, 0.29 mmol) was deprotected according to the procedure for Example 2 (step d) to provide the title compound (131 mg, 82%) as a solid: ¹H NMR (300 MHz, CD₃OD) δ 8.20 (d, J=1.7 Hz, 1H), 7.74 (d, J=8.4 Hz, 2H), 7.55 (d, J=8.0 Hz, 1H), 7.53 (d, J=9.9 Hz, 1H), 7.46 (d, J=7.9 Hz, 2H), 7.40 (dd, J=7.4, 7.4 Hz, 2H), 7.35 (d, J=7.2 Hz, 1H), 7.30 (d, J=8.2 Hz, 2H), 7.20-7.18 (dd, J=8.2, 1.8 Hz, 1H), 6.28-6.26 (dd, J=7.2, 2.6 Hz, 1H), 6.11 (d, J=2.6 Hz, 1H), 5.17 (s, 2H), 4.45 (d, J=5.4 Hz, 1H), 3.98-3.95 (m, 1H), 3.41-3.36 (dd, J=17.7, 4.4 Hz, 1H), 2.92 (d, J=17.7 Hz, 1H), 2.33 (s, 3H), 2.16-2.08 (m, 1H), 2.05-1.97 (m, 1H), 1.92-1.85 (m, 1H), 1.52-1.47 (m, 1H).

d) 4-(Benzyloxy)-1-(5,6,7,8,9,10-hexahydro-7,10-iminocyclohept[b]indol-3-yl)pyridin-2(1H)-one hydrochloride

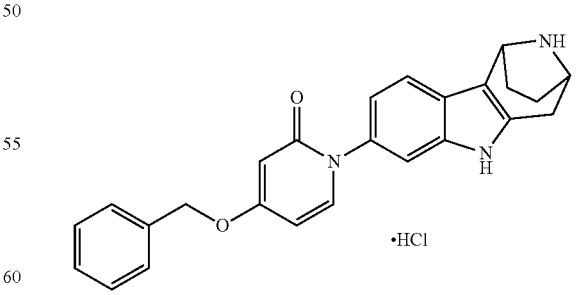

Chemical Formula: $C_{25}H_{24}ClN_3O_2$
Exact Mass: 433.16
Molecular Weight: 433.93

4-(Benzyloxy)-1-(5-tosyl-5,6,7,8,9,10-hexahydro-7,10-iminocyclohept[b]indol-3-yl)pyridin-2(1H)-one (130 mg, 0.24 mmol) and NaOH (594 mg, 14.8 mmol) were added to 1:1 MeOH/CH$_2$Cl$_2$ (20 mL) under N$_2$, and the resulting suspension was stirred at reflux for 16 h. The reaction was cooled, H$_2$O was added, and the resulting suspension was filtered. The obtained solid was purified by flash chromatography (silica gel, CH$_2$Cl$_2$/(9:1 MeOH/NH$_4$OH), 100:0 to 80:20) afforded the free-base that was subsequently converted to the hydrochloride salt according to the procedure for Example 2 (step d) to provide the title compound (41 mg, 39%) as a white solid: mp 209-214° C.; $^1$H NMR (300 MHz, DMSO-d$_6$) δ 11.39 (s, 1H), 9.54 (br s, 1H), 9.14 (d, J=9.8 Hz, 1H), 7.60 (d, J=8.4 Hz, 1H), 7.55 (d, J=7.6 Hz, 1H), 7.48-7.44 (m, 2H), 7.44-7.40 (m, 2H), 7.37 (dd, J=8.0, 8.0 Hz, 1H), 7.29 (d, J=1.8 Hz, 1H), 6.95-6.93 (dd, J=8.3, 1.8 Hz, 1H), 6.09-6.07 (dd, J=7.6, 2.6 Hz, 1H), 5.96 (d, J=2.7 Hz, 1H), 5.18 (br s, 1H), 5.14 (s, 2H), 4.40 (br m, 1H), 3.44-3.40 (dd, J=17.0, 4.0 Hz, 1H), 2.90 (d, J=17.0 Hz, 1H), 2.29-2.26 (m, 2H), 2.07-2.04 (m, 1H), 1.80-1.75 (m, 1H); ESI MS m/z 398 [M+H]$^+$; HPLC (Method B)>99% (AUC), t$_R$=12.7 min.

Example 9

Preparation of 4-((5-Fluoropyridin-2-yl)methoxy)-1-(5,6,7,8,9,10-hexahydro-7,10-iminocyclohept[b]indol-3-yl)pyridin-2(1H)-one dihydrochloride a) tert-Butyl 3-(4-((5-fluoropyridin-2-yl)methoxy)-2-oxopyridin-1(2H)-yl)-5-tosyl-5,6,7,8,9,10-hexahydro-7,10-iminocyclohept[b]indole-11-carboxylate

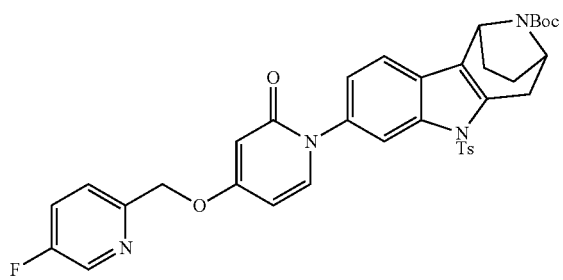

Chemical Formula: C$_{36}$H$_{35}$FN$_4$O$_6$S
Exact Mass: 670.23
Molecular Weight: 670.75 tert-Butyl 3-bromo-5-tosyl-5,6,7,8,9,10-hexahydro-7,10-iminocyclohept[b]indole-11-carboxylate (362 mg, 0.680 mmol) and 4-((5-fluoropyridin-2-yl)methoxy)pyridin-2(1H)-one (150 mg, 0.68 mmol) were reacted following the procedure for Example 2 (step c) to provide the title compound (210 mg, 46%) as a yellow foam: $^1$H NMR (300 MHz, CDCl$_3$) δ 8.47 (s, 1H), 8.16 (br s, 1H), 7.66 (d, J=7.8 Hz, 2H), 7.52-7.34 (m, 3H), 7.34-7.17 (m, 4H), 6.14-6.11 (dd, J=7.6, 2.6, 1H), 6.06 (d, J=2.4 Hz, 1H), 5.18 (s, 2H), 5.18-5.02 (m, 1H), 4.67-4.47 (m, 1H), 3.72-3.39 (m, 1H), 2.90 (d, J=17.7 Hz, 1H), 2.35-2.27 (m, 4H), 2.27-2.08 (m, 1H), 1.94-1.82 (m, 1H), 1.61-1.51 (m, 1H), 1.46-1.19 (br s, 9H).

b) tert-Butyl 3-(4-((5-fluoropyridin-2-yl)methoxy)-2-oxopyridin-1(2H)-yl)-5,6,7,8,9,10-hexahydro-7,10-iminocyclohept[b]indole-11-carboxylate

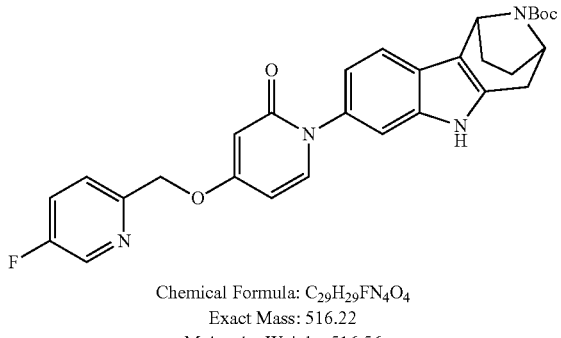

Chemical Formula: C$_{29}$H$_{29}$FN$_4$O$_4$
Exact Mass: 516.22
Molecular Weight: 516.56 tert-Butyl 3-(4-((5-fluoropyridin-2-yl)methoxy)-2-oxopyridin-1(2H)-yl)-5-tosyl-5,6,7,8,9,10-hexahydro-7,10-iminocyclohept[b]indole-11-carboxylate (210 mg, 0.31 mmol) was detosylated according to the procedure for Example 8 (step d) to provide the title compound (260 mg, >100%) as a yellow solid: ESI MS m/z 517 [M+H]$^+$.

c) 4-((5-Fluoropyridin-2-yl)methoxy)-1-(5,6,7,8,9,10-hexahydro-7,10-iminocyclohept[b]indol-3-yl)pyridin-2(1H)-one dihydrochloride

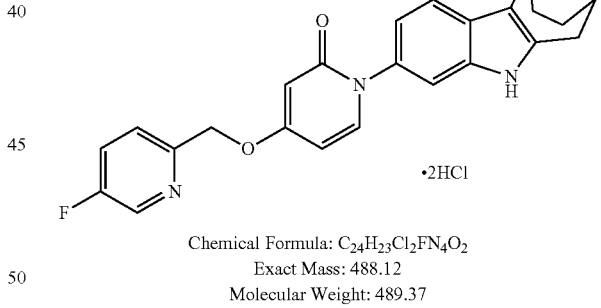

Chemical Formula: C$_{24}$H$_{23}$Cl$_2$FN$_4$O$_2$
Exact Mass: 488.12
Molecular Weight: 489.37 tert-Butyl 3-(4-((5-fluoropyridin-2-yl)methoxy)-2-oxopyridin-1(2H)-yl)-5,6,7,8,9,10-hexahydro-7,10-iminocyclohept[b]indole-11-carboxylate (260 mg (crude), 0.31 mmol) was deprotected and converted to the dihydrochloride salt according to the procedure for Example 2 (step d) to provide the title compound (65 mg, 43%) as a pink solid: mp 205-211° C. (decomp.); $^1$H NMR (300 MHz, DMSO-d$_6$) δ 11.42 (s, 1H), 9.63 (d, J=6.9 Hz, 1H), 9.18 (d, J=9.7 Hz, 1H), 8.62 (d, J=2.9 Hz, 1H), 7.97-7.86 (d, J=8.4 Hz, 1H), 7.68-7.63 (dd, J=8.6, 4.6 Hz, 1H), 7.62 (d, J=8.6 Hz, 1H), 7.57 (d, J=7.6 Hz, 1H), 7.30 (d, J=1.6 Hz, 1H), 6.94-6.92 (dd, J=8.4, 1.9 Hz, 1H), 6.14-6.10 (dd, J=7.6, 2.7 Hz, 1H), 5.97 (d, J=2.7 Hz, 1H), 5.21 (s, 2H), 5.18 (br m, 1H), 4.39 (br m, 1H), 3.46-3.39 (dd, J=17.1, 4.5 Hz, 1H), 2.87 (d, J=16.9 Hz, 1H), 2.34-2.22

(m, 2H), 2.11-2.00 (m, 1H), 1.84-1.74 (m, 1H); ESI MS m/z 417 [M+H]+; HPLC (Method B) 96.9% (AUC), $t_R$=11.4 min.

Example 10

Preparation of 1-(5,6,7,8,9,10-Hexahydro-7,10-iminocyclohept[b]indol-3-yl)-4-(6-(trifluoromethyl)pyridin-3-yl)pyridin-2(1H)-one hydrochloride a) tert-Butyl 3-(2-oxo-4-(6-(trifluoromethyl)pyridin-3-yl)pyridin-1(2H)-yl)-5-tosyl-5,6,7,8,9,10-hexahydro-7,10-iminocyclohept[b]indole-11-carboxylate

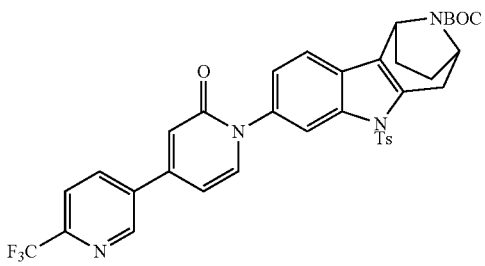

Chemical Formula: $C_{36}H_{33}F_3N_4O_5S$
Exact Mass: 690.21
Molecular Weight: 690.73 tert-Butyl 3-bromo-5-tosyl-5,6,7,8,9,10-hexahydro-7,10-iminocyclohept[b]indole-11-carboxylate (220 mg, 0.41 mmol) and 4-(6-(trifluoromethyl)pyridin-3-yl)pyridin-2(1H)-one (100 mg, 0.41 mmol) were reacted following the procedure for Example 2 (step c) to provide the title compound (150 mg, 53%) as a colorless oil: ESI MS m/z 691 [M+H]+.

b) 1-(5-Tosyl-5,6,7,8,9,10-hexahydro-7,10-iminocyclohept[b]indol-3-yl)-4-(6-(trifluoromethyl)pyridin-3-yl)pyridin-2(1H)-one

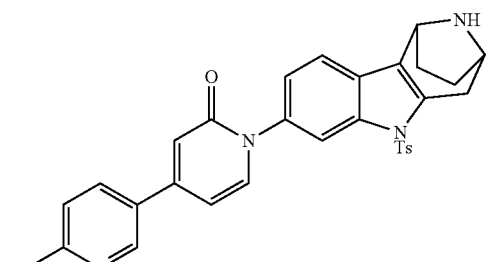

Chemical Formula: $C_{31}H_{25}F_3N_4O_3S$
Exact Mass: 590.16
Molecular Weight: 590.62 tert-Butyl 3-(2-oxo-4-(6-(trifluoromethyl)pyridin-3-yl)pyridin-1(2H)-yl)-5-tosyl-5,6,7,8,9,10-hexahydro-7,10-iminocyclohept[b]indole-11-carboxylate (150 mg, 0.22 mmol) was deprotected according to the procedure for Example 2 (step d) to provide the title compound (124 mg, 96%) as a yellow solid; ESI MS m/z 591 [M+H]+.

c) 1-(5,6,7,8,9,10-Hexahydro-7,10-iminocyclohept[b]indol-3-yl)-4-(6-(trifluoromethyl)pyridin-3-yl)pyridin-2(1H)-one hydrochloride

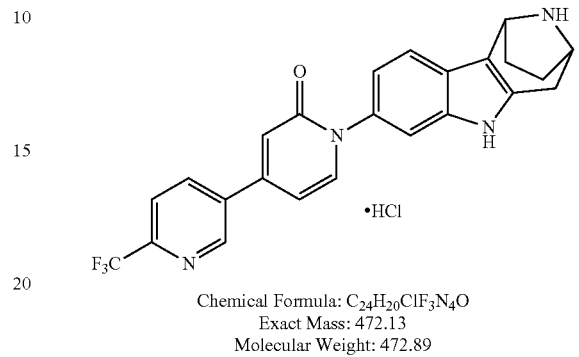

Chemical Formula: $C_{24}H_{20}ClF_3N_4O$
Exact Mass: 472.13
Molecular Weight: 472.89

1-(5-Tosyl-5,6,7,8,9,10-hexahydro-7,10-iminocyclohept[b]indol-3-yl)-4-(6-(trifluoromethyl)pyridin-3-yl)pyridin-2(1H)-one (120 mg, 0.21 mmol) was detosylated and converted to the hydrochloride salt according to the procedure for Example 8 (step d) to provide the title compound (46 mg, 46%) as an orange solid: mp 215-235° C. (decomp.); 1H NMR (300 MHz, DMSO-$d_6$) δ 11.48 (s, 1H), 9.58-9.47 (br m, 1H), 9.20-9.15 (m, 2H), 8.51-8.47 (dd, J=8.4, 1.8 Hz, 1H), 8.04 (d, J=8.1 Hz, 1H), 7.84 (d, J=7.1 Hz, 1H), 7.67 (d, J=8.4 Hz, 1H), 7.42 (d, J=1.8 Hz, 1H), 7.07-7.04 (dd, J=8.4, 1.8 Hz, 1H), 7.00 (d, J=1.8 Hz, 1H), 6.80-6.77 (dd, J=7.2, 2.0 Hz, 1H), 5.21 (br m, 1H), 4.42 (br m, 1H), 3.47-3.40 (dd, J=17.3, 4.4 Hz, 1H), 2.90 (d, J=16.9 Hz, 1H), 2.30-2.23 (m, 2H), 2.07 (t, J=9.8 Hz, 1H), 1.85-1.75 (m, 1H); ESI MS m/z 437 [M+H]+; HPLC (Method B)>99% (AUC), $t_R$=12.3 min.

Example 11

Preparation of 4-((5-Fluoropyridin-2-yl)methoxy)-1-(5-methyl-6,7,8,9,10,11-hexahydro-7,11-imino-5H-cyclooct[b]indol-3-yl)pyridin-2(1H)-one dihydrochloride a) tert-Butyl 3-bromo-5-methyl-6,7,8,9,10,11-hexahydro-7,11-imino-5H-cyclooct[b]indole-12-carboxylate

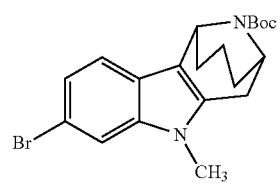

Chemical Formula: $C_{20}H_{25}BrN_2O_2$
Exact Mass: 404.11
Molecular Weight: 405.33

1-(3-Bromophenyl)-1-methylhydrazine (2.64 g, 13.1 mmol) and (3.2 g, 13 mmol) tert-butyl 3-oxo-9-azabicyclo[3.3.1]nonane-9-carboxylate were reacted according to the procedure in Example 2 (step a) to provide the title compound (1.38 g, 26%) as a white solid: ¹H NMR (300 MHz, CDCl₃) δ 7.42 (d, J=6.8 Hz, 1H), 7.29 (d, J=8.0 Hz, 1H), 7.19-7.14 (m, 1H), 5.57-5.41 (m, 1H), 4.84-4.68 (m, 1H), 3.59 (s, 3H), 3.25-3.13 (ddd, J=16.3, 7.4, 7.4 Hz, 1H), 2.53 (d, J=16.5 Hz, 1H), 1.95-1.60 (m, 2H), 1.65-0.60 (m, 2H), 1.48-1.38 (m, 1H), 1.49-1.35 (m, 10H).

b) tert-Butyl 3-(4-((5-fluoropyridin-2-yl)methoxy)-2-oxopyridin-1(2H)-yl)-5-methyl-6,7,8,9,10,11-hexahydro-7,11-imino-5H-cyclooct[b]indole-12-carboxylate

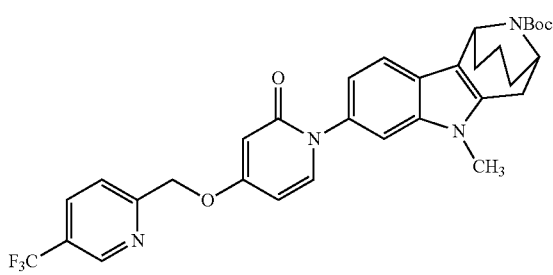

Chemical Formula: C₃₁H₃₃FN₄O₄
Exact Mass: 544.25
Molecular Weight: 544.62 tert-Butyl 3-bromo-5-methyl-6,7,8,9,10,11-hexahydro-7,11-imino-5H-cyclooct[b]indole-12-carboxylate (130 mg, 0.32 mmol) and 4-((5-fluoropyridin-2-yl)methoxy)pyridin-2(1H)-one (70 mg, 0.32 mmol) were reacted following the procedure for Example 2 (step c) to provide the title compound (30 mg, 17%) as a brown oil: ¹H NMR (300 MHz, CDCl₃) δ 8.48 (d, J=2.2 Hz, 1H), 7.51-7.45 (m, 3H), 7.36-7.30 (m, 1H), 7.29-7.26 (m, 1H), 7.04-6.96 (m, 1H), 6.14-6.05 (m, 2H), 5.64-5.45 (m, 1H), 5.17 (s, 2H), 4.86-4.70 (br m 1H), 3.63 (s, 3H), 3.30-3.16 (ddd, J=16.9, 7.1, 7.1 Hz, 1H), 2.57 (d, J=16.9 Hz, 1H), 1.95-1.58 (m, 5H), 1.50-1.35 (m, 10H).

c) 4-((5-Fluoropyridin-2-yl)methoxy)-1-(5-methyl-6,7,8,9,10,11-hexahydro-7,11-imino-5H-cyclooct[b]indol-3-yl)pyridin-2(1H)-one dihydrochloride

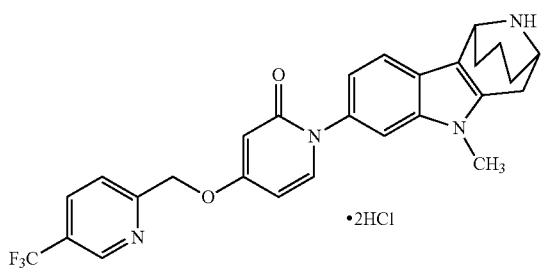

Chemical Formula: C₂₆H₂₇Cl₂FN₄O₂
Exact Mass: 516.15
Molecular Weight: 517.42 tert-Butyl 3-(4-((5-fluoropyridin-2-yl)methoxy)-2-oxopyridin-1(2H)-yl)-5-methyl-6,7,8,9,10,11-hexahydro-7,11-imino-5H-cyclooct[b]indole-12-carboxylate (30 mg, 0.055 mmol) was deprotected and converted to the dihydrochloride salt according to the procedure for Example 2 (step d) to provide the title compound (25 mg, 89%) as a orange solid: ¹H NMR (300 MHz, CD₃OD) δ 8.60 (s, 1H), 7.88-7.80 (ddd, J=8.2, 2.8, 2.8 Hz, 1H), 7.80-7.70 (m, 2H), 7.60 (d, J=8.4 Hz, 1H), 7.52 (d, J=1.5 Hz, 1H), 7.09-7.05 (dd, J=8.4, 1.8 Hz, 1H), 6.52-6.48 (dd, J=7.6, 2.8 Hz, 1H), 6.26 (d, J=2.6 Hz, 1H), 5.35 (s, 2H), 5.09 (br m 1H), 4.18-4.15 (m, 1H), 3.76 (s, 3H), 3.54-3.42 (dd, J=18.0, 7.3 Hz, 1H), 3.13 (d, J=18.0 Hz, 1H), 2.23-1.84 (m, 4H), 1.61-1.40 (m, 2H); ESI MS m/z 445 [M+H]⁺; HPLC (Method B) 97.4% (AUC), t_R=11.9 min.

Example 12

Preparation of 4-(Benzyloxy)-1-(5-methyl-6,7,8,9,10,11-hexahydro-7,11-imino-5H-cyclooct[b]indol-3-yl)pyridin-2(1H)-one hydrochloride a) tert-Butyl 3-(4-(benzyloxy)-2-oxopyridin-1(2H)-yl)-5-methyl-6,7,8,9,10,11-hexahydro-7,11-imino-5H-cyclooct[b]indole-12-carboxylate

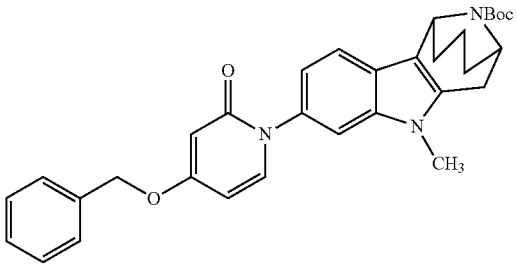

Chemical Formula: C₃₂H₃₅N₃O₄
Exact Mass: 525.26
Molecular Weight: 525.64 tert-Butyl 3-bromo-5-methyl-6,7,8,9,10,11-hexahydro-7,11-imino-5H-cyclooct[b]indole-12-carboxylate (130 mg, 0.32 mmol) and 4-(benzyloxy)pyridin-2(1H)-one (64 mg, 0.32 mmol) were reacted following the procedure for Example 2 (step c) to provide the title compound (60 mg, 35%) as a yellow oil: ¹H NMR (300 MHz, CDCl₃) δ 7.51-7.26 (m, 8H), 7.03-6.96 (m, 1H), 6.12-6.03 (m, 2H), 5.61-5.45 (m, 1H), 5.02 (s, 2H), 4.86-4.70 (br m 1H), 3.63 (s, 3H), 3.30-3.18 (ddd, J=17.0, 7.4, 7.4 Hz, 1H), 2.56 (d, J=17.0 Hz, 1H), 1.97-1.78 (m, 2H), 1.72-1.56 (m, 3H), 1.51-1.33 (m, 10H).

b) 4-(Benzyloxy)-1-(5-methyl-6,7,8,9,10,11-hexahydro-7,11-imino-5H-cyclooct[b]indol-3-yl)pyridin-2(1H)-one hydrochloride

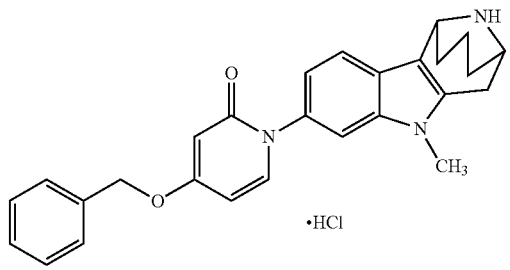

Chemical Formula: C₂₇H₂₈ClN₃O₂
Exact Mass: 461.19
Molecular Weight: 461.98 tert-Butyl 3-(4-(benzyloxy)-2-oxopyridin-1(2H)-yl)-5-methyl-6,7,8,9,10,11-hexahydro-7,11-imino-5H-cyclooct[b]indole-12-carboxylate (60 mg, 0.11 mmol) was deprotected and converted to the hydrochloride salt according to the procedure for Example 2 (step d) to provide the title compound (45 mg, 86%) as a white solid: ¹H NMR (500 MHz, CD₃OD) δ 7.77 (d, J=7.5 Hz, 1H), 7.60 (d, J=8.3 Hz, 1H), 7.53 (d, J=1.7 Hz, 1H), 7.48 (d, J=7.9 Hz, 2H), 7.42 (dd, J=2.9, 2.9 Hz, 2H), 7.39-7.35 (m, 1H), 7.09-7.07 (dd, J=8.3, 1.8 Hz, 1H), 6.54-6.52 (dd, J=7.5, 2.8 Hz, 1H), 6.31 (d, J=2.6 Hz, 1H), 5.26 (s, 2H), 5.09 (br m 1H), 4.17-4.15 (m, 1H), 3.76 (s, 3H), 3.53-3.49 (dd, J=17.9, 7.5 Hz, 1H), 3.12 (d, J=17.9 Hz, 1H), 2.20-2.07 (m, 2H), 2.02-1.89 (m, 2H), 1.62-1.56 (m, 1H), 1.50-1.39 (m, 1H); ESI MS m/z 426 [M+H]⁺; HPLC (Method B)>99% (AUC), t_R=13.4 min.

Example 13

Preparation of 1-(5-Methyl-6,7,8,9,10,11-hexahydro-7,11-imino-5H-cyclooct[b]indol-3-yl)-4-(6-(trifluoromethyl)pyridin-3-yl)pyridin-2(1H)-one hydrochloride a) tert-Butyl 5-methyl-3-(2-oxo-4-(6-(trifluoromethyl)pyridin-3-yl)pyridin-1(2H)-yl)-6,7,8,9,10,11-hexahydro-7,11-imino-5H-cyclooct[b]indole-12-carboxylate

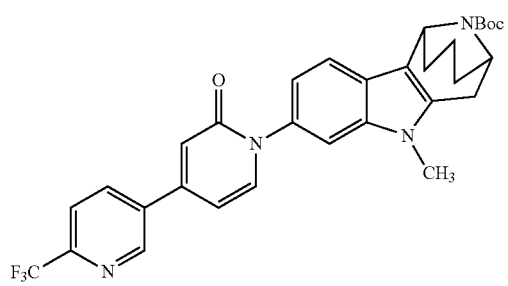

Chemical Formula: C₃₁H₃₁F₃N₄O₃
Exact Mass: 564.23
Molecular Weight: 564.60 tert-Butyl 3-bromo-5-methyl-6,7,8,9,10,11-hexahydro-7,11-imino-5H-cycloocta[b]indole-12-carboxylate (260 mg, 0.64 mmol) and 4-(6-(trifluoromethyl)pyridin-3-yl)pyridin-2(1H)-one (170 mg, 0.71 mmol) were reacted following the procedure for Example 2 (step c) to provide the title compound (190 mg, 52%) as a yellow oil: ESI MS m/z 565 [M+H]⁺.

b) 1-(5-Methyl-6,7,8,9,10,11-hexahydro-7,11-imino-5H-cyclooct[b]indol-3-yl)-4-(6-(trifluoromethyl)pyridin-3-yl)pyridin-2(1H)-one hydrochloride

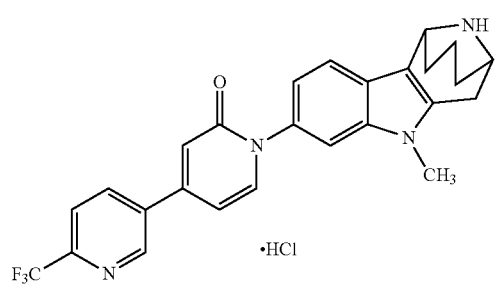

Chemical Formula: C₂₆H₂₄ClF₃N₄O
Exact Mass: 500.16
Molecular Weight: 500.94 tert-Butyl 5-methyl-3-(2-oxo-4-(6-(trifluoromethyl)pyridin-3-yl)pyridin-1(2H)-yl)-6,7,8,9,10,11-hexahydro-7,11-imino-5H-cyclooct[b]indole-12-carboxylate (190 mg, 0.33 mmol) was deprotected and converted to the hydrochloride salt according to the procedure for Example 2 (step d) to provide the title compound (105 mg, 63%) as a yellow solid: mp 265-274° C. (decomp.); ¹H NMR (300 MHz, DMSO-d₆) δ 9.65 (d, J=11.4 Hz, 1H), 9.20 (d, J=2.0 Hz, 1H), 9.10 (d, J=10.5 Hz, 1H), 8.51-8.48 (dd, J=8.0, 1.8 Hz, 1H), 8.05 (d, J=8.2 Hz, 1H), 7.88 (d, J=7.1 Hz, 1H), 7.64-7.61 (m, 2H), 7.10-7.07 (dd, J=8.4, 1.7 Hz, 1H), 7.02 (d, J=1.8 Hz, 1H), 6.83-6.80 (dd, J=7.2, 2.0 Hz, 1H), 5.05 (br m 1H), 4.09 (br m, 1H), 3.72 (s, 3H), 3.44-3.22 (m, 2H), 3.04 (d, J=17.8 Hz, 1H), 2.21-1.96 (m, 2H), 1.88-1.64 (m, 2H), 1.53-1.38 (m, 1H), 1.35-1.17 (m, 1H); ESI MS m/z 465 [M+H]⁺; HPLC (Method B)>99% (AUC), t_R=12.9 min.

Example 14

Preparation of 4-(Benzyloxy)-1-(5-methyl-5,6,7,8,9,10-hexahydro-7,10-iminocyclohept[b]indol-3-yl)pyridin-2(1H)-one hydrochloride (Enantiomer A)

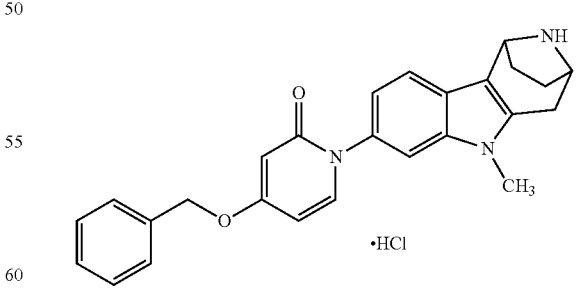

Enantiomer A

Chemical Formula: C₂₆H₂₆ClN₃O₂
Exact Mass: 447.17
Molecular Weight: 447.96

Chiral separation of 4-(benzyloxy)-1-(5-methyl-5,6,7,8,9,10-hexahydro-7,10-iminocyclohept[b]indol-3-yl)pyridin-2(1H)-one was performed by preparative chiral HPLC (CHIRALPAK AD column, 5 cm ID×50 cm L 20μ, flow rate 110 mL/min, using 60:40:0.1 reagent alcohol/heptane/diethylamine as the eluent, 5 mL/injection c=0.07 mol/L, $R_t$=19 min) to give the free base of the title compound (224 mg). The free base was dissolved in methanol (2 mL) and treated with 2 equivalent of 2 M HCl in Et$_2$O (0.5 mL), and the mixture was concentrated to provide the title compound (235 mg) as a yellow solid: Free Base: $^1$H NMR (500 MHz, CDCl$_3$) δ 7.53 (d, J=8.5 Hz, 1H), 7.42-7.39 (m, 4H), 7.37-7.36 (m, 1H), 7.31 (d, J=7.5 Hz, 1H), 7.26 (m, 1H), 7.00 (dd, J=6.5, 2.0 Hz, 1H), 6.08 (d, J=3.0 Hz, 1H), 6.05 (dd, J=5.0, 2.5 Hz, 1H), 5.05 (s, 2H), 4.64 (d, J=5.0 Hz, 1H), 4.16-4.13 (m, 1H), 3.54 (s, 3H), 3.26 (dd, J=12.0, 4.5 Hz, 1H), 2.56 (d, J=16.0 Hz, 1H), 2.28-2.15 (m, 3H), 2.03-1.99 (m, 1H). HCl salt: $^1$H NMR (500 MHz, CD$_3$OD) δ 7.66 (d, J=8.5 Hz, 1H), 7.62 (d, J=7.5 Hz, 1H), 7.48-7.45 (m, 3H), 7.43-7.40 (m, 2H), 7.38-7.34 (m, 1H), 7.08 (dd, J=6.5, 2.0 Hz, 1H), 6.36 (dd, J=5.0, 3.0 Hz, 1H), 6.17 (d, J=2.5 Hz, 1H), 5.24 (d, J=5.5 Hz, 1H), 5.20 (s, 2H), 4.55-4.53 (m, 1H), 3.70 (s, 3H), 3.52 (dd, J=12.5, 4.5 Hz, 1H), 3.09 (dd, J=16.5, 1.0 Hz, 1H), 2.47-2.37 (m, 2H), 2.30-2.25 (m, 1H), 2.00-1.95 (m, 1H); ESI MS m/z 412 [M+H]$^+$; HPLC (Method C) 95.9% (AUC), $t_R$=13.1 min.

Example 15

Preparation of 4-(Benzyloxy)-1-(5-methyl-5,6,7,8,9,10-hexahydro-7,10-iminocyclohept[b]indol-3-yl)pyridin-2(1H)-one hydrochloride (Enantiomer B)

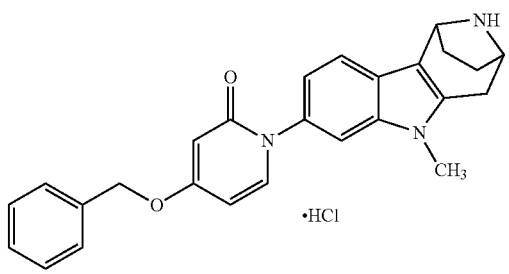

Enantiomer B

Chemical Formula: C$_{26}$H$_{26}$ClN$_3$O$_2$
Exact Mass: 447.17
Molecular Weight: 447.96

Chiral separation 4-(benzyloxy)-1-(5-methyl-5,6,7,8,9,10-hexahydro-7,10-iminocyclohept[b]indol-3-yl)pyridin-2(1H)-one was performed by preparative chiral HPLC (CHIRALPAK AD column, 5 cm ID×50 cm L 20μ, flow rate 110 mL/min, using 60:40:0.1 reagent alcohol/heptane/diethylamine as the eluent, 5 mL/injection c=0.07 mol/L, $R_t$=24 min) to give the free base of title compound (202 mg). The free base was converted to the HCl salt according to the procedure of Example 14 to provide the title compound (204 mg) as a yellow solid: Free Base: $^1$H NMR (500 MHz, CDCl$_3$) δ 7.53 (d, J=8.5 Hz, 1H), 7.42-7.39 (m, 4H), 7.37-7.36 (m, 1H), 7.31 (d, J=7.5 Hz, 1H), 7.26 (m, 1H), 7.00 (dd, J=6.5, 2.0 Hz, 1H), 6.08 (d, J=3.0 Hz, 1H), 6.05 (dd, J=5.0, 2.5 Hz, 1H), 5.05 (s, 2H), 4.64 (d, J=5.0 Hz, 1H), 4.16-4.13 (m, 1H), 3.54 (s, 3H), 3.26 (dd, J=12.0, 4.5 Hz, 1H), 2.56 (d, J=16.0 Hz, 1H), 2.28-2.15 (m, 3H), 2.03-1.99 (m, 1H). HCl salt: $^1$H NMR (500 MHz, CD$_3$OD) δ 7.66 (d, J=8.5 Hz, 1H), 7.62 (d, J=7.5 Hz, 1H), 7.48-7.45 (m, 3H), 7.43-7.40 (m, 2H), 7.38-7.34 (m, 1H), 7.08 (dd, J=6.5, 2.0 Hz, 1H), 6.36 (dd, J=5.0, 3.0 Hz, 1H), 6.17 (d, J=2.5 Hz, 1H), 5.24 (d, J=5.5 Hz, 1H), 5.20 (s, 2H), 4.55-4.53 (m, 1H), 3.70 (s, 3H), 3.52 (dd, J=12.5, 4.5 Hz, 1H), 3.09 (dd, J=16.5, 1.0 Hz, 1H), 2.47-2.37 (m, 2H), 2.30-2.25 (m, 1H), 2.00-1.95 (m, 1H); ESI MS m/z 412 [M+H]$^+$; HPLC (Method C) 98.4% (AUC), $t_R$=13.1 min.

Example 16

Preparation of 1-(5-Methyl-5,6,7,8,9,10-hexahydro-7,10-iminocyclohept[b]indol-3-yl)-4-(5-(trifluoromethyl)pyridin-2-yl)pyridin-2(1H)-one hydrochloride (Enantiomer B)

a) (+)-tert-Butyl 3-bromo-5-methyl-5,6,7,8,9,10-hexahydro-7,10-iminocyclohept[b]indole-11-carboxylate

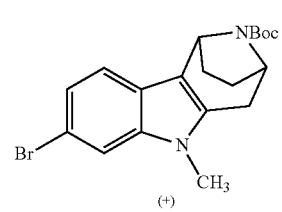

(+)

Chemical Formula: C$_{19}$H$_{23}$BrN$_2$O$_2$
Exact Mass: 390.09
Molecular Weight: 391.30

Chiral separation of tert-butyl 3-bromo-5-methyl-5,6,7,8,9,10-hexahydro-7,10-iminocyclohept[b]indole-11-carboxylate (450 mg, 1.15 mmol) was performed by preparative chiral HPLC(CHIRALPAK OJ column, 5 cm ID×50 cm L 20μ, flow rate 108 mL/min, using 5:95:0.1 reagent alcohol/heptane/diethylamine as the eluent, 40 mL/injection c=0.01 mol/L, $R_t$=40 min) to give the title compound (191 mg) as an off-white solid: $^1$H NMR (500 MHz, CDCl$_3$) δ 6.52 (s, 1H), 6.47 (d, J=8.5 Hz, 1H), 6.30 (d, J=8.0 Hz, 1H), 4.38-4.25 (m, 1H), 3.82-3.73 (m, 1H), 2.67 (s, 3H), 2.53-2.39 (m, 1H), 1.60-1.56 (m, 1H), 1.45-1.37 (m, 1H), 1.32-1.24 (m, 1H), 1.06-1.01 (m, 1H), 0.76-0.70 (m, 1H), 0.55-0.46 (m, 9H); [α]²_D +63.5° (c 0.2, methylene chloride).

b) 1-(5-Methyl-5,6,7,8,9,10-hexahydro-7,10-iminocyclohept[b]indol-3-yl)-4-(5-(trifluoromethyl)pyridin-2-yl)pyridin-2(1H)-one hydrochloride (Enantiomer B)

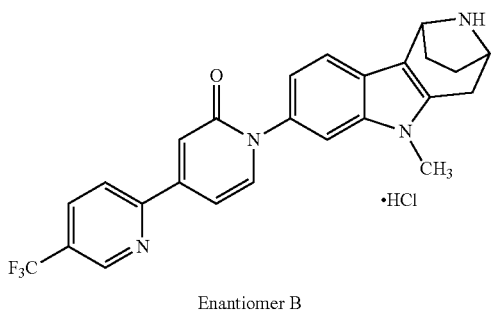

Enantiomer B
Chemical Formula: C₂₅H₂₂ClF₃N₄O
Exact Mass: 486.14
Molecular Weight: 486.92

(+)-tert-Butyl 3-bromo-5-methyl-5,6,7,8,9,10-hexahydro-7,10-iminocyclohept[b]indole-11-carboxylate (191 mg, 0.480 mmol) and 4-(5-(trifluoromethyl)pyridin-2-yl)pyridin-2(1H)-one (140 mg, 0.580 mmol), CuI (45.0 mg, 0.240 mmol), 8-hydroxyquinoline (35.0 mg, 0.240 mmol) and K₂CO₃ (132 mg, 0.960 mmol) in DMSO (10 mL) was degassed under reduced pressure for 45 min. The suspension was put under Ar and stirred at 135° C. overnight. The suspension was cooled, 9:0.9:0.1 CH₂Cl₂/MeOH/NH₄OH (20 mL) was added, and the resulting suspension was stirred at 25° C. for 30 min. The suspension was passed through a plug of silica gel, and the filtrate was washed with brine (3×). The resulting solution was dried over Na₂SO₄ and concentrated under reduced pressure. Purification by preparative thin layer chromatography (silica gel, 93:6:1 methylene chloride/methanol/concentrated ammonium hydroxide) gave a yellow solid (122 mg). The yellow solid was dissolved in MeOH (10 mL), and 2 M HCl in Et₂O (1.1 mL) was added. The reaction was allowed to proceed for 18 h. The mixture was concentrated, and the residue was partitioned between methylene chloride and saturated Na₂CO₃ solution. The organic phase was removed, and the aqueous phase was extracted with methylene chloride. The combined organic extracts were dried over Na₂SO₄, filtered and concentrated to dryness. Purification by preparative thin layer chromatography (silica gel, 90:9:1 methylene chloride/methanol/concentrated ammonium hydroxide) gave the free base of the title compound (64 mg) as a yellow solid. The free base was dissolved in methanol (5 mL) and treated with 2 M HCl in Et₂O (0.14 mL, 0.28 mmol), and the mixture was concentrated to provide the title compound (70 mg, 30%) as a yellow solid: ¹H NMR (500 MHz, CD₃OD) δ 9.05 (d, J=0.5 Hz, 1H), 8.28 (dd, J=8.5, 2.5 Hz, 1H), 8.23 (d, J=8.0 Hz, 1H), 7.83 (d, J=7.0 Hz, 1H), 7.70 (d, J=8.0 Hz, 1H), 7.56 (d, J=2.0 Hz, 1H), 7.39 (d, J=1.5 Hz, 1H), 7.25 (dd, J=7.0, 2.0 Hz, 1H), 7.16 (dd, J=8.5, 2.0 Hz, 1H), 5.26 (d, J=8.0 Hz, 1H), 4.57-4.54 (m, 1H), 3.73 (s, 3H), 3.54-3.49 (dd, J=17.5, 5 Hz, 1H), 3.12-3.07 (dd, J=17.0, 1.0 Hz, 1H), 2.48-2.32 (m, 3H), 2.04-1.97 (m, 1H); ESI MS m/z 451 [M+H]⁺; HPLC (Method D) 97.2% (AUC), t_R=7.6 min; Chiral HPLC (Chiralpak AD, 254 nm, 40:60:0.1 reagent alcohol/heptane/diethylamine) 98.9% (AUC), t_R=31.3 min; [α]²⁰_D -1.96° (c 0.2, CD₃OD).

Example 17

Preparation of 5-((5-Fluoropyridin-2-yl)methoxy)-2-(5-methyl-6,7,8,9,10,11-hexahydro-7,11-imino-5H-cyclooct[b]indol-3-yl)pyridazin-3(2H)-one hydrochloride a) 5-((5-Fluoropyridin-2-yl)methoxy)-2-(tetrahydro-2H-pyran-2-yl)pyridazin-3(2H)-one (CAS Registry Number 1008518-41-3) (WO 2008/022979 to Stenkamp et al., which is hereby incorporated by reference in its entirety)

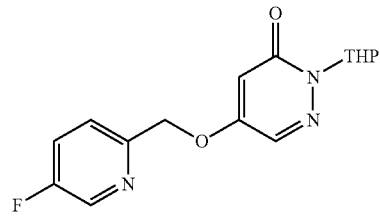

Chemical Formula: C₁₅H₁₆FN₃O₃
Exact Mass: 305.12
Molecular Weight: 305.30

5-Hydroxy-2-(tetrahydro-2H-pyran-2-yl)pyridazin-3(2H)-one (2.62 g, 13.4 mmol) (this compound was prepared in accordance with the procedure of Stenkamp et al., WO 2008022979), 2-(bromomethyl)-5-fluoropyridine (7.6 g, 40.2 mmol) and K₂CO₃ (9.24 g, 67 mmol) were stirred in DMF (40 ml) and CH₂Cl₂ (40 ml) for 48 h. The mixture was diluted with CH₂Cl₂, washed with 5% LiCl solution (4×) and concentrated. The residue was purified by column chromatography (40 g ISCO column column eluting with methylene chloride and a 10:1 methanol/ammonium hydroxide mixture; gradient 100% methylene chloride to 95% methylene chloride) to yield the title compound (1.1 g, 27%) as a light brown solid: ¹H NMR (300 MHz, CDCl₃) δ 8.47 (s, 1H), 7.73 (d, J=2.9 Hz, 1H), 7.47-7.43 (m, 2H), 6.19 (d, J=2.9 Hz, 1H), 6.03-5.98 (dd, J=10.7, 2.0 Hz, 1H), 5.12 (s, 2H), 4.18-4.08 (m, 1H), 3.78-3.69 (td, J=11.6, 2.6 Hz, 1H), 2.21-2.00 (m, 2H), 1.75-1.60 (m, 4H).

b) 5-((5-Fluoropyridin-2-yl)methoxy)pyridazin-3 (2H)-one (CAS Registry Number 1008518-12-4) (WO 2008/022979 to Stenkamp et al., which is hereby incorporated by reference in its entirety)

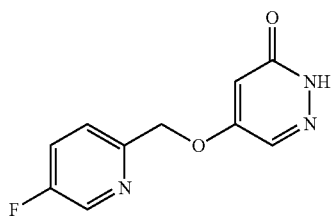

Chemical Formula: $C_{10}H_8FN_3O_2$
Exact Mass: 221.06
Molecular Weight: 221.19

5-((5-Fluoropyridin-2-yl)methoxy)-2-(tetrahydro-2H-pyran-2-yl)pyridazin-3(2H)-one (1.1 g, 3.6 mmol) was stirred in MeOH (5 mL) and 2 N HCl in Et$_2$O (20 mL) was added. After 16 h, the mixture was diluted with Et$_2$O (100 mL), and the solid was filtered off. The solid was stirred in NaHCO$_3$ solution (15 mL) for 15 minutes and then refiltered to provide the title compound (620 mg, 78%) as a pink solid: $^1$H NMR (300 MHz, DMSO-d$_6$) δ 12.69 (s, 1H), 8.60 (d, J=2.8 Hz, 1H), 7.85-7.78 (td, J=8.7, 2.9 Hz, 1H), 7.76 (d, J=2.7 Hz, 1H), 7.67-7.63 (dd, J=8.6, 4.5 Hz, 1H), 6.31 (s, 1H), 5.25 (s, 2H).

c) tert-Butyl 3-(4-((5-fluoropyridin-2-yl)methoxy)-6-oxopyridazin-1(6H)-yl)-5-methyl-6,7,8,9,10,11-hexahydro-7,11-imino-5H-cycloot[b]indole-12-carboxylate

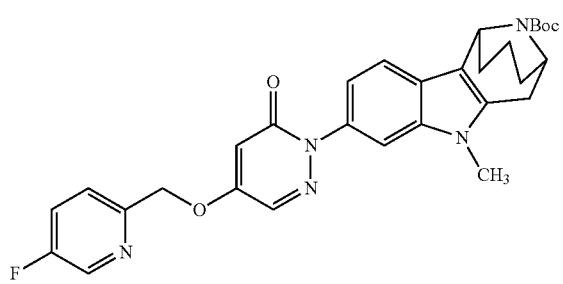

Chemical Formula: $C_{30}H_{32}FN_5O_4$
Exact Mass: 545.24
Molecular Weight: 545.60 tert-Butyl 3-bromo-5-methyl-6,7,8,9,10,11-hexahydro-7,11-imino-5H-cycloot[b]indole-12-carboxylate (260 mg, 0.640 mmol) and 5-((5-fluoropyridin-2-yl)methoxy)pyridazin-3(2H)-one (141 mg, 0.640 mmol) were reacted following the procedure for Example 2 (step c) to provide the title compound (127 mg, 36%) as a yellow oil: ESI MS m/z 546 [M+H]$^+$.

d) 5-((5-Fluoropyridin-2-yl)methoxy)-2-(5-methyl-6, 7,8,9,10,11-hexahydro-7,11-imino-5H-cycloot[b] indol-3-yl)pyridazin-3(2H)-one hydrochloride

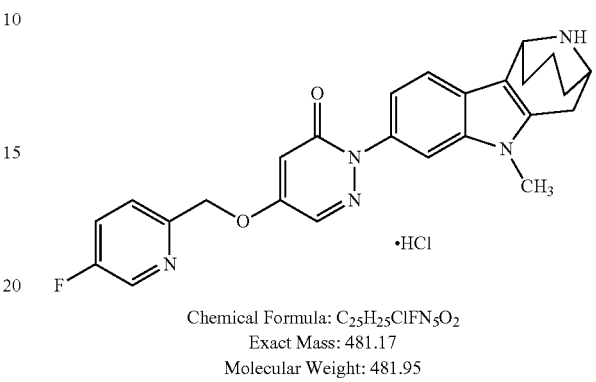

Chemical Formula: $C_{25}H_{25}ClFN_5O_2$
Exact Mass: 481.17
Molecular Weight: 481.95 tert-Butyl 3-(4-((5-fluoropyridin-2-yl)methoxy)-6-oxopyridazin-1(6H)-yl)-5-methyl-6,7,8,9,10,11-hexahydro-7,11-imino-5H-cycloot[b]indole-12-carboxylate (127 mg, 0.230 mmol) was reacted following the procedure for Example 2 (step d) to provide the title compound (50 mg, 45%) as a yellow solid: $^1$H NMR (500 MHz, DMSO-d$_6$) δ 9.64 (d, J=11.0 Hz, 1H), 9.04 (d, J=11.0 Hz, 1H), 8.63 (d, J=2.9 Hz, 1H), 8.00 (d, J=2.8 Hz, 1H), 7.89-7.82 (dt, J=8.7, 2.7 Hz, 1H), 7.73-7.68 (dd, J=8.7, 4.6 Hz, 1H), 7.59 (d, J=1.6 Hz, 1H), 7.58 (d, J=8.5 Hz, 1H), 7.13-7.09 (dd, J=8.3, 1.8 Hz, 1H), 6.53 (d, J=2.8 Hz, 1H), 5.29 (s, 2H), 5.03 (s, 1H), 4.16-4.05 (m, 1H), 3.70 (s, 3H), 3.41-3.33 (dd, J=18.0, 7.3 Hz, 1H), 3.03 (d, J=18.0 Hz, 1H), 2.16-2.00 (m, 2H), 1.79 (d, J=13.1 Hz, 1H), 1.70 (d, J=12.3 Hz, 1H), 1.48 (d, J=12.6 Hz, 1H), 1.33-1.24 (m, 1H); ESI MS m/z 446 [M+H]$^+$; HPLC (Method B) 97.5% (AUC), $t_R$=11.9 min.

Example 18

Preparation of 2-(5-Methyl-6,7,8,9,10,11-hexahydro-7,11-imino-5H-cycloot[b]indol-3-yl)-5-((6-methylpyridin-3-yl)methoxy)pyridazin-3(2H)-one hydrochloride a) 5-((6-Methylpyridin-3-yl)methoxy)-2-(tetrahydro-2H-pyran-2-yl)pyridazin-3(2H)-one

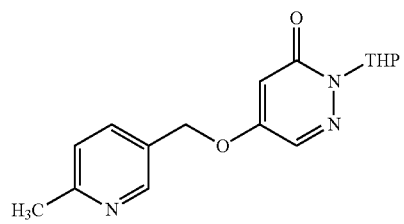

Chemical Formula: $C_{16}H_{19}N_3O_3$
Exact Mass: 301.14
Molecular Weight: 301.34

5-Hydroxy-2-(tetrahydro-2H-pyran-2-yl)pyridazin-3 (2H)-one (2.62 g, 13.4 mmol) and 5-(bromomethyl)-2-methylpyridine (7.47 g, 40.2 mmol) were reacted following the procedure for Example 17 (step a) to provide the title compound (1.76 g, 43%) as a white solid: $^1$H NMR (300 MHz, CDCl$_3$) δ 8.47 (s, 1H), 7.67 (d, J=6.2 Hz, 1H), 7.62-7.59 (dd, J=7.9, 2.3 Hz, 1H), 7.20 (d, J=8.0 Hz, 1H), 6.19 (d, J=2.8 Hz, 1H), 6.03-5.99 (dd, J=10.5, 2.0 Hz, 1H), 4.97 (s, 2H), 4.15-4.08 (m, 1H), 3.78-3.69 (td, J=11.6, 2.6 Hz, 1H), 2.59 (s, 3H), 2.16-2.00 (m, 2H), 1.74-1.54 (m, 4H).

b) 5-((6-Methylpyridin-3-yl)methoxy)pyridazin-3 (2H)-one

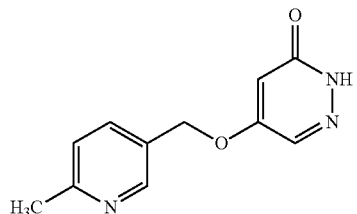

Chemical Formula: C$_{11}$H$_{11}$N$_3$O$_2$
Exact Mass: 217.09
Molecular Weight: 217.22

5-((6-Methylpyridin-3-yl)methoxy)-2-(tetrahydro-2H-pyran-2-yl)pyridazin-3(2H)-one (1.76 g, 0.584 mmol) was reacted following the procedure for Example 17 (step b) to provide the title compound (971 mg, 76%) as a white solid: ESI MS m/z 218 [M+H]$^+$.

c) tert-Butyl 3-(4-((6-methylpyridin-2-yl)methoxy)-6-oxopyridazin-1(6H)-yl)-5-methyl-6,7,8,9,10,11-hexahydro-7,11-imino-5H-cyclooct[b]indole-12-carboxylate

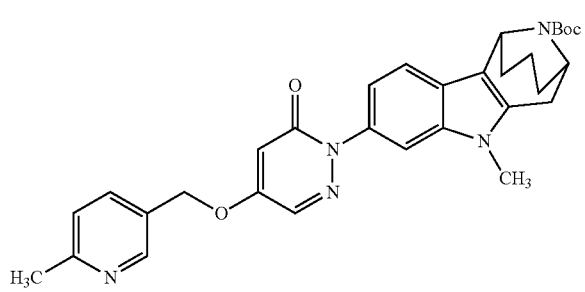

Chemical Formula: C$_{31}$H$_{35}$N$_5$O$_4$
Exact Mass: 541.27
Molecular Weight: 541.64 tert-Butyl 3-bromo-5-methyl-6,7,8,9,10,11-hexahydro-7,11-imino-5H-cyclooct[b]indole-12-carboxylate (180 mg, 0.440 mmol) and 5-((6-methylpyridin-3-yl)methoxy)pyridazin-3(2H)-one (76 mg, 0.44 mmol) were reacted following the procedure for Example 2 (step c) to provide the title compound (78 mg, 32%) as a yellow oil ESI MS m/z 542 [M+H]$^+$ d) 2-(5-Methyl-6,7,8,9,10,11-hexahydro-7,11-imino-5H-cyclooct[b]indol-3-yl)-5-((6-methylpyridin-3-yl)methoxy)pyridazin-3(2H)-one hydrochloride

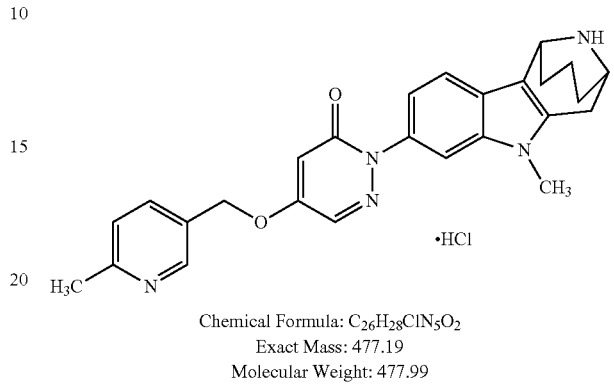

Chemical Formula: C$_{26}$H$_{28}$ClN$_5$O$_2$
Exact Mass: 477.19
Molecular Weight: 477.99 tert-Butyl 3-(4-((6-methylpyridin-2-yl)methoxy)-6-oxopyridazin-1(6H)-yl)-5-methyl-6,7,8,9,10,11-hexahydro-7,11-imino-5H-cyclooct[b]indole-12-carboxylate (78 mg, 0.14 mmol) was reacted following the procedure for Example 2 (step d) to provide the title compound (65 mg, 97%) as a white solid; mp 190-200° C. deliquesc; $^1$H NMR (300 MHz, DMSO-d$_6$) δ 9.63 (d, J=10.8 Hz, 1H), 9.06 (d, J=10.3 Hz, 1H), 8.76 (d, J=1.7 Hz, 1H), 8.19 (d, J=8.0 Hz, 1H), 7.97 (d, J=2.9 Hz, 1H), 7.66 (d, J=8.1 Hz, 1H), 7.59 (d, J=1.8 Hz, 1H), 7.57 (d, J=8.5 Hz, 1H), 7.12-7.09 (dd, J=8.3, 1.8 Hz, 1H), 6.58 (d, J=2.8 Hz, 1H), 5.34 (s, 2H), 5.03 (s, 1H), 4.08-4.01 (m, 1H), 3.70 (s, 3H), 3.41-3.33 (dd, J=18.0, 7.5 Hz, 1H), 3.06 (d, J=17.8 Hz, 1H), 2.63 (s, 3H), 2.17-2.01 (m, 2H), 1.90-1.61 (m, 2H), 1.59-1.44 (m, 1H), 1.32-1.23 (m, 1H); ESI MS m/z 442 [M+H]$^+$; HPLC (Method B) 98.2% (AUC), t$_R$=9.5 min.

Example 19

Preparation of 1-(5-Methyl-6,7,8,9,10,11-hexahydro-7,11-imino-5H-cyclooct[b]indol-3-yl)-4-β6-(trifluoromethyl)pyridin-3-yl)methoxy)pyridin-2(1H)-one hydrochloride a) 2-Methoxy-4-((6-(trifluoromethyl)pyridin-3-yl)methoxy)pyridine

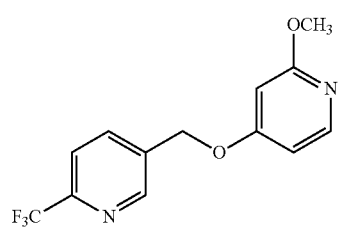

Chemical Formula: C$_{13}$H$_{11}$F$_3$N$_2$O$_2$
Exact Mass: 284.08
Molecular Weight: 284.23

4-Bromo-2-methoxypyridine (3.06 g, 16.2 mmol), (6-(trifluoromethyl)pyridin-3-yl)methanol (2.74 g, 15.5 mmol), 3,4,7,8-tetramethylphenanthroline (0.36 g, 0.15 mmol), CuI (0.14 g, 0.74 mmol) and $Cs_2CO_3$ (7.57 g, 23.2 mmol) were combined in toluene (15 mL) and heated to reflux under a nitrogen atmosphere for 16 h. Upon cooling the mixture was purified by flash column chromatography (silica gel, hexanes/EtOAc, 1:0 to 1:1) to provide the title compound (3.19 g, 72%) as a red oil: $^1$H NMR (300 MHz, $CDCl_3$) δ 8.78 (s, 1H), 8.02 (d, J=5.9 Hz, 1H), 7.95 (d, J=8.1 Hz, 1H), 7.32 (d, J=8.0 Hz, 1H), 6.55 (dd, J=5.9, 2.2 Hz, 1H), 6.26 (d, J=2.2 Hz, 1H), 5.16 (s, 2H), 3.93 (s, 3H).

b) 4-((6-(Trifluoromethyl)pyridin-3-yl)methoxy)pyridin-2(1H)-one

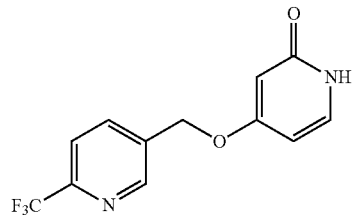

Chemical Formula: $C_{12}H_9F_3N_2O_2$
Exact Mass: 270.06
Molecular Weight: 270.21

2-Methoxy-4-(6-(trifluoromethyl)pyridin-3-yl)methoxy)pyridine (3.19 g, 11.2 mmol) was reacted according to the procedure of Example 3 (step b) to provide the title compound (2.04 g, 67%) as a white solid: $^1$H NMR (300 MHz, DMSO-$d_6$) δ 11.2 (br s, 1H), 8.84 (s, 1H), 8.14 (d, J=8.5 Hz, 1H), 7.96 (d, J=8.0 Hz, 1H), 7.28 (d, J=7.3 Hz, 1H), 5.95 (dd, J=7.3, 2.5 Hz, 1H), 5.82 (d, J=2.4 Hz, 1H), 5.25 (s, 2H).

c) tert-Butyl 5-methyl-3-(2-oxo-4-((6-(trifluoromethyl)pyridin-3-yl)methoxy)pyridin-1(2H)-yl)-6,7,8,9,10,11-hexahydro-7,11-imino-5H-cyclooct[b]indol-3-yl-12-carboxylate

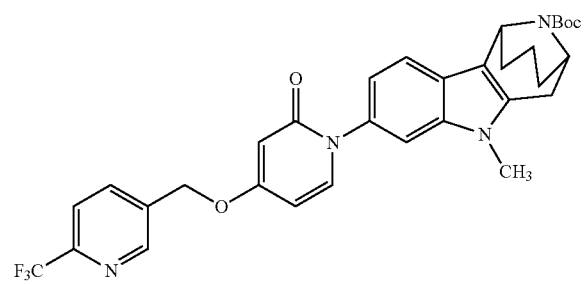

Chemical Formula: $C_{32}H_{33}F_3N_4O_4$
Exact Mass: 594.25
Molecular Weight: 594.62 tert-Butyl 3-bromo-5-methyl-6,7,8,9,10,11-hexahydro-7,11-imino-5H-cyclooct[b]indole-12-carboxylate (230 mg, 0.570 mmol) and 4-((6-(trifluoromethyl)pyridin-3-yl)methoxy)pyridin-2(1H)-one (154 mg, 0.570 mmol) were reacted following the procedure for Example 2 (step c) to provide the title compound (171 mg, 50%) as a yellow oil: ESI MS m/z 595 [M+H]$^+$.

d) 1-(5-Methyl-6,7,8,9,10,11-hexahydro-7,11-imino-5H-cyclooct[b]indol-3-yl)-4-((6-(trifluoromethyl)pyridin-3-yl)methoxy)pyridin-2 (1H)-one hydrochloride

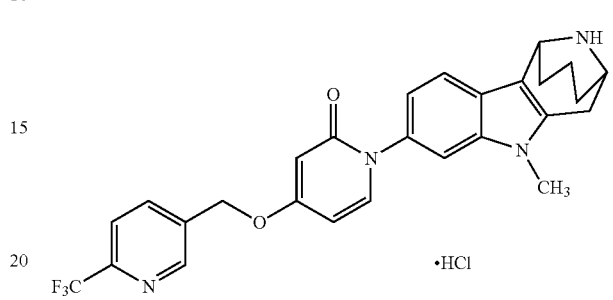

Chemical Formula: $C_{27}H_{26}ClF_3N_4O_2$
Exact Mass: 530.17
Molecular Weight: 530.97 tert-Butyl 5-methyl-3-(2-oxo-4-((6-(trifluoromethyl)pyridin-3-yl)methoxy)pyridin-1(2H)-yl)-6,7,8,9,10,11-hexahydro-7,11-imino-5H-cyclooct[b]indol-3-yl-12-carboxylate (171 mg, 0.228 mmol) was reacted following the procedure for Example 2 (step d) to provide the title compound (107 mg, 88%) as a white solid: mp 240-250° C.; $^1$H NMR (300 MHz, DMSO-$d_6$) δ 9.71 (d, J=11.3 Hz, 1H), 9.12 (d, J=11.1 Hz, 1H), 8.89 (s, 1H), 8.21-8.18 (dd, J=8.1, 1.4 Hz, 1H), 8.0 (d, J=8.1 Hz, 1H), 7.64 (d, J=7.6 Hz, 1H), 7.58 (d, J=8.3 Hz, 1H), 7.51 (d, J=1.6 Hz, 1H), 7.00-6.96 (dd, J=8.3, 1.8 Hz, 1H), 6.17-6.13 (dd, J=7.6, 2.8 Hz, 1H), 6.02 (d, J=2.8 Hz, 1H), 5.38 (s, 2H), 5.02 (s, 1H), 4.12-4.00 (m, 1H), 3.70 (s, 3H), 3.41-3.33 (dd, J=17.9, 7.3 Hz, 1H), 3.03 (d, J=17.9 Hz, 1H), 2.18-2.02 (m, 2H), 1.80 (d, J=13.3 Hz, 1H), 1.70 (d, J=12.9 Hz, 1H), 1.47-1.23 (m, 2H); ESI MS m/z 495 [M+H]$^+$; HPLC (Method B)>99% (AUC), $t_R$=13.1 min.

Example 20

Preparation of (−)-4-(Benzyloxy)-1-(5,6,7,8,9,10-hexahydro-7,10-iminocyclohept[b]indol-3-yl)pyridin-2(1H)-one hydrochloride (Enantiomer B)

a) Di-tert-butyl 3-bromo-5,6,7,8,9,10-hexahydro-7,10-iminocyclohept[b]indole-5,11-dicarboxylate (Enantiomer B)

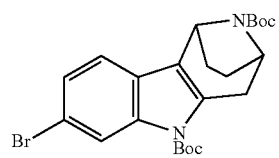

Chemical Formula: $C_{23}H_{29}BrN_2O_4$
Exact Mass: 476.13
Molecular Weight: 477.39 tert-Butyl 3-bromo-5,6,7,8,9,10-hexahydro-7,10-iminocyclohept[b]indole-11-carboxylate (enantiomer B) was obtained from the racemate by preparative chiral HPLC (CHIRALPAK OJ column, 5 cm ID×50 cm L 20μ, flow rate 108 mL/min, using 90:10:0.1 iso-propyl alcohol/heptane/diethylamine as the eluent; enantiomer B was the second peak to elute). Enantiomer B (1.55 g, 4.11 mmol) was dissolved in DMF (20 mL), NaH (60% disp, 180 mg, 4.52 mmol) was added, and the mixture was stirred for 15 minutes. Di-tert-butyl dicarbonate (980 mg, 4.52 mmol) was added, and the reaction was stirred for 1.5 h. Ethyl acetate and water were added, and the organic layer was removed, dried and concentrated to provide the product (1.99 g, >100%) as a tan solid: ESI MS m/z 477 [M+H]$^+$.

b) tert-Butyl 3-(4-(benzyloxy)-2-oxopyridin-1(2H)-yl)-5,6,7,8,9,10-hexahydro-7,10-iminocyclohept[b]indole-11-carboxylate (Enantiomer B)

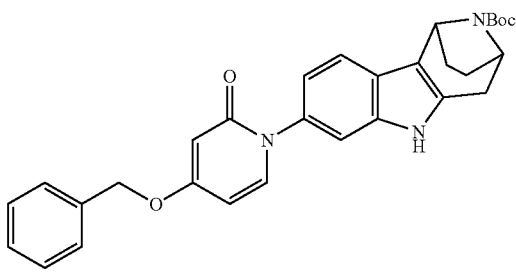

Chemical Formula: $C_{30}H_{31}N_3O_4$
Exact Mass: 497.23
Molecular Weight: 497.58

Di-tert-butyl 3-bromo-5,6,7,8,9,10-hexahydro-7,10-iminocyclohept[b]indole-5,11-dicarboxylate (enantiomer B) (1.99 g (crude), 4.11 mmol estimated) and 4-(benzyloxy)pyridin-2(1H)-one (0.74 g, 3.70 mmol) were reacted following the procedure for Example 2 (step c) to provide the title compound (800 mg, 40%) as a yellow solid: ESI MS m/z 498 [M+H]$^+$.

c) (−)-4-(Benzyloxy)-1-(5,6,7,8,9,10-hexahydro-7,10-iminocyclohept[b]indol-3-yl)pyridin-2(1H)-one hydrochloride (Enantiomer B)

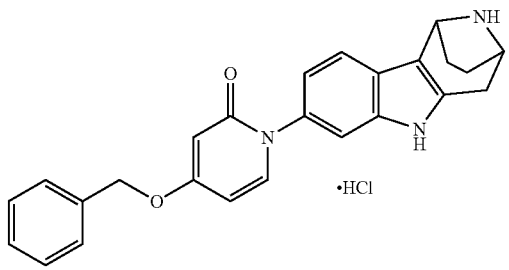

Chemical Formula: $C_{25}H_{24}ClN_3O_2$
Exact Mass: 433.16
Molecular Weight: 433.93 tert-Butyl 3-(4-(benzyloxy)-2-oxopyridin-1(2H)-yl)-5,6,7,8,9,10-hexahydro-7,10-iminocyclohept[b]indole-11-carboxylate (enantiomer B) (800 mg, 1.60 mmol) was reacted following the procedure for Example 2 (step d) to provide the title compound (302 mg, 41%) as a white solid: mp 211-217° C.; $^1$H NMR (500 MHz, DMSO-$d_6$) δ 11.37 (s, 1H), 9.26-8.83 (s, 2H), 7.60 (d, J=8.4 Hz, 1H), 7.56 (d, J=7.6 Hz, 1H), 7.49-7.34 (m, 5H), 7.29 (d, J=1.6 Hz, 1H), 6.95-6.92 (dd, J=8.4, 1.9 Hz, 1H), 6.13-6.05 (dd, J=7.6, 2.8 Hz, 1H), 5.90 (d, J=2.8 Hz, 1H), 5.14 (s, 3H), 4.44-4.37 (m, 1H), 3.44-3.37 (dd, J=17.2, 4.4 Hz, 1H), 2.85 (d, J=16.8 Hz, 1H), 2.25-2.19 (m, 2H), 2.07-1.98 (m, 1H), 1.79-1.75 (m, 1H); ESI MS m/z 398 [M+H]$^+$; HPLC (Method B)>99% (AUC), $t_R$=12.7 min; $[\alpha]^{22}_D$ -11.8° (c 1.00, Methanol).

Example 21

Preparation of (+)-4-(Benzyloxy)-1-(5,6,7,8,9,10-hexahydro-7,10-iminocyclohept[b]indol-3-yl)pyridin-2(1H)-one hydrochloride (Enantiomer A)

a) Di-tert-butyl 3-bromo-5,6,7,8,9,10-hexahydro-7,10-iminocyclohept[b]indole-5,11-dicarboxylate (Enantiomer A)

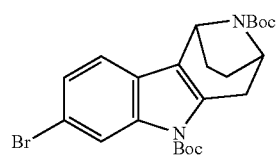

Chemical Formula: $C_{23}H_{29}BrN_2O_4$
Exact Mass: 476.13
Molecular Weight: 477.39 tert-Butyl 3-bromo-5,6,7,8,9,10-hexahydro-7,10-iminocyclohept[b]indole-11-carboxylate (enantiomer A) was obtained from the racemate by preparative chiral HPLC (CHIRALPAK OJ column, 5 cm ID×50 cm L 20μ, flow rate 108 mL/min, using 90:10:0.1 iso-propyl alcohol/heptane/diethylamine as the eluent; enantiomer A was the first peak to elute). Enantiomer A (1.26 g, 3.34 mmol) was dissolved in DMF (20 mL), NaH (60% disp, 150 mg, 3.67 mmol) was added and the mixture was stirred for 15 minutes. Di-tert-butyl dicarbonate (800 mg, 3.67 mmol) was added, and the reaction stirred for 1.5 h. Ethyl acetate and water were added, and the organic layer was removed, dried and concentrated to provide the product (1.64 g, >100%) as a tan solid: ESI MS m/z 477 [M+H]+.

b) tert-Butyl 3-(4-(benzyloxy)-2-oxopyridin-1(2H)-yl)-5,6,7,8,9,10-hexahydro-7,10-iminocyclohept[b]indole-11-carboxylate (Enantiomer A)

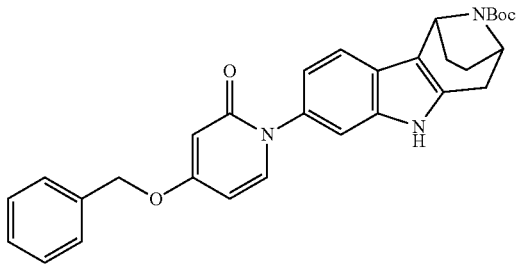

Chemical Formula: C30H31N3O4
Exact Mass: 497.23
Molecular Weight: 497.58

Di-tert-butyl 3-bromo-5,6,7,8,9,10-hexahydro-7,10-iminocyclohept[b]indole-5,11-dicarboxylate (enantiomer A) (1.67 g (crude), 3.34 mmol estimated) and 4-(benzyloxy)pyridin-2(1H)-one (0.60 g, 3.0 mmol) were reacted following the procedure for Example 2 (step c) to provide the title compound (660 mg, 40%) as a yellow solid: ESI MS m/z 498 [M+H]+.

c) (+)-4-(Benzyloxy)-1-(5,6,7,8,9,10-hexahydro-7,10-iminocyclohept[b]indol-3-yl)pyridin-2(1H)-one hydrochloride (Enantiomer A)

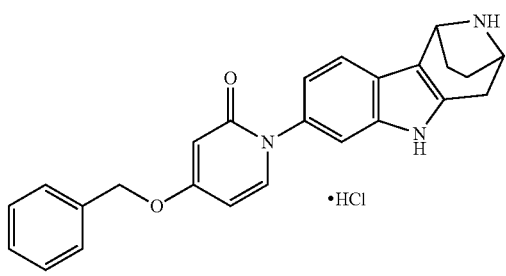

Chemical Formula: C25H24ClN3O2
Exact Mass: 433.16
Molecular Weight: 433.93 tert-Butyl 3-(4-(benzyloxy)-2-oxopyridin-1(2H)-yl)-5,6,7,8,9,10-hexahydro-7,10-iminocyclohept[b]indole-11-carboxylate (enantiomer A) (660 mg, 1.32 mmol) was reacted following the procedure for Example 2 (step d) to provide the title compound (269 mg, 54%) as a white solid: mp 211-212° C.; $^1$H NMR (300 MHz, DMSO-$d_6$) δ 11.41 (s, 1H), 9.58 (s, 1H), 9.16 (s, 1H), 7.60 (d, J=8.4 Hz, 1H), 7.55 (d, J=7.6 Hz, 1H), 7.49-7.34 (m, 5H), 7.29 (d, J=1.6 Hz, 1H), 6.95-6.92 (dd, J=8.4, 1.9 Hz, 1H), 6.10-6.07 (dd, J=7.6, 2.8 Hz, 1H), 5.90 (d, J=2.6 Hz, 1H), 5.18 (s, 1H), 5.14 (s, 2H), 4.48-4.25 (m, 1H), 3.46-3.39 (dd, J=17.2, 4.4 Hz, 1H), 2.88 (d, J=16.7 Hz, 1H), 2.38-2.15 (m, 2H), 2.07-1.98 (m, 1H), 1.85-1.66 (m, 1H); ESI MS m/z 398 [M+H]+; HPLC (Method B)>99% (AUC), $t_R$=12.7 min; $[α]^{22}_D$+5.4° (c 1.00, Methanol).

Example 22

Preparation of 1-(5,6,7,8,9,10-Hexahydro-7,10-iminocyclohept[b]indol-3-yl)-4-((pyridin-2-yl)methoxy)pyridin-2(1H)-one hydrochloride a) 2-Chloro-4-(pyridin-2-ylmethoxy)pyridine

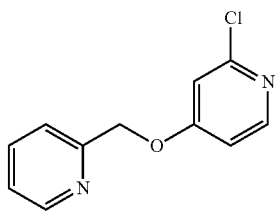

Chemical Formula: C11H9ClN2O
Exact Mass: 220.04
Molecular Weight: 220.65

Pyridin-2-ylmethanol (3.00 g, 27.5 mmol), 2-chloro-4-iodopyridine (6.0 g, 25 mmol), cesium carbonate (10.6 g, 32.5 mmol), CuI (0.95 g, 5.0 mmol) and 1,10-phenanthroline (0.90 g, 5.0 mmol) were stirred in toluene (15 mL) and purged with a nitrogen stream for 10 minutes. The mixture was heated to 105° C. for 16 h, allowed cool and filtered through a silica plug eluting with ethyl acetate. The filtrate was concentrated, and the residue was purified by column chromatography (80 g ISCO column column eluting with ethyl acetate/hexanes; gradient 100% hexanes to 100% ethyl acetate) to provide the title compound (4.1 g, 74%) as a white solid: ESI MS m/z 221 [M+H]+.

b) 4-(Pyridin-2-ylmethoxy)pyridin-2(1H)-one (CAS Registry Number 1008518-20-4) (WO 2007/043835 to Kim et al., which is hereby incorporated by reference in its entirety)

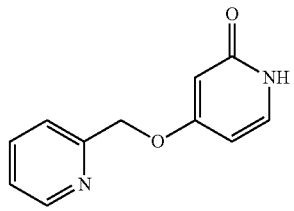

Chemical Formula: C11H10N2O2
Exact Mass: 202.07
Molecular Weight: 202.21

2-Chloro-4-(pyridin-2-ylmethoxy)pyridine (4.10 g, 18.5 mmol) and ammonium acetate (7.21 g, 92.3 mmol) were heated to 110° C. in a mixture of formic acid (20 mL) and water (20 mL) for 5 days. The mixture was concentrated to remove most of the liquid and then adjusted to pH 8 with NaHCO₃ solution. The resulting solid was filtered off to provide the title compound (3.1 g, 83%) as a white solid: ESI MS m/z 203 [M+H]⁺.

c) tert-Butyl 3-(2-oxo-4-(pyridin-2-ylmethoxy)pyridin-1(2H)-yl)-5,6,7,8,9,10-hexahydro-7,10-iminocyclohept[b]indole-11-carboxylate

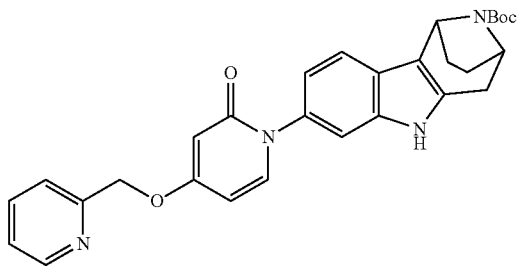

Chemical Formula: C₂₉H₃₀N₄O₄
Exact Mass: 498.23
Molecular Weight: 498.57 tert-Butyl 3-bromo-5,6,7,8,9,10-hexahydro-7,10-iminocyclohept[b]indole-11-carboxylate (250 mg, 0.660 mmol) and 4-(pyridin-2-ylmethoxy)pyridin-2(1H)-one (134 mg, 0.660 mmol) were reacted following the procedure for Example 2 (step c) to provide the title compound (160 mg, 48%) as a yellow oil: ESI MS m/z 499 [M+H]⁺.

d) 1-(5,6,7,8,9,10-Hexahydro-7,10-iminocyclohept[b]indol-3-yl)-4-((pyridin-2-yl)methoxy)pyridin-2(1H)-one hydrochloride

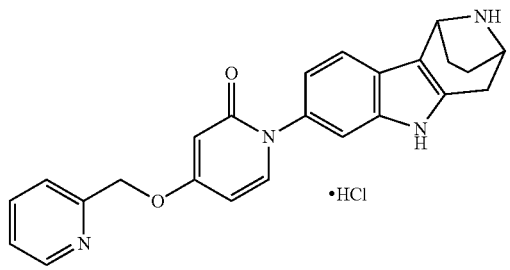

Chemical Formula: C₂₄H₂₃ClN₄O₂
Exact Mass: 434.15
Molecular Weight: 434.92 tert-Butyl 3-(2-oxo-4-(pyridin-2-ylmethoxy)pyridin-1(2H)-yl)-5,6,7,8,9,10-hexahydro-7,10-iminocyclohept[b]indole-11-carboxylate (160 mg, 0.32 mmol) was reacted following the procedure for Example 2 (step d) to provide the title compound (61 mg, 44%) as a pink solid: mp 220-230° C.; ¹H NMR (300 MHz, DMSO-d₆) δ 11.40 (s, 1H), 9.48 (s, 1H), 9.13 (d, J=8.6 Hz, 1H), 8.63-8.60 (m, 1H), 7.93-7.87 (td, J=8.4, 1.8 Hz, 1H), 7.62-7.55 (m, 3H), 7.43-7.38 (m, 1H), 7.29 (d, J=1.6 Hz, 1H), 6.96-6.93 (dd, J=8.4, 1.9 Hz, 1H), 6.14-6.11 (dd, J=7.6, 2.8 Hz, 1H), 5.94 (d, J=2.8 Hz, 1H), 5.21 (s, 2H), 5.18 (s, 1H), 4.41 (s, 1H), 3.40-3.38 (m, 1H), 2.88 (d, J=16.8 Hz, 1H), 2.29-2.21 (m, 2H), 2.05-2.02 (m, 1H), 1.85-1.76 (m, 1H); ESI MS m/z 399 [M+H]⁺; HPLC (Method B) 98.8% (AUC), t_R=9.8 min.

Example 23

Preparation of 1-(5-Methyl-6,7,8,9,10-hexahydro-7,10-iminocyclohept[b]indol-3-yl)-4-((pyridin-2-yl)methoxy)pyridin-2(1H)-one hydrochloride a) tert-Butyl 5-methyl-3-(2-oxo-4-(pyridin-2-ylmethoxy)pyridin-1(2H)-yl)-5,6,7,8,9,10-hexahydro-7,10-iminocyclohept[b]indole-11-carboxylate

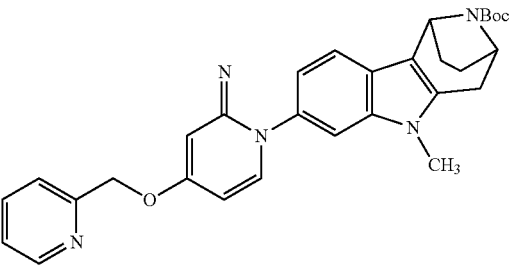

Chemical Formula: C₃₀H₃₂N₄O₄
Exact Mass: 512.24
Molecular Weight: 512.60 tert-Butyl 3-bromo-5-methyl-5,6,7,8,9,10-hexahydro-7,10-iminocyclohept[b]indole-11-carboxylate (191 mg, 0.488 mmol) and 4-(pyridin-2-ylmethoxy)pyridin-2(1H)-one (98 mg, 0.49 mmol) was reacted following the procedure for Example 2 (step c) to provide the title compound (118 mg, 47%) as a yellow foam: ESI MS m/z 513 [M+H]⁺.

d) 1-(5-Methyl-6,7,8,9,10-hexahydro-7,10-iminocyclohept[b]indol-3-yl)-4-((pyridin-2-yl)methoxy)pyridin-2(1H)-one hydrochloride

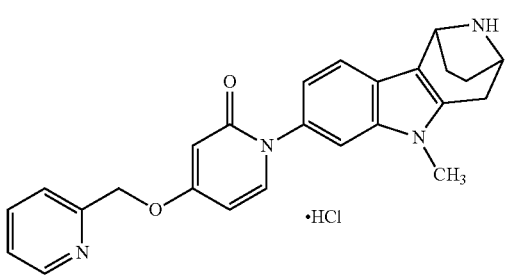

Chemical Formula: C₂₅H₂₅ClN₄O₂
Exact Mass: 448.17
Molecular Weight: 448.94 tert-Butyl 5-methyl-3-(2-oxo-4-(pyridin-2-ylmethoxy)pyridin-1(2H)-yl)-5,6,7,8,9,10-hexahydro-7,10-iminocyclohept[b]indole-11-carboxylate (118 mg, 0.230 mmol) was reacted following the procedure for Example 2 (step d) to provide the title compound (60 mg, 58%) as a yellow solid: mp 175-195° C.; ¹H NMR (300 MHz, DMSO-d₆) δ 9.56 (d, J=7.3 Hz, 1H), 9.16 (d, J=10.1 Hz, 1H), 8.63-8.61 (m, 1H), 7.93-7.87 (td, J=7.7, 2.8 Hz, 1H), 7.65 (d, J=8.4 Hz, 1H), 7.59-7.54 (m, 2H), 7.48 (d, J=1.6 Hz, 1H), 7.43-7.38 (m, 1H), 7.01-6.94 (dd, J=8.3, 1.8 Hz, 1H), 6.16-6.13 (dd, J=7.6, 2.8 Hz, 1H), 5.96 (d, J=2.7 Hz, 1H), 5.22-5.20 (m, 3H), 4.53-4.37 (m, 1H), 3.64 (s, 3H), 3.42-3.35 (dd, J=17.3, 4.6 Hz, 1H), 3.02 (d, J=16.8 Hz, 1H), 2.29-2.21 (m, 2H), 2.11-2.02 (m, 1H), 1.85-1.75 (m, 1H); ESI MS m/z 413 [M+H]$^+$; HPLC (Method B)>99% (AUC), $t_R$=10.1 min.

Example 24

Preparation of (−)-4-((5-Fluoropyridin-2-yl)methoxy)-1-(5-methyl-5,6,7,8,9,10-hexahydro-7,10-iminocyclohept[b]indol-3-yl)pyridin-2(1H)-one hydrochloride (Enantiomer B)

a) tert-Butyl 3-(4-((5-fluoropyridin-2-yl)methoxy)-2-oxopyridin-1(2H)-yl)-5-methyl-5,6,7,8,9,10-hexahydro-7,10-iminocyclohept[b]indole-11-carboxylate (Enantiomer B)

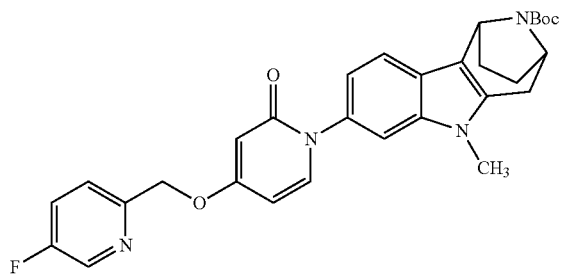

Chemical Formula: C$_{30}$H$_{31}$FN$_4$O$_4$
Exact Mass: 530.23
Molecular Weight: 530.59

(+)-tert-Butyl 3-bromo-5-methyl-5,6,7,8,9,10-hexahydro-7,10-iminocyclohept[b]indole-11-carboxylate (570 mg, 1.45 mmol), 4-((5-fluoropyridin-2-yl)methoxy)pyridin-2(1H)-one (354 mg, 1.60 mmol), CuI (414 mg, 2.20 mmol), 8-hydroxyquinoline (42.0 mg, 0.290 mmol) and Cs$_2$CO$_3$ (519 mg, 1.60 mmol) in DMSO (15 mL) was degassed under reduced pressure for 45 min. The suspension was put under Ar and stirred at 135° C. overnight. The suspension was cooled, 9:0.9:0.1 CH$_2$Cl$_2$/MeOH/NH$_4$OH (20 mL) was added, and the resulting suspension was stirred at 25° C. for 30 min. The suspension was passed through a plug of silica gel, and the filtrate was washed with brine (3×). The resulting solution was dried over Na$_2$SO$_4$ and concentrated under reduced pressure. Purification by flash column chromatography (silica gel, 100% solvent mixture A to 30% solvent mixture B in solvent A; solvent mixture A=30:70 ethyl acetate/hexanes; solvent mixture B=90:10 methanol/concentrated ammonium hydroxide) gave the title compound (415 mg, 54%) as a yellow solid: $^1$H NMR (500 MHz, CDCl$_3$) δ 8.49 (s, 1H), 7.56 (d, J=8.5 Hz, 1H), 7.51-7.44 (m, 2H), 7.33-7.30 (m, 1H), 7.25 (s, 1H), 7.00-6.99 (m, 1H), 6.08 (d, J=7.0 Hz, 1H), 6.07 (s, 1H), 5.30-5.16 (m, 1H), 5.17 (s, 2H), 4.72-4.60 (m, 1H), 3.58 (s, 3H), 3.47-3.30 (m, 1H), 2.50 (d, J=16.0 Hz, 1H), 2.40-2.22 (m, 1H), 2.21-2.14 (m, 1H), 1.96-1.91 (m, 1H), 1.70-1.50 (m, 1H), 1.50-1.30 (m, 9H).

b) (−)-4-((5-Fluoropyridin-2-yl)methoxy)-1-(5-methyl-5,6,7,8,9,10-hexahydro-7,10-iminocyclohept[b]indol-3-yl)pyridin-2(1H)-one hydrochloride (Enantiomer B)

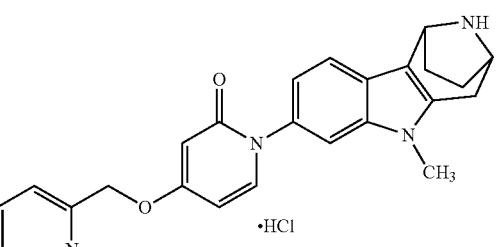

Chemical Formula: C$_{25}$H$_{24}$ClFN$_4$O$_2$
Exact Mass: 466.16
Molecular Weight: 466.94 tert-Butyl 3-(4-((5-fluoropyridin-2-yl)methoxy)-2-oxopyridin-1(2H)-yl)-5-methyl-5,6,7,8,9,10-hexahydro-7,10-iminocyclohept[b]indole-11-carboxylate (enantiomer B) (415 mg, 0.780 mmol) was dissolved in MeOH (20 mL), and 2 M HCl in Et$_2$O (4 mL) was added. The reaction was allowed to proceed for 18 h. The mixture was concentrated, and the residue was partitioned between methylene chloride and saturated Na$_2$CO$_3$ solution. The organic phase was removed, and the aqueous phase was extracted with methylene chloride. The combined organic extracts were dried over Na$_2$SO$_4$, filtered and concentrated to dryness. Purification by preparative thin layer chromatography (silica gel, 90:9:1 methylene chloride/methanol/concentrated ammonium hydroxide) gave the free base of the title compound (158 mg) as a yellow solid. The free base was dissolved in MeOH (10 mL) and treated with 1.25 M HCl in MeOH (0.32 mL). The mixture was concentrated to provide the title compound (179 mg, 59%) as an off-white solid. Free Base: $^1$H NMR (500 MHz, CDCl$_3$) δ 8.49 (d, J=2.5 Hz, 1H), 7.54-7.44 (m, 3H), 7.33 (d, J=7.5 Hz, 1H), 7.25 (d, J=1.5 Hz, 1H), 6.98 (dd, J=8.5, 2.0 Hz, 1H), 6.09-6.06 (m, 2H), 5.17 (s, 2H), 4.59-4.58 (m, 1H), 4.12-4.09 (m, 1H), 3.54 (s, 3H), 3.20-3.15 (dd, J=16.0, 4.5 Hz, 1H), 2.53 (d, J=16.0 Hz, 1H), 2.23-2.18 (m, 1H), 2.15-2.10 (m, 1H), 2.01-1.97 (m, 1H), 1.60-1.53 (m, 1H); HPLC (Method D) 98.4% (AUC), $t_R$=6.7 min. HCl salt: $^1$H NMR (500 MHz, CD$_3$OD) δ 8.50 (s, 1H), 7.72-7.64 (m, 2H), 7.62 (d, J=8.5 Hz, 1H), 7.59 (d, J=7.5 Hz, 1H), 7.42 (d, J=2.0 Hz, 1H), 7.03 (dd, J=8.5, 2.0 Hz, 1H), 6.32 (dd, J=7.5, 2.5 Hz, 1H), 6.12 (d, J=3.0 Hz, 1H), 5.26 (s, 2H), 5.10-5.08 (m, 1H), 4.45-4.42 (m, 1H), 3.68 (s, 3H), 3.44 (dd, J=17.0, 4.5 Hz, 1H), 2.98 (dd, J=17.0, 1.0 Hz, 1H), 2.41-2.28 (m, 2H), 2.24-2.19 (m, 1H), 1.94-1.88 (m, 1H); ESI MS m/z 431 [M+H]$^+$; HPLC (Method C)>99% (AUC), $t_R$=6.7 min; Chiral HPLC (Chiralpak OD, 225 nm, 35:65:0.1 reagent alcohol/heptane/trifluoroacetic acid) 100% (AUC), $t_R$=5.8 min; $[\alpha]^{20}_D$ –8.7° (c 0.1, CD$_3$OD).

Example 25

Preparation of (+)-4-((5-Fluoropyridin-2-yl)methoxy)-1-(5-methyl-5,6,7,8,9,10-hexahydro-7,10-iminocyclohept[b]indol-3-yl)pyridin-2(1H)-one hydrochloride (Enantiomer A)

a) (–)-tert-Butyl 3-bromo-5-methyl-5,6,7,8,9,10-hexahydro-7,10-iminocyclohept[b]indole-11-carboxylate (Enantiomer A)

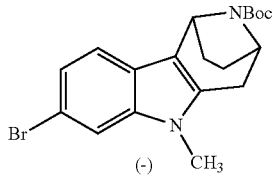

Chemical Formula: C$_{19}$H$_{23}$BrN$_2$O$_2$
Exact Mass: 390.09
Molecular Weight: 391.30

Chiral separation of tert-butyl 3-bromo-5-methyl-5,6,7,8,9,10-hexahydro-7,10-iminocyclohept[b]indole-11-carboxylate (450 mg, 1.15 mmol) was performed by preparative chiral HPLC according to the procedure for Example 16 (step a) to provide the title compound (207 mg) as an off-white solid: $^1$H NMR (500 MHz, CDCl$_3$) δ 6.52 (s, 1H), 6.48 (d, J=8.5 Hz, 1H), 6.30 (d, J=7.5 Hz, 1H), 4.42-4.25 (m, 1H), 3.82-3.73 (m, 1H), 2.67 (s, 3H), 2.53-2.36 (m, 1H), 1.60-1.56 (m, 1H), 1.42-1.38 (m, 1H), 1.32-1.24 (m, 1H), 1.06-1.01 (m, 1H), 0.76-0.70 (m, 1H), 0.55-0.46 (m, 9H); $[\alpha]^{20}_D$ –62.1° (c 0.2, methylene chloride).

b) tert-Butyl 3-(4-((5-fluoropyridin-2-yl)methoxy)-2-oxopyridin-1(2H)-yl)-5-methyl-5,6,7,8,9,10-hexahydro-7,10-iminocyclohept[b]indole-11-carboxylate (Enantiomer A)

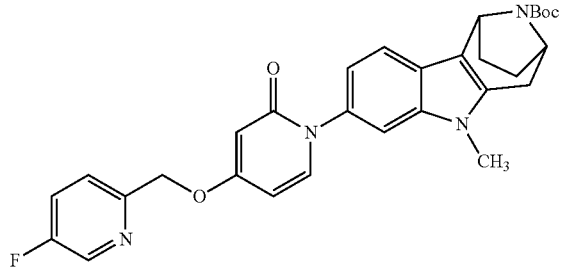

Chemical Formula: C$_{30}$H$_{31}$FN$_4$O$_4$
Exact Mass: 530.23
Molecular Weight: 530.59

(–)-tert-Butyl 3-bromo-5-methyl-5,6,7,8,9,10-hexahydro-7,10-iminocyclohept[b]indole-11-carboxylate (enantiomer A) (600 mg, 1.53 mmol), 4-((5-fluoropyridin-2-yl)methoxy)pyridin-2(1H)-one (373 mg, 1.69 mmol), CuI (437 mg, 2.30 mmol), 8-hydroxyquinoline (44.4 mg, 0.300 mmol) and Cs$_2$CO$_3$ (548 mg, 1.69 mmol) in DMSO (15 mL) were reacted following the procedure for Example 2 (step c) to provide the title compound (434 mg, 53%) as a yellow solid: $^1$H NMR (500 MHz, CDCl$_3$) δ 8.49 (s, 1H), 7.56 (d, J=8.5 Hz, 1H), 7.51-7.44 (m, 2H), 7.33-7.30 (m, 1H), 7.25 (s, 1H), 7.00-6.99 (m, 1H), 6.08 (d, J=7.5 Hz, 1H), 6.07 (s, 1H), 5.30-5.16 (m, 1H), 5.17 (s, 2H), 4.72-4.60 (m, 1H), 3.58 (s, 3H), 3.47-3.30 (m, 1H), 2.50 (d, J=16.0 Hz, 1H), 2.40-2.22 (m, 1H), 2.21-2.14 (m, 1H), 1.96-1.91 (m, 1H), 1.70-1.50 (m, 1H), 1.50-1.30 (m, 9H).

c) (+)-4-((5-Fluoropyridin-2-yl)methoxy)-1-(5-methyl-5,6,7,8,9,10-hexahydro-7,10-iminocyclohept[b]indol-3-yl)pyridin-2(1H)-one hydrochloride (Enantiomer A)

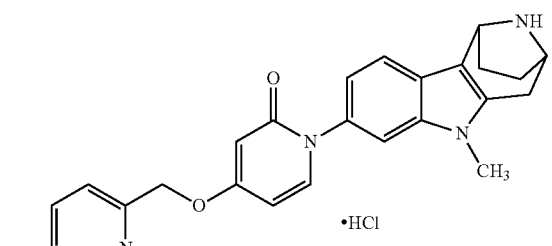

Chemical Formula: C$_{25}$H$_{24}$ClFN$_4$O$_2$
Exact Mass: 466.16
Molecular Weight: 466.94 tert-Butyl 3-(4-((5-fluoropyridin-2-yl)methoxy)-2-oxopyridin-1(2H)-yl)-5-methyl-5,6,7,8,9,10-iminocyclohept[b]indole-11-carboxylate (enantiomer A) (434 mg, 0.820 mmol) was deprotected and converted to the hydrochloride salt according to the procedure for Example 2 (step d) to provide the title compound (206 mg, 65%) as an off-white solid. Free Base: $^1$H NMR (500 MHz, CDCl$_3$) δ 8.48 (d, J=3.0 Hz, 1H), 7.52-7.44 (m, 3H), 7.33 (d, J=7.5 Hz, 1H), 7.25 (d, J=1.5 Hz, 1H), 6.98 (dd, J=8.5, 2.0 Hz, 1H), 6.09-6.06 (m, 2H), 5.16 (s, 2H), 4.64-4.62 (m, 1H), 4.17-4.15 (m, 1H), 3.47 (s, 3H), 3.22-3.17 (dd, J=16.0, 4.0 Hz, 1H), 2.53 (d, J=16.0 Hz, 1H), 2.25-2.15 (m, 2H), 2.03-1.98 (m, 1H), 1.60-1.54 (m, 1H); HPLC (Method D) 98.0% (AUC), $t_R$=6.6 min. HCl salt: $^1$H NMR (500 MHz, CD$_3$OD) δ 8.51 (d, J=2.5 Hz, 1H), 7.72-7.65 (m, 2H), 7.64 (d, J=8.0 Hz, 1H), 7.59 (d, J=7.5 Hz, 1H), 7.43 (d, J=1.5 Hz, 1H), 7.04 (dd, J=8.5, 2.0 Hz, 1H), 6.32 (dd, J=7.5, 2.5 Hz, 1H), 6.12 (d, J=3.0 Hz, 1H), 5.26 (s, 2H), 5.20-5.19 (m, 1H), 4.53-4.50 (m, 1H), 3.69 (s, 3H), 3.48 (dd, J=17.0, 4.5 Hz, 1H), 3.05 (dd, J=17.0, 1.0 Hz, 1H), 2.46-2.33 (m, 2H), 2.28-2.23 (m, 1H), 1.99-1.93 (m, 1H); ESI MS m/z 431 [M+H]$^+$; HPLC (Method C) 99.0% (AUC), $t_R$=6.7 min; Chiral HPLC (Chiralpak OD, 225 nm, 35:65:0.1

Example 26

Preparation of 4-(Benzyloxy)-1-(5,11-dimethyl-5,6,7,8,9,10-hexahydro-7,10-iminocyclohept[b]indol-3-yl)pyridin-2(1H)-one hydrochloride

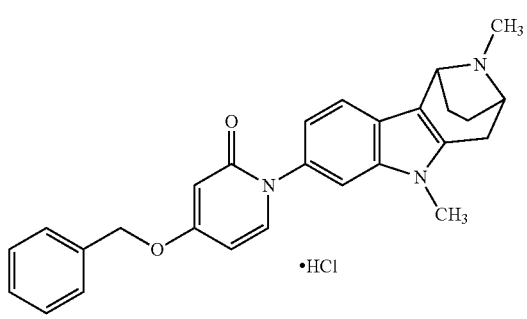

Chemical Formula: C$_{27}$H$_{28}$ClN$_3$O$_2$
Exact Mass: 461.19
Molecular Weight: 461.98

4-(Benzyloxy)-1-(5-methyl-5,6,7,8,9,10-hexahydro-7,10-iminocyclohept[b] indol-3-yl)pyridin-2(1H)-one (100 mg, 0.24 mmol) was reacted following the procedure for Example 31 (step b) to provide the title compound (70 mg, 69%) as a white solid: mp 121-128° C.; $^1$H NMR (300 MHz, DMSO-d$_6$) δ 11.0 (s, 0.5H), 10.30 (s, 0.5H), 7.61-7.4 (m, 2H), 7.49-7.34 (m, 6H), 7.03-6.97 (dt, J=8.4, 1.8 Hz, 1H), 6.12-6.09 (dd, J=7.6, 2.7 Hz, 1H), 5.97 (d, J=2.7 Hz, 1H), 5.15 (s, 2H), 5.11-5.08 (m, 1H), 4.32-4.25 (m, 1H), 3.66 (s, 1.5H), 3.65 (s, 1.5H), 3.53-3.51 (m, 1H), 3.09-3.00 (m, 1H), 2.86 (d, J=5.1 Hz, 1.5H), 2.66 (d, J=5.1 Hz, 1.5H), 2.48-2.20 (m, 2H), 2.11-2.01 (m, 1H), 1.94-1.84 (m, 1H); ESI MS m/z 426 [M+H]$^+$; HPLC (Method B)>99% (AUC), t$_R$=13.1 min.

Example 27

Preparation of 1-(11-Acetyl-5-methyl-5,6,7,8,9,10-hexahydro-7,10-iminocyclohept[b]indol-3-yl)-4-(benzyloxy)pyridin-2(1H)-one

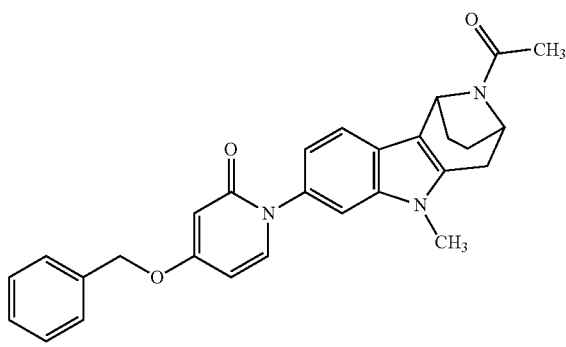

Chemical Formula: C$_{28}$H$_{27}$N$_3$O$_3$
Exact Mass: 453.21
Molecular Weight: 453.53

4-(Benzyloxy)-1-(5-methyl-5,6,7,8,9,10-hexahydro-7,10-iminocyclohept[b]indol-3-yl)pyridin-2(1H)-one (100 mg, 0.24 mmol) was stirred in a mixture of CH$_2$Cl$_2$ (4 mL) and saturated sodium bicarbonate solution (4 mL), and acetyl chloride (~0.2 mL) was added. After 30 minutes, the mixture was concentrated and purified by flash chromatography (12 g ISCO column eluting with methylene chloride and a methanol/ammonia mixture (10:1); gradient 100% methylene chloride to 85% methylene chloride over 30 min) to provide the title compound (92 mg, 84%) as a white solid and as a mixture of rotamers: mp 91-96° C. deliquesc; $^1$H NMR (300 MHz, DMSO-d$_6$) δ 7.64-7.55 (m, 2H), 7.49-7.34 (m, 6H), 6.95-6.87 (m, 1H), 6.10 (m, 1H), 5.96 (d, J=2.7 Hz, 1H), 5.54 (d, J=5.3 Hz, 0.5H), 5.31 (d, J=4.2 Hz, 0.5H), 5.14 (s, 2H), 4.83-4.76 (m, 0.5H), 4.70-4.66 (m, 0.5H), 3.59 (s, 1.5H), 3.58 (s, 1.5H), 3.32-3.29 (m, 1H), 2.76 (d, J=16.3 Hz, 0.5H), 2.63 (d, J=15.9 Hz, 0.5H), 2.37-2.14 (m, 2H), 2.02-1.77 (m, 4H), 1.75-1.59 (m, 1H); ESI MS m/z 454 [M+H]$^+$; HPLC (Method B) 98.5% (AUC), t$_R$=17.2 min.

Example 28

Preparation of 4-(Benzyloxy)-1-(11-isopropyl-5-methyl-5,6,7,8,9,10-hexahydro-7,10-iminocyclohept[b]indol-3-yl)pyridin-2(1H)-one hydrochloride

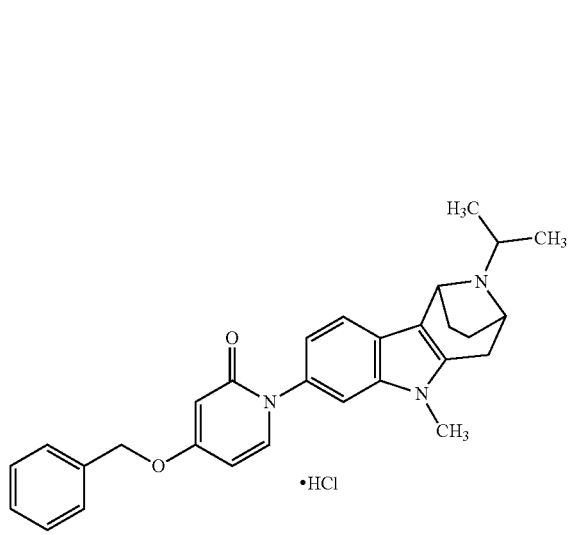

Chemical Formula: C$_{29}$H$_{32}$ClN$_3$O$_2$
Exact Mass: 489.22
Molecular Weight: 490.04

4-(Benzyloxy)-1-(5-methyl-5,6,7,8,9,10-hexahydro-7,10-iminocyclohept[b]indol-3-yl)pyridin-2(1H)-one from (100 mg, 0.24 mmol) was reacted with acetone (5 mL) following the procedure for Example 32 to provide the title compound (89 mg, 75%) as a white solid and as a mixture of rotamers: $^1$H NMR (500 MHz, CD$_3$OD) δ 7.71 (d, J=8.5 Hz, 0.3H), 7.68 (d, J=8.5 Hz, 0.7H), 7.61-7.59 (m, 1H), 7.48-7.46 (m, 3H), 7.43-7.42 (m, 2H), 7.41-7.36 (m, 1H), 7.09-7.08 (m, 1H), 6.35-6.32 (m, 1H), 6.16-6.15 (m, 1H), 5.40-5.38 (m, 1H), 4.91 (s, 2H), 4.71-4.53 (m, 1H), 3.72 (s, 3H), 3.56-3.47 (m, 1H), 3.42-3.32 (m, 1H), 3.21-3.02 (m, 1H), 2.61-2.41 (m, 2H), 2.32-2.18 (m, 1H), 2.15-1.98 (m, 1H), 1.53-1.49 (m, 1H), 1.49-1.43 (m, 2H), 1.32-1.26 (m, 2H); ESI MS m/z 454 [M+H]$^+$; HPLC (Method B) 94.8% (AUC), t$_R$=12.4 min.

Example 29

Preparation of 1-(11-Acetyl-5-methyl-5,6,7,8,9,10-hexahydro-7,10-iminocyclohept[b]indol-3-yl)-4-((5-Fluoropyridin-2-yl)methoxy)pyridin-2(1H)-one (Enantiomer A)

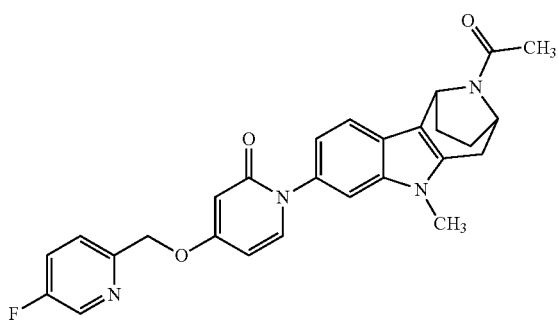

Chemical Formula: $C_{27}H_{25}FN_4O_3$
Exact Mass: 472.19
Molecular Weight: 472.51

To a solution of 4-((5-fluoropyridin-2-yl)methoxy)-1-(5-methyl-5,6,7,8,9,10-hexahydro-7,10-iminocyclohept[b]indol-3-yl)pyridin-2(1l)-one (Enantiomer A) (60.0 mg, 0.130 mmol) in methylene chloride (4 mL) was added $K_2CO_3$ (54.0 mg, 0.390 mmol) and acetyl chloride (18.0 μL, 0.240 mmol). The reaction mixture was stirred at room temperature for 1.5 h. The resulting suspension was filtered and concentrated to dryness. Purification by preparative thin layer chromatography (TLC) (silica gel, 90:9:1 methylene chloride/methanol/concentrated ammonium hydroxide) gave the title compound (46 mg, 75%) as a white solid and as a mixture of rotamers: $^1$H NMR (500 MHz, DMSO-$d_6$) δ 8.62 (d, J=2.5 Hz, 1H), 7.84-7.80 (m, 1H), 7.67-7.64 (m, 1H), 7.61-7.54 (m, 2H), 7.39 (m, 1H), 6.94-6.91 (m, 1H), 6.12 (d, J=7.0 Hz, 1H), 5.97 (s, 1H), 5.56-5.54 (m, 0.4H), 5.40-5.30 (m, 0.6H), 5.20 (s, 2H), 4.90-4.60 (m, 1H), 3.59 (s, 1.2H), 3.58 (s, 1.8H), 2.78 (d, J=16.5 Hz, 0.4H), 2.65 (d, J=16.0 Hz, 0.6H), 2.36-2.15 (m, 2H), 2.03-1.80 (m, 5H), 1.72-1.60 (m, 1H); ESI MS m/z 473 [M+H]$^+$; HPLC (Method A)>99% (AUC), $t_R$=15.0 min.

Example 30

Preparation of 1-(11-Acetyl-5,6,7,8,9,10-hexahydro-7,10-iminocyclohept[b]indol-3-yl)-4-(benzyloxy)pyridin-2(1H)-one hydrochloride (Enantiomer A)

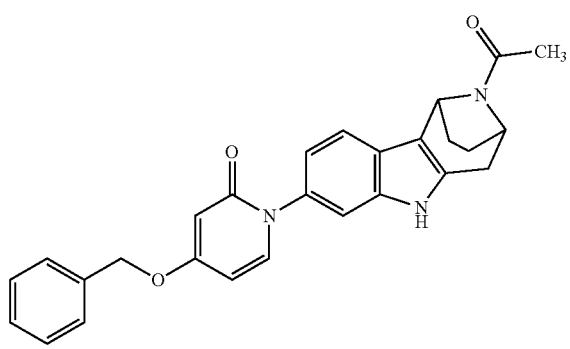

Chemical Formula: $C_{27}H_{25}N_3O_3$
Exact Mass: 439.19
Molecular Weight: 439.51

4-(Benzyloxy)-1-(5,6,7,8,9,10-hexahydro-7,10-iminocyclohept[b]indol-3-yl)pyridin-2(1H)-one hydrochloride (enantiomer A) (100 mg, 0.21 mmol) was reacted with acetyl chloride (22 mg, 0.27 mmol, 20 μL) following the procedure for Example 27 to provide the title compound (67 mg, 73%) as a white solid and as a mixture of rotamers: mp 140-170° C.; $^1$H NMR (500 MHz, CDCl$_3$) δ 9.49 (s, 0.3H), 9.14 (s, 0.7H), 7.43-7.26 (m, 8H), 6.93-6.91 (dd, J=8.2, 1.8 Hz, 0.7H), 6.85-6.83 (dd, J=8.2, 1.8 Hz, 0.3H), 6.09-6.05 (m, 2H), 5.58 (d, J=5.4 Hz, 0.3H), 5.10-5.06 (m, 2.7H), 5.01-4.58 (m, 0.7H), 4.48-4.30 (m, 0.3H), 3.39-3.35 (dd, J=16.1, 4.3 Hz, 0.7H), 3.13-3.09 (dd, J=16.0, 4.0 Hz, 0.3H), 2.43 (d, J=16.0 Hz, 0.7H), 2.38 (d, J=16.0 Hz, 0.3H), 2.30-2.06 (m, 5H), 2.05-1.95 (m, 1H), 1.89-1.75 (m, 0.3H), 1.61-1.52 (m, 0.7H); ESI MS m/z 440 [M+H]$^+$; HPLC (Method B)>99% (AUC), $t_R$=16.2 min.

Example 31

Preparation of 4-(Benzyloxy)-1-(5,12-dimethyl-6,7,8,9,10,11-hexahydro-7,11-imino-5H-cyclooct[b]indol-3-yl)pyridin-2(1H)-one hydrochloride a) 4-(Benzyloxy)-1-(5-methyl-6,7,8,9,10,11-hexahydro-7,11-imino-5H-cyclooct[b]indol-3-yl)pyridin-2(1H)-one

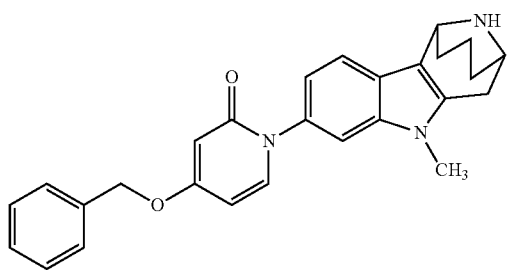

Chemical Formula: $C_{27}H_{27}N_3O_2$
Exact Mass: 425.21
Molecular Weight: 425.52 tert-Butyl 3-(4-(benzyloxy)-2-oxopyridin-1(2H)-yl)-5-methyl-6,7,8,9,10,11-hexahydro-7,11-imino-5H-cyclooct[b]indole-12-carboxylate (400 mg, 0.761 mmol) was stirred in TFA (2 mL) and CH$_2$Cl$_2$ (2 mL) for 1 h and then concentrated. The residue was purified by Flash chromatography (silica gel, CH$_2$Cl$_2$/(9:1 MeOH/NH$_4$OH), 100:0 to 80:20) to provide the free base (227 mg, 70%) as a yellow oil: ESI MS m/z 426 [M+H]$^+$.

b) 4-(Benzyloxy)-1-(5,12-dimethyl-6,7,8,9,10,11-hexahydro-7,11-imino-5H-cyclooct[b]indol-3-yl)pyridin-2(1H)-one hydrochloride Chemical Formula: $C_{28}H_{30}ClN_3O_2$
Exact Mass: 475.20
Molecular Weight: 476.01

4-(Benzyloxy)-1-(5-methyl-6,7,8,9,10,11-hexahydro-7,11-imino-5H-cyclooct[b]indol-3-yl)pyridin-2(1H)-one (76 mg, 0.18 mmol) and 37% aqueous formaldehyde (~0.5 mL) were dissolved in MeOH (2 mL) and $CH_2Cl_2$ (2 mL) and stirred at room temperature for 0.5 h. Sodium triacetoxyborohydride (75 mg, 0.358 mmol) was then added, and the reaction was stirred at room temperature for an additional 1 h. The mixture was concentrated, and the residue was partitioned between $CH_2Cl_2$ and saturated $Na_2CO_3$ solution. The organic phase was removed, and the aqueous phase was extracted with $CH_2Cl_2$. The combined organics were dried over $Na_2SO_4$, filtered and concentrated to dryness. Purification by column chromatography (120 g ISCO column eluting with methylene chloride and a methanol/ammonia mixture (10:1); gradient 100% methylene chloride to 85% methylene chloride over 60 min) provided the free base of the title compound. The free base was converted to the HCl salt using 2 N HCl in $Et_2O$ to provide the title compound (69 mg, 81%) as a white solid: mp 161-180° C.; $^1$H NMR (300 MHz, DMSO-$d_6$) δ 10.96 (s, 1H), 7.60-7.51 (m, 3H), 7.49-7.35 (m, 5H), 6.99-6.96 (dd, J=8.3, 1.8 Hz, 1H), 6.12-6.09 (dd, J=7.6, 2.7 Hz, 1H), 5.97 (d, J=2.7 Hz, 1H), 5.15 (s, 2H), 5.02 (s, 1H), 3.98-3.93 (m, 1H), 3.70 (s, 3H), 3.43-3.35 (dd, J=18.3, 7.3 Hz, 1H), 3.07 (d, J=18.4 Hz, 1H), 2.65 (d, J=4.9 Hz, 3H), 2.36-2.16 (m, 2H), 1.86 (d, J=13.7 Hz, 1H), 1.74 (d, J=13.4 Hz, 1H), 1.42 (d, J=13.2 Hz, 1H), 1.26-1.14 (m, 1H); ESI MS m/z 440 [M+H]$^+$; HPLC (Method B) 98.9% (AUC), $t_R$=13.4 min.

Example 32

Preparation of 4-(Benzyloxy)-1-(12-ethyl-5-methyl-6,7,8,9,10,11-hexahydro-7,11-imino-5H-cyclooct[b]indol-3-yl)pyridin-2(1H)-one hydrochloride

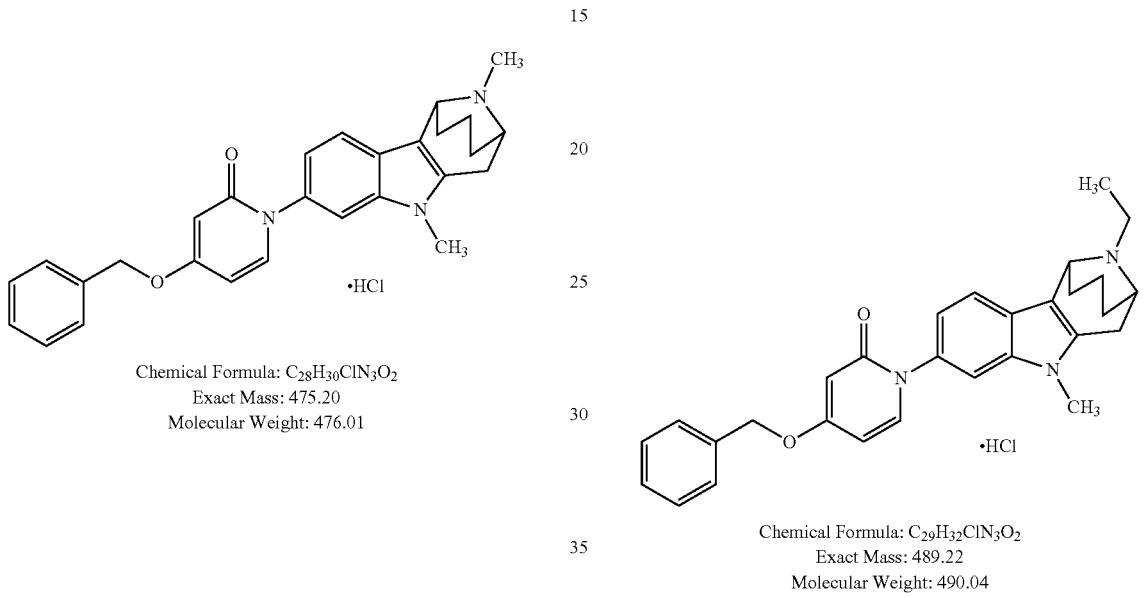

Chemical Formula: $C_{29}H_{32}ClN_3O_2$
Exact Mass: 489.22
Molecular Weight: 490.04

Picoline-borane complex (57 mg, 0.54 mmol) was added to a suspension of 4-(benzyloxy)-1-(5-methyl-6,7,8,9,10,11-hexahydro-7,11-imino-5H-cyclooct[b]indol-3-yl)pyridin-2(1H)-one (76 mg, 0.18 mmol) and acetylaldehyde (~0.2 mL) in 9:1 $CH_2Cl_2$/AcOH (10 mL) under $N_2$, and the resulting solution was stoppered and stirred for 2 h. The solution was neutralized with saturated $NaHCO_3$ solution, and the phases were separated. The organic phase was dried over $Na_2SO_4$ and concentrated under reduced pressure. Purification by flash chromatography (12 g ISCO column eluting with methylene chloride and a methanol/ammonia mixture (10:1); gradient 100% methylene chloride to 85% methylene chloride over 30 min) provided the free base of the title compound. The free base was converted to the HCl salt using 2 N HCl in $Et_2O$ to provide the title compound (35 mg, 44%) as a white solid: $^1$H NMR (500 MHz, DMSO-$d_6$) δ 10.46-10.26 (s, 1H), 7.59-7.57 (m, 2H), 7.51 (d, J=1.7 Hz, 1H), 7.48-7.46 (m, 2H), 7.44-7.41 (m, 2H), 7.39-7.37 (m, 1H), 6.98-6.96 (dd, J=8.3, 1.8 Hz, 1H), 6.16-6.09 (dd, J=7.6, 2.7 Hz, 1H), 5.97 (d, J=2.7 Hz, 1H), 5.15 (s, 3H), 4.15-4.01 (m, 1H), 3.69 (s, 3H), 3.40 (dd, J=18.2, 6.7 Hz, 1H), 3.09-3.04 (d, J=18.2 Hz, 1H), 3.04-2.93 (m, 2H), 2.37-2.17 (m, 2H), 1.92-1.84 (d, J=13.9 Hz, 1H), 1.75 (d, J=13.8 Hz, 1H), 1.49-1.41 (m, 1H), 1.32-1.19 (m, 4H); ESI MS m/z 454 [M+H]⁺; HPLC (Method B) 93.8% (AUC), $t_R$=13.6 min.

Example 33

Preparation of 1-(5-Methyl-5,6,7,8,9,10-hexahydro-7,10-iminocyclohept[b]indol-3-yl)-4-phenethylpiperazin-2-one dihydrochloride (Enantiomer B)

a) 4-Phenethylpiperazin-2-one (CAS Registry Number 23099-72-1) (JP 43017188 to Irikura et al., which is hereby incorporated by reference in its entirety)

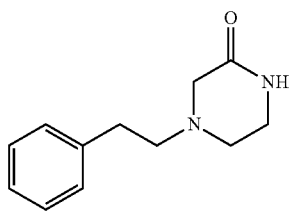

Chemical Formula: $C_{12}H_{16}N_2O$
Exact Mass: 204.13
Molecular Weight: 204.27

A suspension of (2-bromoethyl)benzene (4.10 mL, 30.0 mmol), piperazin-2-one (3.00 g, 30.0 mmol) and $K_2CO_3$ (4.90 g, 36.0 mmol) in DMSO (60.0 mL) was stirred at 80° C. for 5 h. The reaction mixture was cooled to room temperature and filtered. The filtrate was then washed with water (200 mL) and extracted with methylene chloride (2×). The combined organic layers were washed with brine, dried over $MgSO_4$, filtered, and concentrated. The result yellow solid was then dissolved in 1 N HCl (120 mL) and washed with methylene chloride. The aqueous layer was separated, basified with 6 N NaOH, and extracted with methylene chloride (3×). The combined organic layers were dried over $MgSO_4$, filtered, and concentrated. The residue was titrated with hexanes and filtered. The filtered solid was dried under reduced pressure to give the title compound (4.50 g, 74%) as an off-white solid: ¹H NMR (500 MHz, $CDCl_3$) δ 7.31-7.28 (m, 2H), 7.23-7.19 (m, 3H), 6.17 (brs, 1H), 3.40-3.37 (m, 2H), 3.23 (s, 2H), 2.83-2.79 (m, 2H), 2.73-2.67 (m, 4H).

b) 11-tert-Butyl 5-((1S,2R,5S)-2-isopropyl-5-methylcyclohexyl) 3-bromo-5,6,7,8,9,10-hexahydro-7,10-iminocyclohept[b]indole-5,11-dicarboxylate

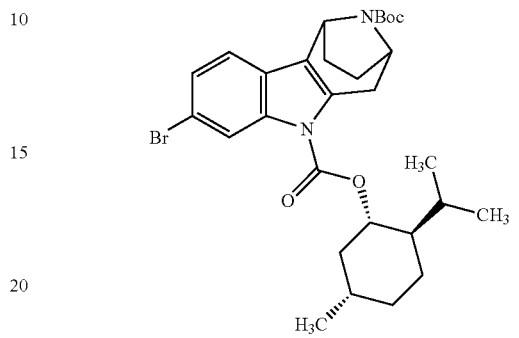

Chemical Formula: $C_{29}H_{39}BrN_2O_4$
Exact Mass: 558.21
Molecular Weight: 559.53

A solution of sodium hexamethyl disilazide in THF (130 mL, 1.0 M, 130 mmol) was added to a solution of tert-butyl 3-bromo-5,6,7,8,9,10-hexahydro-7,10-iminocyclohept[b]indole-11-carboxylate (4.50 g, 11.9 mmol) in THF (60 mL) at −78° C. The reaction was stirred at −78° C. for 40 min, and then (1S)-(+)-menthyl chloroformate (5.00 mL, 23.7 mmol) was added dropwise over 5 min. The reaction was stirred at −78° C. for an additional 5 min. Then the cooling bath was removed, and stirring continued for 2.5 h. The reaction mixture was treated with saturated aqueous $NH_4Cl$ (60 mL) and extracted with ethyl acetate (3×). The combined organic extracts were dried over $Na_2SO_4$, filtered and concentrated to dryness. Purification by flash column chromatography (silica gel, ethyl acetate/hexanes, 0:100 to 30:70) gave the title compound (5.00 g, 76%) as a yellow solid: ¹H NMR (500 MHz, $CDCl_3$) δ 8.36 (br s, 1H), 7.36 (d, J=8.0 Hz, 1H), 7.31 (d, J=8.5 Hz, 1H), 5.30-5.00 (m, 1H), 4.95-4.89 (m, 1H), 4.65-4.55 (m, 1H), 3.70-3.40 (m, 1H), 2.80 (d, J=17.5 Hz, 1H), 2.33-2.13 (m, 3H), 1.99-1.92 (m, 2H), 1.79-1.73 (m, 2H), 1.67-1.57 (m, 3H), 1.50-1.30 (br s, 9H), 1.21-1.10 (m, 2H), 1.10-0.81 (m, 10H).

c) (+)-tert-Butyl 3-bromo-5,6,7,8,9,10-hexahydro-7,10-iminocyclohept[b]indole-11-carboxylate (Enantiomer B)

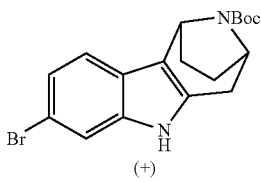

Chemical Formula: $C_{18}H_{21}BrN_2O_2$
Exact Mass: 376.08
Molecular Weight: 377.28

11-tert-Butyl 5-((1S,2R,5S)-2-isopropyl-5-methylcyclohexyl) 3-bromo-5,6,7,8,9,10-hexahydro-7,10-iminocyclohept[b]indole-5,11-dicarboxylate (5.00 g, 9.00 mmol) was dissolved in hexanes (80 mL). After 3 days at −15° C. the mixture was filtered and washed with ice-cold hexanes to give a white crystal (1.6 g), which was then dissolved in THF/MeOH/water (49 mL, 4:2:1). Lithium hydroxide monohydrate (352 mg, 8.59 mmol) was added to the solution, and the reaction was stirred at room temperature for 5 h. The reaction mixture was neutralized with saturated aqueous NH$_4$Cl and extracted with ethyl acetate (3×). The combined organic extracts were dried over Na$_2$SO$_4$, filtered and concentrated to dryness. Purification by flash column chromatography (silica gel, ethyl acetate/hexanes, 0:100 to 30:70) gave the title compound (1.10 g, 31%) as a white solid: $^1$H NMR (500 MHz, CDCl$_3$) δ 7.76 (br s, 1H), 7.43 (br s, 1H), 7.36 (d, J=8.0 Hz, 1H), 7.20 (d, J=6.5 Hz, 1H), 5.30-5.10 (m, 1H), 4.70-4.50 (m, 1H), 3.50-3.30 (m, 1H), 2.46 (d, J=15.5 Hz, 1H), 2.33-2.26 (m, 1H), 2.21-2.13 (m, 1H), 1.96-1.91 (m, 1H), 1.66-1.60 (m, 1H), 1.50-1.30 (m, 9H); HPLC (Method A) 97.8% (AUC), t$_R$=23.0 min; Chiral HPLC (Chiralpak OJ, 260 nm, 80:20:0.1 reagent alcohol/heptane/trifluoroacetic acid) 94.8% (AUC), t$_R$=23.8 min; [α]$^{20}_D$+68.2° (c 0.2, CDCl$_3$).

d) (+)-tert-Butyl 3-bromo-5-methyl-5,6,7,8,9,10-hexahydro-7,10-iminocyclohept[b]indole-11-carboxylate (Enantiomer B)

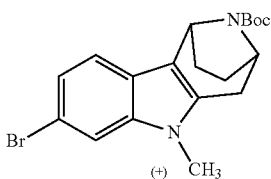

Chemical Formula: C$_{19}$H$_{23}$BrN$_2$O$_2$
Exact Mass: 390.09
Molecular Weight: 391.30

Sodium hydride (60% weight dispersion in mineral oil, 135 mg, 3.40 mmol) and methyl iodide (482 mg, 210 μL, 3.40 mmol) were added to a solution of (+)-tert-butyl 3-bromo-5,6,7,8,9,10-hexahydro-7,10-iminocyclohept[b]indole-11-carboxylate (enantiomer B) (1.10 g, 2.80 mmol) in DMF (8 mL) at 0° C. under N$_2$. The reaction was allowed to warm to room temperature for 3.5 h. The mixture was quenched with H$_2$O at 0° C., and a solid precipitated out of solution. The solids were filtered off to provide the title compound (1.10 g, 100%) as a yellow solid: $^1$H NMR (500 MHz, CDCl$_3$) δ 6.52 (s, 1H), 6.47 (d, J=8.5 Hz, 1H), 6.30 (d, J=8.0 Hz, 1H), 4.38-4.25 (m, 1H), 3.82-3.73 (m, 1H), 2.67 (s, 3H), 2.53-2.39 (m, 1H), 1.60-1.56 (m, 1H), 1.45-1.37 (m, 1H), 1.32-1.24 (m, 1H), 1.06-1.01 (m, 1H), 0.76-0.70 (m, 1H), 0.55-0.46 (m, 9H).

e) tert-Butyl 5-methyl-3-(2-oxo-4-phenethylpiperazin-1-yl)-5,6,7,8,9,10-hexahydro-7,10-iminocyclohept[b]indole-11-carboxylate (Enantiomer B)

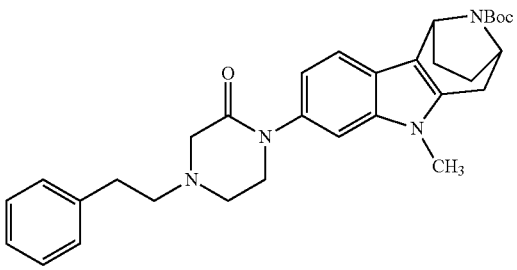

Chemical Formula: C$_{31}$H$_{38}$N$_4$O$_3$
Exact Mass: 514.29
Molecular Weight: 514.66

(+)-tert-Butyl 3-bromo-5-methyl-5,6,7,8,9,10-hexahydro-7,10-iminocyclohept[b]indole-11-carboxylate (enantiomer B) (150 mg, 0.380 mmol) and 4-phenethylpiperazin-2-one (86.0 mg, 0.420 mmol), CuI (145 mg, 0.760 mmol), trans-N,N'-dimethylcyclohexane-1,2-diamine (12.0 μL, 0.080 mmol) and Cs$_2$CO$_3$ (248 mg, 0.760 mmol) in dioxane (5 mL) were reacted following the procedure for Example 2 (step c) to provide the title compound (82.0 mg, 42%) as a yellow solid: $^1$H NMR (500 MHz, CDCl$_3$) δ 7.51 (d, J=8.0 Hz, 1H), 7.33-7.30 (m, 2H), 7.25-7.21 (m, 3H), 7.18 (d, J=1.5 Hz, 1H), 7.00-6.90 (m, 1H), 5.30-5.17 (m, 1H), 4.71-4.59 (m, 1H), 3.75 (br s, 2H), 3.55 (s, 3H), 3.44 (br s, 2H), 3.44-3.30 (m, 1H), 2.92-2.85 (m, 4H), 2.77-2.73 (m, 2H), 2.47 (d, J=15.5 Hz, 1H), 2.40-2.20 (m, 1H), 2.20-2.12 (m, 1H), 1.94-1.90 (m, 1H), 1.70-1.50 (m, 1H), 1.50-1.30 (m, 9H).

f) 1-(5-Methyl-5,6,7,8,9,10-hexahydro-7,10-iminocyclohept[b]indol-3-yl)-4-phenethylpiperazin-2-one dihydrochloride (Enantiomer B)

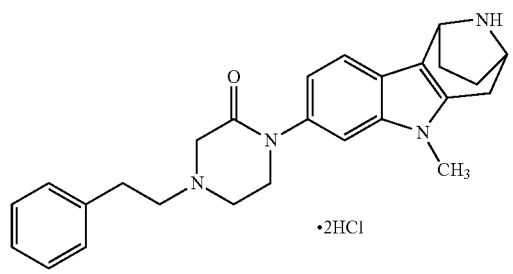

Chemical Formula: C$_{26}$H$_{32}$Cl$_2$N$_4$O
Exact Mass: 486.20
Molecular Weight: 487.46 tert-Butyl 5-methyl-3-(2-oxo-4-phenethylpiperazin-1-yl)-5,6,7,8,9,10-hexahydro-7,10-iminocyclohept[b]indole-11-carboxylate (enantiomer B) (82.0 mg, 0.160 mmol) was deprotected and converted to the hydrochloride salt according to the procedure for Example 2 (step d) to provide the title compound (33.0 mg, 33%) as a yellow solid. Free Base: ¹H NMR (500 MHz, CDCl₃) δ 7.47 (d, J=8.5 Hz, 1H), 7.33-7.30 (m, 2H), 7.26-7.23 (m, 3H), 7.19 (s, 1H), 6.96 (dd, J=8.0, 1.5 Hz, 1H), 4.70-4.69 (m, 1H), 4.21 (m, 1H), 3.76-3.73 (m, 2H), 3.44 (s, 2H), 3.40 (s, 3H), 3.25 (dd, J=16.0, 4.0 Hz, 1H), 2.92-2.86 (m, 4H), 2.77-2.74 (m, 2H), 2.52 (d, J=16.5 Hz, 1H), 2.31-2.19 (m, 2H), 2.03-2.00 (m, 1H), 1.60-1.55 (m, 1H); HPLC (Method A) 98.0% (AUC), $t_R$=10.1 min. HCl salt: ¹H NMR (500 MHz, CD₃OD) δ 7.62 (d, J=8.5 Hz, 1H), 7.44 (d, J=2.0 Hz, 1H), 7.40-7.35 (m, 4H), 7.32-7.28 (m, 1H), 7.08 (dd, J=8.5, 2.0 Hz, 1H), 5.22 (d, J=5.5 Hz, 1H), 4.55-4.52 (m, 1H), 4.30-3.80 (m, 6H), 3.70 (s, 3H), 3.63-3.59 (m, 2H), 3.52-3.47 (m, 1H), 3.22-3.18 (m, 2H), 3.08-3.04 (m, 1H), 2.47-2.35 (m, 2H), 2.29-2.24 (m, 1H), 2.00-1.94 (m, 1H); ESI MS m/z 415 [M+H]⁺; HPLC (Method A) 98.6% (AUC), $t_R$=10.1 min.

Example 34

Preparation of 1-(5-Methyl-5,6,7,8,9,10-hexahydro-7,10-iminocyclohept[b]indol-3-yl)-4-phenethylpiperazin-2-one dihydrochloride (Enantiomer A)

a) 11-tert-Butyl 5-((1R,2S,5R)-2-isopropyl-5-methylcyclohexyl)3-bromo-5,6,7,8,9,10-hexahydro-7,10-iminocyclohept[b]indole-5,11-dicarboxylate

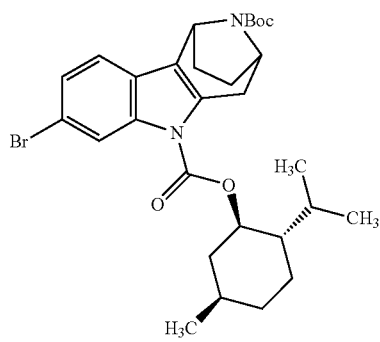

Chemical Formula: C₂₉H₃₉BrN₂O₄
Exact Mass: 558.21
Molecular Weight: 559.53

Sodium hexamethyl disilazide in THF (2.90 mL, 1.0 M, 2.80 mmol), (1R)-(−)-menthyl chloroformate (1.10 mL, 5.20 mmol) and tert-butyl 3-bromo-5,6,7,8,9,10-hexahydro-7,10-iminocyclohept[b]indole-11-carboxylate (1.00 g, 2.60 mmol) in THF (15 mL) were reacted following the procedure for Example 33 (step b) to provide the title compound (1.20 mg, 85%) as a yellow solid: ¹H NMR (500 MHz, CDCl₃) δ 8.36 (br s, 1H), 7.36 (d, J=8.5 Hz, 1H), 7.31 (d, J=8.5 Hz, 1H), 5.30-5.00 (m, 1H), 4.95-4.89 (m, 1H), 4.65-4.55 (m, 1H), 3.70-3.40 (m, 1H), 2.80 (d, J=17.5 Hz, 1H), 2.40-2.10 (m, 3H), 2.10-1.90 (m, 2H), 1.79-1.73 (m, 2H), 1.67-1.57 (m, 3H), 1.50-1.30 (br s, 9H), 1.21-1.10 (m, 2H), 1.10-0.81 (m, 10H).

b) (−)-tert-Butyl 3-bromo-5,6,7,8,9,10-hexahydro-7,10-iminocyclohept[b]indole-11-carboxylate (Enantiomer A)

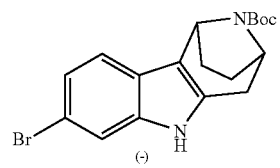

Chemical Formula: C₁₈H₂₁BrN₂O₂
Exact Mass: 376.08
Molecular Weight: 377.28

Crystallization of 11-tert-Butyl 5-((1R,2S,5R)-2-isopropyl-5-methylcyclohexyl)3-bromo-5,6,7,8,9,10-hexahydro-7,10-iminocyclohept[b]indole-5,11-dicarboxylate (1.20 g, 2.20 mmol) in hexanes (20 mL) was performed following the procedure for Example 33 (step c) to provide a white crystal (229 mg), which was then dissolved in THF/MeOH/water (7 mL, 4:2:1). The resulting solution was reacted with lithium hydroxide monohydrate (50.0 mg, 1.20 mmol) following the procedure for Example 33 (step c) to give the title compound (155 mg, 16%) as a white solid: ¹H NMR (500 MHz, CDCl₃) δ 7.95 (br s, 1H), 7.41 (br s, 1H), 7.34 (d, J=7.5 Hz, 1H), 7.18 (br s, 1H), 5.30-5.10 (m, 1H), 4.70-4.50 (m, 1H), 3.50-3.30 (m, 1H), 2.46 (d, J=16.0 Hz, 1H), 2.40-2.20 (m, 1H), 2.20-2.10 (m, 1H), 1.96-1.91 (m, 1H), 1.70-1.60 (m, 1H), 1.50-1.30 (m, 9H); HPLC (Method A) 99.4% (AUC), $t_R$=23.0 min; Chiral HPLC (Chiralpak OJ, 260 nm, 80:20:0.1 reagent alcohol/heptane/trifluoroacetic acid) 100% (AUC), $t_R$=22.7 min.

c) (−)-tert-Butyl 3-bromo-5-methyl-5,6,7,8,9,10-hexahydro-7,10-iminocyclohept[b]indole-11-carboxylate (Enantiomer A)

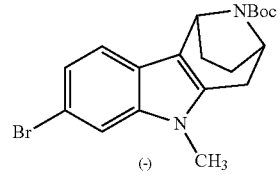

Chemical Formula: C₁₉H₂₃BrN₂O₂
Exact Mass: 390.09
Molecular Weight: 391.30

Sodium hydride (60% weight dispersion in mineral oil, 27.0 mg, 0.680 mmol), methyl iodide (96.5 mg, 42.0 μL, 0.680 mmol) and (−)-tert-butyl 3-bromo-5,6,7,8,9,10-hexahydro-7,10-iminocyclohept[b]indole-11-carboxylate (213 mg, 0.560 mmol) in DMF (3 mL) were reacted following the procedure for Example 33 (step d) to provide the title compound (144 mg, 66%) as a yellow solid: ¹H NMR (500 MHz, CDCl₃) δ 6.52 (s, 1H), 6.48 (d, J=8.5 Hz, 1H), 6.30 (d, J=7.5 Hz, 1H), 4.42-4.25 (m, 1H), 3.82-3.73 (m, 1H), 2.67 (s, 3H), 2.53-2.36 (m, 1H), 1.60-1.56 (m, 1H), 1.42-1.38 (m, 1H), 1.32-1.24 (m, 1H), 1.06-1.01 (m, 1H), 0.76-0.70 (m, 1H), 0.55-0.46 (m, 9H).

d) 1-(5-Methyl-5,6,7,8,9,10-hexahydro-7,10-iminocyclohept[b]indol-3-yl)-4-phenethylpiperazin-2-one dihydrochloride (Enantiomer A)

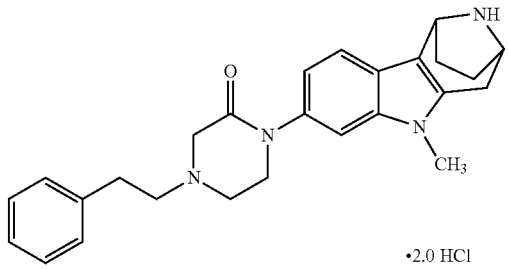

Chemical Formula: $C_{26}H_{32}Cl_2N_4O$
Exact Mass: 486.20
Molecular Weight: 487.46

(−)-tert-Butyl 3-bromo-5-methyl-5,6,7,8,9,10-hexahydro-7,10-iminocyclohept[b]indole-11-carboxylate (enantiomer A) (70.0 mg, 0.180 mmol), 4-phenethylpiperazin-2-one (40.0 mg, 0.200 mmol), CuI (69.0 mg, 0.360 mmol), trans-N,N'-dimethylcyclohexane-1,2-diamine (5.60 μL, 0.0400 mmol) and $Cs_2CO_3$ (117 mg, 0.360 mmol) in dioxane (5 mL) were reacted following the procedure for Example 2 (step c) to give tert-butyl 5-methyl-3-(2-oxo-4-phenethylpiperazin-1-yl)-5,6,7,8,9,10-hexahydro-7,10-iminocyclohept[b]indole-11-carboxylate (580 mg) as a yellow solid. The yellow solid was deprotected and converted to the hydrochloride salt according to the procedure for Example 2 (step d) to provide the title compound (12.8 mg, 15%) as a yellow solid. Free Base: $^1$H NMR (500 MHz, $CDCl_3$) δ 7.47 (d, J=8.5 Hz, 1H), 7.33-7.30 (m, 2H), 7.26-7.23 (m, 3H), 7.19 (d, J=1.5 Hz, 1H), 6.96 (dd, J=8.0, 1.5 Hz, 1H), 4.70-4.69 (m, 1H), 4.21-4.40 (m, 1H), 3.76-3.73 (m, 2H), 3.44 (s, 2H), 3.43 (s, 3H), 3.42 (dd, J=16.0, 4.0 Hz, 1H), 2.92-2.86 (m, 4H), 2.77-2.74 (m, 2H), 2.56 (d, J=16.0 Hz, 1H), 2.40-2.20 (m, 2H), 2.08-2.04 (m, 1H), 1.63-1.60 (m, 1H); HPLC (Method A) 96.0% (AUC), $t_R$=10.1 min. HCl salt: $^1$H NMR (500 MHz, $CD_3OD$) δ 7.64 (d, J=8.5 Hz, 1H), 7.44 (d, J=1.5 Hz, 1H), 7.40-7.35 (m, 4H), 7.32-7.28 (m, 1H), 7.08 (dd, J=8.0, 1.5 Hz, 1H), 5.22 (d, J=5.5 Hz, 1H), 4.55-4.52 (m, 1H), 4.30-3.80 (m, 6H), 3.70 (s, 3H), 3.62-3.58 (m, 2H), 3.50 (dd, J=17.5, 4.5 Hz, 1H), 3.21-3.16 (m, 2H), 3.06 (d, J=17.0 Hz, 1H), 2.49-2.34 (m, 2H), 2.29-2.24 (m, 1H), 2.00-1.97 (m, 1H); ESI MS m/z 415 [M+H]$^+$; HPLC (Method A) 97.8% (AUC), $t_R$=10.0 min.

Example 35

Preparation of 1-(5-Methyl-5,6,7,8,9,10-hexahydro-7,10-iminocyclohept[b]indol-3-yl)-4-(6-methylpyridin-3-yl)-pyridin-2(1H)-one hydrochloride (Enantiomer B)

a) 2'-Methoxy-6-methyl-3,4'-bipyridine (CAS Registry Number 1173156-60-9) (WO 2009/089482 to Guzzo et al., which is hereby incorporated by reference in its entirety)

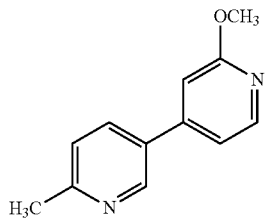

Chemical Formula: $C_{12}H_{12}N_2O$
Exact Mass: 200.09
Molecular Weight: 200.24

2-Methyl-5-(4,4,5,5-tetramethyl-1,3,2-dioxaborolan-2-yl)pyridine (3.5 g, 16 mmol) and 4-bromo-2-methoxypyridine (2.0 g, 11 mmol) were reacted according to Example 3 (step a) to provide the title compound (2.1 g, 98%) as a brown solid: $^1$H NMR (300 MHz, $CDCl_3$) δ 8.75 (d, J=2.1 Hz, 1H), 8.23 (d, J=5.4 Hz, 1H), 7.78 (dd, J=8.0, 2.4 Hz, 1H), 7.24 (d, J=8.1, 1H), 7.08 (dd, J=5.4, 1.5 Hz, 1H), 6.84 (d, J=1.0, 1H), 3.98 (s, 3H), 2.61 (s, 3H).

b) 4-(6-Methylpyridin-3-yl)pyridin-2(1H)-one (CAS Registry Number 1173156-63-2) (WO 2009/089482 to Guzzo et al., which is hereby incorporated by reference in its entirety)

Chemical Formula: $C_{11}H_{10}N_2O$
Exact Mass: 186.08
Molecular Weight: 186.21

2'-Methoxy-6-methyl-3,4'-bipyridine (2.1 g, 10.4 mmol) was reacted according to Example 3 (step b) to provide the title compound (1.36 mg, 68%) as a white solid: $^1$H NMR (300 MHz, DMSO-$d_6$) δ 11.65 (s, 1H) 8.78 (d, J=2.1 Hz, 1H), 8.01 (dd, J=8.1, 2.5 Hz, 1H), 7.47 (d, J=6.9 Hz, 1H), 7.36 (d, J=8.1, 1H), 6.66 (d, J=1.4 Hz, 1H), 6.55 (dd, J=6.9, 1.8 Hz, 1H), 2.51 (s, 3H).

a) tert-Butyl 5-methyl-3-(4-(6-methylpyridin-3-yl)-2-oxopyridin-1(2H)-yl)-5,6,7,8,9,10-hexahydro-7,10-iminocyclohept[b]indole-11-carboxylate (Enantiomer B)

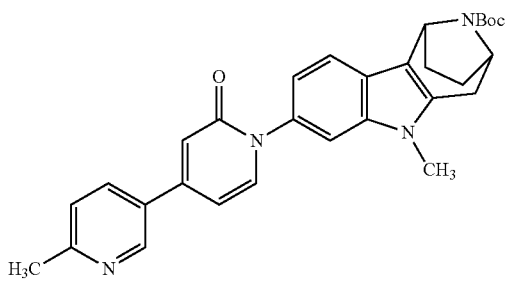

Chemical Formula: $C_{30}H_{32}N_4O_3$
Exact Mass: 496.25
Molecular Weight: 496.60

(+)-tert-Butyl 3-bromo-5-methyl-5,6,7,8,9,10-hexahydro-7,10-iminocyclohept[b]indole-11-carboxylate (enantiomer B) (150 mg, 0.380 mmol), 4-(6-methylpyridin-3-yl)pyridin-2(1H)-one (85.0 mg, 0.460 mmol), CuI (108 mg, 0.570 mmol), 8-hydroxyquinoline (11.0 mg, 80.0 µmol) and $Cs_2CO_3$ (248 mg, 0.760 mmol) in DMSO (5 mL) were reacted following the procedure for Example 2 (step c) to provide the title compound (32.0 mg, 17%) as a yellow solid: $^1$H NMR (500 MHz, CDCl$_3$) δ 8.79 (d, J=2.0 Hz, 1H), 7.83 (dd, J=8.5, 2.5 Hz, 1H), 7.60 (d, J=8.5 Hz, 1H), 7.52 (br s, 1H), 7.33 (d, J=1.5 Hz, 1H), 7.29-7.22 (m, 1H), 7.06 (br s, 1H), 6.90 (d, J=1.5 Hz, 1H), 6.49 (d, J=7.0 Hz, 1H), 5.40-5.20 (m, 1H), 4.80-4.60 (m, 1H), 3.60 (s, 3H), 3.50-3.30 (m, 1H), 2.64 (s, 3H), 2.51 (d, J=15.5 Hz, 1H), 2.40-2.30 (m, 1H), 2.23-2.15 (m, 1H), 1.97-1.92 (m, 1H), 1.70-1.50 (m, 1H), 1.50-1.30 (m, 9H); HPLC (Method A) 98.0% (AUC), $t_R$=14.3 min.

b) 1-(5-Methyl-5,6,7,8,9,10-hexahydro-7,10-iminocyclohept[b]indol-3-yl)-4-(6-methylpyridin-3-yl)pyridin-2(1H)-one hydrochloride (Enantiomer B)

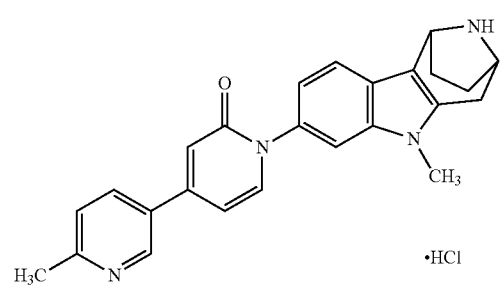

Chemical Formula: $C_{25}H_{25}ClN_4O$
Exact Mass: 432.17
Molecular Weight: 432.95 tert-Butyl 5-methyl-3-(4-(6-methylpyridin-3-yl)-2-oxopyridin-1(2H)-yl)-5,6,7,8,9,10-hexahydro-7,10-iminocyclohept[b]indole-11-carboxylate (Enantiomer B) (32.0 mg, 0.064 mmol) was deprotected and converted to the hydrochloride salt according to the procedure for Example 2 (step d) to provide the title compound (21.0 mg, 81%) as a yellow solid: $^1$H NMR (500 MHz, CD$_3$OD) δ 9.15 (d, J=2.0 Hz, 1H), 8.85 (dd, J=8.5, 2.5 Hz, 1H), 8.05 (d, J=8.5 Hz, 1H), 7.89 (d, J=7.0 Hz, 1H), 7.71 (d, J=8.5 Hz, 1H), 7.55 (d, J=2.0 Hz, 1H), 7.15 (dd, J=8.0, 1.5 Hz, 1H), 7.08 (d, J=2.0 Hz, 1H), 6.90 (dd, J=7.0, 2.0 Hz, 1H), 5.26 (d, J=5.0 Hz, 1H), 4.58-4.56 (m, 1H), 3.73 (s, 3H), 3.52 (dd, J=17.0, 4.5 Hz, 1H), 3.10 (dd, J=17.0, 1.0 Hz, 1H), 2.87 (s, 3H), 2.51-2.36 (m, 2H), 2.32-2.27 (m, 1H), 2.03-1.99 (m, 1H); ESI MS m/z 397 [M+H]$^+$; HPLC (Method A) 96.7% (AUC), $t_R$=9.2 min.

Example 36

Preparation of 1-(5-Methyl-5,6,7,8,9,10-hexahydro-7,10-iminocyclohept[b]indol-3-yl)-4-(6-(trifluoromethyl)pyridin-3-yl)pyridin-2(1H)-one hydrochloride (Enantiomer B)

a) tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate (Enantiomer B)

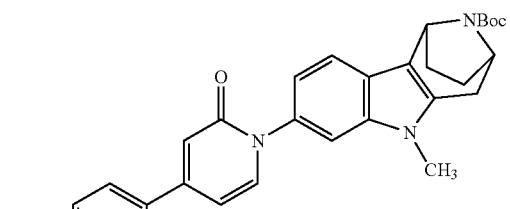

Chemical Formula: $C_{30}H_{29}F_3N_4O_3$
Exact Mass: 550.22
Molecular Weight: 550.57

(+)-tert-Butyl 3-bromo-5-methyl-5,6,7,8,9,10-hexahydro-7,10-iminocyclohept[b]indole-11-carboxylate (enantiomer B) (150 mg, 0.380 mmol), 4-(6-(trifluoromethyl)pyridin-3-yl)pyridin-2(1H)-one (110 mg, 0.460 mmol), CuI (108 mg, 0.570 mmol), 8-hydroxyquinoline (11.0 mg, 0.0800 mmol) and $Cs_2CO_3$ (248 mg, 0.760 mmol) in DMSO (5 mL) were reacted following the procedure for Example 2 (step c) to provide the title compound (68.0 mg, 33%) as a yellow solid: $^1$H NMR (500 MHz, CDCl$_3$) δ 8.99 (d, J=1.5 Hz, 1H), 8.10 (dd, J=8.0, 1.5 Hz, 1H), 7.82 (d, J=8.5 Hz, 1H), 7.61 (d, J=8.5 Hz, 2H), 7.33 (d, J=1.5 Hz, 1H), 7.06 (br s, 1H), 6.93 (d, J=1.5 Hz, 1H), 6.48 (dd, J=7.0, 2.0 Hz, 1H), 5.40-5.30 (m, 1H), 4.80-4.60 (m, 1H), 3.61 (s, 3H), 3.49-3.34 (m, 1H), 2.53-2.49 (d, J=16.0 Hz, 1H), 2.40-2.30 (m, 1H), 2.24-2.16 (m, 1H), 1.97-1.93 (m, 1H), 1.70-1.50 (m, 1H), 1.50-1.30 (m, 9H); HPLC (Method A) 97.8% (AUC), $t_R$=21.8 min.

b) 1-(5-Methyl-5,6,7,8,9,10-hexahydro-7,10-iminocyclohept[b]indol-3-yl)-4-(6-(trifluoromethyl)pyridin-3-yl)pyridin-2(1H)-one hydrochloride (Enantiomer B)

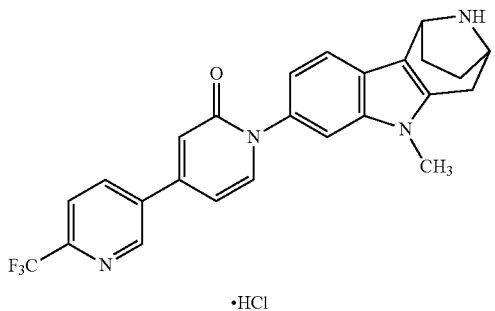

Chemical Formula: C$_{25}$H$_{22}$ClF$_3$N$_4$O
Exact Mass: 486.14
Molecular Weight: 486.92 tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate (enantiomer B) (68.0 mg, 0.124 mmol) was deprotected and converted to the hydrochloride salt according to the procedure for Example 2 (step d) to provide the title compound (50.0 mg, 86%) as a yellow solid: $^1$H NMR (500 MHz, CD$_3$OD) δ 9.10 (s, 1H), 8.41 (d, J=8.0 Hz, 1H), 7.97 (d, J=8.5 Hz, 1H), 7.84 (d, J=7.0 Hz, 1H), 7.71 (d, J=8.0 Hz, 1H), 7.55 (d, J=1.0 Hz, 1H), 7.15 (dd, J=8.0, 1.5 Hz, 1H), 7.02 (d, J=1.5 Hz, 1H), 6.89 (dd, J=7.0, 1.5 Hz, 1H), 5.26 (d, J=5.0 Hz, 1H), 4.58-4.55 (m, 1H), 3.73 (s, 3H), 3.52 (dd, J=17.5, 4.5 Hz, 1H), 3.10 (d, J=17.0, 1H), 2.51-2.36 (m, 2H), 2.32-2.27 (m, 1H), 2.03-1.99 (m, 1H); ESI MS m/z 451 [M+H]$^+$; HPLC (Method C) 98.5% (AUC), t$_R$=13.9 min.

Example 37

Preparation of 1-(5-Methyl-5,6,7,8,9,10-hexahydro-7,10-iminocyclohept[b]indol-3-yl)-4-(6-(trifluoromethyl)pyridin-3-yl)pyridin-2(1H)-one hydrochloride (Enantiomer A)

a) tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate (Enantiomer A)

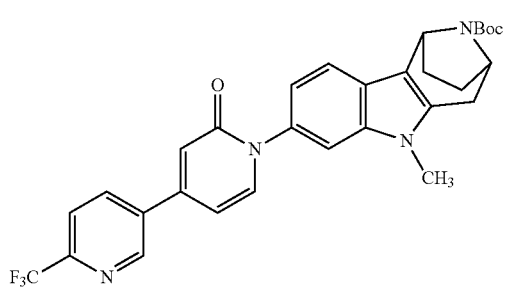

Chemical Formula: C$_{30}$H$_{29}$F$_3$N$_4$O$_3$
Exact Mass: 550.22
Molecular Weight: 550.57

(−)-tert-Butyl 3-bromo-5-methyl-5,6,7,8,9,10-hexahydro-7,10-iminocyclohept[b]indole-11-carboxylate (enantiomer A) (71.0 mg, 0.180 mmol), 4-(6-(trifluoromethyl)pyridin-3-yl)pyridin-2(1H)-one (52.0 mg, 0.220 mmol), CuI (51.0 mg, 0.270 mmol), 8-hydroxyquinoline (5.20 mg, 0.040 mmol) and Cs$_2$CO$_3$ (117 mg, 0.360 mmol) in DMSO (5 mL) were reacted following the procedure for Example 2 (step c) to provide the title compound (19 mg, 19%) as a yellow solid: $^1$H NMR (500 MHz, CDCl$_3$) δ 8.99 (s, 1H), 8.10 (d, J=8.0 Hz, 1H), 7.82 (d, J=8.0 Hz, 1H), 7.61 (d, J=8.0 Hz, 2H), 7.47 (s, 1H), 7.06 (br s, 1H), 6.94 (s, 1H), 6.48 (d, J=6.5 Hz, 1H), 5.40-5.20 (m, 1H), 4.80-4.60 (m, 1H), 3.61 (s, 3H), 3.57-3.35 (m, 1H), 2.53-2.49 (d, J=16.0 Hz, 1H), 2.40-2.30 (m, 1H), 2.24-2.16 (m, 1H), 1.97-1.93 (m, 1H), 1.62-1.57 (m, 1H), 1.50-1.30 (m, 9H); HPLC (Method A) 95.8% (AUC), t$_R$=21.8 min.

b) 1-(5-Methyl-5,6,7,8,9,10-hexahydro-7,10-iminocyclohept[b]indol-3-yl)-4-(6-(trifluoromethyl)pyridin-3-yl)pyridin-2(1H)-one hydrochloride (Enantiomer A)

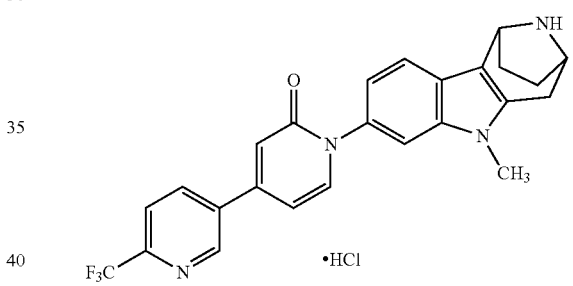

Chemical Formula: C$_{25}$H$_{22}$ClF$_3$N$_4$O
Exact Mass: 486.14
Molecular Weight: 486.92 tert-Butyl 5-methyl-3-(2-oxo-4-(6-(trifluoromethyl)pyridin-3-yl)pyridin-1(2H)-yl)-5,6,7,8,9,10-hexahydro-7,10-iminocyclohept[b]indole-11-carboxylate (enantiomer A) (19.0 mg, 34.5 μmol) was deprotected and converted to the hydrochloride salt according to the procedure for Example 2 (step d) to provide the title compound (13 mg, 89%) as a yellow solid: $^1$H NMR (500 MHz, CD$_3$OD) δ 9.10 (d, J=2.0 Hz, 1H), 8.41 (dd, J=8.0, 2.0 Hz, 1H), 7.97 (d, J=8.5 Hz, 1H), 7.84 (d, J=7.0 Hz, 1H), 7.71 (d, J=8.0 Hz, 1H), 7.55 (d, J=1.5 Hz, 1H), 7.15 (dd, J=8.0, 1.5 Hz, 1H), 7.02 (d, J=2.0 Hz, 1H), 6.89 (dd, J=7.0, 2.0 Hz, 1H), 5.26 (d, J=5.0 Hz, 1H), 4.57-4.54 (m, 1H), 3.73 (s, 3H), 3.52 (dd, J=17.5, 5.0 Hz, 1H), 3.10 (dd, J=17.0, 1.0 Hz, 1H), 2.51-2.36 (m, 2H), 2.32-2.28 (m, 1H), 2.04-2.01 (m, 1H); ESI MS m/z 451 [M+H]$^+$; HPLC (Method C) 97.9% (AUC), t$_R$=13.8 min.

Example 38

Preparation of 1-(5-Methyl-5,6,7,8,9,10-hexahydro-7,10-iminocyclohept[b]indol-3-yl)-4-((6-(trifluoromethyl)pyridin-3-yl)methoxy)pyridin-2(1H)-one hydrochloride (Enantiomer B)

a) tert-Butyl 5-methyl-3-(2-oxo-4-((6-(trifluoromethyl)pyridin-3-yl)methoxy)pyridin-1(2H)-yl)-5,6,7,8,9,10-hexahydro-7,10-iminocyclohept[b]indole-11-carboxylate (Enantiomer B)

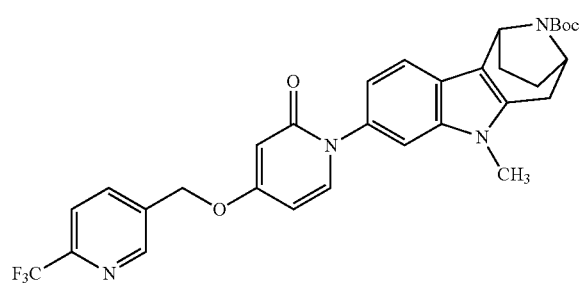

Chemical Formula: C₃₁H₃₁F₃N₄O₄
Exact Mass: 580.23
Molecular Weight: 580.60

(+)-tert-Butyl 3-bromo-5-methyl-5,6,7,8,9,10-hexahydro-7,10-iminocyclohept[b]indole-11-carboxylate (enantiomer B) (150 mg, 0.380 mmol), 4-((6-(trifluoromethyl)pyridin-3-yl)methoxy)pyridin-2(1H)-one (124 mg, 0.460 mmol), CuI (108 mg, 0.570 mmol), 8-hydroxyquinoline (11.0 mg, 0.080 mmol) and Cs₂CO₃ (248 mg, 0.760 mmol) in DMSO (5 mL) were reacted following the procedure for Example 2 (step c) to provide the title compound (22.0 mg, 10%) as a yellow solid: ¹H NMR (300 MHz, CDCl₃) δ 8.81 (s, 1H), 7.96 (d, J=8.4 Hz, 1H), 7.75 (d, J=8.1 Hz, 1H), 7.56 (d, J=8.1 Hz, 1H), 7.35 (d, J=6.9 Hz, 1H), 7.25 (s, 1H), 6.99 (br s, 1H), 6.07-6.03 (m, 2H), 5.40-5.20 (m, 1H), 5.16 (s, 2H), 4.80-4.60 (m, 1H), 3.59 (s, 3H), 3.50-3.20 (m, 1H), 2.53-2.47 (d, J=16.2 Hz, 1H), 2.40-2.10 (m, 2H), 1.97-1.90 (m, 1H), 1.70-1.50 (m, 1H), 1.50-1.30 (m, 9H).

b) 1-(5-Methyl-5,6,7,8,9,10-hexahydro-7,10-iminocyclohept[b]indol-3-yl)-4-((6-(trifluoromethyl)pyridin-3-yl)methoxy)pyridin-2(1H)-one hydrochloride (Enantiomer B)

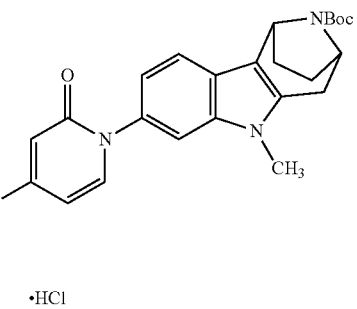

Chemical Formula: C₂₆H₂₄ClF₃N₄O₂
Exact Mass: 516.15
Molecular Weight: 516.94 tert-Butyl 5-methyl-3-(2-oxo-4-(6-(trifluoromethyl)pyridin-3-yl)methoxy)pyridin-(2H)-yl)-5,6,7,8,9,10-hexahydro-7,10-iminocyclohept[b]indole-11-carboxylate (enantiomer B) (25.0 mg, 43.1 µmol) was deprotected and converted to the hydrochloride salt according to the procedure for Example 2 (step d) to provide the title compound (18.0 mg, 87%) as a yellow solid: ¹H NMR (500 MHz, CD₃OD) δ 8.84 (s, 1H), 8.16 (d, J=8.0 Hz, 1H), 7.89 (d, J=8.0 Hz, 1H), 7.65 (d, J=8.5 Hz, 1H), 7.61 (d, J=7.5 Hz, 1H), 7.46 (d, J=2.0 Hz, 1H), 7.07 (dd, J=8.5, 2.0 Hz, 1H), 6.35 (dd, J=8.0, 3.0 Hz, 1H), 6.17 (d, J=2.5 Hz, 1H), 5.36 (s, 2H), 5.24 (d, J=5.5 Hz, 1H), 4.56-4.53 (m, 1H), 3.70 (s, 3H), 3.50 (dd, J=17.0, 4.5 Hz, 1H), 3.08 (dd, J=17.5, 1.5 Hz, 1H), 2.48-2.36 (m, 2H), 2.31-2.26 (m, 1H), 2.02-2.00 (m, 1H); ESI MS m/z 481 [M+H]⁺; HPLC (Method A) 96.8% (AUC), $t_R$=13.1 min.

Example 39

Preparation of 4-(Benzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride a) 1-Chloroethyl 3-oxo-8-azabicyclo[3.2.1]octane-8-carboxylate (CAS Registry Number 799283-74-2) (WO 2004/100946 to Borcherding et al., which is hereby incorporated by reference in its entirety)

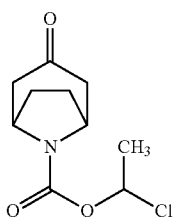

Chemical Formula: C₁₀H₁₄ClNO₃
Exact Mass: 231.07
Molecular Weight: 231.68

To a solution of 8-methyl-8-azabicyclo[3.2.1]octan-3-one (30.0 g, 210 mmol) in 1,2-dichloroethane (100 mL) was added 1-chloroethyl chloroformate (25.8 mL, 240 mmol). The reaction mixture was heated to reflux for 18 h. The mixture was cooled to room temperature and filtered. The filtrate was concentrated and purified by flash column chromatography (silica gel, hexanes/ethyl acetate, 100:0 to 80:20) to give the title compound (40.2 g, 83%) as a yellow oil: ¹H NMR (500 MHz, CDCl₃) δ 6.67-3.63 (m, 1H), 4.65-4.57 (m, 2H), 2.83-2.56 (m, 2H), 2.42 (d, J=5.5 Hz, 1H), 2.38 (d, J=5.5 Hz, 1H), 2.30-2.10 (m, 2H), 1.85 (d, J=6.0 Hz, 3H), 1.80-1.70 (m, 2H).

b) 2-Bromo-6-(1-methylhydrazinyl)pyridine

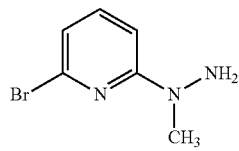

Chemical Formula: C₆H₈BrN₃
Exact Mass: 200.99
Molecular Weight: 202.05

A suspension of 2,6-dibromopyridine (10.0 g, 42.0 mmol) in anhydrous methylhydrazine (10 mL) was heated at 100° C. for 2 h. The mixture was cooled to room temperature and washed with water (3×20 mL). The combined organic extracts were dried over sodium sulfate, filtered, and concentrated under reduced pressure. Purification by flash column chromatography (silica gel, hexanes/EtOAc, 80:20) gave the title compound (5.70 g, 66%) as white solid: ¹H NMR (500 MHz, CDCl₃) δ 7.30-7.26 (dd, J=8.5, 7.8 Hz, 1H), 6.83 (d, J=8.0 Hz, 1H), 6.73 (d, J=7.0 Hz, 1H), 4.03 (br s, 2H), 3.36 (s, 3H).

c) 1-Chloroethyl 3-(2-(6-bromopyridin-2-yl)-2-methylhydrazono)-8-azabicyclo[3.2.1]octane-8-carboxylate

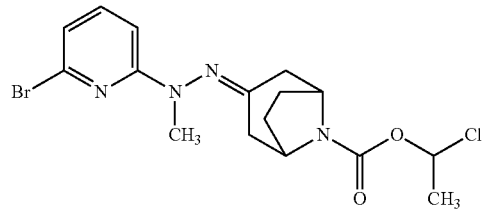

Chemical Formula: C₁₆H₂₀BrClN₄O₂
Exact Mass: 414.05
Molecular Weight: 415.71

A solution of 2-bromo-6-(1-methylhydrazinyl)pyridine (1.60 g, 7.90 mmol), 1-chloroethyl 3-oxo-8-azabicyclo[3.2.1]octane-8-carboxylate (1.80 g, 7.90 mmol) and p-toluenesulphonic acid (300 mg, 1.60 mmol) in toluene (50 mL) was heated under reflux, with water removal (azeotrope), for 3 h. The mixture was cooled to room temperature and concentrated. The residue was purified by flash column chromatography (silica gel, 0%-100% solvent mixture B in methylene chloride; solvent mixture B=80:18:2 methylene chloride/methanol/concentrated ammonium hydroxide) to give the title compound (676 mg, 28%) as a yellow solid: ¹H NMR (500 MHz, CDCl₃) δ 7.31 (t, J=7.5 Hz, 1H), 6.88 (d, J=7.5 Hz, 1H), 6.68-6.65 (m, 1H), 6.62 (d, J=8.0 Hz, 1H), 4.63-4.40 (m, 3H), 3.17 (s, 3H), 2.93-2.90 (m, 1H), 265-2.62 (m, 1H), 2.42-2.37 (dd, J=16.0, 6.0 Hz, 1H), 2.13-2.00 (m, 3H), 1.85 (d, J=6.0 Hz, 3H), 1.80-1.73 (m, 1H).

d) 4-(Benzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride

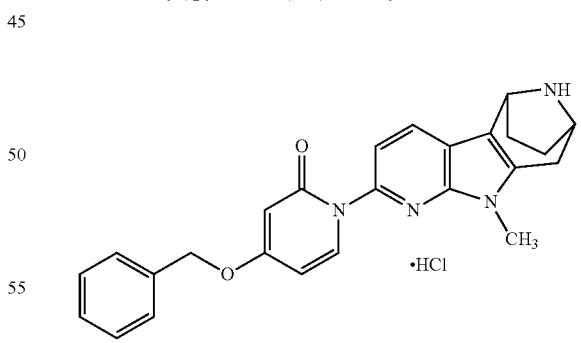

Chemical Formula: C₂₅H₂₅ClN₄O₂
Exact Mass: 448.17
Molecular Weight: 448.94

A mixture of 1-chloroethyl 3-(2-(6-bromopyridin-2-yl)-2-methylhydrazono)-8-azabicyclo[3.2.1]octane-8-carboxylate (676 mg, 1.57 mmol) and polyphosphoric acid (2 mL) was heated at 180° C. for 25 min. After cooling to room temperature, the reaction mixture was basified with 6N NaOH and extracted with methylene chloride (3×). The combined organic extracts were dried over Na$_2$SO$_4$, filtered and concentrated to dryness. The residue was purified by flash column chromatography (silica gel, 0%-100% solvent mixture B in methylene chloride; solvent mixture B=80:18:2 methylene chloride/methanol/concentrated ammonium hydroxide) to give 2-bromo-10-methyl-5,6,7,8,9,10-hexahydro-5,8-iminocyclohepta[4,5]pyrrolo[2,3-b]pyridine (185 mg) as a brown oil.

2-bromo-10-methyl-5,6,7,8,9,10-hexahydro-5,8-iminocyclohepta[4,5]pyrrolo[2,3-b]pyridine (185 mg, 0.640 mmol), 4-(benzyloxy)pyridin-2(1H)-one (154 mg, 0.760 mmol), CuI (183 mg, 0.960 mmol), 8-hydroxyquinoline (18.6 mg, 0.130 mmol) and Cs$_2$CO$_3$ (417 mg, 1.20 mmol) in DMSO (5 mL) were reacted following the procedure for Example 2 (steps c and d) to provide the free base of the title compound (8.0 mg) as a yellow solid. 1.25 M HCl in methanol (0.02 mL, 0.03 mmol) was added to a solution of the solid in MeOH (3 mL). Concentration under vacuum provided the title compound (6.5 mg, 3%) as a yellow solid. Free Base: $^1$H NMR (500 MHz, CDCl$_3$) δ 7.85 (d, J=8.0 Hz, 1H), 7.67 (d, J=7.5 Hz, 1H), 7.44-7.33 (m, 7H), 6.11-6.05 (m, 1H), 6.05 (d, J=2.5 Hz, 1H), 5.06 (s, 2H), 4.75 (d, J=4.5 Hz, 1H), 4.30-4.20 (m, 1H), 3.66 (s, 3H), 3.44-3.40 (dd, J=16.5, 4.5 Hz, 1H), 2.63 (d, J=16.5 Hz, 1H), 2.36-2.26 (m, 2H), 2.08-2.03 (m, 1H), 1.69-1.65 (m, 1H); HPLC (Method D) 97.1% (AUC), t$_R$=7.2 min. HCl salt: $^1$H NMR (500 MHz, CD$_3$OD) δ 8.10 (d, J=8.0 Hz, 1H), 7.82 (d, J=7.5 Hz, 1H), 7.48-7.35 (m, 6H), 6.37 (dd, J=7.5, 2.5 Hz, 1H), 6.15 (d, J=2.5 Hz, 1H), 5.26 (d, J=5.5 Hz, 1H), 5.21 (s, 2H), 4.58-4.55 (m, 1H), 3.75 (s, 3H), 3.54 (dd, J=17.5, 4.5 Hz, 1H), 3.15-3.11 (dd, J=17.5, 1.0 Hz, 1H), 2.51-2.36 (m, 2H), 2.33-2.28 (m, 1H), 2.04-2.02 (m, 1H); ESI MS m/z 413 [M+H]$^+$; HPLC (Method D) 97.6% (AUC), t$_R$=10.2 min.

Example 40

Preparation of 4-((5-Fluoropyridin-2-yl)methoxy)-1-(11-methyl-5,6,7,8,9,10-hexahydro-5,9-imino-11H-cycloocta[4,5]pyrrolo[2,3-b]pyridin-2-yl)pyridin-2(1H)-one hydrochloride a) tert-Butyl 3-(2-(6-bromopyridin-2-yl)hydrazono)-9-azabicyclo[3.3.1]nonane-9-carboxylate

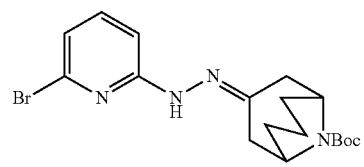

Chemical Formula: C$_{18}$H$_{25}$BrN$_4$O$_2$
Exact Mass: 408.12
Molecular Weight: 409.32

2-Bromo-6-hydrazinylpyridine (393 mg, 2.09 mmol) and tert-butyl 3-oxo-9-azabicyclo[3.3.1]nonane-9-carboxylate (500 mg, 2.09 mmol) were heated at reflux in EtOH (5 mL) for 16 h and the mixture concentrated to provide the title compound (855 mg, 100%) as a yellow solid: ESI MS m/z 409 [M+H]$^+$.

b) tert-Butyl 3-(2-(6-bromopyridin-2-yl)-2-methylhydrazono)-9-azabicyclo[3.3.1]nonane-9-carboxylate

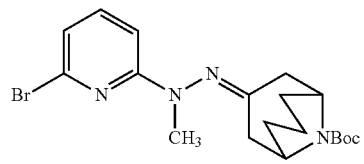

Chemical Formula: C$_{19}$H$_{27}$BrN$_4$O$_2$
Exact Mass: 422.13
Molecular Weight: 423.35 tert-Butyl 3-(2-(6-bromopyridin-2-yl)hydrazono)-9-azabicyclo[3.3.1]nonane-9-carboxylate (609 mg, 1.49 mmol) was dissolved in DMF, and NaH (60%, 65 mg, 1.63 mmol) was added. After 30 min, MeI (232 mg, 1.63 mmol, 102 µL) was added, and stirring continued for 30 min. The mixture was poured into water and extracted with ethyl acetate. The ethyl acetate was concentrated to provide the crude product (655 mg, >100%) as a red oil: ESI MS m/z 423 [M+H]$^+$.

c) tert-Butyl 2-bromo-11-methyl-5,6,7,8,9,10-hexahydro-5,9-imino-11H-cycloocta[4,5]pyrrolo[2,3-b]pyridine-12-carboxylate

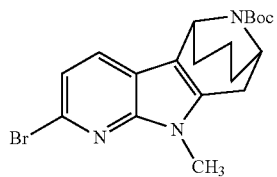

Chemical Formula: C$_{19}$H$_{24}$BrN$_3$O$_2$
Exact Mass: 405.11
Molecular Weight: 406.32 tert-Butyl 3-(2-(6-bromopyridin-2-yl)-2-methylhydrazono)-9-azabicyclo[3.3.1]nonane-9-carboxylate (655 mg, 1.49 mmol, estimated) was combined with p-toluenesulphonic acid (579 mg, 3.14 mmol) and heated to 160° C. for 15 minutes. The mixture was allowed to cool and isopropanol (20 mL), water (10 mL), potassium carbonate (1.03 g, 7.45 mmol), and di-tert-butyl dicarbonate (0.65 g, 4.9 mmol) were added. After stirring for 16 h, the mixture was partitioned between methylene chloride and water. The organic layer was removed, dried and concentrated, and the residue was purified by column chromatography eluting with ethyl acetate/hexanes (1:4) to provide the title compound (300 mg, 50%) as a orange oil: ESI MS m/z 406 [M+H]⁺.

d) tert-Butyl 2-(4-((5-fluoropyridin-2-yl)methoxy)-2-oxopyridin-1(2H)-yl)-11-methyl-5,6,7,8,9,10-hexahydro-5,9-imino-11H-cycloocta[4,5]pyrrolo[2,3-b]pyridine-12-carboxylate

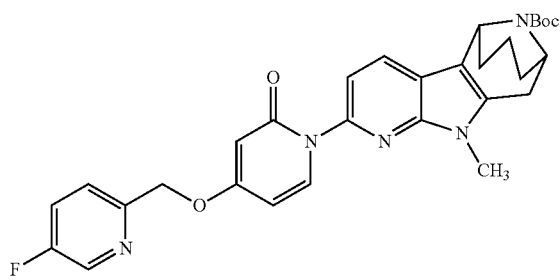

Chemical Formula: C₃₀H₃₂FN₅O₄
Exact Mass: 545.24
Molecular Weight: 545.60 tert-Butyl 2-bromo-11-methyl-5,6,7,8,9,10-hexahydro-5,9-imino-11H-cycloocta[4,5]pyrrolo[2,3-b]pyridine-12-carboxylate (150 mg, 0369 mmol) and 4-((5-fluoropyridin-2-yl)methoxy)pyridin-2(1H)-one (73 mg, 0.33 mmol) were reacted following the procedure for Example 2 (step c) to provide the title compound (106 mg, 52%) as a yellow oil: ESI MS m/z 546 [M+H]⁺.

e) 4-((5-Fluoropyridin-2-yl)methoxy)-1-(11-methyl-5,6,7,8,9,10-hexahydro-5,9-imino-11H-cycloocta[4,5]pyrrolo[2,3-b]pyridin-2-yl)pyridin-2(1H)-one hydrochloride

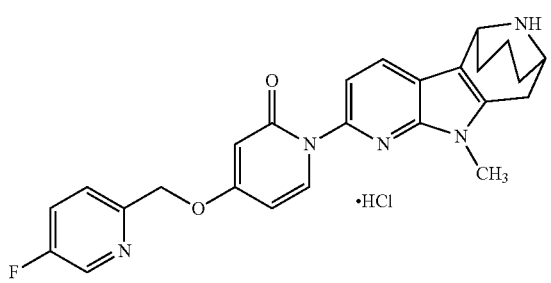

Chemical Formula: C₂₅H₂₅ClFN₅O₂
Exact Mass: 481.17
Molecular Weight: 481.95 tert-Butyl 2-(4-((5-fluoropyridin-2-yl)methoxy)-2-oxopyridin-1(2H)-yl)-11-methyl-5,6,7,8,9,10-hexahydro-5,9-imino-11H-cycloocta[4,5]pyrrolo[2,3-b]pyridine-12-carboxylate (106 mg, 0.194 mmol) was reacted following the procedure for Example 2 (step d) to provide the title compound (64 mg, 69%) as a white solid: mp 170-180° C. deliquesc; ¹H NMR (300 MHz, DMSO-d₆) δ 9.61 (d, J=11.3 Hz, 1H), 9.13 (d, J=10.7 Hz, 1H), 8.63 (d, J=2.8 Hz, 1H), 8.09 (d, J=8.3 Hz, 1H), 7.86-7.79 (m, 2H), 7.68-7.63 (dd, J=8.6, 4.5 Hz, 1H), 7.33 (d, J=8.2 Hz, 1H), 6.22-6.18 (dd, J=7.7, 2.6 Hz, 1H), 6.00 (d, J=2.6 Hz, 1H), 5.23 (s, 2H), 5.03 (s, 1H), 4.11-3.96 (m, 1H), 3.73 (s, 3H), 3.49-3.39 (dd, J=18.3, 7.5 Hz, 1H), 3.16 (d, J=18.2 Hz, 1H), 2.16-1.94 (m, 2H), 1.82 (d, J=13.9 Hz, 1H), 1.72 (d, J=13.9 Hz, 1H), 1.49-1.45 (m, 1H), 1.34-1.25 (m, 1H); ESI MS m/z 446 [M+H]⁺; HPLC (Method B)>99% (AUC), t_R=11.7 min.

Example 41

Preparation of 4-(Benzyloxy)-1-(11-methyl-5,6,7,8,9,10-hexahydro-5,9-imino-11H-cycloocta[4,5]pyrrolo[2,3-b]pyridin-2-yl)pyridin-2(1H)-one hydrochloride a) tert-Butyl 2-(4-(benzyloxy)-2-oxopyridin-1(2H)-yl)-11-methyl-5,6,7,8,9,10-hexahydro-5,9-imino-11H-cycloocta[4,5]pyrrolo[2,3-b]pyridine-12-carboxylate

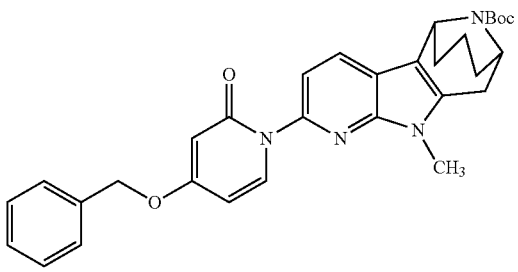

Chemical Formula: C₃₁H₃₄N₄O₄
Exact Mass: 526.26
Molecular Weight: 526.63 tert-Butyl 2-bromo-11-methyl-5,6,7,8,9,10-hexahydro-5,9-imino-11H-cycloocta[4,5]pyrrolo[2,3-b]pyridine-12-carboxylate (150 mg, 0.369 mmol) and 4-(benzyloxy)pyridin-2(1H)-one (67 mg, 0.33 mmol) were reacted following the procedure for Example 2 (step c) to provide the title compound (90 mg, 43%) as a yellow oil: ESI MS m/z 527 [M+H]⁺.

b) 4-(Benzyloxy)-1-(11-methyl-5,6,7,8,9,10-hexahydro-5,9-imino-11H-cycloocta[4,5]pyrrolo[2,3-b]pyridin-2-yl)pyridin-2(1H)-one hydrochloride

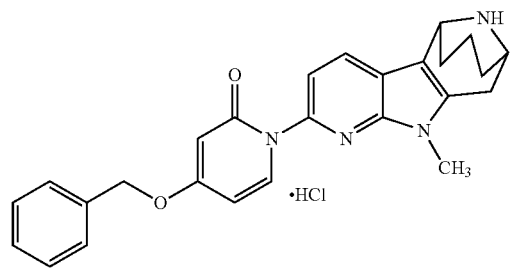

Chemical Formula: C₂₆H₂₇ClN₄O₂
Exact Mass: 462.18
Molecular Weight: 462.97 tert-Butyl 2-(4-(benzyloxy)-2-oxopyridin-1(2H)-yl)-11-methyl-5,6,7,8,9,10-hexahydro-5,9-imino-11H-cycloocta[4,5]pyrrolo[2,3-b]pyridine-12-carboxylate (90 mg, 0171 mmol) was reacted following the procedure for Example 2 (step d) to provide the title compound (60 mg, 76%) as a white solid: mp 191-206° C.; ¹H NMR (300 MHz, DMSO-d₆) δ

9.52 (d, J=10.6 Hz, 1H), 9.10 (d, J=10.5 Hz, 1H), 8.09 (d, J=8.3 Hz, 1H), 7.82 (d, J=7.7 Hz, 1H), 7.49 (m, 6H), 6.19-6.15 (dd, J=7.6, 2.7 Hz, 1H), 6.00 (dd, J=2.7 Hz, 1H), 5.17 (s, 2H), 5.06 (s, 1H), 4.18-4.00 (m, 1H), 3.73 (s, 3H), 3.44-3.36 (dd, J=18.3, 7.4 Hz, 1H), 3.09 (d, J=18.1 Hz, 1H), 2.15-2.00 (m, 2H), 1.83 (d, J=13.3 Hz, 1H), 1.72 (d, J=13.4 Hz, 1H), 1.49-1.45 (m, 1H), 1.34-1.14 (m, 1H); ESI MS m/z 427 [M+H]$^+$; HPLC (Method B)>99% (AUC), $t_R$=13.1 min.

Example 42

Preparation of 4-(Benzyloxy)-1-(10,11-dimethyl-5,6,7,8,9,10-hexahydro-5,8-iminocyclohepta[4,5]pyrrolo[2,3-b]pyridin-2-yl)pyridin-2(1H)-one hydrochloride a) 2-bromo-10,11-dimethyl-5,6,7,8,9,10-hexahydro-5,8-iminocyclohepta[4,5]pyrrolo[2,3-b]pyridine

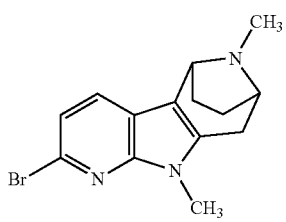

Chemical Formula: C$_{14}$H$_{16}$BrN$_3$
Exact Mass: 305.05
Molecular Weight: 306.20

2-Bromo-6-(1-methylhydrazinyl)pyridine (202 mg, 1.00 mmol), 8-methyl-8-azabicyclo[3.2.1]octan-3-one (139 mg, 1.00 mmol) and p-toluenesulphonic acid (19.0 mg, 100 μmol) in toluene (10 mL) were reacted following the procedure for Example 39 (step c). The result crude product was then reacted with polyphosphoric acid (3.23 g) following the procedure for Example 39 (step d) to give the title compound (33.0 mg, 11%) as brown solid: $^1$H NMR (500 MHz, CDCl$_3$) δ 7.58 (d, J=8.0 Hz, 1H), 7.67 (d, J=8.5 Hz, 1H), 4.15 (d, J=5.0 Hz, 1H), 3.68 (s, 3H), 3.67-3.64 (m, 1H), 3.45-3.43 (m, 1H), 3.19-3.15 (dd, J=16.0, 4.5 Hz, 1H), 2.38 (s, 3H), 2.22-2.17 (dd, J=17.5, 1.5 Hz, 1H), 2.13-2.10 (m, 1H), 1.90-1.86 (m, 1H), 1.62-1.56 (m, 1H).

b) 4-(Benzyloxy)-1-(10,11-dimethyl-5,6,7,8,9,10-hexahydro-5,8-iminocyclohepta[4,5]pyrrolo[2,3-b]pyridin-2-yl)pyridin-2(1H)-one hydrochloride

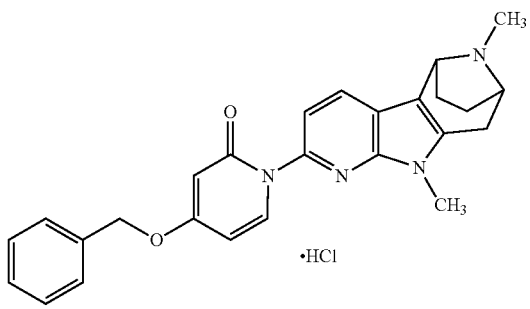

Chemical Formula: C$_{26}$H$_{27}$ClN$_4$O$_2$
Exact Mass: 462.18
Molecular Weight: 462.97

2-Bromo-10,11-dimethyl-5,6,7,8,9,10-hexahydro-5,8-iminocyclohepta[4,5]pyrrolo[2,3-b]pyridine (33.0 mg, 100 μmol) and 4-(benzyloxy)pyridin-2(1H)-one (26.0 mg, 0.130 mmol), CuI (28.5 mg, 0.150 mmol), 8-hydroxyquinoline (2.90 mg, 20.0 μmol) and Cs$_2$CO$_3$ (65.0 mg, 20.0 μmol) in DMSO (2 mL) were reacted following the procedure for Example 2 (steps c and d) to provide the free base of the title compound (8.00 mg) as a yellow solid. 1.25 M HCl in methanol (0.5 mL, 0.6 mmol) was added to a solution of the solid in MeOH (1 mL). Concentration under vacuum provided the title compound (7.70 mg, 17%) as a yellow solid. Free Base: $^1$H NMR (500 MHz, CDCl$_3$) δ 7.85 (d, J=8.0 Hz, 1H), 7.67 (d, J=8.0 Hz, 1H), 7.48 (d, J=8.5 Hz, 1H), 7.43-7.35 (m, 5H), 6.13-6.10 (dd, J=8.0, 2.5 Hz, 1H), 6.06 (d, J=2.0 Hz, 1H), 5.07 (s, 2H), 4.70-4.50 (m, 1H), 4.10-4.00 (m, 1H), 3.73 (s, 3H), 3.50-3.30 (m, 1H), 2.72-2.57 (m, 6H), 2.10-2.06 (m, 1H), 1.77-1.73 (m, 1H); HPLC (Method C) 96.6% (AUC), $t_R$=14.3 min. HCl salt: $^1$H NMR (500 MHz, CD$_3$OD) δ 8.07 (d, J=8.0 Hz, 1H), 7.79 (dd, J=8.0, 3.5 Hz, 1H), 7.47 (d, J=7.0 Hz, 2H), 7.40-7.39 (m, 2H), 7.34-7.36 (m, 2H), 6.32 (dd, J=7.5, 2.5 Hz, 1H), 6.11 (d, J=2.5 Hz, 1H), 5.19 (s, 2H), 5.18-5.10 (m, 1H), 4.39-4.35 (m, 1H), 3.79 (s, 1H), 3.76 (s, 2H), 3.63-3.50 (m, 1H), 3.18-3.15 (m, 1H), 2.99 (s, 2H), 2.86 (s, 1H), 2.66-2.50 (m, 2H), 2.35-2.29 (m, 1H), 2.11-2.06 (m, 1H); ESI MS m/z 427 [M+H]$^+$; HPLC (Method A) 95.8% (AUC), $t_R$=12.9 min.

Example 43

Preparation of 4-((5-Fluoropyridin-2-yl)methoxy)-1-(10-methyl-5,6,7,8,9,10-hexahydro-5,8-iminocyclohepta[4,5]pyrrolo[2,3-b]pyridin-2-yl)pyridin-2(1H)-one hydrochloride a) tert-Butyl 2-bromo-10-methyl-5,6,7,8,9,10-hexahydro-5,8-iminocyclohepta[4,5]pyrrolo[2,3-b]pyridine-11-carboxylate

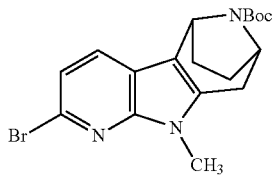

Chemical Formula: $C_{18}H_{22}BrN_3O_2$
Exact Mass: 391.09
Molecular Weight: 392.29

To a solution of 2-bromo-10-methyl-5,6,7,8,9,10-hexahydro-5,8-iminocyclohepta[4,5]pyrrolo[2,3-b]pyridine (283 mg, 0.970 mol) in methylene chloride (10 mL) was added $Boc_2O$ (209 mg, 0.970 mmol), DMAP (59.0 mg, 0.40 mmol) and triethylamine (400 µL, 2.90 mmol), and the reaction progressed at room temperature for 18 h. The mixture was washed with water (10 mL) and saturated aqueous sodium bicarbonate (2×10 mL). The organic phase was removed, dried over $Na_2SO_4$, filtered and concentrated to dryness. The resulting mixture was purified by flash column chromatography (silica gel, hexanes/EtOAc, 100:0 to 0:100) to give the title compound (163 mg, 43%) as a yellow oil: $^1$H NMR (500 MHz, $CDCl_3$) δ 7.62 (d, J=8.0 Hz, 1H), 7.16 (d, J=6.5 Hz, 1H), 5.30-5.00 (m, 1H), 4.80-4.60 (m, 1H), 3.67 (s, 3H), 3.52-3.30 (m, 1H), 2.51-2.47 (d, J=16.0 Hz, 1H), 2.20-2.14 (m, 1H), 2.10-2.00 (m, 1H), 1.93-1.89 (m, 1H), 1.67-1.65 (m, 1H), 1.43-1.34 (m, 9H).

b) 4-((5-Fluoropyridin-2-yl)methoxy)-1-(10-methyl-5,6,7,8,9,10-hexahydro-5,8-iminocyclohepta[4,5]pyrrolo[2,3-b]pyridin-2-yl)pyridin-2(1H)-one hydrochloride

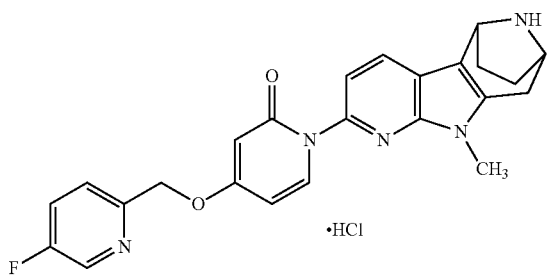

Chemical Formula: $C_{24}H_{23}ClFN_5O_2$
Exact Mass: 467.15
Molecular Weight: 467.92 tert-Butyl 2-bromo-10-methyl-5,6,7,8,9,10-hexahydro-5,8-iminocyclohepta[4,5]pyrrolo[2,3-b]pyridine-11-carboxylate (80 mg, 200 µmol), 4-((5-fluoropyridin-2-yl)methoxy)pyridin-2(1H)-one (53 mg, 240 µmol), CuI (46 mg, 240 µmol), 8-hydroxyquinoline (5.8 mg, 40 µmol) and $Cs_2CO_3$ (130 mg, 400 µmol) in DMSO (2 mL) were reacted following the procedure for Example 2 (step c) to provide tert-butyl 2-(4-((5-fluoropyridin-2-yl)methoxy)-2-oxopyridin-1(2H)-yl)-10-methyl-5,6,7,8,9,10-hexahydro-5,8-iminocyclohepta[4,5]pyrrolo[2,3-b]pyridine-11-carboxylate (37 mg) as a yellow solid.

tert-Butyl 2-(4-((5-fluoropyridin-2-yl)methoxy)-2-oxopyridin-1(2H)-yl)-10-methyl-5,6,7,8,9,10-hexahydro-5,8-iminocyclohepta[4,5]pyrrolo[2,3-b]pyridine-11-carboxylate (37.0 mg, 69.8 µmol) was deprotected and converted to the hydrochloride salt according to the procedure for Example 2 (step d) to provide the title compound (31.0 mg, 33%) as an off-white solid: $^1$H NMR (500 MHz, $CD_3OD$) δ 8.54 (d, J=2.5 Hz, 1H), 8.10 (d, J=8.5 Hz, 1H), 7.81 (d, J=7.5 Hz, 1H), 7.77-7.73 (m, 1H), 7.71-7.67 (m, 1H), 7.36 (d, J=8.5 Hz, 1H), 6.37 (dd, J=7.5, 2.5 Hz, 1H), 6.13 (d, J=2.5 Hz, 1H), 5.29 (s, 2H), 5.25 (d, J=5.0 Hz, 1H), 4.58-4.55 (m, 1H), 3.76 (s, 3H), 3.56-3.51 (dd, J=18.0, 5.0 Hz, 1H), 3.15-3.10 (dd, J=17.5, 1.0 Hz, 1H), 2.51-2.29 (m, 3H), 2.05-2.01 (m, 1H); ESI MS m/z 432 [M+H]$^+$; HPLC (Method A) 98.0% (AUC), $t_R$=11.4 min.

Example 44

Preparation of 1-(10-Methyl-5,6,7,8,9,10-hexahydro-5,8-iminocyclohepta[4,5]pyrrolo[2,3-b]pyridin-2-yl)-4-(6-(trifluoromethyl)pyridin-3-yl)pyridin-2(1H)-one hydrochloride a) tert-Butyl 10-methyl-2-(2-oxo-4-(6-(trifluoromethyl)pyridin-3-yl)pyridin-1(2H)-yl)-5,6,7,8,9,10-hexahydro-5,8-iminocyclohepta[4,5]pyrrolo[2,3-b]pyridine-11-carboxylate

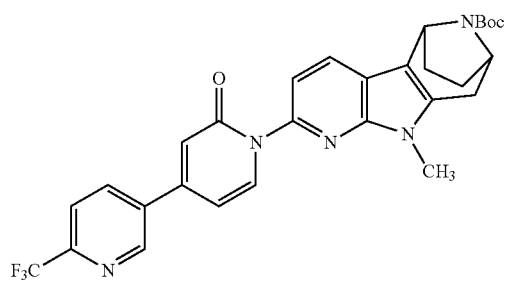

Chemical Formula: $C_{29}H_{28}F_3N_5O_3$
Exact Mass: 551.21
Molecular Weight: 551.56 tert-Butyl 2-bromo-10-methyl-5,6,7,8,9,10-hexahydro-5,8-iminocyclohepta[4,5]pyrrolo[2,3-b]pyridine-11-carboxylate (278 mg, 0.700 mmol), 4-(6-(trifluoromethyl)pyridin-3-yl)pyridin-2(1H)-one (169 mg, 0.700 mmol), CuI (202 mg, 1.10 mmol), 8-hydroxyquinoline (20.0 mg, 0.140 mmol) and $Cs_2CO_3$ (462 mg, 1.40 mmol) in DMSO (10 mL) were reacted following the procedure for Example 2 (step c) to provide the title compound (60.4 mg, 15%) as a yellow solid: $^1$H NMR (500 MHz, $CDCl_3$) δ 8.99 (d, J=1.5 Hz, 1H), 8.10 (dd, J=8.5, 2.0 Hz, 1H), 7.99-7.91 (m, 2H), 7.82 (d, J=8.0 Hz, 1H), 7.53-7.46 (m, 1H), 6.92 (d, J=1.5 Hz, 1H), 6.54 (d, J=7.0 Hz, 1H), 5.40-5.10 (m, 1H), 4.80-4.60 (m, 1H), 3.70 (s, 3H), 3.60-3.30 (m, 1H), 2.57-2.53 (d, J=16.5 Hz, 1H), 2.35-2.33 (m, 1H), 2.26-2.18 (m, 1H), 1.97-1.93 (m, 1H), 1.70-1.60 (m, 1H), 1.50-1.30 (m, 9H).

b) 1-(10-Methyl-5,6,7,8,9,10-hexahydro-5,8-iminocyclohepta[4,5]pyrrolo[2,3-b]pyridin-2-yl)-4-(6-(trifluoromethyl)pyridin-3-yl)pyridin-2(1H)-one hydrochloride

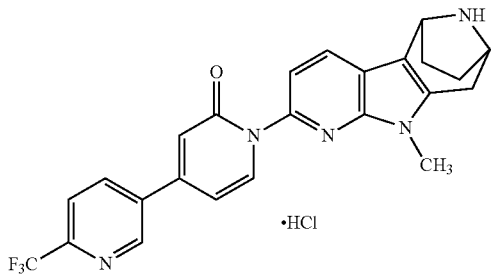

Chemical Formula: $C_{24}H_{21}ClF_3N_5O$
Exact Mass: 487.14
Molecular Weight: 487.90 tert-Butyl 10-methyl-2-(2-oxo-4-(6-(trifluoromethyl)pyridin-3-yl)pyridin-1(2H)-yl)-5,6,7,8,9,10-hexahydro-5,8-iminocyclohepta[4,5]pyrrolo[2,3-b]pyridine-11-carboxylate (60.0 mg, 0.100 mmol) was deprotected and converted to the hydrochloride salt according to the procedure for Example 2 (step d) to provide the title compound (27.0 mg, 56%) as a yellow solid: $^1$H NMR (500 MHz, CD$_3$OD) δ 9.11 (s, 1H), 8.42 (d, J=8.0 Hz, 1H), 8.15 (d, J=8.5 Hz, 1H), 8.06 (d, J=7.0 Hz, 1H), 7.98 (d, J=8.5 Hz, 1H), 7.49 (d, J=8.0 Hz, 1H), 7.03 (d, J=1.5 Hz, 1H), 6.92 (dd, J=7.5, 2.0 Hz, 1H), 5.28 (d, J=5.0 Hz, 1H), 4.59 (m, 1H), 3.79 (s, 3H), 3.58-3.53 (dd, J=17.5, 5.0 Hz, 1H), 3.17-3.13 (d, J=17.5 Hz, 1H), 2.52-2.31 (m, 3H), 2.06-2.03 (m, 1H); ESI MS m/z 452 [M+H]$^+$; HPLC (Method A) 96.3% (AUC), $t_R$=12.6 min.

Example 45

Preparation of 4-(2,4-Difluorobenzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride a) 4-(2,4-Difluorobenzyloxy)pyridin-2(1H)-one (CAS Registry Number 586373-58-2) (WO 2003/068230 to Devadas et al., which is hereby incorporated by reference in its entirety)

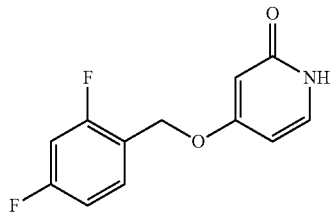

Chemical Formula: $C_{12}H_9F_2NO_2$
Exact Mass: 237.06
Molecular Weight: 237.20

A suspension of (2,4-difluorophenyl)methanol (4.86 g, 33.7 mmol), 2-chloro-4-iodopyridine (7.35 g, 30.7 mmol), Cs$_2$CO$_3$ (14.3 g, 43.8 mmol), CuI (5.83 g, 30.7 mmol) and 1,10-phenanthroline (1.11 g, 6.14 mmol) in toluene (20 mL) was degassed by bubbling N$_2$ through the suspension for 15 min. The suspension was put under N$_2$, and heated at 105° C. for 18 h. The suspension was cooled, EtOAc (50 mL) was added, and the resulting suspension was passed through a plug of SiO$_2$. The resulting solution was concentrated under reduced pressure. Flash chromatography on silica gel (hexanes/(1:1 EtOAc/hexanes), 100:0 to 0:100) afforded a white solid. A suspension of the white solid and NH$_4$OAc (8.21 g, 107 mmol) in 1:1 HCO$_2$H/H$_2$O (40 mL) was heated at reflux with stirring for 4 d. The solution was cooled and concentrated under reduced pressure. The resulting residue was made basic with saturated NaHCO$_3$ solution, and the resulting suspension was filtered. The solid was washed with H$_2$O and dried under reduced pressure to afford 3.16 g (44%) of the title compound as a white solid: $^1$H NMR (300 MHz, DMSO-d$_6$) δ 11.14 (br s, 1H), 7.62 (br dd, J=15.3, 8.7 Hz, 1H), 7.33 (ddd, J=10.5, 10.5, 2.4 Hz, 1H), 7.25 (d, J=7.2 Hz, 1H), 7.12 (ddd, J=8.4, 8.4, 1.8 Hz, 1H), 5.91-5.82 (m, 2H), 5.06 (s, 2H).

b) tert-Butyl 2-(4-(2,4-difluorobenzyloxy)-2-oxopyridin-1(2H)-yl)-10-methyl-5,6,7,8,9,10-hexahydro-5,8-iminocyclohepta[4,5]pyrrolo[2,3-b]pyridine-11-carboxylate

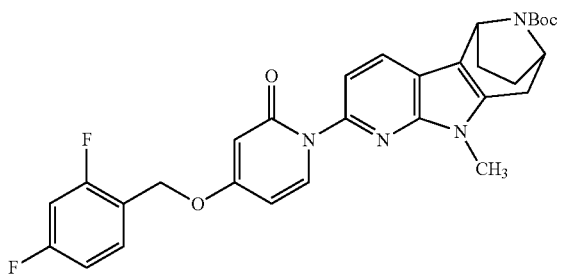

Chemical Formula: $C_{30}H_{30}F_2N_4O_4$
Exact Mass: 548.22
Molecular Weight: 548.58 tert-Butyl 2-bromo-10-methyl-5,6,7,8,9,10-hexahydro-5,8-iminocyclohepta[4,5]pyrrolo[2,3-b]pyridine-11-carboxylate (130 mg, 0.330 mmol), 4-(2,4-difluorobenzyloxy)pyridin-2(1H)-one (78.0 mg, 0.330 mmol), CuI (94.0 mg, 0.500 mmol), 8-hydroxyquinoline (9.50 mg, 0.060 mmol) and Cs$_2$CO$_3$ (215 mg, 0.660 mmol) in DMSO (8 mL) were reacted following the procedure for Example 2 (step c) to provide the title compound (46.5 mg, 26%) as an off-white solid: $^1$H NMR (500 MHz, CDCl$_3$) δ 7.87 (d, J=8.0 Hz, 1H), 7.80-7.60 (m, 1H), 7.47-7.42 (m, 2H), 6.95-6.86 (m, 2H), 6.07-6.05 (m, 2H), 5.30-5.10 (m, 1H), 5.07 (s, 2 H), 4.80-4.60

(m, 1H), 3.67 (s, 3H), 3.55-3.36 (m, 1H), 2.54-2.51 (d, J=16.0 Hz, 1H), 2.40-2.30 (m, 1H), 2.24-2.16 (m, 1H), 1.95-1.91 (m, 1H), 1.70-1.60 (m, 1H), 1.50-1.30 (m, 9H).

c) 4-(2,4-Difluorobenzyloxy)-1-(10-methyl-5,6,7,8, 9,10-hexahydro-5,8-iminocyclohepta[4,5]pyrrolo[2, 3-b]pyridin-2-yl)pyridin-2(1H)-one hydrochloride

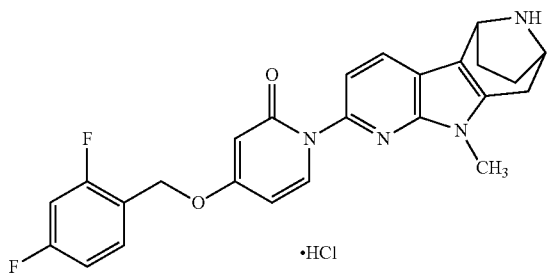

Chemical Formula: $C_{25}H_{23}ClF_2N_4O_2$
Exact Mass: 484.15
Molecular Weight: 484.93 tert-Butyl 2-(4-(2,4-difluorobenzyloxy)-2-oxopyridin-1 (2H)-yl)-10-methyl-5,6,7,8,9,10-hexahydro-5,8-iminocyclohepta[4,5]pyrrolo[2,3-b]pyridine-11-carboxylate (46 mg, 0.080 mmol) was deprotected and converted to the hydrochloride salt according to the procedure for Example 2 (step d) to provide the title compound (35.0 mg, 90%) as an off-white solid: $^1$H NMR (500 MHz, CD$_3$OD) δ 8.10 (d, J=8.5 Hz, 1H), 7.79 (d, J=7.5 Hz, 1H), 7.59 (m, 1H), 7.38 (d, J=8.5 Hz, 1H), 7.07-7.02 (m, 2H), 6.29 (dd, J=7.5, 2.5 Hz, 1H), 6.15 (d, J=2.5 Hz, 1H), 5.40-5.25 (m, 1H), 5.20 (s, 2H), 4.70-4.50 (m, 1H), 3.76 (s, 3H), 3.55-3.51 (dd, J=17.5, 4.5 Hz, 1H), 3.15-3.11 (d, J=18.0 Hz, 1H), 2.51-2.29 (m, 3H), 2.05-1.99 (m, 1H); ESI MS m/z 449 [M+H]$^+$; HPLC (Method A) 97.6% (AUC), $t_R$=13.2 min.

Example 46

Preparation of 4-(4-Chlorophenethyl)-1-(10-methyl-5,6,7,8,9,10-hexahydro-5,8-iminocyclohepta[4,5] pyrrolo[2,3-b]pyridin-2-yl)-piperazin-2-one dihydrochloride a) 4-(4-Chlorophenethyl)piperazin-2-one

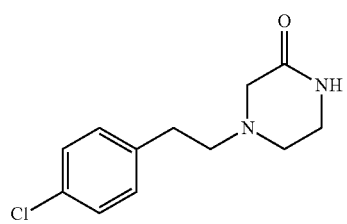

Chemical Formula: $C_{12}H_{15}ClN_2O$
Exact Mass: 238.09
Molecular Weight: 238.71

Piperazinone (1.04 g, 10.4 mmol), 1-chloro-4-(2-chloroethyl)benzene (2.28 g, 10.4 mmol) and K$_2$CO$_3$ (1.72 g, 12.4 mmol) were combined in DMSO (12 mL) and heated to 85° C. for 2 h. The mixture was partitioned between H$_2$O (20 mL) and CH$_2$Cl$_2$ (20 mL), and the organic layer was removed. The aqueous layer was extracted with CH$_2$Cl$_2$ (3×20 mL), the combined organics were concentrated, and the residue was dissolved in 2 N HCl (50 mL). This acidic mixture was washed with CH$_2$Cl$_2$ (3×20 mL) and then made basic with 6 N NaOH. The basic mixture was extracted with CH$_2$Cl$_2$ (3×20 mL), and the extracts were combined, dried and concentrated to provide the title compound (1.51 g, 60%) as an orange solid: $^1$H NMR (500 MHz, DMSO-d$_6$) δ 7.72 (s, 1H), 7.32 (d, J=8.8 Hz, 2H), 7.26 (d, J=8.8 Hz, 2H), 3.14-3.10 (m, 2H), 2.96 (s, 2H), 2.74 (t, J=6.6 Hz, 2H), 2.62-2.53 (m, 4H).

b) 4-(4-Chlorophenethyl)-1-(10-methyl-5,6,7,8,9,10-hexahydro-5,8-iminocyclohepta[4,5]pyrrolo[2,3-b] pyridin-2-yl)-piperazin-2-one dihydrochloride

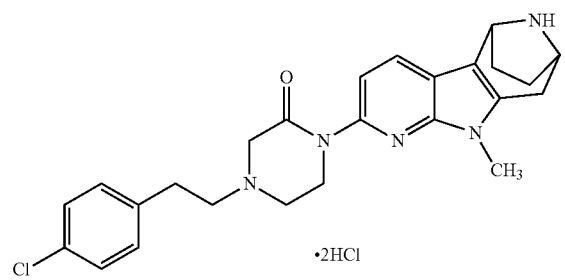

Chemical Formula: $C_{25}H_{30}Cl_3N_5O$
Exact Mass: 521.15
Molecular Weight: 522.90 tert-Butyl 2-bromo-10-methyl-5,6,7,8,9,10-hexahydro-5, 8-iminocyclohepta[4,5]pyrrolo[2,3-b]pyridine-11-carboxylate (214 mg, 0.550 mmol), 4-(4-chlorophenethyl)piperazin-2-one (131 mg, 0.550 mmol), CuI (157 mg, 0.530 mmol), trans-N,N'-dimethylcyclohexane-1,2-diamine (17.0 µL, 0.110 mmol) and Cs$_2$CO$_3$ (358 mg, 1.10 mmol) in dioxane (5 mL) were reacted following the procedure for Example 2 (step c) to give tert-butyl 2-(4-(4-chlorophenethyl)-2-oxopiperazin-1-yl)-10-methyl-5,6,7,8,9,10-hexahydro-5,8-iminocyclohepta[4,5]pyrrolo[2,3-b]pyridine-11-carboxylate (83.3 mg) as a yellow oil.

tert-Butyl 2-(4-(4-chlorophenethyl)-2-oxopiperazin-1-yl)-10-methyl-5,6,7,8,9,10-hexahydro-5,8-iminocyclohepta[4,5]pyrrolo[2,3-b]pyridine-11-carboxylate (83.3 mg, 0.150 mmol) was deprotected and converted to the hydrochloride salt according to the procedure for Example 2 (step d) to provide the title compound (30 mg, 11%) as an off-white solid: $^1$H NMR (500 MHz, CD$_3$OD) δ 8.03 (d, J=8.5 Hz, 1H), 7.57 (d, J=8.0 Hz, 1H), 7.40-7.34 (m, 4H), 5.22 (d, J=5.5 Hz, 1H), 4.57-4.54 (m, 1H), 4.40-4.20 (m, 4H), 4.00-3.80 (m, 2H), 3.74 (s, 3H), 3.60 (t, J=8.5 Hz, 2H), 3.54-3.50 (dd, J=17.5, 4.5 Hz, 1H), 3.20-3.16 (m, 2H), 3.12-3.08 (d, J=17.5

Hz, 1H), 2.50-2.26 (m, 3H), 2.03-2.00 (m, 1H); ESI MS m/z 450 [M+H]⁺; HPLC (Method A) 98.7% (AUC), $t_R$=11.0 min.

Example 47

Preparation of 4-(4-Chloro-2-fluorobenzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride a) 4-(4-Chloro-2-fluorobenzyloxy)pyridin-2(1H)-one

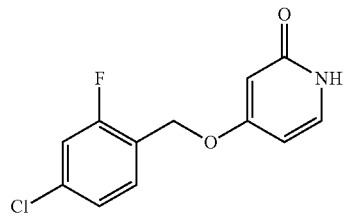

Chemical Formula: $C_{12}H_9ClFNO_2$
Exact Mass: 253.03
Molecular Weight: 253.66

A suspension of (4-chloro-2-fluorophenyl)methanol (3.24 g, 20.1 mmol), 2-chloro-4-iodopyridine (4.40 g, 18.3 mmol), $Cs_2CO_3$ (7.76 g, 23.8 mmol), CuI (3.48 g, 18.7 mmol) and 1,10-phenanthroline (659 mg, 3.66 mmol) in toluene (20 mL) was degassed by bubbling $N_2$ through the suspension for 15 min. The suspension was put under $N_2$ and heated at 105° C. for 18 h. The suspension was cooled, 9:0.9:0.1 $CH_2Cl_2$/MeOH/NH$_4$OH (10 mL) was added, and the resulting suspension was passed through a plug of $SiO_2$. The resulting solution was concentrated under reduced pressure. Flash chromatography on silica gel (hexanes/(1:1 EtOAc/hexanes), 100:0 to 0:100) afforded a white solid. A suspension of the white solid and NH$_4$OAc (2.66 g, 34.6 mmol) in 1:1 HCO$_2$H/H$_2$O (20 mL) was heated at reflux with stirring for 4 d. The solution was cooled and concentrated under reduced pressure. The resulting residue was made basic with saturated NaHCO$_3$ solution, and the resulting suspension was filtered. The solid was washed with H$_2$O and CH$_2$Cl$_2$, and dried under reduced pressure to afford 1.28 g (28%) of the title compound as a white solid: ¹H NMR (300 MHz, DMSO-$d_6$) δ 11.14 (br s, 1H), 7.59 (dd, J=8.1, 8.1 Hz, 1H), 7.52 (dd, J=10.2, 1.8 Hz, 1H), 7.36 (dd, J=8.1, 1.8 Hz, 1H), 7.25 (d, J=7.2 Hz, 1H), 5.89 (d, J=7.2, 2.4 Hz, 1H), 5.83 (d, J=2.4 Hz, 1H), 5.06 (s, 2H).

b) tert-Butyl 2-(4-(4-chloro-2-fluorobenzyloxy)-2-oxopyridin-1(2H)-yl)-10-methyl-5,6,7,8,9,10-hexahydro-5,8-iminocyclohepta[4,5]pyrrolo[2,3-b]pyridine-11-carboxylate

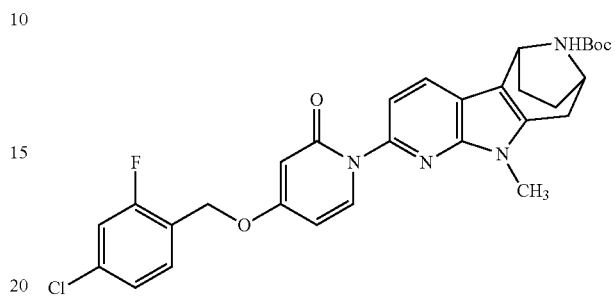

Chemical Formula: $C_{30}H_{30}ClFN_4O_4$
Exact Mass: 564.19
Molecular Weight: 565.04 tert-Butyl 2-bromo-10-methyl-5,6,7,8,9,10-hexahydro-5,8-iminocyclohepta[4,5]pyrrolo[2,3-b]pyridine-11-carboxylate (220 mg, 0.560 mmol), 4-(4-chloro-2-fluorobenzyloxy)pyridin-2(1H)-one (142 mg, 0.560 mmol), CuI (160 mg, 0.84 mmol), 8-hydroxyquinoline (16 mg, 0.11 mmol) and $Cs_2CO_3$ (365 mg, 1.10 mmol) in DMSO (8 mL) were reacted following the procedure for Example 2 (step c) to provide the title compound (85.0 mg, 27%) as a yellow solid: ¹H NMR (500 MHz, CDCl$_3$) δ 7.88 (d, J=8.5 Hz, 1H), 7.80-7.60 (m, 1H), 7.43-7.39 (m, 2H), 7.21-7.14 (m, 2H), 6.08-6.05 (m, 2H), 5.30-5.10 (m, 1H), 5.08 (s, 2H), 4.80-4.60 (m, 1H), 3.67 (s, 3H), 3.55-3.36 (m, 1H), 2.54-2.51 (d, J=16.5 Hz, 1H), 2.40-2.30 (m, 1H), 2.30-2.10 (m, 1H), 1.95-1.91 (m, 1H), 1.70-1.60 (m, 1H), 1.50-1.30 (m, 9H).

c) 4-(4-Chloro-2-fluorobenzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride

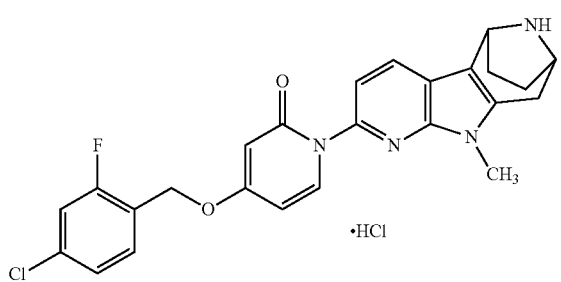

Chemical Formula: $C_{25}H_{23}Cl_2FN_4O_2$
Exact Mass: 500.12
Molecular Weight: 501.38 tert-Butyl 2-(4-(4-chloro-2-fluorobenzyloxy)-2-oxopyridin-1(2H)-yl)-10-methyl-5,6,7,8,9,10-hexahydro-5,8-iminocyclohepta[4,5]pyrrolo[2,3-b]pyridine-11-carboxylate (85.0 mg, 0.150 mmol) was deprotected and converted to the hydrochloride salt according to the procedure for Example 2

(step d) to provide the title compound (48.0 mg, 64%) as an off-white solid: $^1$H NMR (500 MHz, CD$_3$OD) δ 8.10 (d, J=8.5 Hz, 1H), 7.79 (d, J=8.0 Hz, 1H), 7.57-7.53 (m, 1H), 7.38 (d, J=8.0 Hz, 1H), 7.32-7.28 (m, 2H), 6.30 (dd, J=8.0, 3.0 Hz, 1H), 6.14 (d, J=2.5 Hz, 1H), 5.26 (d, J=5.5 Hz, 1H), 5.22 (s, 2H), 4.58-4.55 (m, 1H), 3.76 (s, 3H), 3.55-3.51 (dd, J=17.5, 4.5 Hz, 1H), 3.15-3.11 (d, J=17.5 Hz, 1H), 2.51-2.29 (m, 3H), 2.05-2.01 (m, 1H); ESI MS m/z 465 [M+H]$^+$; HPLC (Method A) 97.7% (AUC), $t_R$=13.9 min.

Example 48

Preparation of 4-(2,4-Dichlorobenzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride a) 4-(2,4-Dichlorobenzyloxy)pyridin-2(1H)-one (CAS Registry Number 1182243-20-4) (WO 2007/043835 to Kim et al., which is hereby incorporated by reference in its entirety)

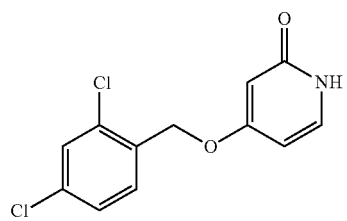

Chemical Formula: C$_{12}$H$_9$Cl$_2$NO$_2$
Exact Mass: 269.00
Molecular Weight: 270.11

A suspension of (2,4-dichlorophenyl)methanol (4.10 g, 23.2 mmol), 2-chloro-4-iodopyridine (5.05 g, 21.1 mmol), Cs$_2$CO$_3$ (8.94 g, 27.4 mmol), CuI (4.01 g, 21.1 mmol) and 1,10-phenanthroline (760 mg, 4.22 mmol) in toluene (20 mL) was degassed by bubbling N$_2$ through the suspension for 15 min. The suspension was put under N$_2$, and heated at 105° C. for 18 h. The suspension was cooled, EtOAc (50 mL) was added, and the resulting suspension was passed through a plug of SiO$_2$. The resulting solution was concentrated under reduced pressure. Flash chromatography on silica gel (hexanes/(1:1 EtOAc/hexanes), 100:0 to 0:100) afforded a white solid. A suspension of the white solid and NH$_4$OAc (6.13 g, 79.5 mmol) in 1:1 HCO$_2$H/H$_2$O (40 mL) was heated at reflux with stirring for 4 d. The solution was cooled and concentrated under reduced pressure. The resulting residue was made basic with saturated NaHCO$_3$ solution and the resulting suspension was filtered. The solid was washed with H$_2$O and dried under reduced pressure. Flash chromatography on silica gel ((1:1 EtOAc/hexanes)/(9:0.9:0.1 CH$_2$Cl$_2$/MeOH/NH$_4$OH), 100:0 to 0:100) afforded 1.36 g (24%) of the title compound as a white solid: $^1$H NMR (300 MHz, DMSO-d$_6$) δ 11.16 (br s, 1H), 7.71 (d, J=2.1 Hz, 1H), 7.61 (d, J=8.1 Hz, 1H), 7.50 (dd, J=8.4, 2.1 Hz, 1H), 7.26 (d, J=7.2 Hz, 1H), 5.91 (dd, J=7.5, 2.7 Hz, 1H), 5.81 (d, J=2.4 Hz, 1H), 5.10 (s, 2H).

b) tert-Butyl 2-(4-(2,4-dichlorobenzyloxy)-2-oxopyridin-1(2H)-yl)-10-methyl-5,6,7,8,9,10-hexahydro-5,8-iminocyclohepta[4,5]pyrrolo[2,3-b]pyridine-11-carboxylate

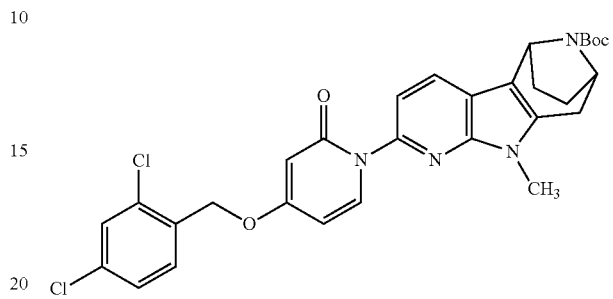

Chemical Formula: C$_{30}$H$_{30}$Cl$_2$N$_4$O$_4$
Exact Mass: 580.16
Molecular Weight: 581.49 tert-Butyl 2-bromo-10-methyl-5,6,7,8,9,10-hexahydro-5,8-iminocyclohepta[4,5]pyrrolo[2,3-b]pyridine-11-carboxylate (232 mg, 0.590 mmol), 4-(2,4-dichlorobenzyloxy)pyridin-2(1H)-one (159 mg, 0.590 mmol), CuI (168 mg, 0.880 mmol), 8-hydroxyquinoline (17.0 mg, 0.120 mmol) and Cs$_2$CO$_3$ (384 mg, 1.20 mmol) in DMSO (8 mL) were reacted following the procedure for Example 2 (step c) to provide the title compound (114 mg, 33%) as a yellow solid: $^1$H NMR (500 MHz, CDCl$_3$) δ 8.19 (d, J=8.5 Hz, 1H), 7.80-7.60 (m, 1H), 7.50-7.40 (m, 3H), 7.30 (d, J=7.0 Hz, 1H), 6.11 (d, J=7.5 Hz, 1H), 6.05 (s, 1H), 5.30-5.10 (m, 1H), 5.02 (s, 2H), 4.80-4.60 (m, 1H), 3.67 (s, 3H), 3.55-3.36 (m, 1H), 2.54-2.51 (d, J=16.5 Hz, 1H), 2.40-2.30 (m, 1H), 2.30-2.10 (m, 1H), 2.00-1.90 (m, 1H), 1.70-1.60 (m, 1H), 1.50-1.30 (m, 9H).

c) 4-(2,4-Dichlorobenzyloxy)-1-(10-methyl-5,6,7,8,9,10-hexahydro-5,8-iminocyclohepta[4,5]pyrrolo[2,3-b]pyridin-2-yl)pyridin-2(1H)-one hydrochloride

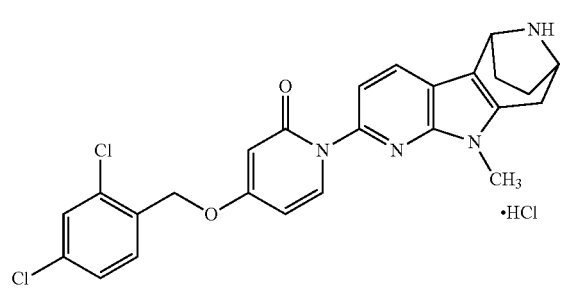

Chemical Formula: C$_{25}$H$_{23}$Cl$_3$N$_4$O$_2$
Exact Mass: 516.09
Molecular Weight: 517.83 tert-Butyl 2-(4-(2,4-dichlorobenzyloxy)-2-oxopyridin-1(2H)-yl)-10-methyl-5,6,7,8,9,10-hexahydro-5,8-iminocyclohepta[4,5]pyrrolo[2,3-b]pyridine-11-carboxylate (114 mg, 0.190 mmol) was deprotected and converted to the hydrochloride salt according to the procedure for Example 2 (step d) to provide the title compound (44.0 mg, 45%) as an off-white solid: $^1$H NMR (500 MHz, CD$_3$OD) δ 8.10 (d, J=8.0 Hz, 1H), 7.80 (d, J=7.5 Hz, 1H), 7.59-7.57 (m, 2H), 7.42 (dd, J=8.5, 2.0 Hz, 1H), 7.38 (d, J=8.0 Hz, 1H), 6.32 (dd, J=8.0, 2.5 Hz, 1H), 6.12 (d, J=2.5 Hz, 1H), 5.25 (m, 3H), 4.58-4.56 (m, 1H), 3.76 (s, 3H), 3.55-3.51 (dd, J=18.0, 4.5 Hz, 1H), 3.15-3.11 (d, J=17.5 Hz, 1H), 2.51-2.29 (m, 3H), 2.05-1.99 (m, 1H); ESI MS m/z 481 [M+H]$^+$; HPLC (Method A) 99.1% (AUC), t$_R$=14.4 min.

Example 49

Preparation of 1-(10-Methyl-5,6,7,8,9,10-hexahydro-5,8-iminocyclohepta[4,5]pyrrolo[2,3-b]pyridin-2-yl)-4-(6-(trifluoromethyl)pyridin-2-yl)pyridin-2(1H)-one hydrochloride a) tert-Butyl 10-methyl-2-(2-oxo-4-(6-(trifluoromethyl)pyridin-2-yl)pyridin-1(2H)-yl)-5,6,7,8,9,10-hexahydro-5,8-iminocyclohepta[4,5]pyrrolo[2,3-b]pyridine-11-carboxylate

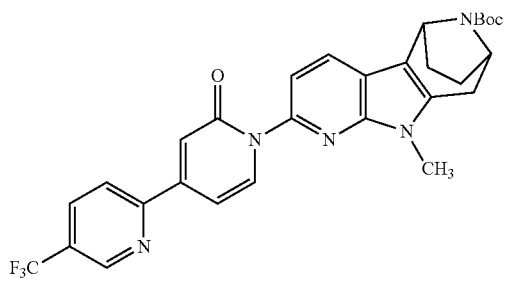

Chemical Formula: C$_{29}$H$_{28}$F$_3$N$_5$O$_3$
Exact Mass: 551.21
Molecular Weight: 551.56 tert-Butyl 2-bromo-10-methyl-5,6,7,8,9,10-hexahydro-5,8-iminocyclohepta[4,5]pyrrolo[2,3-b]pyridine-11-carboxylate (250 mg, 0.630 mmol), 4-(6-(trifluoromethyl)pyridin-2-yl)pyridin-2(1H)-one (152 mg, 0.630 mmol), CuI (180 mg, 0.940 mmol), 8-hydroxyquinoline (18.0 mg, 0.120 mmol) and Cs$_2$CO$_3$ (410 mg, 1.20 mmol) in DMSO (10 mL) were reacted following the procedure for Example 2 (step c) to provide the title compound (25.5 mg, 7%) as a yellow solid: $^1$H NMR (500 MHz, CDCl$_3$) δ 9.00 (d, J=2.0 Hz, 1H), 8.06 (dd, J=8.5, 2.5 Hz, 1H), 7.99-7.91 (m, 3H), 7.60-7.40 (m, 2H), 7.08 (d, J=7.5 Hz, 1H), 5.40-5.10 (m, 1H), 4.80-4.60 (m, 1H), 3.70 (s, 3H), 3.60-3.40 (m, 1H), 2.57-2.53 (d, J=16.5 Hz, 1H), 2.40-2.30 (m, 1H), 2.30-2.20 (m, 1H), 2.00-1.90 (m, 1H), 1.70-1.60 (m, 1H), 1.50-1.30 (m, 9H).

b) 1-(10-Methyl-5,6,7,8,9,10-hexahydro-5,8-iminocyclohepta[4,5]pyrrolo[2,3-b]pyridin-2-yl)-4-(6-(trifluoromethyl)pyridin-2-yl)pyridin-2(1H)-one hydrochloride

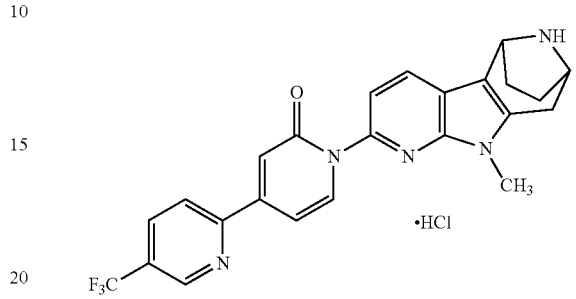

Chemical Formula: C$_{24}$H$_{21}$ClF$_3$N$_5$O
Exact Mass: 487.14
Molecular Weight: 487.90 tert-Butyl 10-methyl-2-(2-oxo-4-(6-(trifluoromethyl)pyridin-2-yl)pyridin-1(2H)-yl)-5,6,7,8,9,10-hexahydro-5,8-iminocyclohepta[4,5]pyrrolo[2,3-b]pyridine-11-carboxylate (25.0 mg, 40.0 μmol) was deprotected and converted to the hydrochloride salt according to the procedure for Example 2 (step d) to provide the title compound (5.8 mg, 30%) as a yellow solid: $^1$H NMR (500 MHz, CD$_3$OD) δ 9.06 (s, 1H), 8.30-8.27 (m, 1H), 8.23 (d, J=8.5 Hz, 1H), 8.15 (d, J=8.5 Hz, 1H), 8.05 (d, J=7.0 Hz, 1H), 7.49 (d, J=8.0 Hz, 1H), 7.40 (d, J=1.5 Hz, 1H), 7.28 (dd, J=7.0, 1.5 Hz, 1H), 5.28 (d, J=5.5 Hz, 1H), 4.59-4.56 (m, 1H), 3.79 (s, 3H), 3.57-3.52 (dd, J=17.5, 4.5 Hz, 1H), 3.17-3.13 (d, J=17.5 Hz, 1H), 2.52-2.31 (m, 3H), 2.06-2.03 (m, 1H); ESI MS m/z 452 [M+H]$^+$; HPLC (Method A) 90.2% (AUC), t$_R$=13.0 min.

Example 50

Preparation of 1-(10-Methyl-5,6,7,8,9,10-hexahydro-5,8-iminocyclohepta[4,5]pyrrolo[2,3-b]pyridin-2-yl)-4-(4-(trifluoromethyl)phenyl)pyridin-2(1H)-one hydrochloride a) 4-(4-(Trifluoromethyl)phenyl)pyridine 1-oxide (CAS Registry Number 545396-52-9) (WO 2003/049702 to Bo et al., which is hereby incorporated by reference in its entirety)

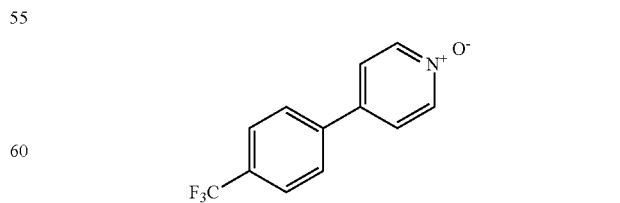

Chemical Formula: C$_{12}$H$_8$F$_3$NO
Exact Mass: 239.06
Molecular Weight: 239.19

4-Chloropyridine-N-oxide (3.0 g, 23 mmol), 4-trifluoromethylphenylboronic acid (6.57 g, 34.6 mmol), K$_2$CO$_3$ (4.8 g, 35 mmol) and PdCl$_2$(dppf) (470 mg, 0.57 mmol) were stirred in DMSO (40 mL) under vacuum for 30 min. The flask was flushed with nitrogen, and the mixture was heated to 80° C. for 10 min. Upon cooling, the mixture was diluted with methylene chloride and washed with 5% lithium chloride solution (5×), dried, concentrated, and the residue was purified by flash column chromatography (40 g ISCO column eluting with methylene chloride and a methanol/ammonia mixture (10:1); gradient 100% methylene chloride to 80% methylene chloride over 30 min at 40 mL/min) to provide the title compound (1.90 g, 34%) as a tan solid: ESI MS m/z 240 [M+H]$^+$.

b) 4-(4-(Trifluoromethyl)phenyl)pyridin-2(1H)-one (CAS Registry Number 942947-10-6) (U.S. Published Patent Application No. 2007/149513 to Chen et al., which is hereby incorporated by reference in its entirety)

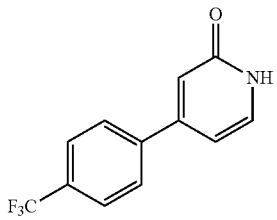

Chemical Formula: C$_{12}$H$_8$F$_3$NO
Exact Mass: 239.06
Molecular Weight: 239.19

4-(4-(Trifluoromethyl)phenyl)pyridine-1-oxide (1.9 g, 7.9 mmol) was heated to 140° C. in acetic anhydride (80 mL) for 5 h. The mixture was concentrated and then heated at 80° C. for 1 h in a mixture of MeOH (20 mL) and aqueous 1 N NaOH (15 mL). The resulting black solution was concentrated to a volume of 15 mL, and the solid was filtered off, rinsed with CH$_2$Cl$_2$ and dried under vacuum to provide the title compound (1.26 g, 66%) as a brown solid: $^1$H NMR (300 MHz, CD$_3$OD) δ 7.80-7.74 (br m, 5H), 6.85-6.66 (br m, 2H).

c) 1-(10-Methyl-5,6,7,8,9,10-hexahydro-5,8-iminocyclohepta[4,5]pyrrolo[2,3-b]pyridin-2-yl)-4-(4-(trifluoromethyl)phenyl)pyridin-2(1H)-one hydrochloride

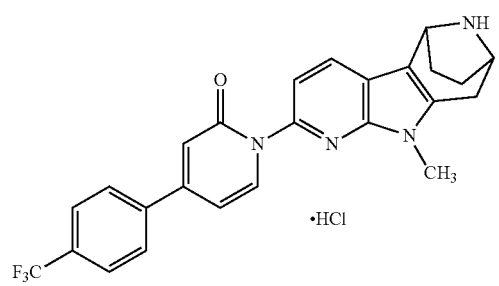

Chemical Formula: C$_{25}$H$_{22}$ClF$_3$N$_4$O
Exact Mass: 486.14
Molecular Weight: 486.92 tert-Butyl 2-bromo-10-methyl-5,6,7,8,9,10-hexahydro-5,8-iminocyclohepta[4,5]pyrrolo[2,3-b]pyridine-11-carboxylate (470 mg, 1.20 mmol), 4-(4-(trifluoromethyl)phenyl)pyridin-2(1H)-one (228 mg, 0.960 mmol), CuI (342 mg, 1.80 mmol), 8-hydroxyquinoline (34.0 mg, 0.240 mmol) and Cs$_2$CO$_3$ (782 mg, 2.40 mmol) in DMSO (15 mL) were reacted following the procedure for Example 2 (step c) to provide tert-butyl 10-methyl-2-(2-oxo-4-(4-(trifluoromethyl)phenyl)pyridin-1(2H)-yl)-5,6,7,8,9,10-hexahydro-5,8-iminocyclohepta[4,5]pyrrolo[2,3-b]pyridine-11-carboxylate (82.0 mg) as a brown oil.

tert-butyl 10-methyl-2-(2-oxo-4-(4-(trifluoromethyl)phenyl)pyridin-1(2H)-yl)-5,6,7,8,9,10-hexahydro-5,8-iminocyclohepta[4,5]pyrrolo[2,3-b]pyridine-11-carboxylate (82.0 mg, 0.150 mmol) was deprotected and converted to the hydrochloride salt according to the procedure for Example 2 (step d) to provide the title compound (25 mg, 4%) as a yellow solid: $^1$H NMR (500 MHz, CD$_3$OD) δ 8.15 (d, J=8.0 Hz, 1H), 8.01 (d, J=7.0 Hz, 1H), 7.97 (d, J=8.0 Hz, 2H), 7.84 (d, J=8.0 Hz, 2H), 7.48 (d, J=8.0 Hz, 1H), 6.96 (d, J=1.5 Hz, 1H), 6.89 (dd, J=7.5, 2.0 Hz, 1H), 5.28 (d, J=5.0 Hz, 1H), 4.59-4.56 (m, 1H), 3.79 (s, 3H), 3.57-3.52 (dd, J=17.5, 4.5 Hz, 1H), 3.17-3.13 (d, J=17.5 Hz, 1H), 2.52-2.31 (m, 3H), 2.07-2.00 (m, 1H); ESI MS m/z 451 [M+H]$^+$; HPLC (Method A) 95.8% (AUC), t$_R$=14.0 min.

Example 51

Binding Assay for Human Melanin-Concentrating Hormone (MCH-1) Receptor

Evaluation of the affinity of compounds for the human MCH-1 receptor was accomplished using 4-(3,4,5-tritritiumbenzyloxy)-1-(1-(2-(pyrrolidin-1-yl)ethyl)-1H-indazol-5-yl)pyridin-2(1H)-one and membranes prepared from stable CHO-K1 cells expressing the human MCH1 receptor obtained from Euroscreen (Batch 1138). Cell membrane homogenates (8.92 µg protein) were incubated for 60 min at 25° C. with 1.4 µM of the [$^3$H]-labeled compound in the absence or presence of the test compound in 50 mM Tris-HCl buffer, pH 7.4. Nonspecific binding was determined in the presence of 50 µM 1-(5-(4-cyanophenyl)bicyclo[3.1.0]hexan-2-yl)-3-(4-fluoro-3-(trifluoromethyl)phenyl)-1-(3-(4-methylpiperazin-1-yl)propyl)urea. Following incubation, the samples were filtered rapidly under vacuum through Skatron 11731 filters, pre-soaked in 0.5% polyethylenimine, and washed with ice-cold 50 mM Tris-HCl buffer, pH 7.4, (wash setting 9,9,0) using a Skatron cell harvester. The filters were counted for radioactivity in a liquid scintillation counter (Tri-Carb 2100TR, Packard) using a scintillation cocktail (Ultima Gold MV, Perkin Elmer).

The results are expressed as a percent inhibition of the control radioligand specific binding. The IC$_{50}$ value (concentration causing a half-maximal inhibition of control specific binding) and Hill coefficient (n$_H$) were determined by nonlinear regression analysis of the competition curve using Hill equation curve fitting. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor.

By methods as described above, the compounds listed in Table 1 were synthesized and tested for biological activity.

TABLE 1

Compounds Tested for Biological Activity

| Ex. No. | Structure | MCH-1 K$_i$ (nM) | Mass Spec | $^1$H NMR Data |
|---|---|---|---|---|
| 2 | (structure) ·HCl | 10.5 | 412 | $^1$H NMR (300 MHz, CD$_3$OD) δ 7.64 (d, J = 8.4 Hz, 1H), 7.58 (d, J = 7.6 Hz, 1H), 7.49-7.30 (m, 6H), 7.07-7.04 (dd, J = 8.3, 1.7 Hz, 1H), 6.33-6.30 (dd, J = 7.6, 2.6 Hz, 1H), 6.14 (d, J = 2.6 Hz, 1H), 5.23 (d, J = 4.6 Hz, 1H), 5.19 (s, 2H), 4.59-4.48 (m, 1H), 3.69 (s, 3H), 3.55-3.46 (dd, J = 17.3, 4.4 Hz, 1H), 3.05 (d, J = 17.3 Hz, 1H), 2.53-2.23 (m, 3H), 2.04-1.90 (m, 1H) |
| 3 | (structure) ·HCl | 24.4 | 452 | $^1$H NMR (300 MHz, CD$_3$OD) δ 8.53 (d, J = 8.9 Hz, 1H), 8.27 (d, J = 8.9 Hz, 1H), 7.90 (d, J = 7.1 Hz, 1H), 7.71 (d, J = 8.4 Hz, 1H), 7.58 (d, J = 1.3 Hz, 1H), 7.43 (d, J = 1.3 Hz, 1H), 7.35-7.32 (dd, J = 7.1, 2.0 Hz, 1H), 7.19-7.15 (dd, J = 8.4, 1.8 Hz, 1H), 5.26 (d, J = 4.6 Hz, 1H), 4.57-4.54 (m, 1H), 3.78 (s, 3H), 3.55-3.48 (dd, J = 17.0, 4.6 Hz, 1H), 3.09 (d, J = 17.5 Hz, 1H), 2.53-2.24 (m, 3H), 2.06-1.95 (m, 1H) |
| 4 | (structure) ·2HCl | 16.1 | 451 | $^1$H NMR (500 MHz, CD$_3$OD) δ 9.05 (s, 1H), 8.29-8.27 (dd, J = 8.4, 2.0 Hz, 1H), 8.23 (d, J = 8.3 Hz, 1H), 7.82 (d, J = 7.1 Hz, 1H), 7.70 (d, J = 8.3 Hz, 1H), 7.55 (d, J = 1.5 Hz, 1H), 7.39 (d, J = 1.4 Hz, 1H), 7.25-7.24 (dd, J = 7.1, 2.0 Hz, 1H), 7.17-7.14 (dd, J = 8.3, 1.8 Hz, 1H), 5.26 (d, J = 5.2 Hz, 1H), 4.58-4.53 (m, 1H), 3.72 (s, 3H), 3.53-3.49 (dd, J = 17.2, 4.5 Hz, 1H), 3.09 (d, J = 17.2 Hz, 1H), 2.53-2.35 (m, 2H), 2.32-2.27 (dd, J = 11.7, 9.7 Hz, 1H), 2.03-1.96 (m, 1H) |
| 5 | (structure) ·2HCl | 6.5 | 451 | $^1$H NMR (300 MHz, CD$_3$OD) δ 9.10 (s, 1H), 8.43-8.39 (dd, J = 8.9, 1.9 Hz, 1H), 7.97 (d, J = 8.2 Hz, 1H), 7.84 (d, J = 7.1 Hz, 1H), 7.70 (d, J = 8.4 Hz, 1H), 7.55 (d, J = 1.5 Hz, 1H), 7.15 (dd, J = 8.4, 1.8 Hz, 1H), 7.02 (d, J = 1.6 Hz, 1H), 6.90-6.87 (dd, J = 7.1, 2.0 Hz, 1H), 5.27 (d, J = 4.7 Hz, 1H), 4.59-4.53 (m, 1H), 3.72 (s, 3H), 3.53-3.48 (dd, J = 17.5, 4.5 Hz, 1H), 3.08 (d, J = 17.1 Hz, 1H), 2.52-2.26 (m, 3H), 2.04-2.00 (m, 1H) |
| 6 | (structure) ·2HCl | 13.5 | 431 | $^1$H NMR (300 MHz, CD$_3$OD) δ 8.54 (d, J = 2.7 Hz, 1H), 7.79-7.63 (m, 4H), 7.46 (d, J = 1.6 Hz, 1H), 7.08-7.04 (dd, J = 8.4, 1.8 Hz, 1H), 6.40-6.37 (dd, J = 7.6, 2.7 Hz, 1H), 6.18 (d, J = 2.6 Hz, 1H), 5.29 (s, 2H), 5.24 (d, J = 4.7 Hz, 1H), 4.58-4.50 (m, 1H), 3.70 (s, 3H), 3.54-3.46 (dd, J = 17.2, 4.9 Hz, 1H), 3.07 (d, J = 17.1 Hz, 1H), 2.51-2.23 (m, 3H), 2.02-1.99 (m, 1H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 7 | 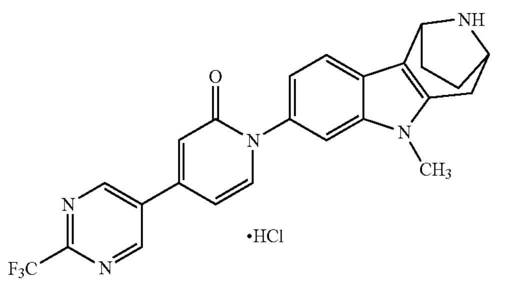 [SMILES: Cn1c2c(c3ccc(-n4ccc(-c5cnc(C(F)(F)F)nc5)cc4=O)cc31)C1CCC(C2)N1 ; Cl] | 68.1 | 452 | $^1$H NMR (300 MHz, CD$_3$OD) δ 9.36 (s, 2H), 7.87 (d, J = 7.1 Hz, 1H), 7.70 (d, J = 8.4 Hz, 1H), 7.55 (d, J = 1.5 Hz, 1H), 7.16-7.13 (dd, J = 8.4, 1.8 Hz, 1H), 7.09 (d, J = 1.5 Hz, 1H), 6.93-6.93 (dd, J = 7.1, 2.0 Hz, 1H), 5.26 (d, J = 4.7 Hz, 1H), 4.58-4.52 (m, 1H), 3.79 (s, 3H), 3.56-3.47 (dd, J = 17.3, 4.4 Hz, 1H), 3.12 (dd, J = 17.3, 1.4 Hz, 1H), 2.53-2.23 (m, 3H), 2.04-1.98 (m, 1H) |
| 8 | 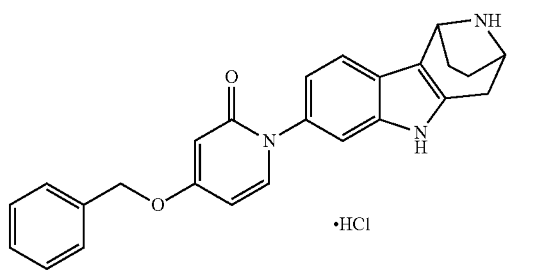 [SMILES: O=c1cc(OCc2ccccc2)ccn1-c1ccc2c3c([nH]c2c1)CC1CCC3N1 ; Cl] | 9.8 | 398 | $^1$H NMR (300 MHz, DMSO-d$_6$) δ 11.39 (s, 1H), 9.54 (br s, 1H), 9.14 (d, J = 9.8 Hz, 1H), 7.60 (d, J = 8.4 Hz, 1H), 7.55 (d, J = 7.6 Hz, 1H), 7.48-7.44 (m, 2H), 7.44-7.40 (m, 2H), 7.37 (dd, J = 8.0, 8.0 Hz, 1H), 7.29 (d, J = 1.8 Hz, 1H), 6.95-6.93 (dd, J = 8.3, 1.8 Hz, 1H), 6.09-6.07 (dd, J = 7.6, 2.6 Hz, 1H), 5.96 (d, J = 2.7 Hz, 1H), 5.18 (br s, 1H), 5.14 (s, 2H), 4.40 (br m, 1H), 3.44-3.40 (dd, J = 17.0, 4.0 Hz, 1H), 2.90 (d, J = 17.0 Hz, 1H), 2.29-2.26 (m, 2H), 2.07-2.04 (m, 1H), 1.80-1.75 (m, 1H) |
| 9 | 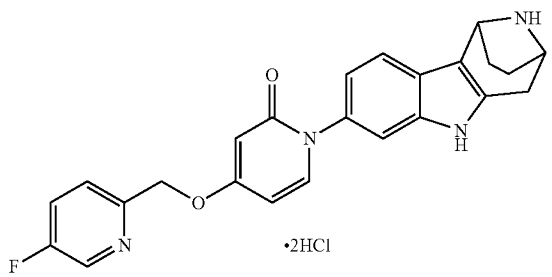 [SMILES: O=c1cc(OCc2ccc(F)cn2)ccn1-c1ccc2c3c([nH]c2c1)CC1CCC3N1 ; "·2HCl"] | 25.3 | 417 | $^1$H NMR (300 MHz, DMSO-d$_6$) δ 11.42 (s, 1H), 9.63 (d, J = 6.9 Hz, 1H), 9.18 (d, J = 9.7 Hz, 1H), 8.62 (d, J = 2.9 Hz, 1H), 7.97-7.86 (d, J = 8.4 Hz, 1H), 7.68-7.63 (dd, J = 8.6, 4.6 Hz, 1H), 7.62 (d, J = 8.6 Hz, 1H), 7.57 (d, J = 7.6 Hz, 1H), 7.30 (d, J = 1.6 Hz, 1H), 6.94-6.92 (dd, J = 8.4, 1.9 Hz, 1H), 6.14-6.10 (dd, J = 7.6, 2.7 Hz, 1H), 5.97 (d, J = 2.7 Hz, 1H), 5.21 (s, 2H), 5.18 (br m, 1H), 4.39 (br m, 1H), 3.46-3.39 (dd, J = 17.1, 4.5 Hz, 1H), 2.87 (d, J = 16.9 Hz, 1H), 2.34-2.22 (m, 2H), 2.11-2.00 (m, 1H), 1.84-1.74 (m, 1H) |
| 10 | 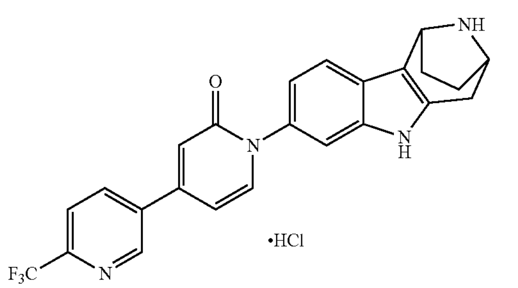 [SMILES: O=c1cc(-c2ccc(C(F)(F)F)nc2)ccn1-c1ccc2c3c([nH]c2c1)CC1CCC3N1 ; Cl] | 22.7 | 437 | $^1$H NMR (300 MHz, DMSO-d$_6$) δ 11.48 (s, 1H), 9.58-9.47 (br m, 1H), 9.20-9.15 (m, 2H), 8.51-8.47 (dd, J = 8.4, 1.8 Hz, 1H), 8.04 (d, J = 8.1 Hz, 1H), 7.84 (d, J = 7.1 Hz, 1H), 7.67 (d, J = 8.4 Hz, 1H), 7.42 (d, J = 1.8 Hz, 1H), 7.07-7.04 (dd, J = 8.4, 1.8 Hz, 1H), 7.00 (d, J = 1.8 Hz, 1H), 6.80-6.77 (dd, J = 7.2, 2.0 Hz, 1H), 5.21 (br m, 1H), 4.42 (br m, 1H), 3.47-3.40 (dd, J = 17.3, 4.4 Hz, 1H), 2.90 (d, J = 16.9 Hz, 1H), 2.30-2.23 (m, 2H), 2.07 (t, J = 9.8 Hz, 1H), 1.85-1.75 (m, 1H) |
| 11 | 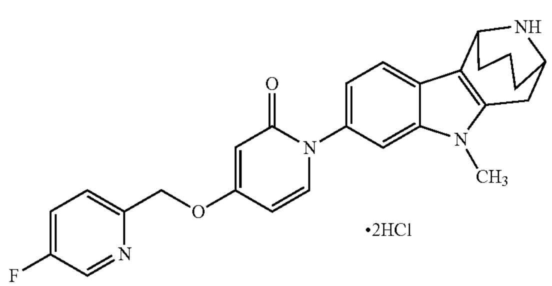 [SMILES: Cn1c2c(c3ccc(-n4ccc(OCc5ccc(F)cn5)cc4=O)cc31)C1CCCC(C2)N1 ; "·2HCl"] | 21.3 | 445 | $^1$H NMR (300 MHz, CD$_3$OD) δ 8.60 (s, 1H), 7.88-7.80 (ddd, J = 8.2, 2.8, 2.8 Hz, 1H), 7.80-7.70 (m, 2H), 7.60 (d, J = 8.4 Hz, 1H), 7.52 (d, J = 1.5 Hz, 1H), 7.09-7.05 (dd, J = 8.4, 1.8 Hz, 1H), 6.52-6.48 (dd, J = 7.6, 2.8 Hz, 1H), 6.26 (d, J = 2.6 Hz, 1H), 5.35 (s, 2H), 5.09 (br m 1H), 4.18-4.15 (m, 1H), 3.76 (s, 3H), 3.54-3.42 (dd, J = 18.0, 7.3 Hz, 1H), 3.13 (d, J = 18.0 Hz, 1H), 2.23-1.84 (m, 4H), 1.61-1.40 (m, 2H) |

TABLE 1-continued

Compounds Tested for Biological Activity

| Ex. No. | Structure | MCH-1 K$_i$ (nM) | Mass Spec | $^1$H NMR Data |
|---|---|---|---|---|
| 12 | (structure) ·HCl | 9.3 | 426 | $^1$H NMR (500 MHz, CD$_3$OD) δ 7.77 (d, J = 7.5 Hz, 1H), 7.60 (d, J = 8.3 Hz, 1H), 7.53 (d, J = 1.7 Hz, 1H), 7.48 (d, J = 7.9 Hz, 2H), 7.42 (dd, J = 2.9, 2.9 Hz, 2H), 7.39-7.35 (m, 1H), 7.09-7.07 (dd, J = 8.3, 1.8 Hz, 1H), 6.54-6.52 (dd, J = 7.5, 2.8 Hz, 1H), 6.31 (d, J = 2.6 Hz, 1H), 5.26 (s, 2H), 5.09 (br m 1H), 4.17-4.15 (m, 1H), 3.76 (s, 3H), 3.53-3.49 (dd, J = 17.9, 7.5 Hz, 1H), 3.12 (d, J = 17.9 Hz, 1H), 2.20-2.07 (m, 2H), 2.02-1.89 (m, 2H), 1.62-1.56 (m, 1H), 1.50-1.39 (m, 1H) |
| 13 | (structure) ·HCl | 46.3 | 465 | $^1$H NMR (300 MHz, DMSO-d$_6$) δ 9.65 (d, J = 11.4 Hz, 1H), 9.20 (d, J = 2.0 Hz, 1H), 9.10 (d, J = 10.5 Hz, 1H), 8.51-8.48 (dd, J = 8.0, 1.8 Hz, 1H), 8.05 (d, J = 8.2 Hz, 1H), 7.88 (d, J = 7.1 Hz, 1H), 7.64-7.61 (m, 2H), 7.10-7.07 (dd, J = 8.4, 1.7 Hz, 1H), 7.02 (d, J = 1.8 Hz, 1H), 6.83-6.80 (dd, J = 7.2, 2.0 Hz, 1H), 5.05 (br m 1H), 4.09 (br m, 1H), 3.72 (s, 3H), 3.44-3.22 (m, 1H), 3.04 (d, J = 17.8 Hz, 1H), 2.21-1.96 (m, 2H), 1.88-1.64 (m, 2H), 1.53-1.38 (m, 1H), 1.35-1.17 (m, 1H) |
| 14 | (structure) ·HCl Enantiomer A | 15.8 | 412 | $^1$H NMR (500 MHz, CD$_3$OD) δ 7.66 (d, J = 8.5 Hz, 1H), 7.62 (d, J = 7.5 Hz, 1H), 7.48-7.45 (m, 3H), 7.43-7.40 (m, 2H), 7.38-7.34 (m, 1H), 7.08 (dd, J = 6.5, 2.0 Hz, 1H), 6.36 (dd, J = 5.0, 3.0 Hz, 1H), 6.17 (d, J = 2.5 Hz, 1H), 5.24 (d, J = 5.5 Hz, 1H), 5.20 (s, 2H), 4.55-4.53 (m, 1H), 3.70 (s, 3H), 3.52 (dd, J = 12.5, 4.5 Hz, 1H), 3.09 (dd, J = 16.5, 1.0 Hz, 1H), 2.47-2.37 (m, 2H), 2.30-2.25 (m, 1H), 2.00-1.95 (m, 1H) |
| 15 | (structure) ·HCl Enantiomer B | 7.8 | 412 | $^1$H NMR (500 MHz, CD$_3$OD) δ 7.66 (d, J = 8.5 Hz, 1H), 7.62 (d, J = 7.5 Hz, 1H), 7.48-7.45 (m, 3H), 7.43-7.40 (m, 2H), 7.38-7.34 (m, 1H), 7.08 (dd, J = 6.5, 2.0 Hz, 1H), 6.36 (dd, J = 5.0, 3.0 Hz, 1H), 6.17 (d, J = 2.5 Hz, 1H), 5.24 (d, J = 5.5 Hz, 1H), 5.20 (s, 2H), 4.55-4.53 (m, 1H), 3.70 (s, 3H), 3.52 (dd, J = 12.5, 4.5 Hz, 1H), 3.09 (dd, J = 16.5, 1.0 Hz, 1H), 2.47-2.37 (m, 2H), 2.30-2.25 (m, 1H), 2.00-1.95 (m, 1H) |
| 16 | (structure) ·HCl Enantiomer B | 14 | 451 | $^1$H NMR (500 MHz, CD$_3$OD) δ 9.05 (d, J = 0.5 Hz, 1H), 8.28 (dd, J = 8.5, 2.5 Hz, 1H), 8.23 (d, J = 8.0 Hz, 1H), 7.83 (d, J = 7.0 Hz, 1H), 7.70 (d, J = 8.0 Hz, 1H), 7.56 (d, J = 2.0 Hz, 1H), 7.39 (d, J = 1.5 Hz, 1H), 7.25 (dd, J = 7.0, 2.0 Hz, 1H), 7.16 (dd, J = 8.5, 2.0 Hz, 1H), 5.26 (d, J = 8.0 Hz, 1H), 4.57-4.54 (m, 1H), 3.73 (s, 3H), 3.54-3.49 (dd, J = 17.5, 5 Hz, 1H), 3.12-3.07 (dd, J = 17.0, 1.0 Hz, 1H), 2.48-2.32 (m, 3H), 2.04-1.97 (m, 1H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 17 | (pyridazinone with 5-fluoropyridin-2-ylmethoxy group and N-methyl carbazole-bridged amine) ·HCl | 28 | 446 | $^1$H NMR (500 MHz, DMSO-d$_6$) δ 9.64 (d, J = 11.0 Hz, 1H), 9.04 (d, J = 11.0 Hz, 1H), 8.63 (d, J = 2.9 Hz, 1H), 8.00 (d, J = 2.8 Hz, 1H), 7.89-7.82 (dt, J = 8.7, 2.7 Hz, 1H), 7.73-7.68 (dd, J = 8.7, 4.6 Hz, 1H), 7.59 (d, J = 1.6 Hz, 1H), 7.58 (d, J = 8.5 Hz, 1H), 7.13-7.09 (dd, J = 8.3, 1.8 Hz, 1H), 6.53 (d, J = 2.8 Hz, 1H), 5.29 (s, 2H), 5.03 (s, 1H), 4.16-4.05 (m, 1H), 3.70 (s, 3H), 3.41-3.33 (dd, J = 18.0, 7.3 Hz, 1H), 3.03 (d, J = 18.0 Hz, 1H), 2.16-2.00 (m, 2H), 1.79 (d, J = 13.1 Hz, 1H), 1.70 (d, J = 12.3 Hz, 1H), 1.48 (d, J = 12.6 Hz, 1H), 1.33-1.24 (m, 1H) |
| 18 | (pyridazinone with 6-methylpyridin-3-ylmethoxy group and N-methyl carbazole-bridged amine) ·HCl | 73 | 442 | $^1$H NMR (300 MHz, DMSO-d$_6$) δ 9.63 (d, J = 10.8 Hz, 1H), 9.06 (d, J = 10.3 Hz, 1H), 8.76 (d, J = 1.7 Hz, 1H), 8.19 (d, J = 8.0 Hz, 1H), 7.97 (d, J = 2.9 Hz, 1H), 7.66 (d, J = 8.1 Hz, 1H), 7.59 (d, J = 1.8 Hz, 1H), 7.57 (d, J = 8.5 Hz, 1H), 7.12-7.09 (dd, J = 8.3, 1.8 Hz, 1H), 6.58 (d, J = 2.8 Hz, 1H), 5.34 (s, 2H), 5.03 (s, 1H), 4.08-4.01 (m, 1H), 3.70 (s, 3H), 3.41-3.33 (dd, J = 18.0, 7.5 Hz, 1H), 3.06 (d, J = 17.8 Hz, 1H), 2.63 (s, 3H), 2.17-2.01 (m, 2H), 1.90-1.61 (m, 2H), 1.59-1.44 (m, 1H), 1.32-1.23 (m, 1H) |
| 19 | (pyridinone with 6-trifluoromethylpyridin-3-ylmethoxy group and N-methyl carbazole-bridged amine) ·HCl | 13 | 495 | $^1$H NMR (300 MHz, DMSO-d$_6$) δ 9.71 (d, J = 11.3 Hz, 1H), 9.12 (d, J = 11.1 Hz, 1H), 8.89 (s, 1H), 8.21-8.18 (dd, J = 8.1, 1.4 Hz, 1H), 8.0 (d, J = 8.1 Hz, 1H), 7.64 (d, J = 7.6 Hz, 1H), 7.58 (d, J = 8.3 Hz, 1H), 7.51 (d, J = 1.6 Hz, 1H), 7.00-6.96 (dd, J = 8.3, 1.8 Hz, 1H), 6.17-6.13 (dd, J = 7.6, 2.8 Hz, 1H), 6.02 (d, J = 2.8 Hz, 1H), 5.38 (s, 2H), 5.02 (s, 1H), 4.12-4.00 (m, 1H), 3.70 (s, 3H), 3.41-3.33 (dd, J = 17.9, 7.3 Hz, 1H), 3.03 (d, J = 17.9 Hz, 1H), 2.18-2.02 (m, 2H), 1.80 (d, J = 13.3 Hz, 1H), 1.70 (d, J = 12.9 Hz, 1H), 1.47-1.23 (m, 2H) |
| 20 | (pyridinone with benzyloxy group and carbazole-bridged amine) ·HCl (−)-Enantiomer | 9.3 | 398 | $^1$H NMR (500 MHz, DMSO-d$_6$) δ 11.37 (s, 1H), 9.26-8.83 (s, 2H), 7.60 (d, J = 8.4 Hz, 1H), 7.56 (d, J = 7.6 Hz, 1H), 7.49-7.34 (m, 5H), 7.29 (d, J = 1.6 Hz, 1H), 6.95-6.92 (dd, J = 8.4, 1.9 Hz, 1H), 6.13-6.05 (dd, J = 7.6, 2.8 Hz, 1H), 5.90 (d, J = 2.8 Hz, 1H), 5.14 (s, 3H), 4.44-4.37 (m, 1H), 3.44-3.37 (dd, J = 17.2, 4.4 Hz, 1H), 2.85 (d, J = 16.8 Hz, 1H), 2.25-2.19 (m, 2H), 2.07-1.98 (m, 1H), 1.79-1.75 (m, 1H) |
| 21 | (pyridinone with benzyloxy group and carbazole-bridged amine) ·HCl (+)-Enantiomer | 39 | 398 | $^1$H NMR (300 MHz, DMSO-d$_6$) δ 11.41 (s, 1H), 9.58 (s, 1H), 9.16 (s, 1H), 7.60 (d, J = 8.4 Hz, 1H), 7.55 (d, J = 7.6 Hz, 1H), 7.49-7.34 (m, 5H), 7.29 (d, J = 1.6 Hz, 1H), 6.95-6.92 (dd, J = 8.4, 1.9 Hz, 1H), 6.10-6.07 (dd, J = 7.6, 2.8 Hz, 1H), 5.90 (d, J = 2.6 Hz, 1H), 5.18 (s, 1H), 5.14 (s, 2H), 4.48-4.25 (m, 1H), 3.46-3.39 (dd, J = 17.2, 4.4 Hz, 1H), 2.88 (d, J = 16.7 Hz, 1H), 2.38-2.15 (m, 2H), 2.07-1.98 (m, 1H), 1.85-1.66 (m, 1H) |

TABLE 1-continued

Compounds Tested for Biological Activity

| Ex. No. | Structure | MCH-1 K$_i$ (nM) | Mass Spec | $^1$H NMR Data |
|---|---|---|---|---|
| 22 | ·HCl | 25 | 399 | $^1$H NMR (300 MHz, DMSO-d$_6$) δ 11.40 (s, 1H), 9.48 (s, 1H), 9.13 (d, J = 8.6 Hz, 1H), 8.63-8.60 (m, 1H), 7.93-7.87 (td, J = 8.4, 1.8 Hz, 1H), 7.62-7.55 (m, 3H), 7.43-7.38 (m, 1H), 7.29 (d, J = 1.6 Hz, 1H), 6.96-6.93 (dd, J = 8.4, 1.9 Hz, 1H), 6.14-6.11 (dd, J = 7.6, 2.8 Hz, 1H), 5.94 (d, J = 2.8 Hz, 1H), 5.21 (s, 2H), 5.18 (s, 1H), 4.41 (s, 1H), 3.40-3.38 (m, 1H), 2.88 (d, J = 16.8 Hz, 1H), 2.29-2.21 (m, 2H), 2.05-2.02 (m, 1H), 1.85-1.76 (m, 1H) |
| 23 | ·HCl | 17 | 413 | $^1$H NMR (300 MHz, DMSO-d$_6$) δ 9.56 (d, J = 7.3 Hz, 1H), 9.16 (d, J = 10.1 Hz, 1H), 8.63-8.61 (m, 1H), 7.93-7.87 (td, J = 7.7, 2.8 Hz, 1H), 7.65 (d, J = 8.4 Hz, 1H), 7.59-7.54 (m, 2H), 7.48 (d, J = 1.6 Hz, 1H), 7.43-7.38 (m, 1H), 7.01-6.94 (dd, J = 8.3, 1.8 Hz, 1H), 6.16-6.13 (dd, J = 7.6, 2.8 Hz, 1H), 5.96 (d, J = 2.7 Hz, 1H), 5.22-5.20 (m, 3H), 4.53-4.37 (m, 1H), 3.64 (s, 3H), 3.42-3.35 (dd, J = 17.3, 4.6 Hz, 1H), 3.02 (d, J = 16.8 Hz, 1H), 2.29-2.21 (m, 2H), 2.11-2.02 (m, 1H), 1.85-1.75 (m, 1H) |
| 24 | ·HCl Enantiomer B | 7.4 | 431 | $^1$H NMR (500 MHz, CD$_3$OD) δ 8.50 (s, 1H), 7.72-7.64 (m, 2H), 7.62 (d, J = 8.5 Hz, 1H), 7.59 (d, J = 7.5 Hz, 1H), 7.42 (d, J = 2.0 Hz, 1H), 7.03 (dd, J = 8.5, 2.0 Hz, 1H), 6.32 (dd, J = 7.5, 2.5 Hz, 1H), 6.12 (d, J = 3.0 Hz, 1H), 5.26 (s, 2H), 5.10-5.08 (m, 1H), 4.45-4.42 (m, 1H), 3.68 (s, 3H), 3.44 (dd, J = 17.0, 4.5 Hz, 1H), 2.98 (dd, J = 17.0, 1.0 Hz, 1H), 2.41-2.28 (m, 2H), 2.24-2.19 (m, 1H), 1.94-1.88 (m, 1H) |
| 25 | ·HCl Enantiomer A | 19 | 431 | $^1$H NMR (500 MHz, CD$_3$OD) δ 8.51 (d, J = 2.5 Hz, 1H), 7.72-7.65 (m, 2H), 7.64 (d, J = 8.0 Hz, 1H), 7.59 (d, J = 7.5 Hz, 1H), 7.43 (d, J = 1.5 Hz, 1H), 7.04 (dd, J = 8.5, 2.0 Hz, 1H), 6.32 (dd, J = 7.5, 2.5 Hz, 1H), 6.12 (d, J = 3.0 Hz, 1H), 5.26 (s, 2H), 5.20-5.19 (m, 1H), 4.53-4.50 (m, 1H), 3.69 (s, 3H), 3.48 (dd, J = 17.0, 4.5 Hz, 1H), 3.05 (dd, J = 17.0, 1.0 Hz, 1H), 2.46-2.33 (m, 2H), 2.28-2.23 (m, 1H), 1.99-1.93 (m, 1H) |
| 26 | ·HCl | 9.7 | 426 | $^1$H NMR (300 MHz, DMSO-d$_6$) δ 11.0 (s, 0.5H), 10.30 (s, 0.5H), 7.61-7.4 (m, 2H), 7.49-7.34 (m, 6H), 7.03-6.97 (dt, J = 8.4, 1.8 Hz, 1H), 6.12-6.09 (dd, J = 7.6, 2.7 Hz, 1H), 5.97 (d, J = 2.7 Hz, 1H), 5.15 (s, 2H), 5.11-5.08 (m, 1H), 4.32-4.25 (m, 1H), 3.66 (s, 1.5H), 3.65 (s, 1.5H), 3.53-3.51 (m, 1H), 3.09-3.00 (m, 1H), 2.86 (d, J = 5.1 Hz, 1.5H), 2.66 (d, J = 5.1 Hz, 1.5H), 2.48-2.20 (m, 2H), 2.11-2.01 (m, 1H), 1.94-1.84 (m, 1H) |

TABLE 1-continued

Compounds Tested for Biological Activity

| Ex. No. | Structure | MCH-1 K$_i$ (nM) | Mass Spec | $^1$H NMR Data |
|---|---|---|---|---|
| 27 | 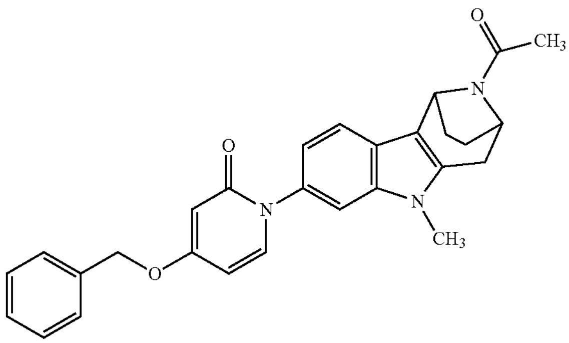 [SMILES: CC(=O)N1C2CCC1c1c(n(C)c3cc(-n4ccc(OCc5ccccc5)cc4=O)ccc13)C2] | 131 | 454 | $^1$H NMR (300 MHz, DMSO-d$_6$) δ 7.64-7.55 (m, 2H), 7.49-7.34 (m, 6H), 6.95-6.87 (m, 1H), 6.10 (m, 1H), 5.96 (d, J = 2.7 Hz, 1H), 5.54 (d, J = 5.3 Hz, 0.5H), 5.31 (d, J = 4.2 Hz, 0.5H), 5.14 (s, 2H), 4.83-4.76 (m, 0.5H), 4.70-4.66 (m, 0.5H), 3.59 (s, 1.5 H), 3.58 (s, 1.5H), 3.32-3.29 (m, 1H), 2.76 (d, J = 16.3 Hz, 0.5H), 2.63 (d, J = 15.9 Hz, 0.5H), 2.37-2.14 (m, 2H), 2.02-1.77 (m, 4H), 1.75-1.59 (m, 1H) |
| 28 | 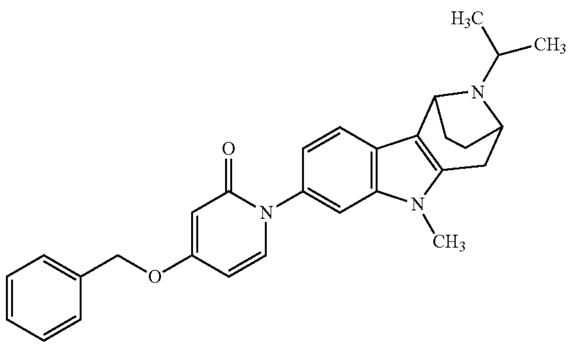 [SMILES: CC(C)N1C2CCC1c1c(n(C)c3cc(-n4ccc(OCc5ccccc5)cc4=O)ccc13)C2] | 12 | 454 | $^1$H NMR (500 MHz, CD$_3$OD) δ 7.71 (d, J = 8.5 Hz, 0.3H), 7.68 (d, J = 8.5 Hz, 0.7H), 7.61-7.59 (m, 1H), 7.48-7.46 (m, 3H), 7.43-7.42 (m, 2H), 7.41-7.36 (m, 1H), 7.09-7.08 (m, 1H), 6.35-6.32 (m, 1H), 6.16-6.15 (m, 1H), 5.40-5.38 (m, 1H), 4.91 (s, 2H), 4.71-4.53 (m, 1H), 3.72 (s, 3H), 3.56-3.47 (m, 1H), 3.42-3.32 (m, 1H), 3.21-3.02 (m, 1H), 2.61-2.41 (m, 2H), 2.32-2.18 (m, 1H), 2.15-1.98 (m, 1H), 1.53-1.49 (m, 2H), 1.49-1.43 (m, 2H), 1.32-1.26 (m, 2H) |
| 29 | Enantiomer A | 75 | 473 | $^1$H NMR (500 MHz, DMSO-d$_6$) δ 8.62 (d, J = 2.5 Hz, 1H), 7.84-7.80 (m, 1H), 7.67-7.64 (m, 1H), 7.61-7.54 (m, 2H), 7.39 (m, 1H), 6.94-6.91 (m, 1H), 6.12 (d, J = 7.0 Hz, 1H), 5.97 (s, 1H), 5.56-5.54 (m, 0.4H), 5.40-5.30 (m, 0.6H), 5.20 (s, 2H), 4.90-4.60 (m, 1H), 3.59 (s, 1.2H), 3.58 (s, 1.8H), 2.78 (d, J = 16.5 Hz, 0.4H), 2.65 (d, J = 16.0 Hz, 0.6H), 2.36-2.15 (m, 2H), 2.03-1.80 (m, 5H), 1.72-1.60 (m, 1H) |
| 30 | Enantiomer A | 97 | 440 | $^1$H NMR (500 MHz, CDCl$_3$) δ 9.49 (s, 0.3H), 9.14 (s, 0.7H), 7.43-7.26 (m, 8H), 6.93-6.91 (dd, J = 8.2, 1.8 Hz, 0.7H), 6.85-6.83 (dd, J = 8.2, 1.8 Hz, 0.3H), 6.09-6.05 (m, 2H), 5.58 (d, J = 5.4 Hz, 0.3H), 5.10-5.06 (m, 2.7H), 5.01-4.58 (m, 0.7H), 4.48-4.30 (m, 0.3H), 3.39-3.35 (dd, J = 16.1, 4.3 Hz, 0.7H), 3.13-3.09 (dd, J = 16.0, 4.0 Hz, 0.3H), 2.43 (d, J = 16.0 Hz, 0.7H), 2.38 (d, J = 16.0 Hz, 0.3H), 2.30-2.06 (m, 5H), 2.05-1.95 (m, 1H), 1.89-1.75 (m, 0.3H), 1.61-1.52 (m, 0.7H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 31 | 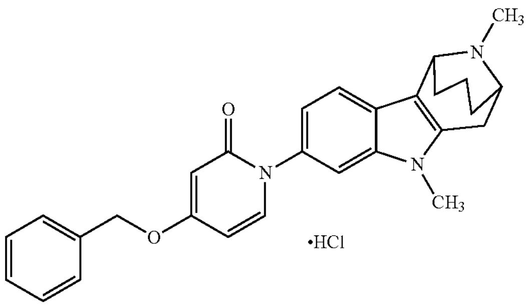 [SMILES: CN1C2CCCC1c1c(n(C)c3cc(-n4ccc(OCc5ccccc5)cc4=O)ccc13)C2 ; Cl] | 14 | 440 | $^1$H NMR (300 MHz, DMSO-d$_6$) δ 10.96 (s, 1H), 7.60-7.51 (m, 3H), 7.49-7.35 (m, 5H), 6.99-6.96 (dd, J = 8.3, 1.8 Hz, 1H), 6.12-6.09 (dd, J = 7.6, 2.7 Hz, 1H), 5.97 (d, J = 2.7 Hz, 1H), 5.15 (s, 2H), 5.02 (s, 1H), 3.98-3.93 (m, 1H), 3.70 (s, 3H), 3.43-3.35 (dd, J = 18.3, 7.3 Hz, 1H), 3.07 (d, J = 18.4 Hz, 1H), 2.65 (d, J = 4.9 Hz, 3H), 2.36-2.16 (m, 2H), 1.86 (d, J = 13.7 Hz, 1H), 1.74 (d, J = 13.4 Hz, 1H), 1.42 (d, J = 13.2 Hz, 1H), 1.26-1.14 (m, 1H) |
| 32 | 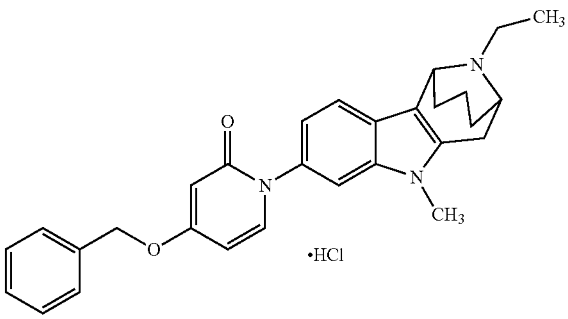 [SMILES: CCN1C2CCCC1c1c(n(C)c3cc(-n4ccc(OCc5ccccc5)cc4=O)ccc13)C2 ; Cl] | 15 | 454 | $^1$H NMR (500 MHz, DMSO-d$_6$) δ 10.46-10.26 (s, 1H), 7.59-7.57 (m, 2H), 7.51 (d, J = 1.7 Hz, 1H), 7.48-7.46 (m, 2H), 7.44-7.41 (m, 2H), 7.39-7.37 (m, 1H), 6.98-6.96 (dd, J = 8.3, 1.8 Hz, 1H), 6.16-6.09 (dd, J = 7.6, 2.7 Hz, 1H), 5.97 (d, J = 2.7 Hz, 1H), 5.15 (s, 3H), 4.15-4.01 (m, 1H), 3.69 (s, 3H), 3.40 (dd, J = 18.2, 6.7 Hz, 1H), 3.09-3.04 (d, J = 18.2 Hz, 1H), 3.04-2.93 (m, 2H), 2.37-2.17 (m, 2H), 1.92-1.84 (d, J = 13.9 Hz, 1H), 1.75 (d, J = 13.8 Hz, 1H), 1.49-1.41 (m, 1H), 1.32-1.19 (m, 4H) |
| 33 | Enantiomer B | 17 | 415 | $^1$H NMR (500 MHz, CD$_3$OD) δ 7.62 (d, J = 8.5 Hz, 1H), 7.44 (d, J = 2.0 Hz, 1H), 7.40-7.35 (m, 4H), 7.32-7.28 (m, 1H), 7.08 (dd, J = 8.5, 2.0 Hz, 1H), 5.22 (d, J = 5.5 Hz, 1H), 4.55-4.52 (m, 1H), 4.30-3.80 (m, 6H), 3.70 (s, 3H), 3.63-3.59 (m, 2H), 3.52-3.47 (m, 1H), 3.22-3.18 (m, 2H), 3.08-3.04 (m, 1H), 2.47-2.35 (m, 2H), 2.29-2.24 (m, 1H), 2.00-1.94 (m, 1H) |
| 34 | Enantiomer A | 68% @ 1 uM | 415 | $^1$H NMR (500 MHz, CD$_3$OD) δ 7.64 (d, J = 8.5 Hz, 1H), 7.44 (d, J = 1.5 Hz, 1H), 7.40-7.35 (m, 4H), 7.32-7.28 (m, 1H), 7.08 (dd, J = 8.0, 1.5 Hz, 1H), 5.22 (d, J = 5.5 Hz, 1H), 4.55-4.52 (m, 1H), 4.30-3.80 (m, 6H), 3.70 (s, 3H), 3.62-3.58 (m, 2H), 3.50 (dd, J = 17.5, 4.5 Hz, 1H), 3.21-3.16 (m, 2H), 3.06 (d, J = 17.0 Hz, 1H), 2.49-2.34 (m, 2H), 2.29-2.24 (m, 1H), 2.00-1.97 (m, 1H) |
| 35 | Enantiomer B | 59 | 397 | $^1$H NMR (500 MHz, CD$_3$OD) δ 9.15 (d, J = 2.0 Hz, 1H), 8.85 (dd, J = 8.5, 2.5 Hz, 1H), 8.05 (d, J = 8.5 Hz, 1H), 7.89 (d, J = 7.0 Hz, 1H), 7.71 (d, J = 8.5 Hz, 1H), 7.55 (d, J = 2.0 Hz, 1H), 7.15 (dd, J = 8.0, 1.5 Hz, 1H), 7.08 (d, J = 2.0 Hz, 1H), 6.90 (dd, J = 7.0, 2.0 Hz, 1H), 5.26 (d, J = 5.0 Hz, 1H), 4.58-4.56 (m, 1H), 3.73 (s, 3H), 3.52 (dd, J = 17.0, 4.5 Hz, 1H), 3.10 (dd, J = 17.0, 1.0 Hz, 1H), 2.87 (s, 3H), 2.51-2.36 (m, 2H), 2.32-2.27 (m, 1H), 2.03-1.99 (m, 1H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 36 | 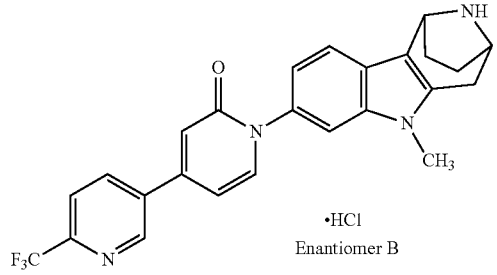 [SMILES: Cn1c2c(c3ccc(-n4ccc(-c5ccc(C(F)(F)F)nc5)cc4=O)cc31)C1CCC(C2)N1 ; Cl] | 5.3 | 451 | $^1$H NMR (500 MHz, CD$_3$OD) δ 9.10 (s, 1H), 8.41 (d, J = 8.0 Hz, 1H), 7.97 (d, J = 8.5 Hz, 1H), 7.84 (d, J = 7.0 Hz, 1H), 7.71 (d, J = 8.0 Hz, 1H), 7.55 (d, J = 1.0 Hz, 1H), 7.15 (dd, J = 8.0, 1.5 Hz, 1H), 7.02 (d, J = 1.5 Hz, 1H), 6.89 (dd, J = 7.0, 1.5 Hz, 1H), 5.26 (d, J = 5.0 Hz, 1H), 4.58-4.55 (m, 1H), 3.73 (s, 3H), 3.52 (dd, J = 17.5, 4.5 Hz, 1H), 3.10 (d, J = 17.0, 1H), 2.51-2.36 (m, 2H), 2.32-2.27 (m, 1H), 2.03-1.99 (m, 1H) |
| 37 | 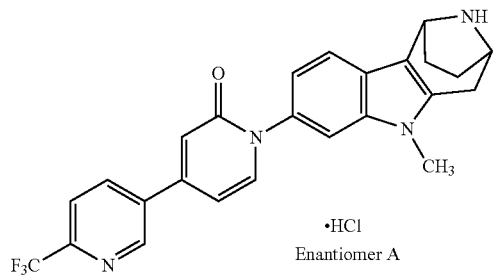 [SMILES: Cn1c2c(c3ccc(-n4ccc(-c5ccc(C(F)(F)F)nc5)cc4=O)cc31)C1CCC(C2)N1 ; Cl] | 72% @ 1 uM | 451 | $^1$H NMR (500 MHz, CD$_3$OD) δ 9.10 (d, J = 2.0 Hz, 1H), 8.41 (dd, J = 8.0, 2.0 Hz, 1H), 7.97 (d, J = 8.5 Hz, 1H), 7.84 (d, J = 7.0 Hz, 1H), 7.71 (d, J = 8.0 Hz, 1H), 7.55 (d, J = 1.5 Hz, 1H), 7.15 (dd, J = 8.0, 1.5 Hz, 1H), 7.02 (d, J = 2.0 Hz, 1H), 6.89 (dd, J = 7.0, 2.0 Hz, 1H), 5.26 (d, J = 5.0 Hz, 1H), 4.57-4.54 (m, 1H), 3.73 (s, 3H), 3.52 (dd, J = 17.5, 5.0 Hz, 1H), 3.10 (dd, J = 17.0, 1.0 Hz, 1H), 2.51-2.36 (m, 2H), 2.32-2.28 (m, 1H), 2.04-2.01 (m, 1H) |
| 38 | 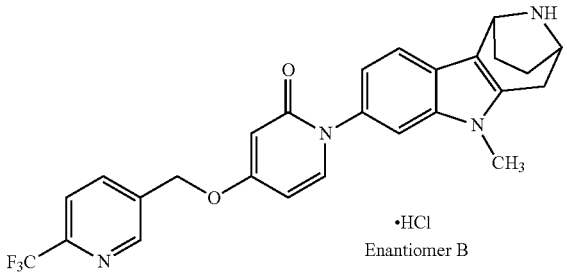 [SMILES: Cn1c2c(c3ccc(-n4ccc(OCc5ccc(C(F)(F)F)nc5)cc4=O)cc31)C1CCC(C2)N1 ; Cl] | 12 | 481 | $^1$H NMR (500 MHz, CD$_3$OD) δ 8.84 (s, 1H), 8.16 (d, J = 8.0 Hz, 1H), 7.89 (d, J = 8.0 Hz, 1H), 7.65 (d, J = 8.5 Hz, 1H), 7.61 (d, J = 7.5 Hz, 1H), 7.46 (d, J = 2.0 Hz, 1H), 7.07 (dd, J = 8.5, 2.0 Hz, 1H), 6.35 (dd, J = 8.0, 3.0 Hz, 1H), 6.17 (d, J = 2.5 Hz, 1H), 5.36 (s, 2H), 5.24 (d, J = 5.5 Hz, 1H), 4.56-4.53 (m, 1H), 3.70 (s, 3H), 3.50 (dd, J = 17.0, 4.5 Hz, 1H), 3.08 (dd, J = 17.5, 1.5 Hz, 1H), 2.48-2.36 (m, 2H), 2.31-2.26 (m, 1H), 2.02-2.00 (m, 1H) |
| 39 | 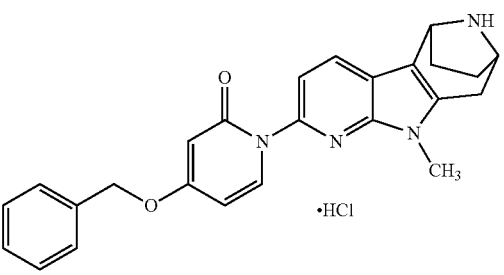 [SMILES: Cn1c2c(c3ccc(-n4ccc(OCc5ccccc5)cc4=O)nc31)C1CCC(C2)N1 ; Cl] | 21 | 413 | $^1$H NMR (500 MHz, CD$_3$OD) δ 8.10 (d, J = 8.0 Hz, 1H), 7.82 (d, J = 7.5 Hz, 1H), 7.48-7.35 (m, 6H), 6.37 (dd, J = 7.5, 2.5 Hz, 1H), 6.15 (d, J = 2.5 Hz, 1H), 5.26 (d, J = 5.5 Hz, 1H), 5.21 (s, 2H), 4.58-4.55 (m, 1H), 3.75 (s, 3H), 3.54 (dd, J = 17.5, 4.5 Hz, 1H), 3.15-3.11 (dd, J = 17.5, 1.0 Hz, 1H), 2.51-2.36 (m, 2H), 2.33-2.28 (m, 1H), 2.04-2.02 (m, 1H) |
| 40 | 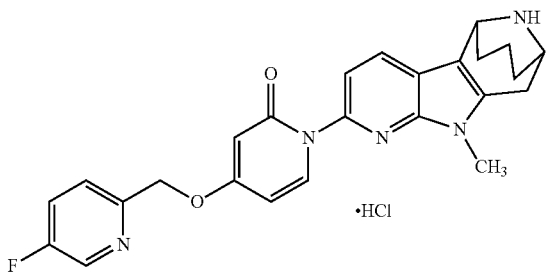 [SMILES: Cn1c2c(c3ccc(-n4ccc(OCc5ccc(F)cn5)cc4=O)nc31)C1CCCC(C2)N1 ; Cl] | 49 | 446 | $^1$H NMR (300 MHz, DMSO-d$_6$) δ 9.61 (d, J = 11.3 Hz, 1H), 9.13 (d, J = 10.7 Hz, 1H), 8.63 (d, J = 2.8 Hz, 1H), 8.09 (d, J = 8.3 Hz, 1H), 7.86-7.79 (m, 2H), 7.68-7.63 (dd, J = 8.6, 4.5 Hz, 1H), 7.33 (d, J = 8.2 Hz, 1H), 6.22-6.18 (dd, J = 7.7, 2.6 Hz, 1H), 6.00 (d, J = 2.6 Hz, 1H), 5.23 (s, 2H), 5.03 (s, 1H), 4.11-3.96 (m, 1H), 3.73 (s, 3H), 3.49-3.39 (dd, J = 18.3, 7.5 Hz, 1H), 3.16 (d, J = 18.2 Hz, 1H), 2.16-1.94 (m, 2H), 1.82 (d, J = 13.9 Hz, 1H), 1.72 (d, J = 13.9 Hz, 1H), 1.49-1.45 (m, 1H), 1.34-1.25 (m, 1H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 41 | 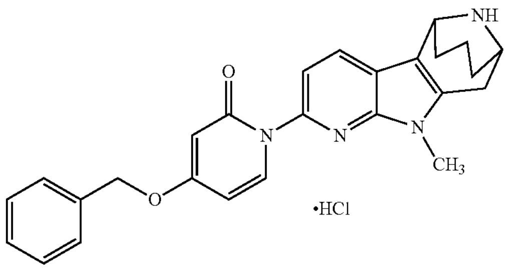 [SMILES: Cn1c2c(c3ccc(-n4ccc(OCc5ccccc5)cc4=O)nc31)C1CCCC(C2)N1 ; Cl] | 30 | 427 | $^1$H NMR (300 MHz, DMSO-d$_6$) δ 9.52 (d, J = 10.6 Hz, 1H), 9.10 (d, J = 10.5 Hz, 1H), 8.09 (d, J = 8.3 Hz, 1H), 7.82 (d, J = 7.7 Hz, 1H), 7.49 (m, 6H), 6.19-6.15 (dd, J = 7.6, 2.7 Hz, 1H), 6.00 (dd, J = 2.7 Hz, 1H), 5.17 (s, 2H), 5.06 (s, 1H), 4.18-4.00 (m, 1H), 3.73 (s, 3H), 3.44-3.36 (dd, J = 18.3, 7.4 Hz, 1H), 3.09 (d, J = 18.1 Hz, 1H), 2.15-2.00 (m, 2H), 1.83 (d, J = 13.3 Hz, 1H), 1.72 (d, J = 13.4 Hz, 1H), 1.49-1.45 (m, 1H), 1.34-1.14 (m, 1H) |
| 42 | 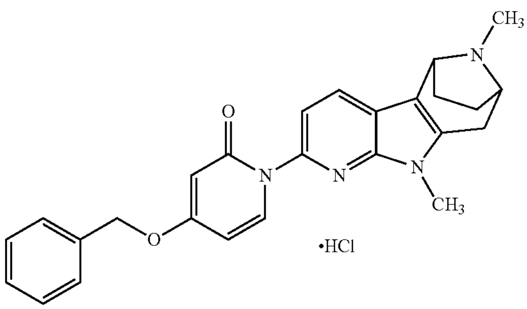 [SMILES: CN1C2CCC1c1c(n(C)c3nc(-n4ccc(OCc5ccccc5)cc4=O)ccc13)C2 ; Cl] | 27 | 427 | $^1$H NMR (500 MHz, CD$_3$OD) δ 8.07 (d, J = 8.0 Hz, 1H), 7.79 (dd, J = 8.0, 3.5 Hz, 1H), 7.47 (d, J = 7.0 Hz, 2H), 7.40-7.39 (m, 2H), 7.34-7.36 (m, 2H), 6.32 (dd, J = 7.5, 2.5 Hz, 1H), 6.11 (d, J = 2.5 Hz, 1H), 5.19 (s, 2H), 5.18-5.10 (m, 1H), 4.39-4.35 (m, 1H), 3.79 (s, 1H), 3.76 (s, 2H), 3.63-3.50 (m, 1H), 3.18-3.15 (m, 1H), 2.99 (s, 2H), 2.86 (s, 1H), 2.66-2.50 (m, 2H), 2.35-2.29 (m, 1H), 2.11-2.06 (m, 1H) |
| 43 | 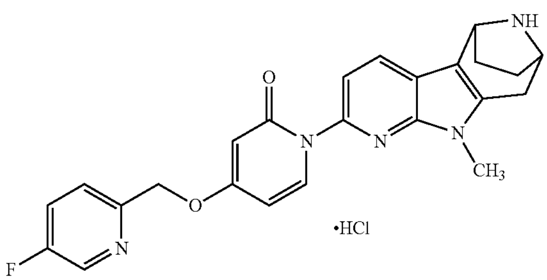 [SMILES: Cn1c2c(c3ccc(-n4ccc(OCc5ccc(F)cn5)cc4=O)nc31)C1CCC(C2)N1 ; Cl] | 38 | 432 | $^1$H NMR (500 MHz, CD$_3$OD) δ 8.54 (d, J = 2.5 Hz, 1H), 8.10 (d, J = 8.5 Hz, 1H), 7.81 (d, J = 7.5 Hz, 1H), 7.77-7.73 (m, 1H), 7.71-7.67 (m, 1H), 7.36 (d, J = 8.5 Hz, 1H), 6.37 (dd, J = 7.5, 2.5 Hz, 1H), 6.13 (d, J = 2.5 Hz, 1H), 5.29 (s, 2H), 5.25 (d, J = 5.0 Hz, 1H), 4.58-4.55 (m, 1H), 3.76 (s, 3H), 3.56-3.51 (dd, J = 18.0, 5.0 Hz, 1H), 3.15-3.10 (dd, J = 17.5, 1.0 Hz, 1H), 2.51-2.29 (m, 3H), 2.05-2.01 (m, 1H) |
| 44 | 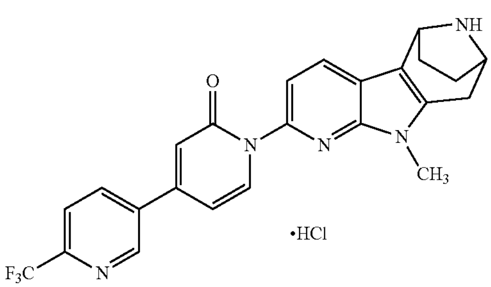 [SMILES: Cn1c2c(c3ccc(-n4ccc(-c5ccc(C(F)(F)F)nc5)cc4=O)nc31)C1CCC(C2)N1 ; Cl] | 110 | 452 | $^1$H NMR (500 MHz, CD$_3$OD) δ 9.11 (s, 1H), 8.42 (d, J = 8.0 Hz, 1H), 8.15 (d, J = 8.5 Hz, 1H), 8.06 (d, J = 7.0 Hz, 1H), 7.98 (d, J = 8.5 Hz, 1H), 7.49 (d, J = 8.0 Hz, 1H), 7.03 (d, J = 1.5 Hz, 1H), 6.92 (dd, J = 7.5, 2.0 Hz, 1H), 5.28 (d, J = 5.0 Hz, 1H), 4.59 (m, 1H), 3.79 (s, 3H), 3.58-3.53 (dd, J = 17.5, 5.0 Hz, 1H), 3.17-3.13 (d, J = 17.5 Hz, 1H), 2.52-2.31 (m, 3H), 2.06-2.03 (m, 1H) |
| 45 | 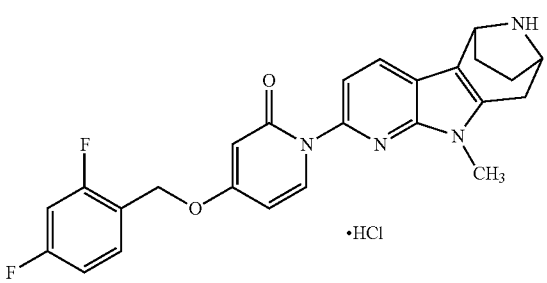 [SMILES: Cn1c2c(c3ccc(-n4ccc(OCc5ccc(F)cc5F)cc4=O)nc31)C1CCC(C2)N1 ; Cl] | 26 | 449 | $^1$H NMR (500 MHz, CD$_3$OD) δ 8.10 (d, J = 8.5 Hz, 1H), 7.79 (d, J = 7.5 Hz, 1H), 7.59 (m, 1H), 7.38 (d, J = 8.5 Hz, 1H), 7.07-7.02 (m, 2H), 6.29 (dd, J = 7.5, 2.5 Hz, 1H), 6.15 (d, J = 2.5 Hz, 1H), 5.40-5.25 (m, 1H), 5.20 (s, 2H), 4.70-4.50 (m, 1H), 3.76 (s, 3H), 3.55-3.51 (dd, J = 17.5, 4.5 Hz, 1H), 3.15-3.11 (d, J = 18.0 Hz, 1H), 2.51-2.29 (m, 3H), 2.05-1.99 (m, 1H) |

TABLE 1-continued

Compounds Tested for Biological Activity

| Ex. No. | Structure | MCH-1 $K_i$ (nM) | Mass Spec | $^1$H NMR Data |
|---|---|---|---|---|
| 46 | 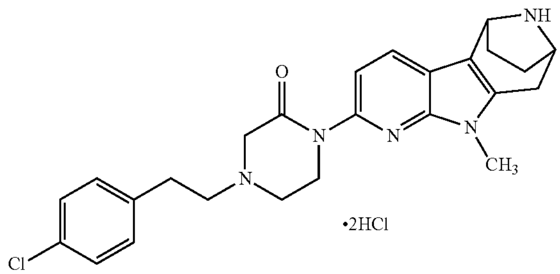 [SMILES: Cn1c2c(c3ccc(N4CCN(CCc5ccc(Cl)cc5)CC4=O)nc31)C1CCC(C2)N1 ; "·2HCl"] | 99 | 450 | $^1$H NMR (500 MHz, CD$_3$OD) δ 8.03 (d, J = 8.5 Hz, 1H), 7.57 (d, J = 8.0 Hz, 1H), 7.40-7.34 (m, 4H), 5.22 (d, J = 5.5 Hz, 1H), 4.57-4.54 (m, 1H), 4.40-4.20 (m, 4H), 4.00-3.80 (m, 2H), 3.74 (s, 3H), 3.60 (t, J = 8.5 Hz, 2H), 3.54-3.50 (dd, J = 17.5, 4.5 Hz, 1H), 3.20-3.16 (m, 2H), 3.12-3.08 (d, J = 17.5 Hz, 1H), 2.50-2.26 (m, 3H), 2.03-2.00 (m, 1H) |
| 47 | 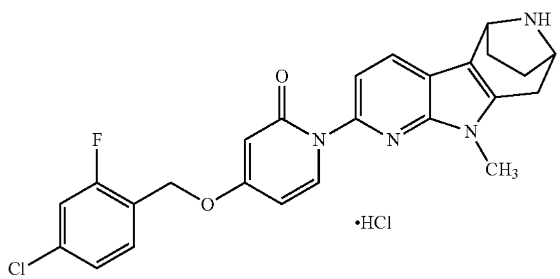 [SMILES: Cn1c2c(c3ccc(-n4ccc(OCc5ccc(Cl)cc5F)cc4=O)nc31)C1CCC(C2)N1 ; Cl] | 14 | 465 | $^1$H NMR (500 MHz, CD$_3$OD) δ 8.10 (d, J = 8.5 Hz, 1H), 7.79 (d, J = 8.0 Hz, 1H), 7.57-7.53 (m, 1H), 7.38 (d, J = 8.0 Hz, 1H), 7.32-7.28 (m, 2H), 6.30 (dd, J = 8.0, 3.0 Hz, 1H), 6.14 (d, J = 2.5 Hz, 1H), 5.26 (d, J = 5.5 Hz, 1H), 5.22 (s, 2H), 4.58-4.55 (m, 1H), 3.76 (s, 3H), 3.55-3.51 (dd, J = 17.5, 4.5 Hz, 1H), 3.15-3.11 (d, J = 17.5 Hz, 1H), 2.51-2.29 (m, 3H), 2.05-2.01 (m, 1H) |
| 48 | 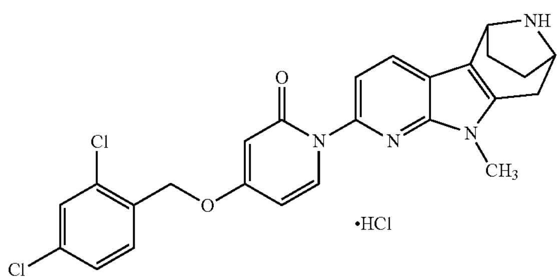 [SMILES: Cn1c2c(c3ccc(-n4ccc(OCc5ccc(Cl)cc5Cl)cc4=O)nc31)C1CCC(C2)N1 ; Cl] | 28 | 481 | $^1$H NMR (500 MHz, CD$_3$OD) δ 8.10 (d, J = 8.0 Hz, 1H), 7.80 (d, J = 7.5 Hz, 1H), 7.59-7.57 (m, 2H), 7.42 (dd, J = 8.5, 2.0 Hz, 1H), 7.38 (d, J = 8.0 Hz, 1H), 6.32 (dd, J = 8.0, 2.5 Hz, 1H), 6.12 (d, J = 2.5 Hz, 1H), 5.25 (m, 3H), 4.58-4.56 (m, 1H), 3.76 (s, 3H), 3.55-3.51 (dd, J = 18.0, 4.5 Hz, 1H), 3.15-3.11 (d, J = 17.5 Hz, 1H), 2.51-2.29 (m, 3H), 2.05-1.99 (m, 1H) |
| 49 | 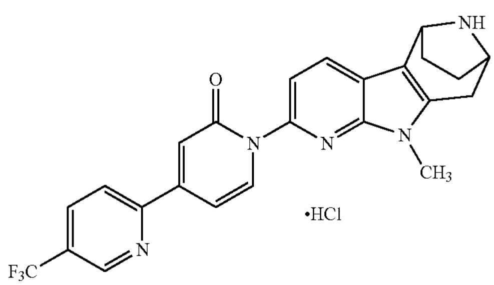 [SMILES: Cn1c2c(c3ccc(-n4ccc(-c5ccc(C(F)(F)F)cn5)cc4=O)nc31)C1CCC(C2)N1 ; Cl] | 53% @ 1 uM | 452 | $^1$H NMR (500 MHz, CD$_3$OD) δ 9.06 (s, 1H), 8.30-8.27 (m, 1H), 8.23 (d, J = 8.5 Hz, 1H), 8.15 (d, J = 8.5 Hz, 1H), 8.05 (d, J = 7.0 Hz, 1H), 7.49 (d, J = 8.0 Hz, 1H), 7.40 (d, J = 1.5 Hz, 1H), 7.28 (dd, J = 7.0, 1.5 Hz, 1H), 5.28 (d, J = 5.5 Hz, 1H), 4.59-4.56 (m, 1H), 3.79 (s, 3H), 3.57-3.52 (dd, J = 17.5, 4.5 Hz, 1H), 3.17-3.13 (d, J = 17.5 Hz, 1H), 2.52-2.31 (m, 3H), 2.06-2.03 (m, 1H) |
| 50 | 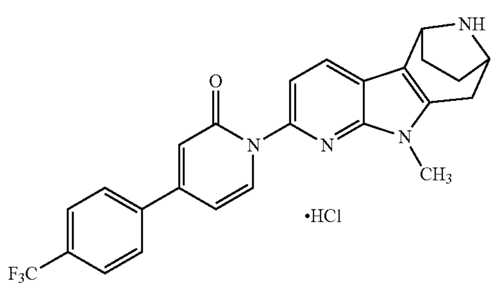 [SMILES: Cn1c2c(c3ccc(-n4ccc(-c5ccc(C(F)(F)F)cc5)cc4=O)nc31)C1CCC(C2)N1 ; Cl] | 19 | 451 | $^1$H NMR (500 MHz, CD$_3$OD) δ 8.15 (d, J = 8.0 Hz, 1H), 8.01 (d, J = 7.0 Hz, 1H), 7.97 (d, J = 8.0 Hz, 2H), 7.84 (d, J = 8.0 Hz, 2H), 7.48 (d, J = 8.0 Hz, 1H), 6.96 (d, J = 1.5 Hz, 1H), 6.89 (dd, J = 7.5, 2.0 Hz, 1H), 5.28 (d, J = 5.0 Hz, 1H), 4.59-4.56 (m, 1H), 3.79 (s, 3H), 3.57-3.52 (dd, J = 17.5, 4.5 Hz, 1H), 3.17-3.13 (d, J = 17.5 Hz, 1H), 2.52-2.31 (m, 3H), 2.07-2.00 (m, 1H) |

As compounds that bind strongly to MCH-1, compounds of formula I are expected to be effective in reducing obesity.

The present invention is not limited to the compounds found in the above examples, and many other compounds falling within the scope of the invention may also be prepared using the procedures set forth in the above synthetic schemes. The preparation of additional compounds of formula (I) using these methods will be apparent to one of ordinary skill in the chemical arts.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula I:

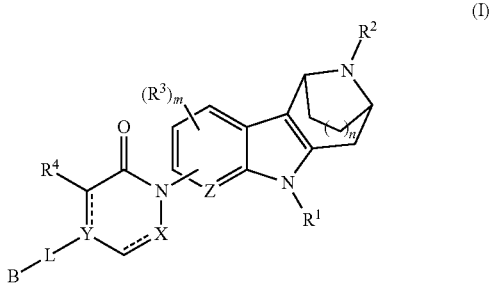

wherein $R^1$ is selected from the group consisting of H, —S(O)$_q$R$^6$, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

$R^2$ is selected from the group consisting of H, —S(O)$_q$R$^6$, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

$R^3$ is independently selected at each location from the group consisting of H, halogen, —OR$^5$, —NR$^5$R$^6$, —NR$^5$C(O)R$^6$, —NR$^5$C(O)$_2$R$^6$, —NR$^6$C(O)NR$^6$R$^7$, —S(O)$_q$R$^6$, —CN, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

$R^4$ is selected from the group consisting of H, halogen, —OR$^5$, —NR$^5$R$^6$, —NR$^5$C(O)R$^6$, —NR$^5$C(O)$_2$R$^6$, —NR$^6$C(O)NR$^6$R$^7$, —S(O)$_q$R$^6$, —CN, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

$R^5$ is H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, —C(O)R$^7$, phenyl, or benzyl, wherein phenyl or benzyl is optionally substituted 1 to 3 times with halogen, cyano, C$_1$-C$_4$ alkyl, C$_1$-C$_4$ haloalkyl, or C$_1$-C$_4$ alkoxy;

$R^6$ is H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, phenyl, or benzyl, wherein phenyl or benzyl is optionally substituted 1 to 3 times with halogen, cyano, C$_1$-C$_4$ alkyl, C$_1$-C$_4$ haloalkyl, or C$_1$-C$_4$ alkoxy;

$R^7$ is C$_1$-C$_4$ alkyl, C$_1$-C$_4$ haloalkyl, or phenyl;

$R^8$ and $R^9$ are each independently H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, —C(O)R$^7$, phenyl, or benzyl, wherein phenyl or benzyl is optionally substituted from 1 to 3 times with a substituent selected independently at each occurrence thereof from the group consisting of halogen, cyano, C$_1$-C$_4$ alkyl, C$_1$-C$_4$ haloalkyl, and C$_1$-C$_4$ alkoxy;

$R^{10}$ is selected from the group consisting of H, halogen, —OR$^5$, —NR$^5$R$^6$, —NR$^5$C(O)R$^6$, —NR$^5$C(O)$_2$R$^6$, NR$^6$C(O)NR$^6$R$^7$, —S(O)$_q$R$^6$, —CN, —C(O)R$^6$, —C(O)NR$^5$R$^6$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^8$, —NR$^8$R$^9$, and phenyl which is optionally substituted 1-3 times with halogen, C$_1$-C$_4$ alkyl, C$_1$-C$_4$ haloalkyl, C$_1$-C$_4$ alkoxy, —CN, —OR$^8$, or —NR$^8$R$^9$;

X is CR$^{10}$, C(R$^{10}$)$_2$, N, or NR$^{10}$;

Y is CR$^{10}$, C, or N;

Z is C, CH, or N;

L is —(CH$_2$)$_p$—O—, —(CH$_2$)$_p$—, —CH=CH—, or a bond;

B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S-alkyl, optionally substituted C$_1$-C$_6$ alkyl, halogen, —CF$_3$, and —CN;

n is 1 or 2;
m is 0, 1, 2, or 3;
p is from 1 to 4;
q is 0, 1, or 2; and
═══ represents an optional double bond, or an oxide thereof, or a pharmaceutically acceptable salt thereof.

2. The compound according to claim 1, wherein $R^1$ is H.
3. The compound according to claim 1, wherein $R^1$ is alkyl.
4. The compound according to claim 1, wherein $R^2$ is H.
5. The compound according to claim 1, wherein X is C.
6. The compound according to claim 1, wherein X is N.
7. The compound according to claim 1, wherein L is a bond.
8. The compound according to claim 1, wherein L is —CH$_2$—O—.
9. The compound according to claim 1, wherein L is —CH$_2$—CH$_2$—.
10. The compound according to claim 1, wherein B is aryl.
11. The compound according to claim 10, wherein B is phenyl.
12. The compound according to claim 1, wherein B is heteroaryl.
13. The compound according to claim 12, wherein B is pyridinyl.
14. The compound according to claim 13, wherein B is pyridin-2-yl.
15. The compound according to claim 13, wherein B is pyridin-3-yl.
16. The compound according to claim 12, wherein B is pyridazinyl.
17. The compound according to claim 16, wherein B is pyridazin-3-yl.
18. The compound according to claim 12, wherein B is pyrimidinyl.
19. The compound according to claim 18, wherein B is pyrimidin-5-yl.
20. The compound according to claim 1, wherein B is unsubstituted.
21. The compound according to claim 1, wherein B is substituted with one substituent selected from the group consisting of methyl, trifluoromethyl, chloro and fluoro.
22. The compound according to claim 1, wherein B is selected from the group consisting of phenyl, 5-(trifluoromethyl)pyridin-2-yl, 5-fluoropyridin-2-yl, 6-(trifluoromethyl)pyridazin-3-yl, 6-(trifluoromethyl)pyridin-3-yl, 2-(trifluoromethyl)pyrimidin-5-yl, 6-methylpyridin-3-yl, pyridin-2-yl, 2,4-difluorophenyl, 4-chlorophenyl, 4-chloro-2-fluorophenyl, 2,4-dichlorophenyl, and 4-(trifluoromethyl)phenyl.
23. The compound according to claim 1, wherein the compound has the formula:

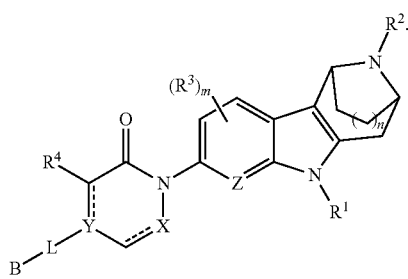

24. The compound according to claim 1, wherein the compound is selected from the group consisting of

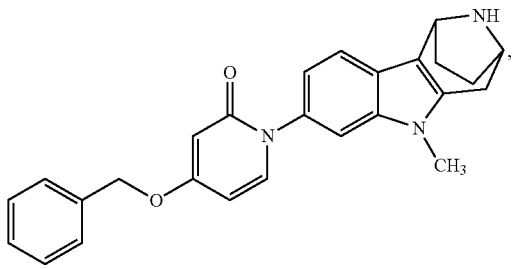

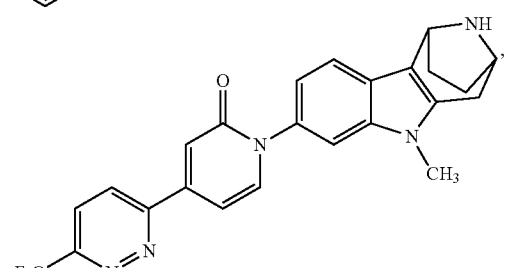

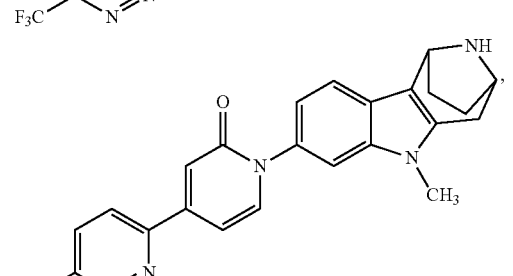

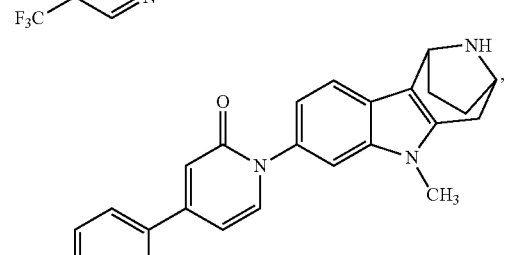

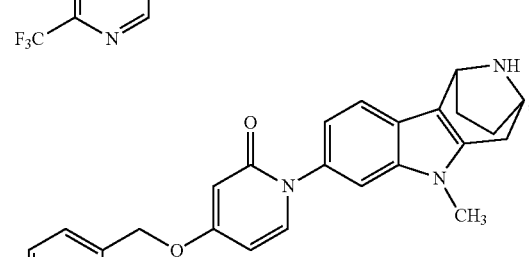

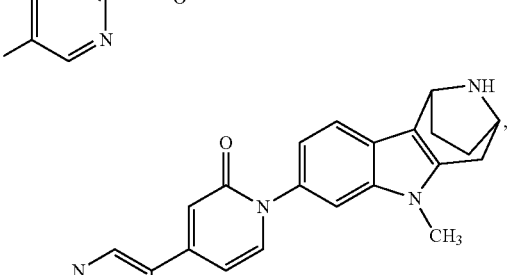

151
-continued
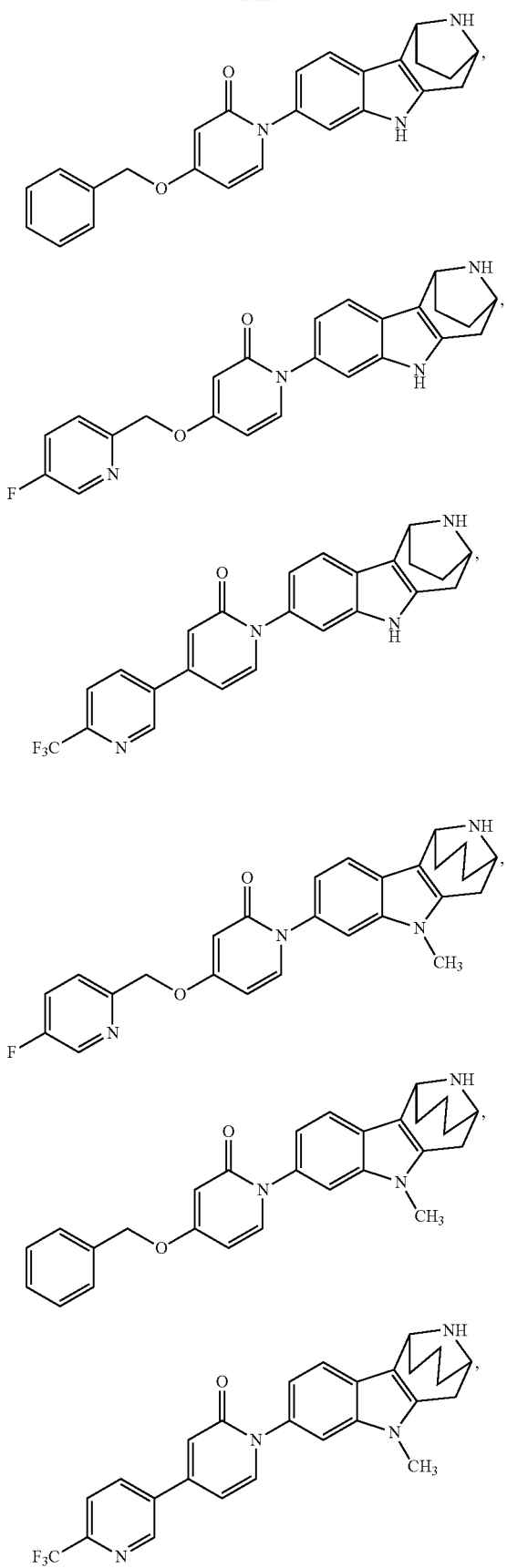
152
-continued
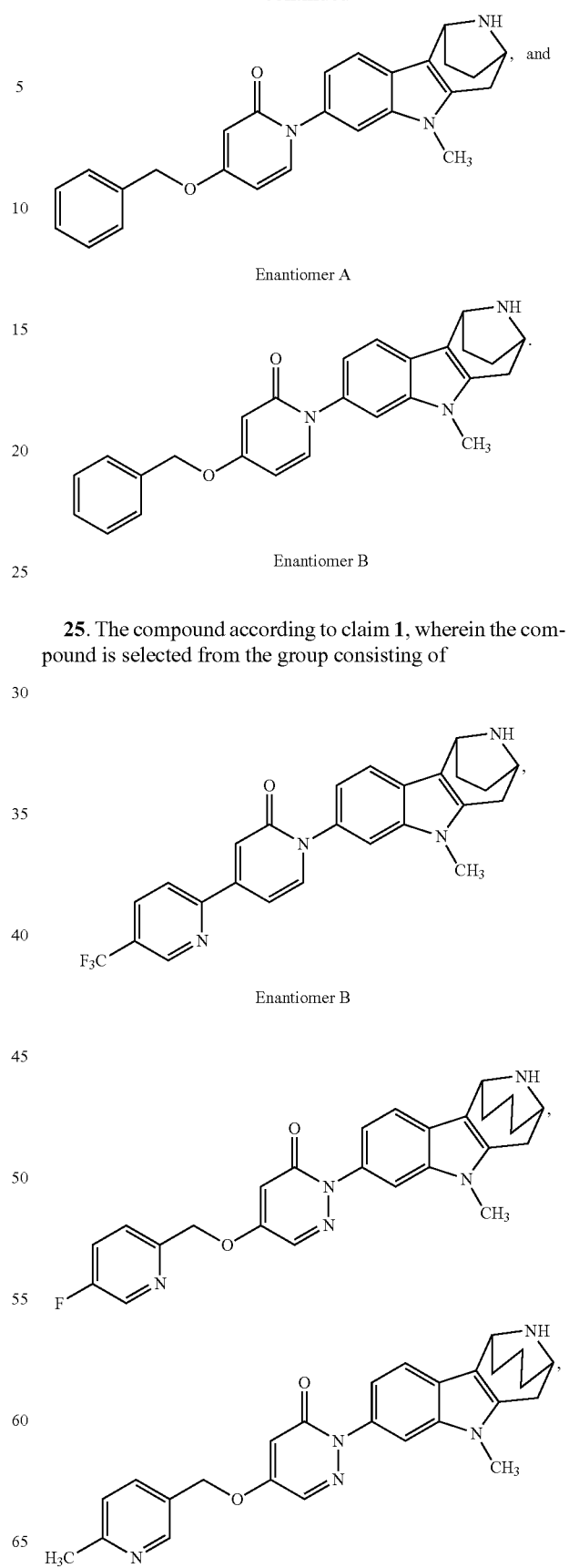
Enantiomer A
Enantiomer B
25. The compound according to claim 1, wherein the compound is selected from the group consisting of
Enantiomer B

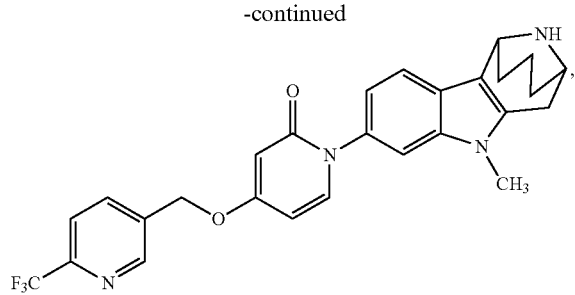
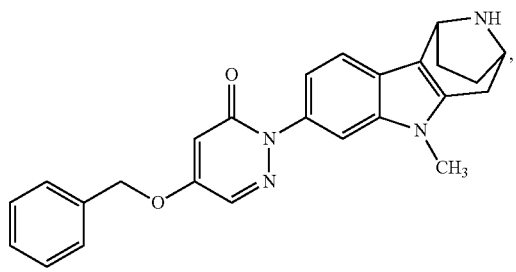
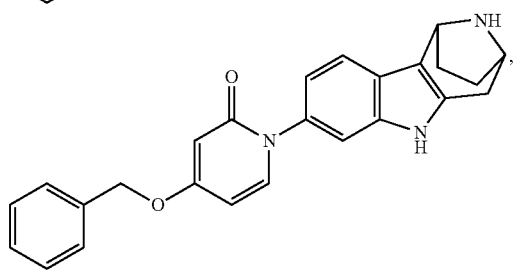
(−)-Enantiomer
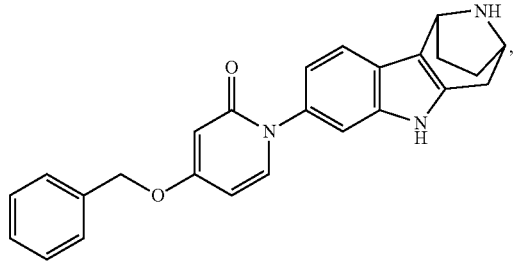
(+)-Enantiomer
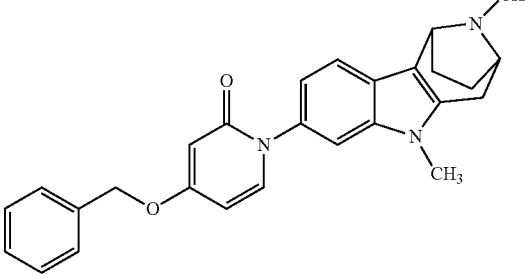
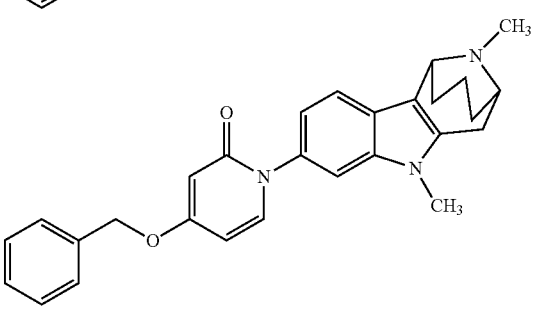
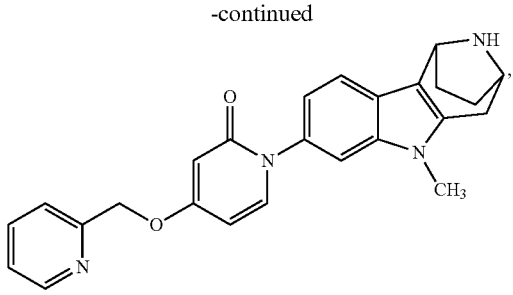
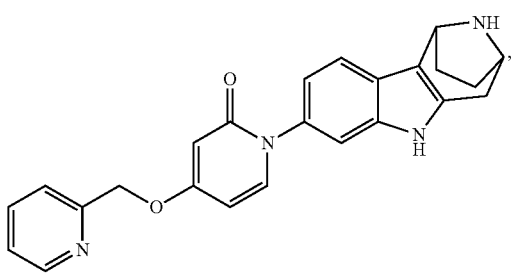
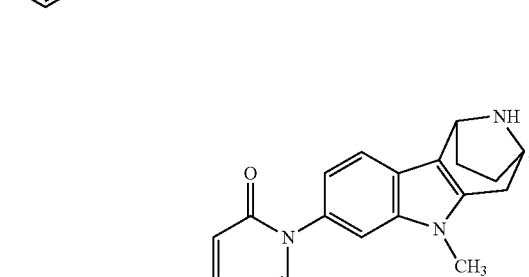
Enantiomer B
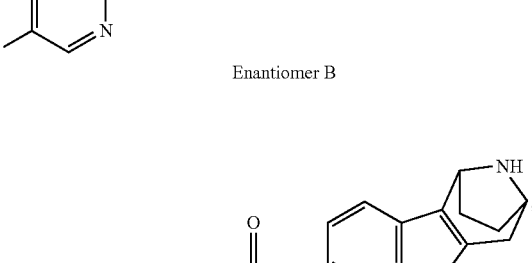
Enantiomer A
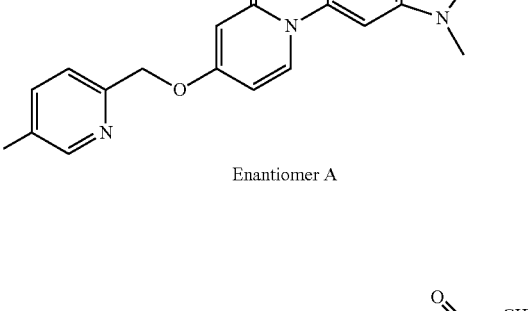

155
-continued
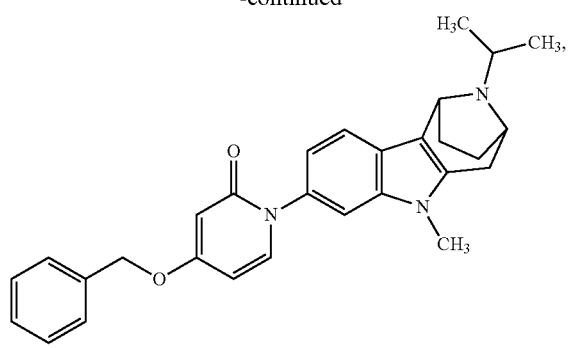
Enantiomer A
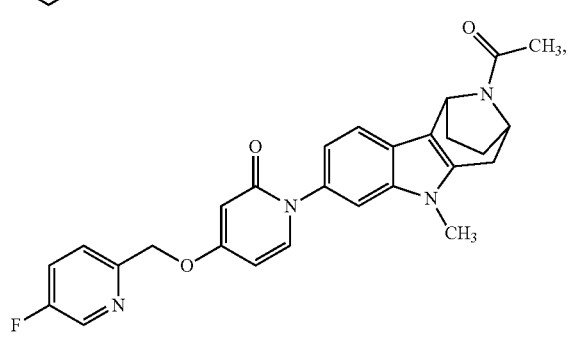
Enantiomer A
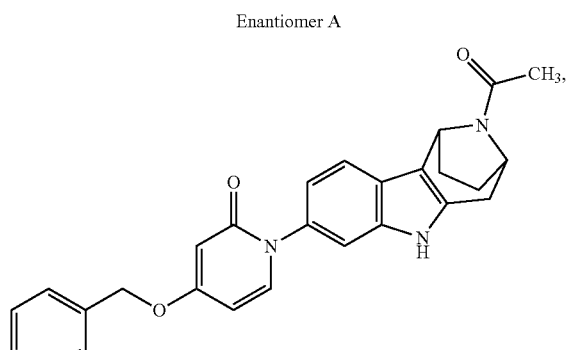
Enantiomer A
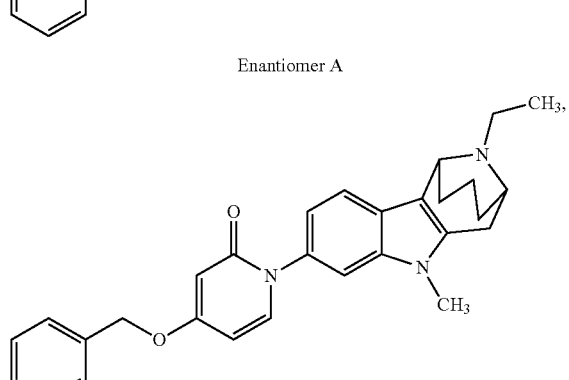
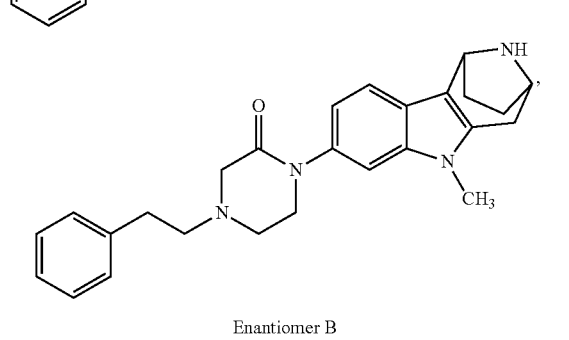
Enantiomer B
156
-continued
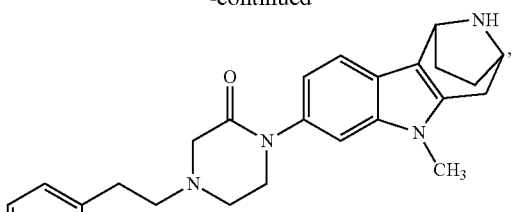
Enantiomer A
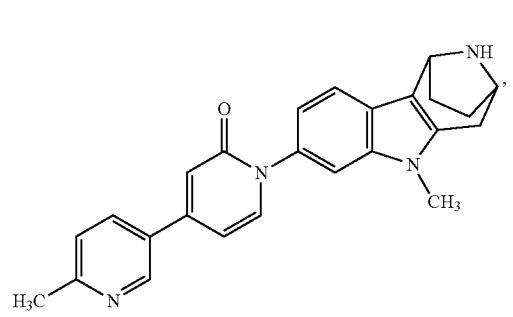
Enantiomer B
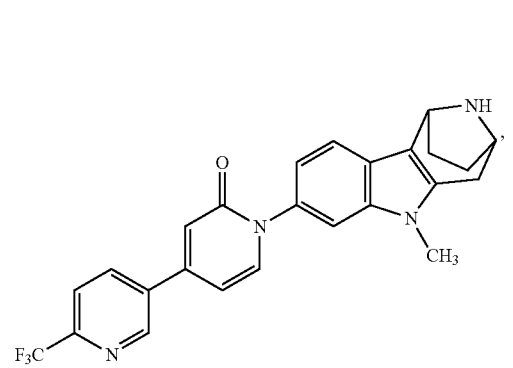
Enantiomer B
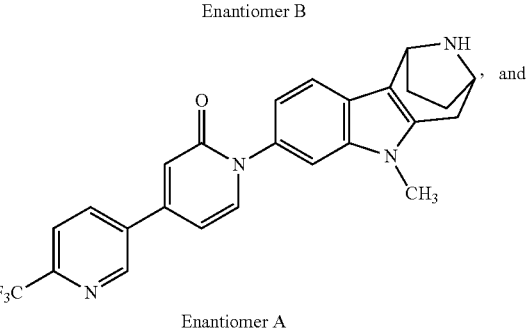
Enantiomer A
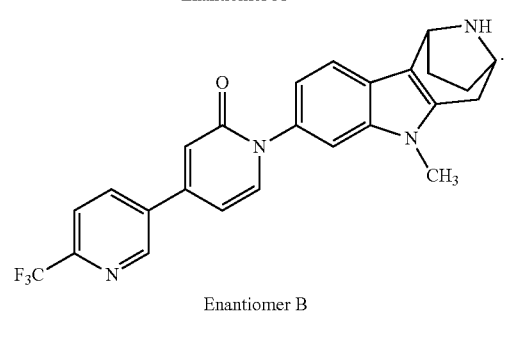
Enantiomer B

26. The compound according to claim 1, wherein the compound is selected from the group consisting of
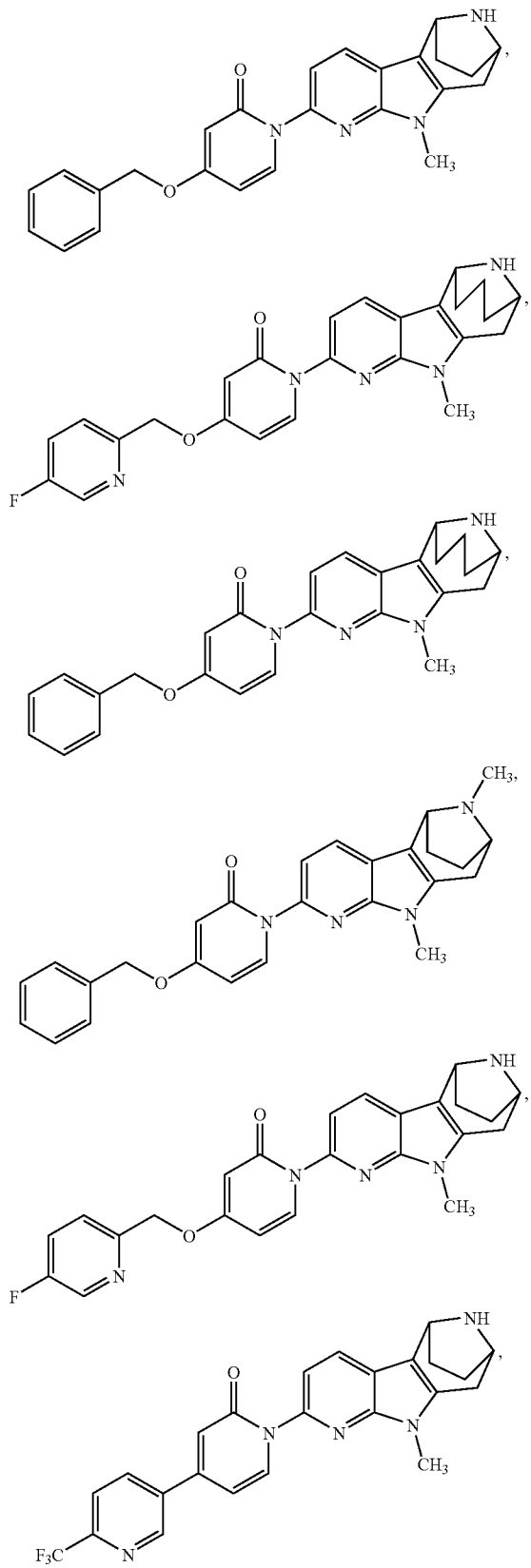
-continued
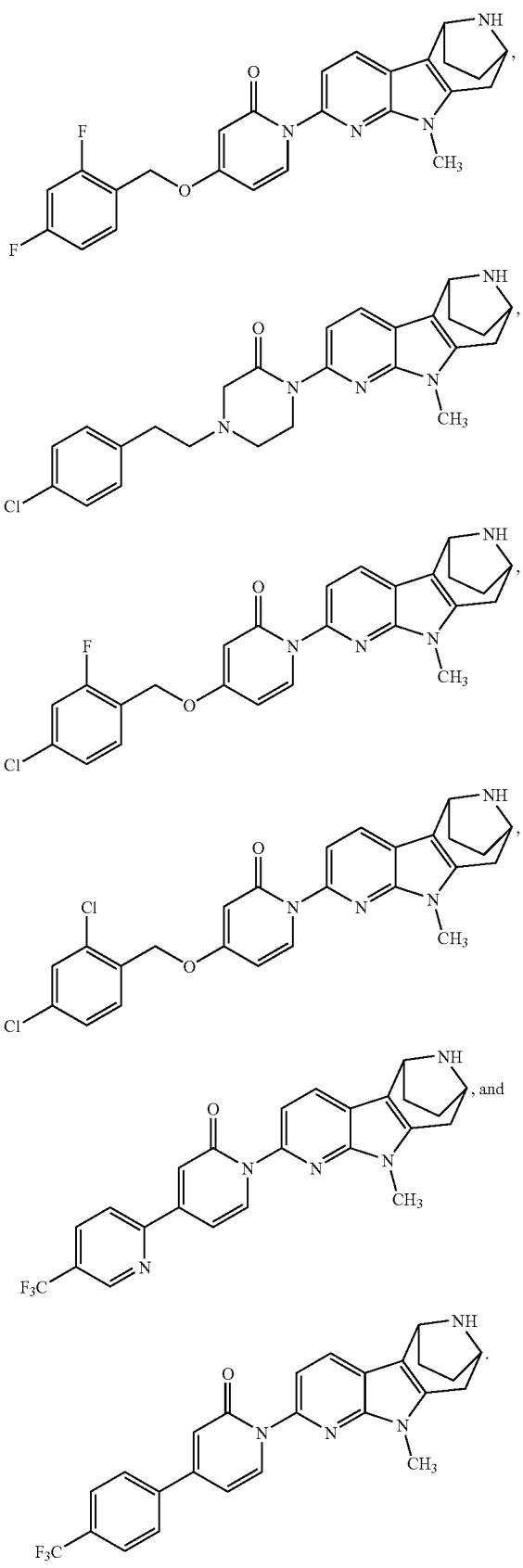
, and 27. The compound according to claim 1, wherein the compound is an HCl salt.

28. A pharmaceutical composition comprising a therapeutically effective amount of the compound according to claim 1 and a pharmaceutically acceptable carrier.

* * * * *